United States Patent
Aubele et al.

(10) Patent No.: US 9,884,828 B2
(45) Date of Patent: Feb. 6, 2018

(54) SUBSTITUTED CINNOLINES AS INHIBITORS OF LRRK2 KINASE ACTIVITY

(75) Inventors: Danielle L. Aubele, Cambridge, MA (US); Albert W. Garofalo, Cambridge, MA (US); Simeon Bowers, Cambridge, MA (US); Anh P. Truong, Cambridge, MA (US); Xiaocong Michael Ye, Cambridge, MA (US); Maurizio Franzini, Cambridge, MA (US); Marc Adler, Cambridge, MA (US); R. Jeffrey Neitz, Cambridge, MA (US); Gary Probst, Cambridge, MA (US)

(73) Assignee: Imago Pharmaceuticals, Inc., Jackson Hole, WY (US)

( * ) Notice: Subject to any disclaimer, the term of this patent is extended or adjusted under 35 U.S.C. 154(b) by 986 days.

(21) Appl. No.: 14/122,199

(22) PCT Filed: May 21, 2012

(86) PCT No.: PCT/US2012/038871
§ 371 (c)(1),
(2), (4) Date: Mar. 25, 2015

(87) PCT Pub. No.: WO2012/162254
PCT Pub. Date: Nov. 29, 2012

(65) Prior Publication Data
US 2015/0284337 A1    Oct. 8, 2015

Related U.S. Application Data

(60) Provisional application No. 61/519,443, filed on May 23, 2011.

(51) Int. Cl.
| | | |
|---|---|---|
| *A61K 31/502* | (2006.01) | |
| *C07D 237/28* | (2006.01) | |
| *C07D 401/04* | (2006.01) | |
| *C07D 401/10* | (2006.01) | |
| *C07D 401/12* | (2006.01) | |
| *C07D 401/14* | (2006.01) | |
| *C07D 403/04* | (2006.01) | |
| *C07D 403/10* | (2006.01) | |
| *C07D 405/04* | (2006.01) | |
| *C07D 405/10* | (2006.01) | |
| *C07D 405/12* | (2006.01) | |
| *C07D 417/04* | (2006.01) | |
| *C07D 413/10* | (2006.01) | |

(52) U.S. Cl.
CPC ......... *C07D 237/28* (2013.01); *C07D 401/04* (2013.01); *C07D 401/10* (2013.01); *C07D 401/12* (2013.01); *C07D 401/14* (2013.01); *C07D 403/04* (2013.01); *C07D 403/10* (2013.01); *C07D 405/04* (2013.01); *C07D 405/10* (2013.01); *C07D 405/12* (2013.01); *C07D 413/10* (2013.01); *C07D 417/04* (2013.01)

(58) Field of Classification Search
CPC .......................... A61K 31/502; C07D 237/28
USPC .......................................... 514/248; 544/235
See application file for complete search history.

(56) References Cited

U.S. PATENT DOCUMENTS

| 2,585,935 A | 2/1952 | Hepworth et al. |
|---|---|---|
| 4,886,800 A | 12/1989 | Resch |
| 7,723,337 B2 | 5/2010 | Dakin et al. |
| 2006/0211715 A1 | 9/2006 | Berthel et al. |
| 2009/0118311 A1 | 5/2009 | Davidson |

FOREIGN PATENT DOCUMENTS

| CN | 86 1 04358 A | 4/1987 |
|---|---|---|
| CN | 101641336 A | 2/2010 |
| DE | 833 818 C | 3/1952 |
| DE | 249011 | 8/1987 |
| WO | WO 2004/043458 A1 | 5/2004 |
| WO | WO 2006/124996 | 11/2006 |
| WO | WO 2007/045861 | 4/2007 |
| WO | WO 2008/090353 A1 | 7/2008 |
| WO | WO 2009/030270 A1 | 3/2009 |
| WO | WO 2009/080835 A1 | 7/2009 |
| WO | WO 2009/127642 A2 | 10/2009 |
| WO | WO 2010/085799 | 7/2010 |

(Continued)

OTHER PUBLICATIONS

Jordan, V. C. Nature Reviews: Drug Discovery, 2, 2003, 205.*
Hackam, et al. JAMA, 296(14), 2006, 1731-1732.*
Lewgowd, et al. Acta Poloniae Pharmaceutica, 62(2), 2005, 105-110.*
Combined Chinese Office Action dated Jan. 12, 2015 in Patent Application No. 201280035024.X (with English language translation).
Richard G. Button, et al., "The Probable Absence of Intramolecular General Base Catalysis in the Hydrolysis of Ethyl 6-Ethyl-4-hydroxycinnoline-3-carboxylate" J. Chem. Research, 1996, 13 pages.

(Continued)

*Primary Examiner* — Douglas M Willis
(74) *Attorney, Agent, or Firm* — Fish & Richardson P.C.

(57) ABSTRACT

The present invention provides compounds having a structure according to Formula I: (I) or a salt or solvate thereof, wherein R1, R2, R3 and R4 are defined herein. The invention further provides pharmaceutical compositions including the compounds of the invention and methods of making and using the compounds and compositions of the invention, e.g., in the treatment and prevention of various disorders, such as Parkinson's disease.

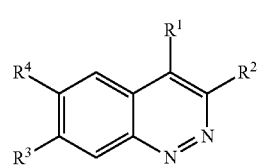

23 Claims, No Drawings

(56) References Cited

FOREIGN PATENT DOCUMENTS

| WO | WO 2010/106333 A1 | 9/2010 |
|----|-------------------|--------|
| WO | WO 2011/038572 A1 | 4/2011 |
| WO | WO 2012/062783    | 5/2012 |

OTHER PUBLICATIONS

David A. Scott, et al., "3-Amido-4-anilinocinnolines as a novel class of CSF-1R inhibitor" Bioorganic & Medicinal Chemistry Letters, vol. 21, 2011, pp. 1382-1384.

Pavadai Parasuraman, et al., "Synthesis, characterization and antimicrobial evaluation of some substituted 4-amino cinnoline-3-carboxamide derivatives" International Journal of Pharmacy & Life Sciences, vol. 3, No. 2, 2012, 8 pages.

J.S. Morley, et al., "495. Cinnolines and Other Heterocyclic Types in Relation to the Chemotherapy of Trypanosomiasis. Part VI. Synthesis of Quaternary Salts of Dicinnolyl- and Diquinolyl-ureas, -thioureas, and -guanidines." Journal of the Chemical Society, 1952, pp. 2617-2622.

Office Action dated Jul. 1, 2015 in Chinese Patent Application No. 201280035024.X (with English language translation).

Office Action dated Jul. 3, 2015 in European Patent Application No. 12 726 282.2.

Office Action dated Jan. 19, 2016 in Chinese Patent Application No. 201280035024.X (with English language translation).

Office Action dated May 19, 2016 in Australian Patent Application No. 2012258977.

Office Action dated Apr. 12, 2016 in Russian Patent Application No. 2013156827/04(088607) (with English language translation).

Japanese Office Action dated Aug. 1, 2016 in Patent Application No. 2014-512929 (with English Translation).

Office Action with Search History dated Feb. 2, 2016 in Canadian Patent Application No. 2,837,199.

International Preliminary Report on Patentability and Written Opinion dated Dec. 4, 2012 in PCT/US2011/038871 filed Jun. 2, 2011.

Office Action dated Dec. 25, 2015 in Japanese Patent Application No. 2014-512929 (with English language translation).

S. M. Hipparagi, et al., "Synthesis of Cinoxacin Derivatives by Phase Transfer Catalysis as Antibacterial Agents" Indian Journal of Heterocyclic Chemistry, vol. 13, No. 2, 2003, pp. 123-126.

Anshu Jakhar, et al., "Synthesis and antibacterial properties of some novel 2-substituted-6-(4-methyl-6-substitutedcinnoline-3-yl)imidazo[2,1-b][1,3,4]thiadiazoles" Indian Journal of Chemistry, vol. 49B, No. 11, Nov. 2010, pp. 1547-1551.

B. Narayana, et al., "Antibacterial and antifungal studies on some new acetylcinnolines and cinnolinyl thiazole derivatives" Indian Journal of Chemistry, vol. 45B, No. 7, Jul. 2006, pp. 1704-1709.

C. B. Kanner, et al., "Reaction of B-Amino-a, B-unsaturated Esters and Amides with Aryl Diazonium Salts" Tetrahedron, vol. 37, No. 20, 1981, pp. 3513-3518.

Atef M. Amer, et al., "On the Chemistry of Cinnoline IV [1]. Synthesis and Reactions of (4-Aminocinnolin-3-yl)-aryl-methanones" Monatshefte fur Chemie, vol. 132, No. 7, 2001, pp. 859-870.

Atef M. Amer, et al., "On the Chemistry of Cinnoline I. Synthesis and Reactions of (4-Amino-cinnolin-3-yl)-p-tolyl-methanones" Monatshefte fur Chemie, vol. 130, No. 11, 1999, pp. 1409-1418.

Andrzej Stanczak, et al., "Synthesis of I-Benzylcinnoline-3-Carboxylic Acids" Acta Poloniae Pharmaceutica, vol. 55, No. 1, 1998, pp. 71-76.

Andrzej Stanczak, et al., "Synthesis and biological activity of some 4-amino-3-cinnoline carboxylic acid derivatives" Pharmazie, vol. 53, No. 3, 1998, pp. 156-161.

A. N. Kaushal, et al., "Thiazolocinnolines" Indian Journal of Chemistry, vol. 10, No. 6 1972, pp. 675-676.

D. E. Ames, et al., "Ames and Lovesey: 1128. Cinnolines. Part VII. Methylation of 4-Hydroxy-6,7-dimethoxycinnoline-3-acetic Acid" Journal of Chemical Society, 1965, pp. 6036-6040.

J. M. Hearn, et al., "733. Ultra-violet Absorption Spectra of Some Derivatives of Quinoline, Quinazoline, and Cinnoline" Journal of the Chemical Society, 1951, pp. 3318-3329.

N. Haider, et al., "Product Class 9: Cinnolines" Science of Synthesis, vol. 16, 2004, pp. 251-313.

Russian Federation Office Action dated Jul. 14, 2016 in Patent Application No. 2013156827 (with English Translation).

Office Action dated Jul. 15, 2016 in European Patent Application No. 12 726 282.2.

Office Action dated Oct. 12, 2016 in Canadian Patent Application No. 2,837,199.

Berge et al., Journal of Pharmaceutical Science, 1977, 66: 1-19.

Biskup et al., "Dynamic and redundant regulation of LRRK2 and LRRK1 expression," BMC Neurosci. 2007, 8: 102.

Deng et al., "Characterization of a selective inhibitor of the Parkinson's disease kinase LRRK2," Nature Chemical Biology, 2011, 7(4): 203-5.

Dzamko et al., "Inhibition of LRRK2 kinase activity leads to dephosphorylation of Ser(910)/Ser(935), disruption of 14-3-3 binding and altered cytoplasmic localization," Biochemical Journal, 2010, 430(3): 405-13.

Gardet et al., "LRRK2 is involved in the IFN-gamma response and host response to pathogens," The Journal of Immunology, 2010, 185(9): 5577-5585.

Lee et al., "Inhibitors of leucine-rich repeat kinase-2 protect against models of Parkinson's disease," Nature Medicine, 2010, 16(9): 998-1000.

Lin et al., "Leucine-rich repeat kinase 2 regulates the progression of neuropathology induced by Parkinson's-disease-related mutant alpha-synuclein," Neuron, 2009, 64: 807-27.

Looyenga et al., "Chromosomal amplification of leucine-rich repeat kinase-2 (LRRK2) is required for oncogenic MET signaling in papillary renal and thyroid carcinomas," PNAS 2011, 108(4): 1439-1444.

Lunniss et al., "Addressing species specific metabolism and solubility issues in a quinolone series of oral PDE4 inhibitors," Bioorganic & Medicinal Chemistry Letters, 2010, 20(1): 137-140.

Melrose, "Update on the functional biology of Lrrk2," Future Neurol., 2008, 3(6): 669-681.

Paisan-Ruiz et al., "Cloning of the gene containing mutations that cause PARK8-linked Parkinson's disease," Neuron, 2004, 44(4): 595.

Pan et al., "The association between Parkinson's disease and melanoma," Internation Journal of Cancer, 2011, 128(10): 2251-2260.

Parisiadou et al., "LRRK2 function on actin and microtubule dynamics in Parkinson disease," Communicative & Integrative Biology, 2010, 3(5): 396-400.

Parkinson, "An essay on the shaking palsy. 1817.," Neuropsychiatry Clin. Neurosci., 2002, 14(2): 223-236.

Purushothaman et al., "Synthesis and antimicrobial studies of some pyrimidocinnolines," Indian Journal of Heterocyclic Chemistry, 1999, 9(1): 43-46.

Saunders-Pullman et al., "LRRK2 G2019S mutations are associated with an increased cancer risk in Parkinson disease," Movement Disorders 2010, 25(15): 2536-2541.

Stanczak et al., "Synthesis, structures, and biological activity of some 4-amino-3-cinnoline-carboxylic acid derivatives. Part 3. 1,3-Oxazino[5,4-c]cinnolines and pyrimido[5,4-c]cinnolines," Pharmazie, 1997, 52(11): 838-843.

Takeda et al., "Abnormal accumulation of NACP/alpha-synuclein in neurodegenerative disorders," J. Pathol. 1998, 152: 367-372.

Thomas and Beal, "Parkinson's disease," Human Molecular Genetics, 2007, 16, Review Issue 2, R183.

Tong et al., "Loss of leucine-rich repeat kinase 2 causes impairment of protein degradation pathways, accumulation of alpha-synuclein, and apoptotic cell death in aged mice," Proc. Natl. Acad. Sci. 2010, 107(21): 9879.

West et al., "Parkinson's disease-associated mutations in leucine-rich repeat kinase 2 augment kinase activity," Proc. Natl. Acad. Sci. 2005, 102(46): 16842.

Zhang et al., "Genomewide association study of leprosy," The New England Journal of Medicine, 2009, 361(27): 2609-2618.

(56) References Cited

OTHER PUBLICATIONS

Zimprich et al., "Mutations in LRRK2 cause autosomal-dominant parkinsonism with pleomorphic pathology," Neuron, 2004, 44(4): 601.
International Search Report and Written Opinion in International Application No. PCT/US2012/038871, dated Jul. 18, 2012, 12 pages.

* cited by examiner

SEQUENCE LISTING

<160> NUMBER OF SEQ ID NOS: 1

<210> SEQ ID NO 1
<211> LENGTH: 15
<212> TYPE: PRT
<213> ORGANISM: Artificial Sequence
<220> FEATURE:
<223> OTHER INFORMATION: Synthetic biotin-linked LRRK2 peptide
<220> FEATURE:
<221> NAME/KEY: MOD_RES

```
<222> LOCATION: (1)..(1)
<223> OTHER INFORMATION: biotin-linked

<400> SEQUENCE: 1

Arg Leu Gly Arg Asp Lys Tyr Lys Thr Leu Arg Gln Ile Arg Gln
1               5                   10                  15
```

SUBSTITUTED CINNOLINES AS INHIBITORS OF LRRK2 KINASE ACTIVITY

CROSS REFERENCE TO RELATED APPLICATIONS

This application claims priority to U.S. Provisional Application Ser. No. 61/519,443 entitled "Inhibitors of LRRK2 Kinase Activity" filed May 23, 2011 which is incorporated herein by reference in its entirety.

BACKGROUND OF THE INVENTION

Parkinson's disease (PD) is the most common form of parkinsonism, a neurodegenerative movement disorder characterized by resting tremors, rigidity, postural instability, impaired speech and bradykinesia (slowed movement). In addition to PD, parkinsonism is exhibited in a range of conditions such as progressive supranuclear palsy, corticobasal degeneration, multiple system atrophy, and dementia with Lewy bodies. PD was first formally described in 1817 by James Parkinson in his monograph titled, "An Essay on the Shaking Palsy" (Parkinson, J.; J. Neuropsychiatry Clin. Neurosci. 2002, 14(2), 223-236 (reprinted)). He noted that the symptoms of this particular disorder include involuntary tremors, decreased muscular strength, bent posture, and difficulty walking. The pathological correlate is the loss of dopaminergic neurons in the substantia nigra of the basal ganglia and the presence of Lewy bodies (LB) in postmortem brain tissues. Aggregated α-synuclein forms the intracellular LB deposits, which are the pathological hallmark of PD and other Lewy body diseases (see e.g., Spillantini et al., Nature 1997, 388:839-840; Takeda et al., J. Pathol. 1998, 152:367-372; and Wakabayashi et al., Neurosci. Lett. 1997, 239:45-48). Most cases of PD appear not to have a genetic component. For that reason the most common form of PD is known as sporadic Parkinson's disease or idiopathic Parkinson's disease (IPD). Other forms of PD include autosomal recessive juvenile parkinsonism (AR-JP) and several rare familial forms. PD affects approximately 1-2% of the population over age 50 (~1.5 million in the US, over 5 million worldwide) and early onset cases can occur as early as 30 (Thomas, B.; Beal, M. F.; Human Molecular Genetics 2007, 16, Review Issue 2, R183).

Current therapeutic strategies for PD focus primarily on reducing the severity of symptoms by using supplement dopaminergic medications. These drugs may lose efficacy after prolonged treatment and display severe side effects. Levodopa, a precursor of dopamine, is the most commonly prescribed drug for treatment. At present, there is no disease-modifying therapy that addresses the underlying neuropathological cause of the disease, thus constituting a significant unmet medical need. Cumulative evidence over the past decade demonstrate that autosomal mutations of several genes might be responsible for a sizable disease sub-population. A prime example is the recent discovery that dominant point mutations in Leucine-rich repeat kinase 2 (LRRK2) cause late-onset PD with clinical and pathological features indistinguishable from idiopathic PD. The extensive genetic analyses undertaken so far indicate that LRRK2 mutations are relatively frequent, accounting for 5-10% of PD cases with a positive family history (familial PD) and 1-2% of sporadic PD cases.

Leucine-rich repeat kinase 2 (also known as dardarin) is a product of the PARK8 gene. It is a member of the tyrosine kinase-like branch of the kinome. LRRK2 encodes a large multi-domain protein that consists of N-terminal leucine-rich repeats (LRR), a ROC (Ras-GTPase in complex proteins) domain, a COR (C-terminal of ROC) domain, a protein kinase domain most homologous to the RIP (Receptor Interacting Protein) kinases, and a C-terminal WD40 domain. It is expressed throughout the brain including regions associated with motor neuron dysfunction. It is also found in various other tissues, most notably in the kidneys, where expression is highest (Biskup, S.; Moore, D. J.; Rea, A.; et al. BMC Neurosci. 2007, 8:102). Levels in kidney are reported to be ~6-fold higher than in brain (Tong, Y.; Yamaguchi, H.; Giaime, E.; et al. Proc. Natl. Acad. Sci. 2010, 107(21), 9879). Mutations in the PARK8 gene have been associated with familial PD (Paisan-Ruiz, C.; Jain, S.; Evans, E. W.; et al. Neuron, 2004, 44(4), 595). All the pathogenic mutations can lead to a wide spectrum of cellular toxicity in a kinase-dependent manner. The most prevalent amino acid substitution found in mutant LRRK2 is G2019S, which is located within the highly conserved DF/YG motif in the activation loop and causes significant increase in kinase activity.

Patients with LRRK2 mutations exhibit Lewy body pathology (Zimprich, A.; Biskup, S.; Leitner, P.; et al. Neuron, 2004, 44(4), 601), and LRRK2 is considered one of the most relevant targets for treating PD and other LB diseases. The G2019S mutation is believed to be responsible for 3-40% of familial and sporadic PD cases, dependent on study population, with Lewy body pathology most often associated with G2019S (Ross, O. A.; Toft, M.; Whittle, A. J.; et al. Ann. Neurol. 2006, 59(2), 388). Because the LRRK2 G2019S mutation has increased kinase activity, inhibition of this activity is a therapeutic target for the treatment of PD (West, A. B.; Moore, D. J.; Biskup, S.; et al. Proc. Natl. Acad. Sci. 2005, 102(46), 16842). Importantly, most of the LRRK2-mediated toxicity and pathology can be prevented by treatment with specific kinase inhibitors, suggesting that kinase inhibitors could be useful therapeutic agents for PD patients with LRRK2 mutations and potentially for sporadic PD as well. Additional LRRK2 mutations, such as 12020T, also in the kinase domain, R1441C and R1441G in the Roc domain, and Y1699C in the COR domain are also associated with PD, and mutations G2385R and R1628P are considered risk factors for sporadic PD in Asian populations (Melrose; Future Neurol. 2008, 3(6), 669-681). Animal models expressing mutant LRRK2 recapitulate certain cardinal features of human PD.

Although the function of LRRK2 is not well known at this time, the recent demonstration that LRRK2 modulates synuclein-mediated toxicity and neurodegeneration in vitro and in vivo further highlights an important role of LRRK2 in PD pathogenesis. For example, transgenic studies in mice have shown that LRRK2 may regulate α-synuclein toxicity by modulating the accumulation of α-synuclein (Lin, X.; Parisiadou, L.; Gu, X-L.; et al. Neuron 2009, 64, 807). It has also been suggested that α-synuclein neurodegeneration is related to LRRK2 regulation of cytoskeletal dynamics (Parisiadou, Loukia and Cai, Huaibin; Communicative & Integrative Biology 2010, 3(5):396-400).

Thus with involvement of LRRK2 in relation to α-synuclein toxicity, and the prevalence of LRRK2 mutant G2019S in familial PD, LRRK2 inhibitors are useful in treating PD, as well as other LBDs, such as Diffuse Lewy body disease, Lewy body variant of Alzheimer's disease, combined Parkinson's disease and Alzheimer's disease, multiple system atrophy, and Dementia with Lewy bodies. Such inhibitors of LRRK2 for the treatment of PD and other LBDs are not well known.

Targeting of LRRK2 kinase may also provide therapeutic benefits in certain cancers, such as melanoma, acute myelogenous leukemia, breast carcinoma, lung adenocarincoma, prostate adenocarcinoma, renal cell carcinoma (e.g. papillary renal cell carcinoma), and papillary thyroid carcinoma (Looyenga et al., PNAS 2011, 108(4):1439-1444; Saunders-Pullman et al., Movement Disorders 2010, 25(15):2536-2541; and Pan et al., Internation Journal of Cancer 2011, 128(10):2251-2260), in certain autoimmune diseases, such as Inflammatory Bowel Disease (e.g. Crohn's disease and ulcerative colitis) (Gardet et al., The Journal of Immunology 2010, 185(9):5577-5585), and in leprosy (Zhang et al., The New England Journal of Medicine 2009, 361(27): 2609-2618).

There are known kinase inhibitors, in particular cFms, or PLK1 inhibitors, that are cinnoline based (U.S. Pat. No. 7,723,337, PCT publication WO 2006/124996). Other compounds have been identified as LRRK2 inhibitors, including those described in PCT publication WO 2012/062783, WO/2011/038572, WO 2010/106333, WO 2010/085799, WO 2009/127642, and WO 2009/030270 and in Deng et al., Nature Chemical Biology 2011, 7:203-205. As there are presently limited therapeutic options, there remains a need for developing potent, selective and brain-penetrant LRRK2 inhibitors for use in the treatment and/or prevention of neurodegenerative diseases or other disorders associated with LRRK2.

SUMMARY OF THE INVENTION

Compounds are provided that are inhibitors of Leucine-rich repeat kinase 2 (LRRK2) kinase activity, including any mutations thereof. In one instance, compounds are provided that are inhibitors of LRRK2 mutant kinase activity, including LRRK2 mutant G2019S, a mutation present in familial PD and having increased kinase activity. Inhibitors of LRRK2 kinase activity, including any mutations thereof, in one instance LRRK2 mutant G2019S, are thus useful for the treatment of neurodegenerative diseases, such as Parkinson's disease, and other Lewy body-type diseases, including Diffuse Lewy body disease, Lewy body variant of Alzheimer's disease, combined Parkinson's disease and Alzheimer's disease, multiple system atrophy, and Dementia with Lewy bodies. Such LRRK2 kinase activity inhibitors are also useful in the treatment of cancers, such as melanoma, acute myelogenous leukemia, breast carcinoma, lung adenocarincoma, prostate adenocarcinoma, renal cell carcinoma, and papillary thyroid carcinoma and autoimmune diseases, such as Inflammatory Bowel Disease (e.g. Crohn's disease and ulcerative colitis). Also provided are pharmaceutical compositions comprising inhibitors of LRRK2 kinase activity, including any mutations thereof, and methods of utilizing those compositions in the treatment and prevention of various neurodegenerative disorders associated with LRRK2, such as Parkinson's Disease and other Lewy body-type diseases and in the treatment of various cancers and autoimmune diseases.

In one instance, compounds described herein that are inhibitors of LRRK2 kinase activity, including LRRK2 mutant kinase activity, including LRRK2 mutant G2019S kinase activity, are selective relative to other kinases.

In one aspect, compounds are provided having a structure according to Formula I:

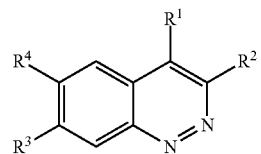

or a salt thereof, wherein:
$R^1$ is $-CR^5R^6R^7$, $-C(=O)R^8$, $-OR^9$, $-SR^{10}$, $-S(=O)_nR^{11}$, or $-NR^{12}R^{13}$;
n is 1 or 2;
$R^5$, $R^6$, and $R^7$ are independently selected from the group consisting of hydrogen, halogen, $-OH$, $C_1$-$C_6$ alkoxy, $-SH$, $-S(=O)_m-C_1$-$C_6$ alkyl, $-NH_2$, $C_1$-$C_6$ alkylamino, $C_1$-$C_6$ dialkylamino, $C_1$-$C_6$ alkyl optionally substituted with one or more substituents $R^{14}$, cycloalkyl optionally substituted with one or more substituents $R^{15}$, heterocycloalkyl optionally substituted with one or more substituents $R^{16}$, aryl optionally substituted with one or more substituents $R^{17}$, and heteroaryl optionally substituted with one or more substituents $R^{18}$, wherein the alkyl chain of $C_1$-$C_6$ alkoxy, $-S(=O)_m-C_6$-$C_6$ alkyl, $C_1$-$C_6$ alkylamino, or $C_1$-$C_6$ dialkylamino is optionally substituted with one or more substituents independently selected from the group consisting of halogen, $-OH$, $C_1$-$C_6$ alkoxy, $C_1$-$C_6$ haloalkoxy, $-SH$, $-S(=O)_m-C_1$-$C_6$ alkyl, $-S(=O)_m-C_1$-$C_6$ haloalkyl, $-NH_2$, $C_1$-$C_6$ alkylamino, $C_1$-$C_6$ dialkylamino, and N-linked-heterocycloalkyl; or any two of $R^5$, $R^6$ and $R^7$ together with the carbon to which they are attached, form a 3-8 membered cycloalkyl optionally substituted with one or more substituents $R^{15}$ or a 4-7 membered heterocycloalkyl optionally substituted with one or more substituents $R^{16}$, and the other of $R^5$, $R^6$ and $R^7$ is selected from the group consisting of hydrogen, halogen, $-OH$, $C_1$-$C_6$ alkoxy, $-SH$, $-S(=O)_m-C_1$-$C_6$ alkyl, $-NH_2$, $C_1$-$C_6$ alkylamino, $C_1$-$C_6$ dialkylamino, and $C_1$-$C_6$ alkyl optionally substituted with one or more substituents $R^{14}$, wherein the alkyl chain of $C_1$-$C_6$ alkoxy, $-S(=O)_m-C_1$-$C_6$ alkyl, $C_1$-$C_6$ alkylamino, or $C_1$-$C_6$ dialkylamino is optionally substituted with one or more substituents independently selected from the group consisting of halogen, $-OH$, $C_1$-$C_6$ alkoxy, $C_1$-$C_6$ haloalkoxy, $-SH$, $-S(=O)_m-C_1$-$C_6$ alkyl, $-S(=O)_m-C_1$-$C_6$ haloalkyl, $-NH_2$, $C_1$-$C_6$ alkylamino, $C_1$-$C_6$ dialkylamino, and N-linked-heterocycloalkyl;

$R^8$, $R^9$, $R^{10}$, and $R^{11}$ are independently selected from the group consisting of $C_1$-$C_6$ alkyl optionally substituted with one or more substituents $R^{14}$, cycloalkyl optionally substituted with one or more substituents $R^{15}$, heterocycloalkyl optionally substituted with one or more substituents $R^{16}$, aryl optionally substituted with one or more substituents $R^{17}$, and heteroaryl optionally substituted with one or more substituents $R^{18}$;

$R^{12}$ is hydrogen or $C_1$-$C_6$ alkyl optionally substituted with one or more substituents $R^{14}$;

$R^{13}$ is selected from the group consisting of hydrogen, $C_1$-$C_6$ alkyl optionally substituted with one or more substituents $R^{14}$, cycloalkyl optionally substituted with one or more substituents $R^{15}$, and heterocycloalkyl optionally substituted with one or more substituents $R^{16}$;

or $R^{12}$ and $R^{13}$, together with the nitrogen to which they are attached, form a 5-7 membered heterocycloalkyl optionally substituted with one or more substituents $R^{16}$;

$R^{14}$ at each occurrence is independently selected from the group consisting of halogen, —OH, $C_1$-$C_6$ alkoxy, —SH, —S(=O)$_m$—$C_1$-$C_6$ alkyl, —NH$_2$, $C_1$-$C_6$ alkylamino, $C_1$-$C_6$ dialkylamino, cycloalkyl optionally substituted with one or more substituents $R^{15}$, heterocycloalkyl optionally substituted with one or more substituents $R^{16}$, aryl optionally substituted with one or more substituents $R^{17}$, and heteroaryl optionally substituted with one or more substituents $R^{18}$, wherein the alkyl chain of $C_1$-$C_6$ alkoxy, —S(=O)$_m$—$C_1$-$C_6$ alkyl, $C_1$-$C_6$ alkylamino, or $C_1$-$C_6$ dialkylamino is optionally substituted with one or more substituents independently selected from the group consisting of halogen, —OH, $C_1$-$C_6$ alkoxy, $C_1$-$C_6$ haloalkoxy, —SH, —S(=O)$_m$—$C_1$-$C_6$ alkyl, —S(=O)$_m$—$C_1$-$C_6$ haloalkyl, —NH$_2$, $C_1$-$C_6$ alkylamino, $C_1$-$C_6$ dialkylamino, and N-linked-heterocycloalkyl;

$R^{15}$ and $R^{16}$, at each occurrence, are independently selected from the group consisting of halogen, $C_1$-$C_6$ alkyl, —OH, =O, $C_1$-$C_6$ alkoxy, —SH, —S(=O)$_m$—$C_1$-$C_6$ alkyl, —NH$_2$, $C_1$-$C_6$ alkylamino, $C_1$-$C_6$ dialkylamino, and N-linked-heterocycloalkyl, wherein the alkyl chain of $C_1$-$C_6$ alkyl, $C_1$-$C_6$ alkoxy, —S(=O)$_m$—$C_1$-$C_6$ alkyl, $C_1$-$C_6$ alkylamino, or $C_1$-$C_6$ dialkylamino is optionally substituted with one or more substituents independently selected from the group consisting of halogen, —OH, $C_1$-$C_6$ alkoxy, $C_1$-$C_6$ haloalkoxy, —SH, —S(=O)$_m$—$C_1$-$C_6$ alkyl, —S(=O)$_m$—$C_1$-$C_6$ haloaloalkyl, —NH$_2$, $C_1$-$C_6$ alkylamino, $C_1$-$C_6$ dialkylamino, and N-linked-heterocycloalkyl;

$R^{17}$ and $R^{18}$ at each occurrence are independently selected from the group consisting of halogen, —CN, —NO$_2$, $C_1$-$C_6$ alkyl, —OH, $C_1$-$C_6$ alkoxy, —SH, —S(=O)$_m$—$C_1$-$C_6$ alkyl, —NH$_2$, $C_1$-$C_6$ alkylamino, $C_1$-$C_6$ dialkylamino, and N-linked-heterocycloalkyl, wherein the alkyl chain of $C_1$-$C_6$ alkyl, $C_1$-$C_6$ alkoxy, —S(=O)$_m$—$C_1$-$C_6$ alkyl, $C_1$-$C_6$ alkylamino, or $C_1$-$C_6$ dialkylamino is optionally substituted with one or more substituents independently selected from the group consisting of halogen, —OH, $C_1$-$C_6$ alkoxy, $C_1$-$C_6$ haloalkoxy, —SH, —S(=O)$_m$—$C_1$-$C_6$ alkyl, —S(=O)$_m$—$C_1$-$C_6$ haloalkyl, —NH$_2$, $C_1$-$C_6$ alkylamino, $C_1$-$C_6$ dialkylamino, and N-linked-heterocycloalkyl;

m is 0, 1 or 2;

$R^2$ is selected from the group consisting of $R^{19}$, $L_1$-$R^{20}$, $C_1$-$C_6$ alkyl, $C_2$-$C_6$ alkenyl, $C_2$-$C_6$ alkynyl, cycloalkyl, heterocycloalkyl, aryl, and heteroaryl, wherein $C_1$-$C_6$ alkyl is optionally substituted with one or more substituents independently selected from the group consisting of $R^{19}$, $L_2$-$R^{20}$, —NR$^{21}$R$^{22}$, cycloalkyl, aryl, heteroaryl, and heterocycloalkyl, provided, however, that heterocycloalkyl is not N-linked-heterocycloalkyl, and wherein $C_2$-$C_6$ alkenyl and $C_2$-$C_6$ alkynyl are optionally substituted with one or more substituents independently selected from the group consisting of $R^{19}$, $L_1$-$R^{20}$, cycloalkyl, heterocycloalkyl, aryl, and heteroaryl, and wherein cycloalkyl and heterocycloalkyl, as $R^2$ or as a substituent of $C_1$-$C_6$ alkyl, $C_2$-$C_6$ alkenyl, or $C_2$-$C_6$ alkynyl, are optionally substituted with one or more substituents independently selected from the group consisting of $R^{19}$, =O, =NR$^{21}$, =NOR$^{21}$, $L_1$-$R^{20}$, and $R^{23}$, and wherein aryl and heteroaryl, as $R^2$ or as a substituent of $C_1$-$C_6$ alkyl, $C_2$-$C_6$ alkenyl, or $C_2$-$C_6$ alkynyl, are optionally substituted with one or more substituents independently selected from the group consisting of $R^{19}$, $L_1$-$R^{20}$, and $R^{23}$;

one of $R^3$ and $R^4$ is selected from the group consisting of hydrogen, $R^{19}$, $L_1$-$R^{20}$, $C_1$-$C_6$ alkyl, $C_2$-$C_6$ alkenyl, $C_2$-$C_6$ alkynyl, cycloalkyl, heterocycloalkyl, aryl, and heteroaryl, wherein $C_1$-$C_6$ alkyl, $C_2$-$C_6$ alkenyl, and $C_2$-$C_6$ alkynyl are optionally substituted with one or more substituents independently selected from the group consisting of $R^{19}$, $L_1$-$R^{20}$, cycloalkyl, heterocycloalkyl, aryl, and heteroaryl, and wherein cycloalkyl and heterocycloalkyl, as $R^3$ or $R^4$ or as a substituent of $C_1$-$C_6$ alkyl, $C_2$-$C_6$ alkenyl, or $C_2$-$C_6$ alkynyl, are optionally substituted with one or more substituents independently selected from the group consisting of $R^{19}$, =O, =NR$^{21}$, =NOR$^{21}$, $L_1$-$R^{20}$, and $R^{23}$, and wherein aryl and heteroaryl, as $R^3$ or $R^4$ or as a substituent of $C_1$-$C_6$ alkyl, $C_2$-$C_6$ alkenyl, or $C_2$-$C_6$ alkynyl, are optionally substituted with one or more substituents independently selected from the group consisting of $R^{19}$, $L_1$-$R^{20}$, and $R^{23}$;

the other of $R^3$ and $R^4$ is selected from the group consisting of $R^{24}$, $L_3$-$R^{20}$, —OR$^{25}$—, —SR$^{25}$, methyl, $C_2$-$C_6$ alkyl, $C_2$-$C_6$ alkenyl, $C_2$-$C_6$ alkynyl, cycloalkyl, heterocycloalkyl, aryl, and heteroaryl, wherein methyl is substituted with one or more substituents independently selected from the group consisting of $R^{19}$, $L_1$-$R^{20}$, cycloalkyl, heterocycloalkyl, aryl, and heteroaryl, and wherein $C_2$-$C_6$ alkyl, $C_2$-$C_6$ alkenyl, and $C_2$-$C_6$ alkynyl are optionally substituted with one or more substituents independently selected from the group consisting of $R^{19}$, $L_1$-$R^{20}$, cycloalkyl, heterocycloalkyl, aryl, and heteroaryl, and wherein cycloalkyl and heterocycloalkyl, as $R^3$ or $R^4$ or as a substituent of methyl, $C_2$-$C_6$ alkyl, $C_2$-$C_6$ alkenyl, or $C_2$-$C_6$ alkynyl, are optionally substituted with one or more substituents independently selected from the group consisting of $R^{19}$, =O, =NR$^{21}$, =NOR$^{21}$, $L_1$-$R^{20}$, and $R^{23}$, and wherein aryl and heteroaryl, as $R^3$ or $R^4$ or as a substituent of methyl, $C_2$-$C_6$ alkyl, $C_2$-$C_6$ alkenyl, or $C_2$-$C_6$ alkynyl, are optionally substituted with one or more substituents independently selected from the group consisting of $R^{19}$, $L_1$-$R^{20}$, and $R^{23}$;

$R^{19}$ at each occurrence is independently selected from the group consisting of halogen, —CN, —NO$_2$, —OH, —SH, —NH$_2$, —NHOH, —C(=X)OH, —C(=X)NH$_2$, —C(=X)NHOH, —OC(=X)NH$_2$, —NHC(=X)NH$_2$, —NHC(=X)OH, —S(=O)$_2$NH$_2$, —S(=O)$_2$NHOH, —NHS(=O)$_2$NH$_2$, and —NHC(NH$_2$)=NH;

$R^{24}$ at each occurrence is independently selected from the group consisting of —CN, —NH$_2$, —NHOH, —C(=X)OH, —C(=X)NH$_2$, —C(=X)NHOH, —OC(=X)NH$_2$, —NHC(=X)NH$_2$, —NHC(=X)OH, —S(=O)$_2$NH$_2$, —S(=O)$_2$NHOH, —NHS(=O)$_2$NH$_2$, and —NHC(NH$_2$)=NH;

$R^{20}$ at each occurrence is independently selected from the group consisting of $C_1$-$C_6$ alkyl, $C_2$-$C_6$ alkenyl, $C_2$-$C_6$ alkynyl, cycloalkyl, heterocycloalkyl, aryl, and heteroaryl, wherein $C_1$-$C_6$ alkyl, $C_2$-$C_6$ alkenyl, and $C_2$-$C_6$ alkynyl are optionally substituted with one or more substituents independently selected from the group consisting of $R^{19}$, $L_4$-$R^{26}$, cycloalkyl, heterocycloalkyl, aryl, and heteroaryl, and wherein cycloalkyl and heterocycloalkyl, as $R^{20}$ or as a substituent of $C_1$-$C_6$ alkyl, $C_2$-$C_6$ alkenyl, or $C_2$-$C_6$ alkynyl, are optionally substituted with one or more substituents independently selected from the group consisting of $R^{19}$, $L_4$-$R^{26}$, =O, =NR$^{21}$, =NOR$^{21}$, and $R^{27}$, and wherein aryl and heteroaryl, as $R^{20}$ or as a substituent of $C_1$-$C_6$ alkyl, $C_2$-$C_6$ alkenyl, or $C_2$-$C_6$ alkynyl, are optionally substituted with one or more substituents independently selected from the group consisting of $R^{19}$, $L_4$-$R^{26}$, and $R^{27}$;

$R^{22}$ at each occurrence is independently selected from the group consisting of aryl, and heteroaryl, wherein aryl and heteroaryl are optionally substituted with one or more substituents independently selected from the group consisting of $R^{19}$, $L_4$-$R^{26}$, and $R^{27}$;

$R^{23}$ at each occurrence is independently selected from the group consisting of $C_1$-$C_6$ alkyl, $C_2$-$C_6$ alkenyl, $C_2$-$C_6$ alkynyl, cycloalkyl, heterocycloalkyl, aryl, and heteroaryl, wherein $C_1$-$C_6$ alkyl, $C_2$-$C_6$ alkenyl, and $C_2$-$C_6$ alkynyl are optionally substituted with one or more substituents independently selected from the group consisting of $R^{19}$, $L_4$-$R^{26}$, cycloalkyl, heterocycloalkyl, aryl, and heteroaryl, and wherein cycloalkyl and heterocycloalkyl as $R^{23}$ or as a substituent of $C_1$-$C_6$ alkyl, $C_2$-$C_6$ alkenyl, or $C_2$-$C_6$ alkynyl, are optionally substituted with one or more substituents independently selected from the group consisting of $R^{19}$, =O, =$NR^{21}$, =$NOR^{21}$, $L_4$-$R^{26}$, and $R^{28}$, and wherein aryl and heteroaryl, as $R^{23}$ or as a substituent of $C_1$-$C_6$ alkyl, $C_2$-$C_6$ alkenyl, or $C_2$-$C_6$ alkynyl, are optionally substituted with one or more substituents independently selected from the group consisting of $R^{19}$, $L_4$-$R^{26}$, and $R^{28}$;

$R^{25}$ at each occurrence is independently selected from the group consisting of methyl, $C_2$-$C_6$ alkyl, $C_2$-$C_6$ alkenyl, $C_2$-$C_6$ alkynyl, cycloalkyl, heterocycloalkyl, aryl, and heteroaryl, wherein methyl is substituted with one or more substituents independently selected from the group consisting of $R^{19}$, $L_4$-$R^{26}$, cycloalkyl, heterocycloalkyl, aryl, and heteroaryl, and wherein $C_2$-$C_6$ alkyl, $C_2$-$C_6$ alkenyl, and $C_2$-$C_6$ alkynyl are optionally substituted with one or more substituents independently selected from the group consisting of $R^{19}$, $L_4$-$R^{26}$, cycloalkyl, heterocycloalkyl, aryl, and heteroaryl, and wherein cycloalkyl and heterocycloalkyl, as $R^{25}$ or as a substituent of methyl, $C_2$-$C_6$ alkyl, $C_2$-$C_6$ alkenyl, or $C_2$-$C_6$ alkynyl, are optionally substituted with one or more substituents independently selected from the group consisting of $R^{19}$, $L_4$-$R^{26}$, =O, =$NR^{21}$, =$NOR^{21}$, and $R^{27}$, and wherein aryl and heteroaryl, as $R^{25}$ or as a substituent of methyl, $C_2$-$C_6$ alkyl, $C_2$-$C_6$ alkenyl, or $C_2$-$C_6$ alkynyl, are optionally substituted with one or more substituents independently selected from the group consisting of $R^{19}$, $L_4$-$R^{26}$, and $R^{27}$;

$R^{26}$ at each occurrence is independently selected from the group consisting of $C_1$-$C_6$ alkyl, $C_2$-$C_6$ alkenyl, $C_2$-$C_6$ alkynyl, cycloalkyl, heterocycloalkyl, aryl, and heteroaryl, wherein $C_1$-$C_6$ alkyl, $C_2$-$C_6$ alkenyl, and $C_2$-$C_6$ alkynyl are optionally substituted with one or more substituents independently selected from the group consisting of $R^{19}$, $L_5$-$R^{29}$, cycloalkyl, heterocycloalkyl, aryl, and heteroaryl, wherein cycloalkyl and heterocycloalkyl as $R^{26}$ or as a substituent of $C_1$-$C_6$ alkyl, $C_2$-$C_6$ alkenyl, or $C_2$-$C_6$ alkynyl, are optionally substituted with one or more substituents independently selected from the group consisting of $R^{19}$, =O, =$NR^{21}$, =$NOR^{21}$, $L_5$-$R^{29}$, and $R^{28}$, and wherein aryl and heteroaryl, as $R^{26}$ or as a substituent of $C_1$-$C_6$ alkyl, $C_2$-$C_6$ alkenyl, or $C_2$-$C_6$ alkynyl, are optionally substituted with one or more substituents independently selected from the group consisting of $R^{19}$, $L_5$-$R^{29}$, and $R^{28}$;

$R^{27}$ at each occurrence is independently selected from the group consisting of $C_1$-$C_6$ alkyl, $C_2$-$C_6$ alkenyl, $C_2$-$C_6$ alkynyl, cycloalkyl, heterocycloalkyl, aryl, and heteroaryl, wherein $C_1$-$C_6$ alkyl, $C_2$-$C_6$ alkenyl, and $C_2$-$C_6$ alkynyl are optionally substituted with one or more substituents independently selected from the group consisting of $R^{19}$, $L_4$-$R^{26}$, cycloalkyl, heterocycloalkyl, aryl, and heteroaryl, wherein cycloalkyl and heterocycloalkyl as $R^{27}$ or as a substituent of $C_1$-$C_6$ alkyl, $C_2$-$C_6$ alkenyl, or $C_2$-$C_6$ alkynyl, are optionally substituted with one or more substituents independently selected from the group consisting of $R^{19}$, =O, =$NR^{21}$, =$NOR^{21}$, $L_4$-$R^{26}$, and $R^{28}$, and wherein aryl and heteroaryl, as $R^{27}$ or as a substituent of $C_1$-$C_6$ alkyl, $C_2$-$C_6$ alkenyl, or $C_2$-$C_6$ alkynyl, are optionally substituted with one or more substituents independently selected from the group consisting of $R^{19}$, $L_4$-$R^{26}$, and $R^{28}$;

$R^{28}$ at each occurrence is independently selected from the group consisting of $C_1$-$C_6$ alkyl, $C_2$-$C_6$ alkenyl, $C_2$-$C_6$ alkynyl, cycloalkyl, heterocycloalkyl, aryl, and heteroaryl, wherein $C_1$-$C_6$ alkyl, $C_2$-$C_6$ alkenyl, and $C_2$-$C_6$ alkynyl are optionally substituted with one or more substituents independently selected from the group consisting of $R^{19}$, $L_5$-$R^{29}$, cycloalkyl, heterocycloalkyl, aryl, and heteroaryl, and wherein cycloalkyl and heterocycloalkyl as $R^{28}$ or as a substituent of $C_1$-$C_6$ alkyl, $C_2$-$C_6$ alkenyl, or $C_2$-$C_6$ alkynyl, are optionally substituted with one or more substituents independently selected from the group consisting of $R^{19}$, =O, =$NR^{21}$, =$NOR^{21}$, $L_5$-$R^{29}$, and $R^{29}$, and wherein aryl and heteroaryl, as $R^{28}$ or a substituent of $C_1$-$C_6$ alkyl, $C_2$-$C_6$ alkenyl, or $C_2$-$C_6$ alkynyl, are optionally substituted with one or more substituents independently selected from the group consisting of $R^{19}$, $L_5$-$R^{29}$, and $R^{29}$;

$R^{29}$ at each occurrence is independently selected from the group consisting of $C_1$-$C_6$ alkyl, $C_2$-$C_6$ alkenyl, $C_2$-$C_6$ alkynyl, cycloalkyl, heterocycloalkyl, aryl, and heteroaryl, wherein $C_1$-$C_6$ alkyl, $C_2$-$C_6$ alkenyl, and $C_2$-$C_6$ alkynyl are optionally substituted with one or more substituents $R^{30}$, and wherein cycloalkyl and heterocycloalkyl are optionally substituted with one or more substituents $R^{31}$, and wherein aryl and heteroaryl are optionally substituted with one or more substituents $R^{32}$;

$L_1$, $L_4$, and $L_5$, at each occurrence, are independently selected from the group consisting of —O—, —S—, —$NR^{21}$—, —$NR^{21}$O—, —C(=X)—, —C(=X)O—, —OC(=X)—, —C(=X)$NR^{21}$—, —C(=X)$NR^{21}$O—, —$NR^{21}$C(=X)—, —OC(=X)$NR^{21}$—, —$NR^{21}$C(=X)$NR^{21}$—, —$NR^{21}$C(=X)O—, —S(=O)—, —S(=O)$_2$—, —S(=O)$_2NR^{21}$—, —S(=O)$_2NR^{21}$O—, —$NR^{21}$S(=O)$_2$—, —$NR^{21}$S(=O)$_2NR^{21}$—, —$NR^{21}$C(=$NR^{21}$)$NR^{21}$—, and —$NR^{21}$C($NR^{21}R^{21}$)=N—;

$L_2$ at each occurrence is independently selected from the group consisting of —O—, —S—, —$NR^{21}$O—, —C(=X)—, —C(=X)O—, —OC(=X)—, —C(=X)$NR^{21}$—, —C(=X)$NR^{21}$O—, —$NR^{21}$C(=X)—, —OC(=X)$NR^{21}$—, —$NR^{21}$C(=X)$NR^{21}$—, —$NR^{21}$C(=X)O—, —S(=O)—, —S(=O)$_2$—, —S(=O)$_2NR^{21}$—, —S(=O)$_2NR^{21}$O—, —$NR^{21}$S(=O)$_2$—, —$NR^{21}$S(=O)$_2NR^{21}$—, —$NR^{21}$C(=$NR^{21}$)$NR^{21}$—, and —$NR^{21}$C($NR^{21}R^{21}$)=N—;

$L_3$ at each occurrence is independently selected from the group consisting of —$NR^{21}$—, —$NR^{21}$O—, —C(=X)—, —C(=X)O—, —OC(=X)—, —C(=X)$NR^{21}$—, —C(=X)$NR^{21}$O—, —$NR^{21}$C(=X)—, —OC(=X)$NR^{21}$—, —$NR^{21}$C(=X)$NR^{21}$—, —$NR^{21}$C(=X)O—, —S(=O)—, —S(=O)$_2$—, —S(=O)$_2NR^{21}$—, —S(=O)$_2NR^{21}$O—, —$NR^{21}$S(=O)$_2$—, —$NR^{21}$S(=O)$_2NR^{21}$—, —$NR^{21}$C(=$NR^{21}$)$NR^{21}$—, and —$NR^{21}$C($NR^{21}R^{21}$)=N—;

X is O or S;

$R^{21}$ at each occurrence is independently selected from the group consisting of hydrogen, $C_1$-$C_6$ alkyl, $C_2$-$C_6$ alkenyl, $C_2$-$C_6$ alkynyl, cycloalkyl, heterocycloalkyl, aryl, and heteroaryl, wherein $C_1$-$C_6$ alkyl, $C_2$-$C_6$ alkenyl, and $C_2$-$C_6$ alkynyl are optionally substituted with one or more substituents R³⁰, cycloalkyl and heterocycloalkyl are optionally substituted with one or more substituents R³¹, and aryl and heteroaryl are optionally substituted with one or more substituents R³²;

R³⁰ at each occurrence is independently selected from the group consisting of halogen, —OH, $C_1$-$C_6$ alkoxy, —SH, —S(=O)$_m$—$C_1$-$C_6$ alkyl, —NH$_2$, $C_1$-$C_6$ alkylamino, $C_1$-$C_6$ dialkylamino, cycloalkyl, heterocycloalkyl, aryl, and heteroaryl, wherein the alkyl chain of $C_1$-$C_6$ alkoxy, —S(=O)$_m$—$C_1$-$C_6$ alkyl, $C_1$-$C_6$ alkylamino, or $C_1$-$C_6$ dialkylamino is optionally substituted with one or more substituents independently selected from the group consisting of halogen, —OH, $C_1$-$C_6$ alkoxy, $C_1$-$C_6$ haloalkoxy, —SH, —S(=O)$_m$—$C_1$-$C_6$ alkyl, —S(=O)$_m$—$C_1$-$C_6$ haloalkyl, —NH$_2$, $C_1$-$C_6$ alkylamino, $C_1$-$C_6$ dialkylamino, and N-linked-heterocycloalkyl, and wherein cycloalkyl and heterocycloalkyl are optionally substituted with one or more substituents R³¹, and aryl and heteroaryl are optionally substituted with one or more substituents R³²;

R³¹ at each occurrence is independently selected from the group consisting of halogen, $C_1$-$C_6$ alkyl, —OH, =O, $C_1$-$C_6$ alkoxy, —SH, —S(=O)$_m$—$C_1$-$C_6$ alkyl, —NH$_2$, $C_1$-$C_6$ alkylamino, $C_1$-$C_6$ dialkylamino, and N-linked-heterocycloalkyl, wherein the alkyl chain of $C_1$-$C_6$ alkyl, $C_1$-$C_6$ alkoxy, —S(=O)$_m$—$C_1$-$C_6$ alkyl, $C_1$-$C_6$ alkylamino, or $C_1$-$C_6$ dialkylamino is optionally substituted with one or more substituents selected from the group consisting of halogen, —OH, $C_1$-$C_6$ alkoxy, $C_1$-$C_6$ haloalkoxy, —SH, —S(=O)$_m$—$C_1$-$C_6$ alkyl, —S(=O)$_m$—$C_1$-$C_6$ haloalkyl, —NH$_2$, $C_1$-$C_6$ alkylamino, $C_1$-$C_6$ dialkylamino, and N-linked-heterocycloalkyl; and R³² at each occurrence is independently selected from the group consisting of halogen, $C_1$-$C_6$ alkyl, —OH, —CN, $C_1$-$C_6$ alkoxy, —SH, —S(=O)$_m$—$C_1$-$C_6$ alkyl, —NH$_2$, $C_1$-$C_6$ alkylamino, $C_1$-$C_6$ dialkylamino, and N-linked-heterocycloalkyl, wherein the alkyl chain of $C_1$-$C_6$ alkyl, $C_1$-$C_6$ alkoxy, —S(=O)$_m$—$C_1$-$C_6$ alkyl, $C_1$-$C_6$ alkylamino, or $C_1$-$C_6$ dialkylamino is optionally substituted with one or more substituents selected from the group consisting of halogen, —OH, $C_1$-$C_6$ alkoxy, $C_1$-$C_6$ haloalkoxy, —SH, —S(=O)$_m$—$C_1$-$C_6$ alkyl, —S(=O)$_m$—$C_1$-$C_6$ haloalkyl, —NH$_2$, $C_1$-$C_6$ alkylamino, $C_1$-$C_6$ dialkylamino, and N-linked-heterocycloalkyl;

provided, however, that when R² is —C(=O)NH$_2$, R⁴ is halogen, R³ is N-linked-heterocycloalkyl or $L_1$-R²⁰ wherein $L_1$ is —NR²¹— and R²⁰ is pyridine, or phenyl optionally substituted with methyl, or $L_1$ is —O— and R²⁰ is $C_{1-6}$ alkyl optionally substituted with methoxy, R¹ is —NR¹²R¹³, and R¹² is hydrogen, R¹³ is selected from the group consisting of $C_1$-$C_6$ alkyl optionally substituted with one or more substituents R¹⁴, cycloalkyl optionally substituted with one or more substituents R¹⁵, and heterocycloalkyl optionally substituted with one or more substituents R¹⁶; or when R² is $L_1$-R²⁰, $L_1$ is —C(=X)— or —C(=X)NR²¹—, one of R³ and R⁴ is hydrogen, the other of R³ and R⁴ is unsubstituted $C_{14}$ alkyl, R¹ is —NR¹²R¹³, and R¹² is hydrogen, R¹³ is selected from the group consisting of $C_1$-$C_6$ alkyl optionally substituted with one or more substituents R¹⁴, cycloalkyl optionally substituted with one or more substituents R¹⁵, and heterocycloalkyl optionally substituted with one or more substituents R¹⁶; and provided that the compound does not have the structure selected from the group consisting of

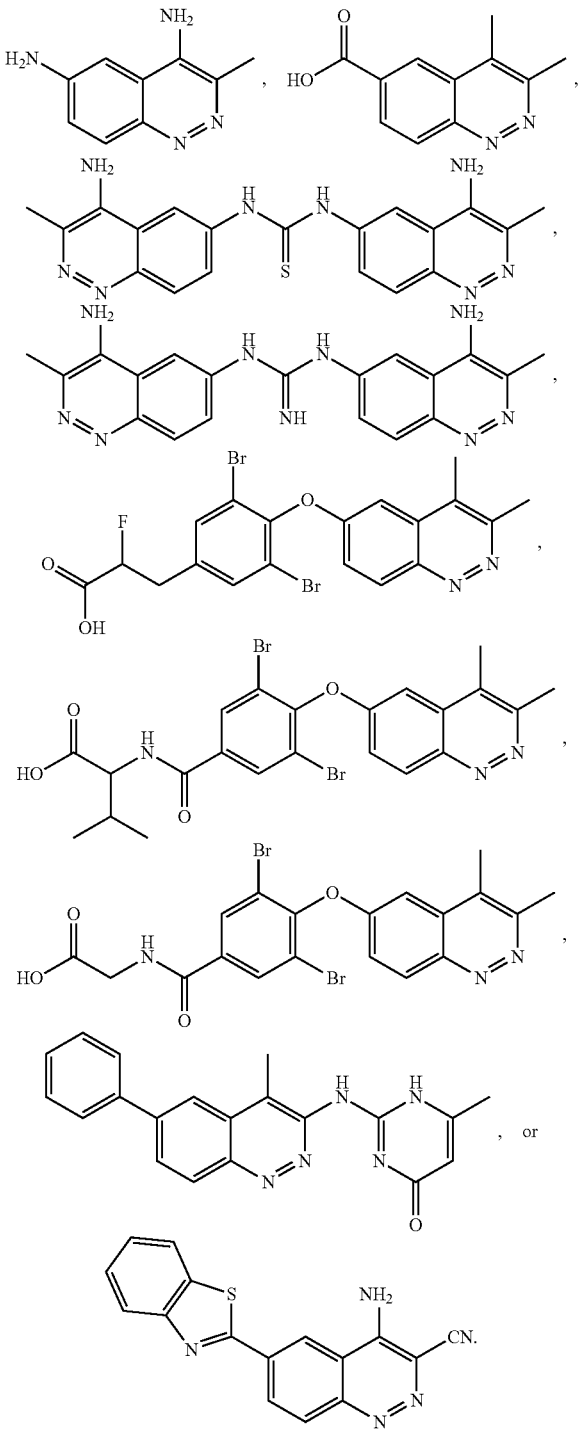

DETAILED DESCRIPTION OF THE INVENTION

Definition

The definitions and explanations below are for the terms as used throughout this entire document including both the specification and the claims. Reference to compounds as described herein (e.g. a compound of Formula I), includes reference to Formula I including any sub-generic embodiments thereof, e.g. Formula Ia or Ib (including all sub-generic embodiments thereof). Throughout the specification and the appended claims, a given formula or name shall encompass all isomers thereof, such as stereoisomers (e.g. diastereomers, enantiomers), geometrical isomers, tautomers, and mixtures thereof where such isomers exist.

It should be noted that, as used in this specification and the appended claims, the singular forms "a", "an", and "the" include plural referents unless the content clearly dictates otherwise. Thus, for example, reference to a composition containing "a compound" includes a composition containing a single compound, as well as a composition containing a mixture of two or more compounds. It should also be noted that the term "or" is generally employed in its sense including "and/or" unless the content clearly dictates otherwise.

Compounds were named using ChemDraw Ultra v. 10.0.4, (available from Cambridgesoft at 100 Cambridge Park Drive, Cambridge, Mass. 02140). Alternatively, the names were generated based on the IUPAC rules or were derived from names originally generated using the aforementioned nomenclature programs. In any instance where there may be any ambiguity between a name given to a compound structure, or if no name is provided for a given structure, the provided structure is intended to clearly define the compound, and those compounds only described by the given structure can be readily named using the above methods, or other methods known to one skilled in the art.

Where multiple substituents are indicated as being attached to a structure, those substituents are independently selected. For example "$C_1$-$C_6$ alkyl optionally substituted with one or more substituents $R^{14}$" indicates that alkyl may be substituted with one or more $R^{14}$ groups, wherein each $R^{14}$ group is independently selected from the Markush group of options (i.e., can be the same or different than another $R^{14}$ group). It is understood that for any optionally substituted group, any such substitution results in a stable molecule. Similarly, when different R groups are described as having the same Markush group of options, each R is independently selected from the Markush group of options. For example "$R^5$, $R^6$, and $R^7$ are independently selected from the group consisting of hydrogen, halogen, etc.", means that $R^5$ is independently selected from hydrogen, halogen etc., $R^6$ is independently selected from hydrogen, halogen, etc., and $R^7$ is independently selected from hydrogen, halogen, etc. As such, these R group definitions can be readily narrowed independently in a subsequent dependent claim.

The term "alkyl", by itself or as part of another substituent, means, unless otherwise stated, a straight or branched chain saturated hydrocarbon radical having from 1 to 24 carbon atoms (i.e. $C_1$-$C_{24}$ alkyl), also from 1 to 12 carbon atoms (i.e. $C_1$-$C_{12}$ alkyl), from 1 to 10 carbon atoms (i.e. $C_1$-$C_{10}$ alkyl), from 1 to 8 carbon atoms (i.e. $C_1$-$C_8$ alkyl), from 1 to 6 carbon atoms (i.e. $C_1$-$C_6$ alkyl) or from 1 to 4 carbon atoms (i.e. $C_1$-$C_4$ alkyl). A "lower alkyl" group is a $C_1$-$C_6$ alkyl, also a $C_1$-$C_4$ alkyl. The term "alkyl" includes di- and multivalent radicals. For example, the term "alkyl" includes "alkylene" wherever appropriate, e.g., when the formula indicates that the alkyl group is divalent or when substituents are joined to form a ring. Examples of alkyl radicals include, but are not limited to methyl, ethyl, n-propyl, iso-propyl, n-butyl, tert-butyl, iso-butyl, sec-butyl, as well as homologs and isomers of, for example, n-pentyl, n-hexyl, n-heptyl and n-octyl. Where it is indicated that alkyl is optionally substituted with one or more substituents, one or more is typically 1, 2, 3, 4, or 5, also 1, 2, 3, or 4, also 1, 2, or 3, also 1 or 2, or one, where multiple substituents are independently selected unless indicated otherwise. It is understood that any substitutions of alkyl, or alkyl substituted on another moiety, are attached at any available atom to provide a stable compound.

The term "alkylene", by itself or as part of another substituent means a divalent (diradical) alkyl group, wherein alkyl is defined herein. "Alkylene" is exemplified, but not limited, by —$CH_2CH_2CH_2CH_2$—. Typically, an "alkylene" group will be $C_1$-$C_{24}$ alkylene, also $C_1$-$C_{10}$ alkylene, $C_1$-$C_8$ alkylene, $C_1$-$C_6$ alkylene or $C_1$-$C_4$ alkylene. A "lower alkylene" group is a $C_1$-$C_6$ alkylene, also a $C_1$-$C_4$ alkylene. Where it is indicated that alkylene is optionally substituted with one or more substituents, one or more is typically 1, 2, 3, 4, or 5, also 1, 2, 3, or 4, also 1, 2, or 3, also 1 or 2, or one, where multiple substituents are independently selected unless indicated otherwise. It is understood that any substitutions of alkylene, or alkylene substituted on other moieties, are attached at any available atom to provide a stable compound.

The term "alkenyl", by itself or as part of another substituent means, unless otherwise stated, a straight or branched chain, hydrocarbon radical that is unsaturated or polyunsaturated so as to have at least one double bond, for example having one, two or three double bonds, and having from 2 to 24 carbon atoms (i.e. $C_2$-$C_{24}$ alkenyl), also $C_2$-$C_{10}$ alkenyl, $C_2$-$C_8$ alkenyl or $C_2$-$C_6$ alkenyl and from 1 to 3 double bonds. Exemplary "alkenyl" groups include vinyl, 2-propenyl, 1-but-3-enyl, crotyl, 2-(butadienyl), 2,4-pentadienyl, 3-(1,4-pentadienyl), 2-isopentenyl, 1-pent-3-enyl, 1-hex-5-enyl and the like. Where it is indicated that alkenyl is optionally substituted with one or more substituents, one or more is typically 1, 2, 3, 4, or 5, also 1, 2, 3, or 4, also 1, 2, or 3, also 1 or 2, or one, where multiple substituents are independently selected unless indicated otherwise. It is understood that any substitutions of alkenyl, or alkenyl substituted on another moiety, are attached at any available atom to provide a stable compound.

The term "alkynyl", by itself or as part of another substituent means, unless otherwise stated, a straight or branched chain, hydrocarbon radical that is unsaturated or polyunsaturated so as to have at least one triple bond, for example having one, two or three triple bonds, and having from 2 to 24 carbon atoms (i.e. $C_2$-$C_{24}$ alkynyl), also $C_2$-$C_{10}$ alkynyl, $C_2$-$C_8$ alkynyl or $C_2$-$C_6$ alkynyl and at least one triple bond. Exemplary "alkynyl" groups include prop-1-ynyl, prop-2-ynyl (i.e., propargyl), ethynyl and 3-butynyl. Where it is indicated that alkynyl is optionally substituted with one or more substituents, one or more is typically 1, 2, 3, 4, or 5, also 1, 2, 3, or 4, also 1, 2, or 3, also 1 or 2, or one, where multiple substituents are independently selected unless indicated otherwise. It is understood that any substitutions of alkynyl, or alkynyl substituted on another moiety, are attached at any available atom to provide a stable compound.

The terms "alkoxy", "alkylamino", "dialkylamino", and "alkylthio" (or thioalkoxy) are used in their conventional sense, and refer to substituted or unsubstituted alkyl groups that are attached to the remainder of the molecule via an oxygen atom, an amino group, or a sulfur atom, respectively. "alkylamino" refers to an amino group substituted with one lower alkyl group and "dialkylamino" refers to an amino group substituted independently with two lower alkyl groups. The alkyl group is as described herein above. Where it is indicated that an alkyl group within alkoxy, alkylamino, dialkylamino, or alkylthio is optionally substituted with one or more substituents, one or more is typically 1, 2, 3, 4, or 5, also 1, 2, 3, or 4, also 1, 2, or 3, also 1 or 2, or one, where multiple substituents are independently selected unless indicated otherwise. It is understood that any substitutions of alkoxy, alkylamino, dialkylamino, or alkylthio, or alkoxy, alkylamino, dialkylamino, or alkylthio substituted on another moiety, are attached at any available atom to provide a stable compound.

The term "N-linked-heterocycloalkyl", by itself or as part of another substituent, means the group —NR'R", where R' and R" combine with the nitrogen to form a 5-7 membered heterocycloalkyl, where the heterocycloalkyl may contain an additional heteroatom within the ring, such as O, N, or S, and may also be further substituted with lower alkyl. The ring is bound to the group it is a substituent of via the nitrogen. Examples of N-linked-heterocycloalkyl include, but are not limited to, piperidine, piperazine, 4-methylpiperazine, morpholine, and thiomorpholine. Where it is indicated that N-linked-heterocycloalkyl is optionally substituted with one or more substituents, one or more is typically 1, 2, 3, 4 or 5, also 1, 2, 3, or 4, also 1, 2, or 3, also 1 or 2, or one, where multiple substituents are independently selected unless indicated otherwise. It is understood that any substitutions of N-linked-heterocycloalkyl, or N-linked-heterocycloalkyl substituted on another moiety, are attached at any available atom to provide a stable compound.

The term "cycloalkyl" by itself or in combination with other terms, means a mono- or polycyclic saturated or unsaturated, non-aromatic carbocyclic radical having from 3 to 24 carbon atoms (i.e. $C_3$-$C_{24}$ cycloalkyl), also 3 to 12 carbon atoms (i.e., $C_3$-$C_{12}$ cycloalkyl), 3 to 10 carbon atoms (i.e. $C_3$-$C_{10}$ cycloalkyl), 3 to 8 carbon atoms (i.e. $C_3$-$C_8$ cycloalkyl) or 3 to 6 carbon atoms (i.e. $C_3$-$C_6$ cycloalkyl). Examples of cycloalkyl include, but are not limited to, cyclopropyl, cyclobutyl, cyclopentyl, cyclohexyl, cycloheptyl, 1-cyclohexenyl, 3-cyclohexenyl, cycloheptyl and the like. The term "cycloalkyl" also includes bridged, polycyclic (e.g., bicyclic) structures, such as norbornyl, adamantyl and bicyclo[2.2.1]heptyl. The "cycloalkyl" group can be fused to at least one (e.g., 1 to 3) other rings selected from aryl (e.g., phenyl), heteroaryl (e.g., pyridyl) and non-aromatic (e.g., carbocyclic or heterocyclic) rings. When the "cycloalkyl" group as a substituent includes a fused aryl, heteroaryl or heterocyclic ring, then the "cycloalkyl" group is attached to the group it is a substituent of via the carbocyclic ring. Where it is indicated that cycloalkyl is optionally substituted with one or more substituents, one or more is typically 1, 2, 3, 4 or 5, also 1, 2, 3, or 4, also 1, 2, or 3, also 1 or 2, or one, where multiple substituents are independently selected unless indicated otherwise. It is understood that any substitutions of cycloalkyl, or cycloalkyl substituted on another moiety, are attached at any available atom to provide a stable compound.

The term "heterocycloalkyl", "heterocyclic", or "heterocycle", by itself or in combination with other terms, means a saturated or unsaturated, non-aromatic ring having, for example, 3- to 10-members or 3- to 8-members, also 4-, 5-, 6- or 7-members, where at least one member and up to 5 members, also up to 3 members, of the ring are heteroatoms selected from, e.g., N, O, S, Si, B and P (in one example N, O and S), remaining ring atoms are carbon atoms, in stable combinations known to those of skill in the art, or a saturated or unsaturated non-aromatic fused ring system having 4- to 8-members (e.g. bicyclic ring system of fused 4- to 8-membered rings), where at least one and up to 5 members, also up to 3 members, are heteroatoms (e.g., from 1 to 5 heteroatoms, also 1 to 3 heteroatoms, selected from N, O and S), and the remaining ring atoms are carbon atoms, in stable combinations known to those of skill in the art. The heterocycloalkyl ring nitrogen, sulfur and phosphorus atoms are optionally oxidized, and the nitrogen atom(s) are optionally quaternized. "4-7 membered heterocycloalkyl" or "5-7 membered heterocycloalkyl" means a monocyclic heterocyclic ring having 4-, 5-, 6-, or 7-members, or 5-, 6-, or 7-members, where 1, 2, or 3, also 1 or 2 members is N, O or S, and the remaining ring atoms are carbon atoms. When the "heterocyclic" group includes a fused aryl, heteroaryl or cycloalkyl ring, then the "heterocyclic" group is attached to the group it is a substituent of via the heterocyclic ring. The point of attachment of heterocycloalkyl to the group it is a substituent of can be via a carbon atom or via a heteroatom. Exemplary heterocycloalkyl groups for compounds described herein (e.g. compounds of Formula I) include morpholinyl, thiomorpholinyl, thiomorpholinyl S-oxide, thiomorpholinyl S,S-dioxide, piperazinyl, homopiperazinyl, pyrrolidinyl, pyrrolinyl, imidazolidinyl, tetrahydropyranyl, piperidinyl, tetrahydrofuranyl, tetrahydrothienyl, piperidinyl, homopiperidinyl, homomorpholinyl, homothiomorpholinyl, homothiomorpholinyl S,S-dioxide, oxazolidinonyl, dihydropyrazolyl, dihydropyrrolyl, dihydropyrazolyl, dihydropyridyl, dihydropyrimidinyl, dihydrofuryl, dihydropyranyl, tetrahydrothienyl S-oxide, tetrahydrothienyl S,S-dioxide, homothiomorpholinyl S-oxide, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. In one example, heterocycloalkyl is cycoalkylamino. Where it is indicated that heterocycloalkyl is optionally substituted with one or more substituents, one or more is typically 1, 2, 3, 4 or 5, also 1, 2, 3, or 4, also 1, 2, or 3, also 1 or 2, or one, where multiple substituents are independently selected unless indicated otherwise. It is understood that any substitutions of heterocycloalkyl, or heterocycloalkyl substituted on another moiety, are attached at any available atom to provide a stable compound.

The term "aryl", by itself or as part of another substituent means, unless otherwise stated, means an aromatic monocyclic or polycyclic carbocyclic group having 6 to 14 carbon atoms, or 6 to 10 carbon atoms, in one example phenyl. Exemplary aryl groups include a fused cycloalkyl, heterocycloalkyl or heteroaryl ring (e.g., from 1 to 3 other rings). When the "aryl" group includes a fused cycloalkyl, heterocycloalkyl or heteroaryl group, then the "aryl" group is attached to the group it is a substituent of via an aryl ring (e.g., a phenyl ring). An "optionally substituted aryl" group is optionally substituted with one or more substituents as described herein (e.g., with 1 to 5 independent substituents). Non-limiting examples of aryl groups include phenyl, 1-naphthyl, 2-naphthyl, indanyl, indenyl, dihydronaphthyl, fluorenyl, tetralinyl, benzo[d][1,3]dioxolyl, 2,3-dihydrobenzo[b][1,4]dioxinyl, or 6,7,8,9-tetrahydro-5H-benzo[a]cycloheptenyl. In one example, "aryl" groups include phenyl, benzo[d][1,3]dioxolyl and naphthyl. In one example, "aryl" is phenyl. Where it is indicated that aryl is optionally substituted with one or more substituents, one or more is typically 1, 2, 3, 4 or 5, also 1, 2, 3, or 4, also 1, 2, or 3, also 1 or 2, or one, where multiple substituents are independently selected unless indicated otherwise. It is understood that any substitutions of aryl, or aryl substituted on another moiety, are attached at any available atom to provide a stable compound.

The term "heteroaryl", by itself or as part of another substituent means, unless otherwise stated, a polyunsaturated, 5-, 6- or 7-membered aromatic moiety containing at least one heteroatom (e.g., 1 to 5 heteroatoms, also 1-3 heteroatoms) selected from N, O, S, Si and B (in one example N, O and S), and the remaining ring atoms are carbon atoms, in stable combinations known to those of skill in the art. Heteroaryl ring nitrogen and sulfur atoms are optionally oxidized, and the nitrogen atom(s) are optionally quaternized. The "heteroaryl" group can be a single ring or be fused to other aryl, heteroaryl, cycloalkyl or heterocycloalkyl rings (e.g., from 1 to 3 other rings). When the "heteroaryl" group includes a fused aryl, cycloalkyl or heterocycloalkyl ring, then the "heteroaryl" group is attached to the group it is a substituent of via a heteroaryl ring. The point of attachment of heteroaryl to the group it is a substituent of can be via a carbon atom or a heteroatom (e.g. nitrogen). In one example, the heteroaryl group has from 1 to 10 carbon atoms and from 1 to 5 heteroatoms selected from O, S and N. "5 or 6 membered heteroaryl" means a monocyclic heteroryl ring having 5- or 6-members, where 1, 2, 3, or 4, also 1, 2 or 3, also 1 or 2, also 1 member(s) is N, O or S. Non-limiting examples of heteroaryl groups include pyridyl, pyrimidinyl, quinolinyl, benzothienyl, indolyl, indolinyl, pryidazinyl, pyrazinyl, isoindolyl, isoquinolyl, quinazolinyl, quinoxalinyl, phthalazinyl, imidazolyl, isoxazolyl, pyrazolyl, oxazolyl, thiazolyl, indolizinyl, indazolyl, benzothiazolyl, benzimidazolyl, benzofuranyl, furanyl, thienyl, pyrrolyl, oxadiazolyl, thiadiazolyl, triazolyl, tetrazolyl, isothiazolyl, naphthyridinyl, isochromanyl, chromanyl, tetrahydroisoquinolinyl, isoindolinyl, isobenzothienyl, benzoxazolyl, pyridopyridyl, purinyl, benzodioxolyl, triazinyl, pteridinyl, benzothiazolyl, imidazopyridyl, imidazothiazolyl, dihydrobenzisoxazinyl, benzisoxazinyl, benzoxazinyl, dihydrobenzisothiazinyl, benzopyranyl, benzothiopyranyl, chromonyl, chromanonyl, pyridyl-N-oxide, tetrahydroquinolinyl, dihydroquinolinyl, dihydroquinolinonyl, dihydroisoquinolinonyl, dihydrocoumarinyl, dihydroisocoumarinyl, isoindolinonyl, benzodioxanyl, benzoxazolinonyl, pyrrolyl N-oxide, pyrimidinyl N-oxide, pyridazinyl N-oxide, pyrazinyl N-oxide, quinolinyl N-oxide, indolyl N-oxide, indolinyl N-oxide, isoquinolyl N-oxide, quinazolinyl N-oxide, quinoxalinyl N-oxide, phthalazinyl N-oxide, imidazolyl N-oxide, isoxazolyl N-oxide, oxazolyl N-oxide, thiazolyl N-oxide, indolizinyl N-oxide, indazolyl N-oxide, benzothiazolyl N-oxide, benzimidazolyl N-oxide, pyrrolyl N-oxide, oxadiazolyl N-oxide, thiadiazolyl N-oxide, triazolyl N-oxide, tetrazolyl N-oxide, benzothiopyranyl S-oxide, benzothiopyranyl S,S-dioxide. In one example, heteroaryl groups include imidazolyl, pyrazolyl, thiadiazolyl, triazolyl, isoxazolyl, oxazolyl, isothiazolyl, thiazolyl, oxadiazolyl, pyridazinyl, pyrazinyl, pyrimidinyl, and pyridyl. Where it is indicated that heteroaryl is optionally substituted with one or more substituents, one or more is typically 1, 2, 3, 4 or 5, also 1, 2, 3, or 4, also 1, 2, or 3, also 1 or 2, or one, where multiple substituents are independently selected unless indicated otherwise. It is understood that any substitutions of heteroaryl, or heteroaryl substituted on another moiety, are attached at any available atom to provide a stable compound.

The terms "halo" or "halogen," by themselves or as part of another substituent, mean at least one of fluorine, chlorine, bromine and iodine.

By "haloalkyl" or "haloalkoxy" is meant an alkyl or alkoxy radical, as defined above, wherein at least one hydrogen atom of alkyl or the alkyl chain of alkoxy is replaced by a halogen atom, where typically 1, 2, 3, 4, or 5, also 1, 2, 3, or 4, also 1, 2, or 3, also 1 or 2, or 1 hydrogen atom is replaced by an independently selected halogen. More typically, 1, 2 or 3 hydrogen atoms on the same carbon are replaced with 1, 2 or 3 halogen atoms. In one example the halogen is fluorine or chlorine, in one example fluorine. The term "haloalkyl" or "haloalkoxy" is meant to include monohaloalkyl and polyhaloalkyl. For example, the term "$C_1$-$C_6$ haloalkyl" is meant to include, but not limited to, chloromethyl, 1-bromoethyl, fluoromethyl, difluoromethyl, trifluoromethyl, 2,2,2-trifluoroethyl, perfluoroethyl, 4-chlorobutyl, and 3-bromopropyl; and the term "$C_1$-$C_6$ haloalkoxy" is meant to include, but not limited to, fluoromethoxy, difluoromethoxy, trifluoromethoxy, 2,2,2-trifluoroethoxy, and perfluoroethoxy.

As used herein, the term "heteroatom" includes oxygen (O), nitrogen (N), sulfur (S), silicon (Si), boron (B) and phosphorus (P). In one example heteroatoms are O, S and N.

By "oxo" is meant the group $=O$.

As used herein, the term "aromatic ring" or "non-aromatic ring" is consistent with the definition commonly used in the art. For example, aromatic rings include phenyl and pyridyl. Non-aromatic rings include cyclohexanes, cyclohexenes, and the like.

As used herein, the term "fused ring system" means at least two rings, wherein each ring has at least 2 atoms in common with another ring. "Fused ring systems can include aromatic as well as non aromatic rings. Examples of "fused ring systems" are naphthalenes, indoles, quinolines, chromenes and the like. Likewise, the term "fused ring" refers to a ring that has at least two atoms in common with the ring to which it is fused.

As used herein, the term "selective" or "selectivity" as it relates to kinase activity, means that a compound as described herein, e.g. a compound of Formula I, is a more potent inhibitor of a particular kinase, such as LRRK2 kinase, when compared to another kinase. While LRRK2 has other enzymatic activities, it is understood that when inhibitory activity or selectivity of LRRK2, or any mutation thereof, is mentioned, it is the LRRK2 kinase activity that is being referred to, unless clearly stated otherwise. As such, selectivity of LRRK2 relative to another kinase indicates a comparison of the $IC_{50}$ of a compound on the kinase activity of LRRK2 to the $IC_{50}$ of the compound on the kinase activity of another kinase. For example, a compound that is 10 fold selective for LRRK2 kinase activity relative to another kinase activity will have a ratio of $IC_{50}$(other kinase)÷$IC_{50}$(LRRK2)=10 (or a ratio of $IC_{50}$(LRRK2)÷$IC_{50}$(other kinase)=0.1).

The phrase "therapeutically effective amount" as used herein means that amount of a compound, material, or composition as described herein (e.g. compounds of Formula I and compositions thereof), which is effective for producing a desired therapeutic effect, at a reasonable benefit/risk ratio applicable to any medical treatment. For example, a "therapeutically effective amount" is an amount effective to reduce or lessen at least one symptom of the disease or condition being treated or to reduce or delay onset of one or more clinical markers or symptoms associated with the disease or condition, or to modify or reverse the disease process.

The terms "treatment" or "treating" when referring to a disease or condition, means producing a desired therapeutic effect. Exemplary therapeutic effects include delaying onset or reducing at least one symptom associated with the disease, positively affecting (e.g., reducing or delaying onset) of a clinical marker associated with the disease and slowing or reversing disease progression.

The term "pharmaceutically acceptable" refers to those properties and/or substances that are acceptable to a patient (e.g., human patient) from a toxicological and/or safety point of view.

The term "pharmaceutically acceptable salts" means salts of the compounds as described herein, e.g. compounds of Formula I, which are prepared with relatively nontoxic acids or bases, depending on the particular substituents found on the compounds described herein. A compound of Formula I may be prepared as a pharmaceutically acceptable salt. Such salts and their preparation for use as pharmaceuticals are readily known to those of skill in the art. Such salts may provide improved properties, e.g. solubility or pharmacokinetic properties, such that the activity of the compound of Formula I is enhanced upon administration to a subject. It is understood that such pharmaceutically acceptable salts are effectively equivalent to compounds of Formula I, i.e. when such a salt is administered into a subject, the administration effectively encompasses the use of a compound of Formula I.

The term "pharmaceutically acceptable solvate" means any solvate, including any hydrate, of a compound as described herein, e.g. a compound of Formula I, which is prepared with a relatively nontoxic solvent or solvents. A compound as described herein, e.g. a compound of Formula I, can exist in unsolvated forms as well as solvated forms, including hydrated forms. Such solvates may provide improved properties, e.g. solubility or pharmacokinetic properties, such that the activity of the compound of Formula I is enhanced upon administration to a subject. It is understood that such pharmaceutically acceptable solvated forms are effectively equivalent to compounds of Formula I, i.e. when such a solvated form is administered into a subject, the administration effectively encompasses the use of a compound of Formula I.

The term "pharmaceutically acceptable carrier" means any pharmaceutically acceptable ingredient known to those of skill in the art, which is typically considered a non-active ingredient.

The term "pharmaceutically acceptable derivative" or "prodrug" means any derivative of a compound of Formula I that is suitable for pharmaceutical use. For example, a prodrug of a compound as described herein which, upon administration to a recipient, is capable of providing either directly or indirectly, a compound as described herein (e.g. a compound of Formula I). In some examples, a prodrug increases the bioavailability of a compound as described herein when such compound is administered to a mammal (e.g., by allowing an orally administered compound to be more readily absorbed into the blood stream) or which enhance delivery of the parent compound to a biological compartment (e.g., the brain) relative to the parent species. It is understood that such a prodrug form is effectively equivalent to a compound of Formula I, i.e. when such a prodrug form is administered into a subject, the administration effectively encompasses the use of a compound of Formula I.

The term "polymorph" refers to a crystal form of a compound as described herein. It is understood that a compound as described herein may occur in many different crystal forms, or polymorphs, or can be made into amorphous form (i.e. solid form without any defined crystal structure). While such varied solid forms may have different pharmaceutical properties, it is understood that any such crystal form comprises a compound as described herein, i.e. it is encompassed by a compound of Formula I. Similarly, a pharmaceutically acceptable salt or solvate of a compound of Formula I may exist as polymorphs, where any such polymorph is encompassed by a pharmaceutically acceptable salt or a pharmaceutically acceptable solvate of a compound of Formula I.

The term "metabolite" refers to a derivative of a compound as described herein resulting from administering such a compound to a recipient, wherein the metabolite results from metabolic processes in the body of a recipient. In some examples, a metabolite may be pharmaceutically active. Any metabolites may be identified using routine techniques known in the art, and their biological activity assessed as described herein.

The term "conjugate" refers to a derivative of a compound as described herein resulting in the linking of a suitable adjunct to provide additional features or uses. A compound of Formula I may be further conjugated via a suitably reactive group to link a moiety to the compound of Formula I, such that the linked moiety provides, for example, improved targeting to certain tissues, improved transport across the blood brain barrier, a suitable binding molecule for use as a probe, or the like. The portion of the conjugate that is derived from a compound of Formula I is expected to have similar properties to a compound of Formula I, for example such portion of the conjugate will readily bind to LRRK2 in a similar manner to the non-derivative compound of Formula I. Such conjugates can be used, for example, for targeted drug delivery, improved delivery to the brain or CNS, as a probe for identifying LRRK2 in a biological mixture or for isolating LRRK2 from a biological mixture, or the like.

The term "isotopically enhanced" or "isotopically enhanced form" means that a compound as described herein, e.g. a compound of Formula I, may be modified to contain unnatural proportions of certain atomic isotopes at one or more of the atoms that constitute such a compound. For example, a compound can be radiolabeled with radioactive isotopes, such as for example tritium ($^3$H), iodine-125 ($^{125}$I) or carbon-14 ($^{14}$C). Such isotopic variations of a compound as described herein, whether radioactive or not, is effectively encompassed by compounds as described herein. For example, a compound in which one or more of the hydrogen atoms are replaced with another stable isotope of hydrogen (i.e., deuterium) or a radioactive isotope (i.e., tritium), is expected to have similar activity to the compound without isotopic enhancement as it relates to LRRK2 kinase inhibition, and such a compound is effectively equivalent to a compound of Formula I. Such an isotopically enhanced compound may be useful, for example, in detection of the compound in vivo or in biological tissue, such as a radiolabelled compound containing $^3$H or $^{14}$C to assess tissue distribution, or a positron emitting compound containing $^{11}$C, $^{15}$O, $^{13}$N, $^{18}$F or the like useful in positron emission tomography for in vivo imaging. Similarly, a deuterated compound may provide a compound with greater metabolic stability than the analogous non-deuterated compound, such that the deuterated compound has better pharmacokinetic properties. Any isotopically enhanced compound is expected to have similar inhibitory activity as it relates to LRRK2 kinase, and other kinases. Such a compound is readily prepared by those of skill in the art, for example by the methods as described herein or other methods known in the art, where suitable isotopically enhanced reagents may be used to provide the isotopically enhanced compounds.

As used herein, the term "chiral", "enantiomerically enriched" or "diastereomerically enriched" refers to a compound having an enantiomeric excess (ee) or a diastereomeric excess (de) of greater than about 50%, also greater than about 70% and also greater than about 90%. In one example, enantiomeric or diastereomeric excess is higher than about 90%, e.g., those compositions with greater than about 95%, greater than about 97% and greater than about 99% ee or de. The terms "enantiomeric excess" and "diastereomeric excess" are used in their conventional sense.

Compounds with a single stereocenter are referred to as being present in "enantiomeric excess", those with at least two stereocenters are referred to as being present in "diastereomeric excess". The value of ee will be a number from 0 to 100, zero being racemic and 100 being enantiomerically pure. For example, a 90% ee reflects the presence of 95% of one enantiomer and 5% of the other(s) in the material in question. Stereoisomers are detectable if a concentration of such stereoisomer in the analyzed mixture can be determined using common analytical methods, such as chiral HPLC.

Hence, in one embodiment, compositions are provided including a first stereoisomer and at least one additional stereoisomer of a compound as described herein, e.g. a compound of Formula I. The first stereoisomer can be present in a diastereomeric or enantiomeric excess of at least about 80%, also at least about 90% and more also at least about 95%. In one embodiment, the first stereoisomer is present in a diastereomeric or enantiomeric excess of at least about 96%, at least about 97%, at least about 98%, at least about 99% or at least about 99.5%. In another embodiment, the compound of Formula I is enantiomerically or diastereomerically pure (diastereomeric or enantiomeric excess is about 100%). Enantiomeric or diastereomeric excess can be determined relative to exactly one other stereoisomer, or can be determined relative to the sum of at least two other stereoisomers. In an exemplary embodiment, enantiomeric or diastereomeric excess is determined relative to all other detectable stereoisomers, which are present in the mixture. Stereoisomers are detectable if a concentration of such stereoisomer in the analyzed mixture can be determined using common analytical methods, such as chiral HPLC.

The terms "use in combination", "combination use" or the like, means use of a compound as described herein with one or more other therapeutics for the treatment, prevention, or amelioration of symptoms of a disease. Combination use includes use of a compound as described herein at any point before, during or after treatment with one or more other therapeutic treatments, for example a compound as described herein and another therapeutic agent can be administered essentially simultaneously, either in different vehicles, or can be administered in the same vehicle (e.g. can be manufactured into the same pill, tablet, solution, etc.); or a compound as described herein can be administered prior to (e.g. minutes, hours, days, or weeks before) administering another therapeutic agent; or a compound as described herein can be administered subsequently to (e.g. minutes, hours, days, or weeks after) administering another therapeutic agent.

The term "LRRK2-mediated condition", "Leucine-rich repeat kinase 2 mediated disorder" or any other variation thereof, as used herein means any disease or other condition in which LRRK2, including any mutations thereof, is known to play a role, or a disease state that is associated with elevated activity or expression of LRRK2, including any mutations thereof. For example, a "LRRK2-mediated condition" may be relieved by inhibiting LRRK2 kinase activity. Such conditions include certain neurodegenerative diseases, such as Lewy body diseases, including, but not limited to, Parkinson's disease, Lewy body variant of Alzheimer's disease, combined Parkinson's disease and Alzheimer's disease, dementia with Lewy bodies, diffuse Lewy body disease, as well as any syndrome identified as multiple system atrophy; certain cancers, such as melanoma; papillary renal cell carcinoma and papillary thyroid carcinoma; certain autoimmune diseases, such as Inflammatory Bowel Disease (e.g. Crohn's disease and ulcerative colitis); and leprosy.

The term "neurodegenerative diseases" includes any disease or condition characterized by problems with movements, such as ataxia, and conditions affecting cognitive abilities (e.g., memory) as well as conditions generally related to all types of dementia. "Neurodegenerative diseases" may be associated with impairment or loss of cognitive abilities, potential loss of cognitive abilities and/or impairment or loss of brain cells. Exemplary "neurodegenerative diseases" include Alzheimer's disease, Parkinson's disease, amyotrophic lateral sclerosis (ALS), Down syndrome, dementia, multi-infarct dementia, mild cognitive impairment (MCI), epilepsy, seizures, Huntington's disease, neurodegeneration induced by viral infection (e.g. AIDS, encephalopathies), traumatic brain injuries, as well as ischemia and stroke. "Neurodegenerative diseases" also includes any undesirable condition associated with the disease. For instance, a method of treating a neurodegenerative disease includes methods of treating or preventing loss of neuronal function characteristic of neurodegenerative disease.

In one aspect, compounds are provided having a structure according to Formula I:

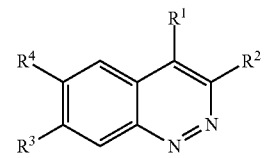

or a salt thereof, wherein:

$R^1$ is —$CR^5R^6R^7$, —$C(=O)R^8$, —$OR^9$, —$SR^{10}$, —$S(=O)_nR^{11}$, or —$NR^{12}R^{13}$;

n is 1 or 2;

$R^5$, $R^6$, and $R^7$ are independently selected from the group consisting of hydrogen, halogen, —OH, $C_1$-$C_6$ alkoxy, —SH, —$S(=O)_m$—$C_1$-$C_6$ alkyl, —$NH_2$, $C_1$-$C_6$ alkylamino, $C_1$-$C_6$ dialkylamino, $C_1$-$C_6$ alkyl optionally substituted with one or more substituents $R^{14}$, cycloalkyl optionally substituted with one or more substituents $R^{15}$, heterocycloalkyl optionally substituted with one or more substituents $R^{16}$, aryl optionally substituted with one or more substituents $R^{17}$, and heteroaryl optionally substituted with one or more substituents $R^{18}$, wherein the alkyl chain of $C_1$-$C_6$ alkoxy, —$S(=O)_m$—$C_1$-$C_6$ alkyl, $C_1$-$C_6$ alkylamino, or $C_1$-$C_6$ dialkylamino is optionally substituted with one or more substituents independently selected from the group consisting of halogen, —OH, $C_1$-$C_6$ alkoxy, $C_1$-$C_6$ haloalkoxy, —SH, —$S(=O)_m$—$C_1$-$C_6$ alkyl, —$S(=O)_m$—$C_1$-$C_6$ haloalkyl, —$NH_2$, $C_1$-$C_6$ alkylamino, $C_1$-$C_6$ dialkylamino, and cycloalkylamino; or any two of $R^5$, $R^6$ and $R^7$ together with the carbon to which they are attached, form a 3-8 membered cycloalkyl optionally substituted with one or more substituents $R^{15}$ or a 4-7 membered heterocycloalkyl optionally substituted with one or more substituents $R^{16}$, and the other of $R^5$, $R^6$ and $R^7$ is selected from the group consisting of hydrogen, halogen, —OH, $C_1$-$C_6$ alkoxy, —SH, —$S(=O)_m$—$C_1$-$C_6$ alkyl, —$NH_2$, $C_1$-$C_6$ alkylamino, $C_1$-$C_6$ dialkylamino, and $C_1$-$C_6$ alkyl optionally substituted with one or more substituents $R^{14}$, wherein the alkyl chain of $C_1$-$C_6$ alkoxy, —$S(=O)_m$—$C_1$-$C_6$ alkyl, $C_1$-$C_6$ alkylamino, or $C_1$-$C_6$ dialkylamino is optionally substituted with one or more substituents independently selected from the group consisting of halogen, —OH, $C_1$-$C_6$ alkoxy, $C_1$-$C_6$ haloalkoxy, —SH, —S(=O)$_m$—$C_1$-$C_6$ alkyl, —S(=O)$_m$—$C_1$-$C_6$ haloalkyl, —NH$_2$, $C_1$-$C_6$ alkylamino, $C_1$-$C_6$ dialkylamino, and N-linked-heterocycloalkyl;

$R^8$, $R^9$, $R^{10}$, and $R^{11}$ are independently selected from the group consisting of $C_1$-$C_6$ alkyl optionally substituted with one or more substituents $R^{14}$, cycloalkyl optionally substituted with one or more substituents $R^{15}$, heterocycloalkyl optionally substituted with one or more substituents $R^{16}$, aryl optionally substituted with one or more substituents $R^{17}$, and heteroaryl optionally substituted with one or more substituents $R^{18}$;

$R^{12}$ is hydrogen or $C_1$-$C_6$ alkyl optionally substituted with one or more substituents $R^{14}$;

$R^{13}$ is selected from the group consisting of hydrogen, $C_1$-$C_6$ alkyl optionally substituted with one or more substituents $R^{14}$, cycloalkyl optionally substituted with one or more substituents $R^{15}$, and heterocycloalkyl optionally substituted with one or more substituents $R^{16}$;

or $R^{12}$ and $R^{13}$, together with the nitrogen to which they are attached, form a 5-7 membered heterocycloalkyl optionally substituted with one or more substituents $R^{16}$;

$R^{14}$ at each occurrence is independently selected from the group consisting of halogen, —OH, $C_1$-$C_6$ alkoxy, —SH, —S(=O)$_m$—$C_1$-$C_6$ alkyl, —NH$_2$, $C_1$-$C_6$ alkylamino, $C_1$-$C_6$ dialkylamino, cycloalkyl optionally substituted with one or more substituents $R^{15}$, heterocycloalkyl optionally substituted with one or more substituents $R^{16}$, aryl optionally substituted with one or more substituents $R^{17}$, and heteroaryl optionally substituted with one or more substituents $R^{18}$, wherein the alkyl chain of $C_1$-$C_6$ alkoxy, —S(=O)$_m$—$C_1$-$C_6$ alkyl, $C_1$-$C_6$ alkylamino, or $C_1$-$C_6$ dialkylamino is optionally substituted with one or more substituents independently selected from the group consisting of halogen, —OH, $C_1$-$C_6$ alkoxy, $C_1$-$C_6$ haloalkoxy, —SH, —S(=O)$_m$—$C_1$-$C_6$ alkyl, —S(=O)$_m$—$C_1$-$C_6$ haloalkyl, —NH$_2$, $C_1$-$C_6$ alkylamino, $C_1$-$C_6$ dialkylamino, and N-linked-heterocycloalkyl;

$R^{15}$ and $R^{16}$, at each occurrence, are independently selected from the group consisting of halogen, $C_1$-$C_6$ alkyl, —OH, =O, $C_1$-$C_6$ alkoxy, —SH, —S(=O)$_m$—$C_1$-$C_6$ alkyl, —NH$_2$, $C_1$-$C_6$ alkylamino, $C_1$-$C_6$ dialkylamino, and N-linked-heterocycloalkyl, wherein the alkyl chain of $C_1$-$C_6$ alkyl, $C_1$-$C_6$ alkoxy, —S(=O)$_m$—$C_1$-$C_6$ alkyl, $C_1$-$C_6$ alkylamino, or $C_1$-$C_6$ dialkylamino is optionally substituted with one or more substituents independently selected from the group consisting of halogen, —OH, $C_1$-$C_6$ alkoxy, $C_1$-$C_6$ haloalkoxy, —SH, —S(=O)$_m$—$C_1$-$C_6$ alkyl, —S(=O)$_m$—$C_1$-$C_6$ haloalkyl, —NH$_2$, $C_1$-$C_6$ alkylamino, $C_1$-$C_6$ dialkylamino, and N-linked-heterocycloalkyl;

$R^{17}$ and $R^{18}$ at each occurrence are independently selected from the group consisting of halogen, —CN, —NO$_2$, $C_1$-$C_6$ alkyl, —OH, $C_1$-$C_6$ alkoxy, —SH, —S(=O)$_m$—$C_1$-$C_6$ alkyl, —NH$_2$, $C_1$-$C_6$ alkylamino, $C_1$-$C_6$ dialkylamino, and N-linked-heterocycloalkyl wherein the alkyl chain of $C_1$-$C_6$ alkyl, $C_1$-$C_6$ alkoxy, —S(=O)$_m$—$C_1$-$C_6$ alkyl, $C_1$-$C_6$ alkylamino, or $C_1$-$C_6$ dialkylamino is optionally substituted with one or more substituents independently selected from the group consisting of halogen, —OH, $C_1$-$C_6$ alkoxy, $C_1$-$C_6$ haloalkoxy, —SH, —S(=O)$_m$—$C_1$-$C_6$ alkyl, —S(=O)$_m$—$C_1$-$C_6$ haloalkyl, —NH$_2$, $C_1$-$C_6$ alkylamino, $C_1$-$C_6$ dialkylamino, and N-linked-heterocycloalkyl;

m is 0, 1 or 2;

$R^2$ is selected from the group consisting of $R^{19}$, $L_1$-$R^{20}$, $C_1$-$C_6$ alkyl, $C_2$-$C_6$ alkenyl, $C_2$-$C_6$ alkynyl, cycloalkyl, heterocycloalkyl, aryl, and heteroaryl, wherein $C_1$-$C_6$ alkyl is optionally substituted with one or more substituents independently selected from the group consisting of $R^{19}$, $L_2$-$R^{20}$, —NR$^{21}$R$^{22}$, cycloalkyl, aryl, heteroaryl, and heterocycloalkyl, provided, however, that heterocycloalkyl is not N-linked-heterocycloalkyl, and wherein $C_2$-$C_6$ alkenyl and $C_2$-$C_6$ alkynyl are optionally substituted with one or more substituents independently selected from the group consisting of $R^{19}$, $L_1$-$R^{20}$, cycloalkyl, heterocycloalkyl, aryl, and heteroaryl, and wherein cycloalkyl and heterocycloalkyl, as $R^2$ or as a substituent of $C_1$-$C_6$ alkyl, $C_2$-$C_6$ alkenyl, or $C_2$-$C_6$ alkynyl, are optionally substituted with one or more substituents independently selected from the group consisting of $R^{19}$, =O, =NR$^{21}$, =NOR$^{21}$, $L_1$-$R^{20}$, and $R^{23}$, and wherein aryl and heteroaryl, as $R^2$ or as a substituent of $C_1$-$C_6$ alkyl, $C_2$-$C_6$ alkenyl, or $C_2$-$C_6$ alkynyl, are optionally substituted with one or more substituents independently selected from the group consisting of $R^{19}$, $L_1$-$R^{20}$, and $R^{23}$;

one of $R^3$ and $R^4$ is selected from the group consisting of hydrogen, $R^{19}$, $L_1$-$R^{20}$, $C_1$-$C_6$ alkyl, $C_2$-$C_6$ alkenyl, $C_2$-$C_6$ alkynyl, cycloalkyl, heterocycloalkyl, aryl, and heteroaryl, wherein $C_1$-$C_6$ alkyl, $C_2$-$C_6$ alkenyl, and $C_2$-$C_6$ alkynyl are optionally substituted with one or more substituents independently selected from the group consisting of $R^{19}$, $L_1$-$R^{20}$, cycloalkyl, heterocycloalkyl, aryl, and heteroaryl, and wherein cycloalkyl and heterocycloalkyl, as $R^3$ or $R^4$ or as a substituent of $C_1$-$C_6$ alkyl, $C_2$-$C_6$ alkenyl, or $C_2$-$C_6$ alkynyl, are optionally substituted with one or more substituents independently selected from the group consisting of $R^{19}$, =O, =NR$^{21}$, =NOR$^{21}$, $L_1$-$R^{20}$, and $R^{23}$, and wherein aryl and heteroaryl, as $R^3$ or $R^4$ or as a substituent of $C_1$-$C_6$ alkyl, $C_2$-$C_6$ alkenyl, or $C_2$-$C_6$ alkynyl, are optionally substituted with one or more substituents independently selected from the group consisting of $R^{19}$, $L_1$-$R^{20}$, and $R^{23}$;

the other of $R^3$ and $R^4$ is selected from the group consisting of $R^{24}$, $L_3$-$R^{20}$, —OR$^{25}$, —SR$^{25}$, methyl, $C_2$-$C_6$ alkyl, $C_2$-$C_6$ alkenyl, $C_2$-$C_6$ alkynyl, cycloalkyl, heterocycloalkyl, aryl, and heteroaryl, wherein methyl is substituted with one or more substituents independently selected from the group consisting of $R^{19}$, $L_1$-$R^{20}$, cycloalkyl, heterocycloalkyl, aryl, and heteroaryl, and wherein $C_2$-$C_6$ alkyl, $C_2$-$C_6$ alkenyl, and $C_2$-$C_6$ alkynyl are optionally substituted with one or more substituents independently selected from the group consisting of $R^{19}$, $L_1$-$R^{20}$, cycloalkyl, heterocycloalkyl, aryl, and heteroaryl, and wherein cycloalkyl and heterocycloalkyl, as $R^3$ or $R^4$ or as a substituent of methyl, $C_2$-$C_6$ alkyl, $C_2$-$C_6$ alkenyl, or $C_2$-$C_6$ alkynyl, are optionally substituted with one or more substituents independently selected from the group consisting of $R^{19}$, =O, =NR$^{21}$, =NOR$^{21}$, $L_1$-$R^{20}$, and $R^{23}$, and wherein aryl and heteroaryl, as $R^3$ or $R^4$ or as a substituent of methyl, $C_2$-$C_6$ alkyl, $C_2$-$C_6$ alkenyl, or $C_2$-$C_6$ alkynyl, are optionally substituted with one or more substituents independently selected from the group consisting of $R^{19}$, $L_1$-$R^{20}$, and $R^{23}$;

$R^{19}$ at each occurrence is independently selected from the group consisting of halogen, —CN, —NO$_2$, —OH, —SH, —NH$_2$, —NHOH, —C(=X)OH, —C(=X)NH$_2$, —C(=X)NHOH, —OC(=X)NH$_2$, —NHC(=X)NH$_2$, —NHC(=X)OH, —S(=O)$_2$NH$_2$, —S(=O)$_2$NHOH, —NHS(=O)$_2$—NH$_2$, and —NHC(NH$_2$)=NH;

$R^{24}$ at each occurrence is independently selected from the group consisting of —CN, —NH$_2$, —NHOH, —C(=X)OH, —C(=X)NH$_2$, —C(=X)NHOH, —OC(=X)NH$_2$, —NHC(=X)NH$_2$, —NHC(=X)OH, —S(=O)$_2$NH$_2$, —S(=O)$_2$NHOH, —NHS(=O)$_2$NH$_2$, and —NHC(NH$_2$)=NH;

$R^{20}$ at each occurrence is independently selected from the group consisting of C$_1$-C$_6$ alkyl, C$_2$-C$_6$ alkenyl, C$_2$-C$_6$ alkynyl, cycloalkyl, heterocycloalkyl, aryl, and heteroaryl, wherein C$_1$-C$_6$ alkyl, C$_2$-C$_6$ alkenyl, and C$_2$-C$_6$ alkynyl are optionally substituted with one or more substituents independently selected from the group consisting of R$^{19}$, L$_4$-R$^{26}$, cycloalkyl, heterocycloalkyl, aryl, and heteroaryl, and wherein cycloalkyl and heterocycloalkyl, as R$^{20}$ or as a substituent of C$_1$-C$_6$ alkyl, C$_2$-C$_6$ alkenyl, or C$_2$-C$_6$ alkynyl, are optionally substituted with one or more substituents independently selected from the group consisting of R$^{19}$, L$_4$-R$^{26}$, =O, =NR$^{21}$, =NOR$^{21}$, and R$^{27}$, and wherein aryl and heteroaryl, as R$^{20}$ or as a substituent of C$_1$-C$_6$ alkyl, C$_2$-C$_6$ alkenyl, or C$_2$-C$_6$ alkynyl, are optionally substituted with one or more substituents independently selected from the group consisting of R$^{19}$, L$_4$-R$^{26}$, and R$^{27}$;

$R^{22}$ at each occurrence is independently selected from the group consisting of aryl, and heteroaryl, wherein aryl and heteroaryl are optionally substituted with one or more substituents independently selected from the group consisting of R$^{19}$, L$_4$-R$^{26}$, and R$^{27}$;

$R^{23}$ at each occurrence is independently selected from the group consisting of C$_1$-C$_6$ alkyl, C$_2$-C$_6$ alkenyl, C$_2$-C$_6$ alkynyl, cycloalkyl, heterocycloalkyl, aryl, and heteroaryl, wherein C$_1$-C$_6$ alkyl, C$_2$-C$_6$ alkenyl, and C$_2$-C$_6$ alkynyl are optionally substituted with one or more substituents independently selected from the group consisting of R$^{19}$, L$_4$-R$^{26}$, cycloalkyl, heterocycloalkyl, aryl, and heteroaryl, and wherein cycloalkyl and heterocycloalkyl as R$^{23}$ or as a substituent of C$_1$-C$_6$ alkyl, C$_2$-C$_6$ alkenyl, or C$_2$-C$_6$ alkynyl, are optionally substituted with one or more substituents independently selected from the group consisting of R$^{19}$, =O, =NR$^{21}$, =NOR$^{21}$, L$_4$-R$^{26}$, and R$^{28}$, and wherein aryl and heteroaryl, as R$^{23}$ or as a substituent of C$_1$-C$_6$ alkyl, C$_2$-C$_6$ alkenyl, or C$_2$-C$_6$ alkynyl, are optionally substituted with one or more substituents independently selected from the group consisting of R$^{19}$, L$_4$-R$^{26}$, and R$^{28}$;

$R^{25}$ at each occurrence is independently selected from the group consisting of methyl, C$_2$-C$_6$ alkyl, C$_2$-C$_6$ alkenyl, C$_2$-C$_6$ alkynyl, cycloalkyl, heterocycloalkyl, aryl, and heteroaryl, wherein methyl is substituted with one or more substituents independently selected from the group consisting of R$^{19}$, L$_4$-R$^{26}$, cycloalkyl, heterocycloalkyl, aryl, and heteroaryl, and wherein C$_2$-C$_6$ alkyl, C$_2$-C$_6$ alkenyl, and C$_2$-C$_6$ alkynyl are optionally substituted with one or more substituents independently selected from the group consisting of R$^{19}$, L$_4$-R$^{26}$, cycloalkyl, heterocycloalkyl, aryl, and heteroaryl, and wherein cycloalkyl and heterocycloalkyl, as R$^{25}$ or as a substituent of methyl, C$_2$-C$_6$ alkyl, C$_2$-C$_6$ alkenyl, or C$_2$-C$_6$ alkynyl, are optionally substituted with one or more substituents independently selected from the group consisting of R$^{19}$, L$_4$-R$^{26}$, =O, =NR$^{21}$, =NOR$^{21}$, and R$^{27}$, and wherein aryl and heteroaryl, as R$^{25}$ or as a substituent of methyl, C$_2$-C$_6$ alkyl, C$_2$-C$_6$ alkenyl, or C$_2$-C$_6$ alkynyl, are optionally substituted with one or more substituents independently selected from the group consisting of R$^{19}$, L$_4$-R$^{26}$, and R$^{27}$;

$R^{26}$ at each occurrence is independently selected from the group consisting of C$_1$-C$_6$ alkyl, C$_2$-C$_6$ alkenyl, C$_2$-C$_6$ alkynyl, cycloalkyl, heterocycloalkyl, aryl, and heteroaryl, wherein C$_1$-C$_6$ alkyl, C$_2$-C$_6$ alkenyl, and C$_2$-C$_6$ alkynyl are optionally substituted with one or more substituents independently selected from the group consisting of R$^{19}$, L$_5$-R$^{29}$, cycloalkyl, heterocycloalkyl, aryl, and heteroaryl, wherein cycloalkyl and heterocycloalkyl as R$^{26}$ or as a substituent of C$_1$-C$_6$ alkyl, C$_2$-C$_6$ alkenyl, or C$_2$-C$_6$ alkynyl, are optionally substituted with one or more substituents independently selected from the group consisting of R$^{19}$, =O, =NR$^{21}$, =NOR$^{21}$, L$_5$-R$^{29}$, and R$^{28}$, and wherein aryl and heteroaryl, as R$^{26}$ or as a substituent of C$_1$-C$_6$ alkyl, C$_2$-C$_6$ alkenyl, or C$_2$-C$_6$ alkynyl, are optionally substituted with one or more substituents independently selected from the group consisting of R$^{19}$, L$_5$-R$^{29}$, and R$^{28}$;

$R^{27}$ at each occurrence is independently selected from the group consisting of C$_1$-C$_6$ alkyl, C$_2$-C$_6$ alkenyl, C$_2$-C$_6$ alkynyl, cycloalkyl, heterocycloalkyl, aryl, and heteroaryl, wherein C$_1$-C$_6$ alkyl, C$_2$-C$_6$ alkenyl, and C$_2$-C$_6$ alkynyl are optionally substituted with one or more substituents independently selected from the group consisting of R$^{19}$, L$_4$-R$^{26}$, cycloalkyl, heterocycloalkyl, aryl, and heteroaryl, wherein cycloalkyl and heterocycloalkyl as R$^{27}$ or as a substituent of C$_1$-C$_6$ alkyl, C$_2$-C$_6$ alkenyl, or C$_2$-C$_6$ alkynyl, are optionally substituted with one or more substituents independently selected from the group consisting of R$^{19}$, =O, =NR$^{21}$, =NOR$^{21}$, L$_4$-R$^{26}$, and R$^{28}$, and wherein aryl and heteroaryl, as R$^{27}$ or as a substituent of C$_1$-C$_6$ alkyl, C$_2$-C$_6$ alkenyl, or C$_2$-C$_6$ alkynyl, are optionally substituted with one or more substituents independently selected from the group consisting of R$^{19}$, L$_4$-R$^{26}$, and R$^{28}$;

$R^{28}$ at each occurrence is independently selected from the group consisting of C$_1$-C$_6$ alkyl, C$_2$-C$_6$ alkenyl, C$_2$-C$_6$ alkynyl, cycloalkyl, heterocycloalkyl, aryl, and heteroaryl, wherein C$_1$-C$_6$ alkyl, C$_2$-C$_6$ alkenyl, and C$_2$-C$_6$ alkynyl are optionally substituted with one or more substituents independently selected from the group consisting of R$^{19}$, L$_5$-R$^{29}$, cycloalkyl, heterocycloalkyl, aryl, and heteroaryl, and wherein cycloalkyl and heterocycloalkyl as R$^{28}$ or as a substituent of C$_1$-C$_6$ alkyl, C$_2$-C$_6$ alkenyl, or C$_2$-C$_6$ alkynyl, are optionally substituted with one or more substituents independently selected from the group consisting of R$^{19}$, =O, =NR$^{21}$, =NOR$^{21}$, L$_5$-R$^{29}$, and R$^{29}$, and wherein aryl and heteroaryl, as R$^{28}$ or a substituent of C$_1$-C$_6$ alkyl, C$_2$-C$_6$ alkenyl, or C$_2$-C$_6$ alkynyl, are optionally substituted with one or more substituents independently selected from the group consisting of R$^{19}$, L$_5$-R$^{29}$, and R$^{29}$;

$R^{29}$ at each occurrence is independently selected from the group consisting of C$_1$-C$_6$ alkyl, C$_2$-C$_6$ alkenyl, C$_2$-C$_6$ alkynyl, cycloalkyl, heterocycloalkyl, aryl, and heteroaryl, wherein C$_1$-C$_6$ alkyl, C$_2$-C$_6$ alkenyl, and C$_2$-C$_6$ alkynyl are optionally substituted with one or more substituents R$^{30}$, and wherein cycloalkyl and heterocycloalkyl are optionally substituted with one or more substituents R$^{31}$, and wherein aryl and heteroaryl are optionally substituted with one or more substituents R$^{32}$;

L$_1$, L$_4$, and L$_5$, at each occurrence, are independently selected from the group consisting of —O—, —S—, —NR$^{21}$—, —NR$^{21}$O—, —C(=X)—, —C(=X)O—, —OC(=X)—, —C(=X)NR$^{21}$—, —C(=X)NR$^{21}$O—, —NR$^{21}$C(=X)—, —OC(=X)NR$^{21}$—, —NR$^{21}$C(=X)NR$^{21}$—, —NR$^{21}$C(=X)O—, —S(=O)—, —S(=O)$_2$—, —S(=O)$_2$NR$^{21}$—, —S(=O)$_2$NR$^{21}$O—, —NR$^{21}$S (=O)$_2$—, —NR$^{21}$S(=O)$_2$NR$^{21}$—, —NR$^{21}$C(=NR$^{21}$) NR$^{21}$—, and —NR$^{21}$C(NR$^{21}$R$^{21}$)=N—;

L$_2$ at each occurrence is independently selected from the group consisting of —O—, —S—, —NR$^{21}$O—, —C(=X)—, —C(=X)O—, —OC(=X)—, —C(=X) NR$^{21}$—, —C(=X)NR$^{21}$O—, —NR$^{21}$C(=X)—, —OC (=X)NR$^{21}$—, —NR$^{21}$C(=X)NR$^{21}$—, —NR$^{21}$C(=X) O—, —S(=O)—, —S(=O)$_2$—, —S(=O)$_2$NR$^{21}$—, —S(=O)$_2$NR$^2$O—, —NR$^{21}$S(=O)$_2$—, —NR$^{21}$S (=O)$_2$NR$^{21}$—, —NR$^{21}$C(=NR$^{21}$)NR$^{21}$—, and —NR$^{21}$C(NR$^{21}$R$^{21}$)=N—;

L$_3$ at each occurrence is independently selected from the group consisting of —NR$^{21}$—, —NR$^{21}$O—, —C(=X)—, —C(=X)O—, —OC(=X)—, —C(=X) NR$^{21}$—, —C(=X)NR$^{21}$O—, —NR$^{21}$C(=X)—, —OC (=X)NR$^{21}$—, —NR$^{21}$C(=X)NR$^{21}$—, —NR$^{21}$C(=X) O—, —S(=O)—, —S(=O)$_2$—, —S(=O)$_2$NR$^{21}$—, —S(=O)$_2$NR$^{21}$O—, —NR$^{21}$S(=O)$_2$—, —NR$^{21}$S (=O)$_2$NR$^{21}$—, —NR$^{21}$C(=NR$^{21}$)NR$^{21}$—, and —NR$^{21}$C(NR$^{21}$R$^{21}$)=N—;

X is O or S;

R$^{21}$ at each occurrence is independently selected from the group consisting of hydrogen, C$_1$-C$_6$ alkyl, C$_2$-C$_6$ alkenyl, C$_2$-C$_6$ alkynyl, cycloalkyl, heterocycloalkyl, aryl, and heteroaryl, wherein C$_1$-C$_6$ alkyl, C$_2$-C$_6$ alkenyl, and C$_2$-C$_6$ alkynyl are optionally substituted with one or more substituents R$^{30}$, cycloalkyl and heterocycloalkyl are optionally substituted with one or more substituents R$^{31}$, and aryl and heteroaryl are optionally substituted with one or more substituents R$^{32}$;

R$^{30}$ at each occurrence is independently selected from the group consisting of halogen, —OH, C$_1$-C$_6$ alkoxy, —SH, —S(=O)$_m$—C$_1$-C$_6$ alkyl, —NH$_2$, C$_1$-C$_6$ alkylamino, C$_1$-C$_6$ dialkylamino, cycloalkyl, heterocycloalkyl, aryl, and heteroaryl, wherein the alkyl chain of C$_1$-C$_6$ alkoxy, —S(=O)$_m$—C$_1$-C$_6$ alkyl, C$_1$-C$_6$ alkylamino, or C$_1$-C$_6$ dialkylamino is optionally substituted with one or more substituents independently selected from the group consisting of halogen, —OH, C$_1$-C$_6$ alkoxy, C$_1$-C$_6$ haloalkoxy, —SH, —S(=O)$_m$—C$_1$-C$_6$ alkyl, —S (=O)$_m$—C$_1$-C$_6$ haloalkyl, —NH$_2$, C$_1$-C$_6$ alkylamino, C$_1$-C$_6$ dialkylamino, and N-linked-heterocycloalkyl, and wherein cycloalkyl and heterocycloalkyl are optionally substituted with one or more substituents R$^{31}$, and aryl and heteroaryl are optionally substituted with one or more substituents R$^{32}$;

R$^{31}$ at each occurrence is independently selected from the group consisting of halogen, C$_1$-C$_6$ alkyl, —OH, =O, C$_1$-C$_6$ alkoxy, —SH, —S(=O)$_m$—C$_1$-C$_6$ alkyl, —NH$_2$, C$_1$-C$_6$ alkylamino, C$_1$-C$_6$ dialkylamino, and N-linked-heterocycloalkyl, wherein the alkyl chain of C$_1$-C$_6$ alkyl, C$_1$-C$_6$ alkoxy, —S(=O)$_m$—C$_1$-C$_6$ alkyl, C$_1$-C$_6$ alkylamino, or C$_1$-C$_6$ dialkylamino is optionally substituted with one or more substituents selected from the group consisting of halogen, —OH, C$_1$-C$_6$ alkoxy, C$_1$-C$_6$ haloalkoxy, —SH, —S(=O)$_m$—C$_1$-C$_6$ alkyl, —S (=O)$_m$—C$_1$-C$_6$ haloalkyl, —NH$_2$, C$_1$-C$_6$ alkylamino, C$_1$-C$_6$ dialkylamino, and N-linked-heterocycloalkyl; and R$^{32}$ at each occurrence is independently selected from the group consisting of halogen, C$_1$-C$_6$ alkyl, —OH, —CN, C$_1$-C$_6$ alkoxy, —SH, —S(=O)$_m$—C$_1$-C$_6$ alkyl, —NH$_2$, C$_1$-C$_6$ alkylamino, C$_1$-C$_6$ dialkylamino, and N-linked-heterocycloalkyl, wherein the alkyl chain of C$_1$-C$_6$ alkyl, C$_1$-C$_6$ alkoxy, —S(=O)$_m$—C$_1$-C$_6$ alkyl, C$_1$-C$_6$ alkylamino, or C$_1$-C$_6$ dialkylamino is optionally substituted with one or more substituents selected from the group consisting of halogen, —OH, C$_1$-C$_6$ alkoxy, C$_1$-C$_6$ haloalkoxy, —SH, —S(=O)$_m$—C$_1$-C$_6$ alkyl, —S (=O)$_m$—C$_1$-C$_6$ haloalkyl, —NH$_2$, C$_1$-C$_6$ alkylamino, C$_1$-C$_6$ dialkylamino, and N-linked-heterocycloalkyl;

provided, however, that when R$^2$ is —C(=O)NH$_2$, R$^4$ is halogen, R$^3$ is N-linked-heterocycloalkyl or L$_1$-R$^{20}$ wherein L$_1$ is —NR$^{21}$— and R$^{20}$ is pyridine, or phenyl optionally substituted with methyl, or L$_1$ is —O— and R$^{20}$ is C$_{1-6}$ alkyl optionally substituted with methoxy, R$^1$ is —NR$^{12}$R$^{13}$, and R$^{12}$ is hydrogen, R$^{13}$ is selected from the group consisting of C$_1$-C$_6$ alkyl optionally substituted with one or more substituents R$^{14}$, cycloalkyl optionally substituted with one or more substituents R$^{15}$, and heterocycloalkyl optionally substituted with one or more substituents R$^{16}$; or when R$^2$ is L$_1$-R$^{20}$, L$_1$ is —C(=X)— or —C(=X)NR$^{21}$—, one of R$^3$ and R$^4$ is hydrogen, the other of R$^3$ and R$^4$ is unsubstituted C$_{1-6}$ alkyl, R$^1$ is —NR$^{12}$R$^{13}$, and R$^{12}$ is hydrogen, R$^{13}$ is selected from the group consisting of C$_1$-C$_6$ alkyl optionally substituted with one or more substituents R$^{14}$, cycloalkyl optionally substituted with one or more substituents R$^{15}$, and heterocycloalkyl optionally substituted with one or more substituents R$^{16}$; and provided that the compound does not have the structure selected from the group consisting of

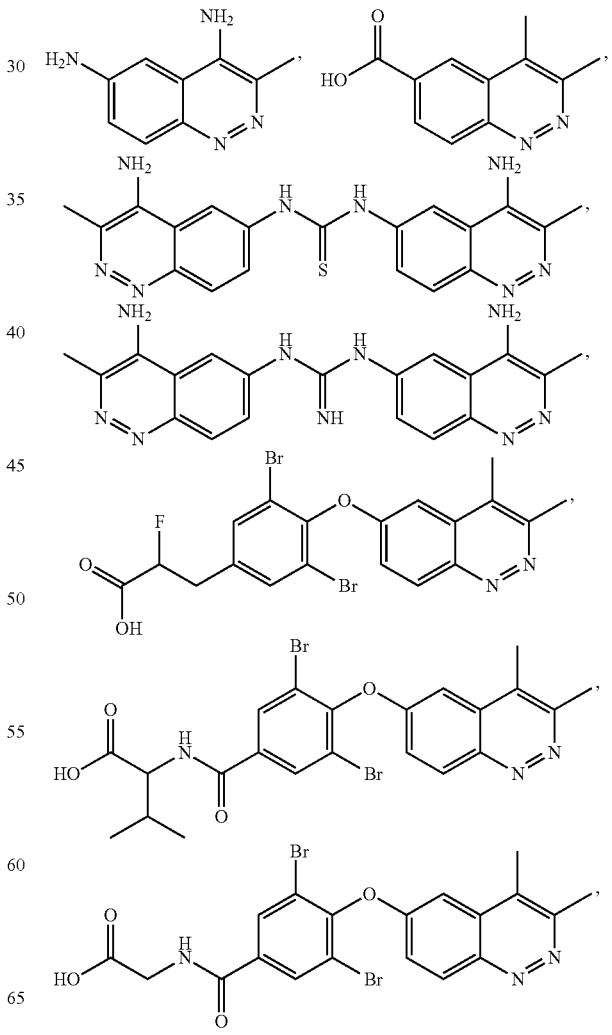

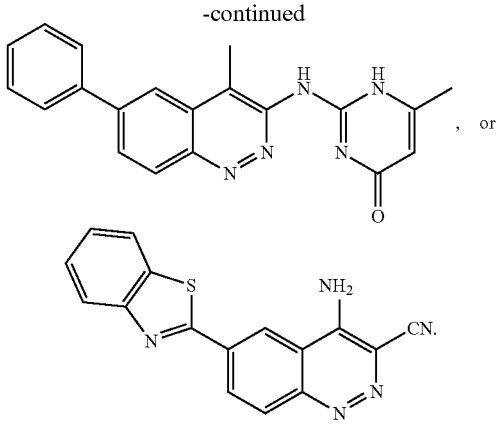

In some embodiments of a compound of Formula I:

$R^1$ is —$CR^5R^6R^7$, —$OR^9$, —$SR^{10}$, or —$NR^{12}R^{13}$;

$R^5$ and $R^6$ are independently selected from the group consisting of hydrogen, halogen, —OH, $C_1$-$C_6$ alkoxy, —SH, —S(=O)$_m$—$C_1$-$C_6$ alkyl, —NH$_2$, $C_1$-$C_6$ alkylamino, $C_1$-$C_6$ dialkylamino, and $C_1$-$C_6$ alkyl optionally substituted with one or more substituents $R^{14}$, wherein the alkyl chain of $C_1$-$C_6$ alkoxy, —S(=O)$_m$—$C_1$-$C_6$ alkyl, $C_1$-$C_6$ alkylamino, or $C_1$-$C_6$ dialkylamino is optionally substituted with one or more substituents independently selected from the group consisting of halogen, —OH, $C_1$-$C_6$ alkoxy, $C_1$-$C_6$ haloalkoxy, —SH, —S(=O)$_m$—$C_1$-$C_6$ alkyl, —S(=O)$_m$—$C_1$-$C_6$ haloalkyl, —NH$_2$, $C_1$-$C_6$ alkylamino, $C_1$-$C_6$ dialkylamino, and N-linked-heterocycloalkyl;

$R^7$ is selected from the group consisting of halogen, —OH, $C_1$-$C_6$ alkoxy, —SH, —S(=O)$_m$—$C_1$-$C_6$ alkyl, —NH$_2$, $C_1$-$C_6$ alkylamino, $C_1$-$C_6$ dialkylamino, $C_1$-$C_6$ alkyl optionally substituted with one or more substituents $R^{14}$, $C_{3-8}$ cycloalkyl optionally substituted with one or more substituents $R^{15}$, 4-7 membered heterocycloalkyl optionally substituted with one or more substituents $R^{17}$, phenyl optionally substituted with one or more substituents $R^{17}$, and 5 or 6 membered heteroaryl optionally substituted with one or more substituents $R^{18}$, wherein the alkyl chain of $C_1$-$C_6$ alkoxy, —S(=O)$_m$—$C_1$-$C_6$ alkyl, $C_1$-$C_6$ alkylamino, or $C_1$-$C_6$ dialkylamino is optionally substituted with one or more substituents independently selected from the group consisting of halogen, —OH, $C_1$-$C_6$ alkoxy, $C_1$-$C_6$ haloalkoxy, —SH, —S(=O)$_m$—$C_1$-$C_6$ alkyl, —S(=O)$_m$—$C_1$-$C_6$ haloalkyl, —NH$_2$, $C_1$-$C_6$ alkylamino, $C_1$-$C_6$ dialkylamino, and N-linked-heterocycloalkyl; or any two of $R^5$, $R^6$ and $R^7$ together with the carbon to which they are attached, form a 3-8 membered cycloalkyl optionally substituted with one or more substituents $R^{15}$ or a 4-7 membered heterocycloalkyl optionally substituted with one or more substituents $R^{16}$, and the other of $R^5$, $R^6$ and $R^7$ is selected from the group consisting of hydrogen, halogen, —OH, $C_1$-$C_6$ alkoxy, —SH, —S(=O)$_m$—$C_1$-$C_6$ alkyl, —NH$_2$, $C_1$-$C_6$ alkylamino, $C_1$-$C_6$ dialkylamino, and $C_1$-$C_6$ alkyl optionally substituted with one or more substituents $R^{14}$, wherein the alkyl chain of $C_1$-$C_6$ alkoxy, —S(=O)$_m$—$C_1$-$C_6$ alkyl, $C_1$-$C_6$ alkylamino, or $C_1$-$C_6$ dialkylamino is optionally substituted with one or more substituents independently selected from the group consisting of halogen, —OH, $C_1$-$C_6$ alkoxy, $C_1$-$C_6$ haloalkoxy, —SH, —S(=O)$_m$—$C_1$-$C_6$ alkyl, —S(=O)$_m$—$C_1$-$C_6$ haloalkyl, —NH$_2$, $C_1$-$C_6$ alkylamino, $C_1$-$C_6$ dialkylamino, and N-linked-heterocycloalkyl;

$R^9$ and $R^{10}$ are independently selected from the group consisting of $C_1$-$C_6$ alkyl optionally substituted with one or more substituents $R^{14}$, $C_{3-8}$ cycloalkyl optionally substituted with one or more substituents $R^{15}$, 4-7 membered heterocycloalkyl optionally substituted with one or more substituents $R^{16}$, phenyl optionally substituted with one or more substituents $R^{17}$, and 5 or 6 membered heteroaryl optionally substituted with one or more substituents $R^{18}$;

$R^{12}$ is hydrogen or $C_1$-$C_6$ alkyl;

$R^{13}$ is selected from the group consisting of $C_1$-$C_6$ alkyl optionally substituted with one or more substituents $R^{14}$, $C_{3-8}$ cycloalkyl optionally substituted with one or more substituents $R^{15}$, and 4-7 membered heterocycloalkyl optionally substituted with one or more substituents $R^{16}$;

or $R^{12}$ and $R^{13}$, together with the nitrogen to which they are attached, form a 5-7 membered heterocycloalkyl optionally substituted with one or more substituents $R^{16}$;

$R^{14}$ at each occurrence is independently selected from the group consisting of halogen, —OH, $C_1$-$C_6$ alkoxy, —SH, —S(=O)$_m$—$C_1$-$C_6$ alkyl, —NH$_2$, $C_1$-$C_6$ alkylamino, $C_1$-$C_6$ dialkylamino, $C_{3-8}$ cycloalkyl optionally substituted with one or more substituents $R^{15}$, 4-7 membered heterocycloalkyl optionally substituted with one or more substituents $R^{16}$, phenyl optionally substituted with one or more substituents $R^{17}$, and 5 or 6 membered heteroaryl optionally substituted with one or more substituents $R^{18}$, wherein the alkyl chain of $C_1$-$C_6$ alkoxy, —S(=O)$_m$—$C_1$-$C_6$ alkyl, $C_1$-$C_6$ alkylamino, or $C_1$-$C_6$ dialkylamino is optionally substituted with one or more substituents independently selected from the group consisting of halogen, —OH, $C_1$-$C_6$ alkoxy, $C_1$-$C_6$ haloalkoxy, —SH, —S(=O)$_m$—$C_1$-$C_6$ alkyl, —S(=O)$_m$—$C_1$-$C_6$ haloalkyl, —NH$_2$, $C_1$-$C_6$ alkylamino, $C_1$-$C_6$ dialkylamino, and N-linked-heterocycloalkyl;

$R^2$ is selected from the group consisting of $R^{19}$, $L_1$-$R^{20}$, $C_{2-6}$ alkynyl, 4-7 membered heterocycloalkyl, and 5 or 6 membered heteroaryl, wherein $C_2$-$C_6$ alkynyl is optionally substituted with one or more substituents independently selected from the group consisting of $R^{19}$ and $L_1$-$R^{20}$, and wherein 4-7 membered heterocycloalkyl is optionally substituted with one or more substituents independently selected from the group consisting of $R^{19}$, =O, =NR$^{21}$, =NOR$^{21}$, $L_1$-$R^{20}$, and $R^{23}$, and wherein 5 or 6 membered heteroaryl is optionally substituted with one or more substituents independently selected from the group consisting of $R^{19}$, $L_1$-$R^{20}$, and $R^{23}$; and m, $L_1$, $R^3$, $R^4$, $R^{15}$, $R^{16}$, $R^{17}$, $R^{18}$, $R^{19}$, $R^{20}$, $R^{21}$, and $R^{23}$, are as defined for Formula I.

In some embodiments of a compound of Formula I:

$R^1$ is —$OR^9$, —$SR^{10}$, or —$NR^{12}R^{13}$;

$R^9$ and $R^{10}$ are independently selected from the group consisting of $C_1$-$C_6$ alkyl optionally substituted with one or more substituents $R^{14}$, $C_{3-8}$ cycloalkyl optionally substituted with one or more substituents $R^{15}$, 4-7 membered heterocycloalkyl optionally substituted with one or more substituents $R^{16}$, phenyl optionally substituted with one or more substituents $R^{17}$, and 5 or 6 membered heteroaryl optionally substituted with one or more substituents $R^{18}$;

$R^{12}$ is hydrogen or $C_1$-$C_6$ alkyl;

$R^{13}$ is selected from the group consisting of $C_1$-$C_6$ alkyl optionally substituted with one or more substituents $R^{14}$, $C_{3-8}$ cycloalkyl optionally substituted with one or more substituents $R^{15}$, and 4-7 membered heterocycloalkyl optionally substituted with one or more substituents $R^{16}$;

or $R^{12}$ and $R^{13}$, together with the nitrogen to which they are attached, form a 5-7 membered heterocycloalkyl optionally substituted with one or more substituents $R^{16}$;

$R^{14}$ at each occurrence is independently selected from the group consisting of halogen, —OH, $C_1$-$C_6$ alkoxy, —SH, —S(═O)$_m$—$C_1$-$C_6$ alkyl, —NH$_2$, $C_1$-$C_6$ alkylamino, $C_1$-$C_6$ dialkylamino, $C_{3-8}$ cycloalkyl optionally substituted with one or more substituents $R^{15}$, 4-7 membered heterocycloalkyl optionally substituted with one or more substituents $R^{16}$, phenyl optionally substituted with one or more substituents $R^{17}$, and 5 or 6 membered heteroaryl optionally substituted with one or more substituents $R^{18}$, wherein the alkyl chain of $C_1$-$C_6$ alkoxy, —S(═O)$_m$—$C_1$-$C_6$ alkyl, $C_1$-$C_6$ alkylamino, or $C_1$-$C_6$ dialkylamino is optionally substituted with one or more substituents independently selected from the group consisting of halogen, —OH, $C_1$-$C_6$ alkoxy, $C_1$-$C_6$ haloalkoxy, —SH, —S(═O)$_m$—$C_1$-$C_6$ alkyl, —S(═O)$_m$—$C_1$-$C_6$ haloalkyl, —NH$_2$, $C_1$-$C_6$ alkylamino, $C_1$-$C_6$ dialkylamino, and N-linked-heterocycloalkyl;

$R^2$ is selected from the group consisting of $R^{19}$, $L_1$-$R^{20}$, $C_{2-6}$ alkynyl, 4-7 membered heterocycloalkyl, and 5 or 6 membered heteroaryl, wherein $C_2$-$C_6$ alkynyl is optionally substituted with one or more substituents independently selected from the group consisting of $R^{19}$ and $L_1$-$R^{20}$, and wherein 4-7 membered heterocycloalkyl is optionally substituted with one or more substituents independently selected from the group consisting of $R^{19}$, ═O, ═NR$^{21}$, ═NOR$^{21}$, $L_1$-$R^{20}$, and $R^{23}$, and wherein 5 or 6 membered heteroaryl is optionally substituted with one or more substituents independently selected from the group consisting of $R^{19}$, $L_1$-$R^{20}$, and $R^{23}$; and m, $L_1$, $R^3$, $R^4$, $R^{15}$, $R^{16}$, $R^{17}$, $R^{18}$, $R^{19}$, $R^{20}$, $R^{21}$, and $R^{23}$, are as defined for Formula I.

In some embodiments of a compound of Formula I:

$R^1$ is —NR$^{12}$R$^{13}$;

$R^{12}$ is hydrogen or $C_1$-$C_6$ alkyl;

$R^{13}$ is selected from the group consisting of $C_1$-$C_6$ alkyl optionally substituted with one or more substituents $R^{14}$, $C_{3-8}$ cycloalkyl optionally substituted with one or more substituents $R^{15}$, and 4-7 membered heterocycloalkyl optionally substituted with one or more substituents $R^{16}$;

or $R^{12}$ and $R^{13}$, together with the nitrogen to which they are attached, form a 5-7 membered heterocycloalkyl optionally substituted with one or more substituents $R^{16}$;

$R^{14}$ at each occurrence is independently selected from the group consisting of halogen, —OH, $C_1$-$C_6$ alkoxy, —SH, —S(═O)$_m$—$C_1$-$C_6$ alkyl, —NH$_2$, $C_1$-$C_6$ alkylamino, $C_1$-$C_6$ dialkylamino, $C_{3-8}$ cycloalkyl optionally substituted with one or more substituents $R^{15}$, 4-7 membered heterocycloalkyl optionally substituted with one or more substituents $R^{16}$, phenyl optionally substituted with one or more substituents $R^{17}$, and 5 or 6 membered heteroaryl optionally substituted with one or more substituents $R^{18}$, wherein the alkyl chain of $C_1$-$C_6$ alkoxy, —S(═O)$_m$—$C_1$-$C_6$ alkyl, $C_1$-$C_6$ alkylamino, or $C_1$-$C_6$ dialkylamino is optionally substituted with one or more substituents independently selected from the group consisting of halogen, —OH, $C_1$-$C_6$ alkoxy, $C_1$-$C_6$ haloalkoxy, —SH, —S(═O)$_m$—$C_1$-$C_6$ alkyl, —S(═O)$_m$—$C_1$-$C_6$ haloalkyl, —NH$_2$, $C_1$-$C_6$ alkylamino, $C_1$-$C_6$ dialkylamino, and N-linked-heterocycloalkyl;

$R^2$ is selected from the group consisting of $R^{19}$, $L_1$-$R^{20}$, $C_{2-6}$ alkynyl, 4-7 membered heterocycloalkyl, and 5 or 6 membered heteroaryl, wherein $C_2$-$C_6$ alkynyl is optionally substituted with one or more substituents independently selected from the group consisting of $R^{19}$ and $L_1$-$R^{20}$, and wherein 4-7 membered heterocycloalkyl is optionally substituted with one or more substituents independently selected from the group consisting of $R^{19}$, ═O, ═NR$^{21}$, ═NOR$^{21}$, $L_1$-$R^{20}$, and $R^{23}$, and wherein 5 or 6 membered heteroaryl is optionally substituted with one or more substituents independently selected from the group consisting of $R^{19}$, $L_1$-$R^{20}$, and $R^{23}$; and m, $L_1$, $R^3$, $R^4$, $R^{15}$, $R^{16}$, $R^{17}$, $R^{18}$, $R^{19}$, $R^{20}$, $R^{21}$, and $R^{23}$, are as defined for Formula I.

In some embodiments of a compound of Formula I:

$R^1$ is —CR$^5$R$^6$R$^7$, —OR$^9$, —SR$^{10}$, or —NR$^{12}$R$^{13}$;

$R^5$ and $R^6$ are independently selected from the group consisting of hydrogen, halogen, —OH, $C_1$-$C_6$ alkoxy, —SH, —S(═O)$_m$—$C_1$-$C_6$ alkyl. —NH$_2$, $C_1$-$C_6$ alkylamino, $C_1$-$C_6$ dialkylamino, and $C_1$-$C_6$ alkyl optionally substituted with one or more substituents $R^{14}$, wherein the alkyl chain of $C_1$-$C_6$ alkoxy, —S(═O)$_m$—$C_1$-$C_6$ alkyl, $C_1$-$C_6$ alkylamino, or $C_1$-$C_6$ dialkylamino is optionally substituted with one or more substituents independently selected from the group consisting of halogen, —OH, $C_1$-$C_6$ alkoxy, $C_1$-$C_6$ haloalkoxy, —SH, —S(═O)$_m$—$C_1$-$C_6$ alkyl, —S(═O)$_m$—$C_1$-$C_6$ haloalkyl, —NH$_2$, $C_1$-$C_6$ alkylamino, $C_1$-$C_6$ dialkylamino, and N-linked-heterocycloalkyl;

$R^7$ is selected from the group consisting of halogen, —OH, $C_1$-$C_6$ alkoxy, —SH, —S(═O)$_m$—$C_1$-$C_6$ alkyl, —NH$_2$, $C_1$-$C_6$ alkylamino, $C_1$-$C_6$ dialkylamino, $C_1$-$C_6$ alkyl optionally substituted with one or more substituents $R^{14}$, $C_{3-8}$ cycloalkyl optionally substituted with one or more substituents $R^{15}$, 4-7 membered heterocycloalkyl optionally substituted with one or more substituents $R^{16}$, phenyl optionally substituted with one or more substituents $R^{17}$, and 5 or 6 membered heteroaryl optionally substituted with one or more substituents $R^{18}$, wherein the alkyl chain of $C_1$-$C_6$ alkoxy, —S(═O)$_m$—$C_1$-$C_6$ alkyl, $C_1$-$C_6$ alkylamino, or $C_1$-$C_6$ dialkylamino is optionally substituted with one or more substituents independently selected from the group consisting of halogen, —OH, $C_1$-$C_6$ alkoxy, $C_1$-$C_6$ haloalkoxy, —SH, —S(═O)$_m$—$C_1$-$C_6$ alkyl, —S(═O)$_m$—$C_1$-$C_6$ haloalkyl, —NH$_2$, $C_1$-$C_6$ alkylamino, $C_1$-$C_6$ dialkylamino, and N-linked-heterocycloalkyl; or any two of $R^5$, $R^6$ and $R^7$ together with the carbon to which they are attached, form a 3-8 membered cycloalkyl optionally substituted with one or more substituents $R^{15}$ or a 4-7 membered heterocycloalkyl optionally substituted with one or more substituents $R^{16}$, and the other of $R^5$, $R^6$ and $R^7$ is selected from the group consisting of hydrogen, halogen, —OH, $C_1$-$C_6$ alkoxy, —SH, —S(═O)$_m$—$C_1$-$C_6$ alkyl, —NH$_2$, $C_1$-$C_6$ alkylamino, $C_1$-$C_6$ dialkylamino, and $C_1$-$C_6$ alkyl optionally substituted with one or more substituents $R^{14}$, wherein the alkyl chain of $C_1$-$C_6$ alkoxy, —S(═O)$_m$—$C_1$-$C_6$ alkyl, $C_1$-$C_6$ alkylamino, or $C_1$-$C_6$ dialkylamino is optionally substituted with one or more substituents independently selected from the group consisting of halogen, —OH, $C_1$-$C_6$ alkoxy, $C_1$-$C_6$ haloalkoxy, —SH, —S(═O)$_m$—$C_1$-$C_6$ alkyl, —S(═O)$_m$—$C_1$-$C_6$ haloalkyl, —NH$_2$, $C_1$-$C_6$ alkylamino, $C_1$-$C_6$ dialkylamino, and N-linked-heterocycloalkyl;

$R^9$ and $R^{10}$ are independently selected from the group consisting of $C_1$-$C_6$ alkyl optionally substituted with one or more substituents $R^{14}$, $C_{3-8}$ cycloalkyl optionally substituted with one or more substituents $R^{15}$, 4-7 membered heterocycloalkyl optionally substituted with one or more substituents $R^{16}$, phenyl optionally substituted with one or more substituents $R^{17}$, and 5 or 6 membered heteroaryl optionally substituted with one or more substituents $R^{18}$;

$R^{12}$ is hydrogen or $C_1$-$C_6$ alkyl;

$R^{13}$ is selected from the group consisting of $C_1$-$C_6$ alkyl optionally substituted with one or more substituents $R^{14}$, $C_{3-8}$ cycloalkyl optionally substituted with one or more substituents $R^{15}$, and 4-7 membered heterocycloalkyl optionally substituted with one or more substituents $R^{16}$;

or $R^{12}$ and $R^{13}$, together with the nitrogen to which they are attached, form a 5-7 membered heterocycloalkyl optionally substituted with one or more substituents $R^{16}$;

$R^{14}$ at each occurrence is independently selected from the group consisting of halogen, —OH, $C_1$-$C_6$ alkoxy, —SH, —S(=O)$_m$—$C_1$-$C_6$ alkyl, —NH$_2$, $C_1$-$C_6$ alkylamino, $C_1$-$C_6$ dialkylamino, $C_{3-8}$ cycloalkyl optionally substituted with one or more substituents $R^{15}$, 4-7 membered heterocycloalkyl optionally substituted with one or more substituents $R^{16}$, phenyl optionally substituted with one or more substituents $R^{17}$, and 5 or 6 membered heteroaryl optionally substituted with one or more substituents $R^{18}$, wherein the alkyl chain of $C_1$-$C_6$ alkoxy, —S(=O)$_m$— $C_1$-$C_6$ alkyl, $C_1$-$C_6$ alkylamino, or $C_1$-$C_6$ dialkylamino is optionally substituted with one or more substituents independently selected from the group consisting of halogen, —OH, $C_1$-$C_6$ alkoxy, $C_1$-$C_6$ haloalkoxy, —SH, —S(=O)$_m$—$C_1$-$C_6$ alkyl, —S(=O)$_m$—$C_1$-$C_6$ haloalkyl, —NH$_2$, $C_1$-$C_6$ alkylamino, $C_1$-$C_6$ dialkylamino, and N-linked-heterocycloalkyl;

$R^2$ is selected from the group consisting of $R^{19}$, $L_1$-$R^{20}$, $C_{2-6}$ alkynyl, 4-7 membered heterocycloalkyl, and 5 or 6 membered heteroaryl, wherein $C_2$-$C_6$ alkynyl is optionally substituted with one or more substituents independently selected from the group consisting of $R^{19}$ and $L_1$-$R^{20}$, and wherein 4-7 membered heterocycloalkyl is optionally substituted with one or more substituents independently selected from the group consisting of $R^{19}$, =O, =NR$^{21}$, =NOR$^{21}$, $L_1$-$R^{20}$, and $R^{23}$, and wherein 5 or 6 membered heteroaryl is optionally substituted with one or more substituents independently selected from the group consisting of $R^{19}$, $L_1$-$R^{20}$, and $R^{23}$;

$R^4$ is selected from the group consisting of hydrogen, $R^{19}$, $L_1$-$R^{20}$, $C_1$-$C_6$ alkyl, $C_2$-$C_6$ alkenyl, $C_2$-$C_6$ alkynyl, cycloalkyl, heterocycloalkyl, aryl, and heteroaryl, wherein $C_1$-$C_6$ alkyl, $C_2$-$C_6$ alkenyl, and $C_2$-$C_6$ alkynyl are optionally substituted with one or more substituents independently selected from the group consisting of $R^{19}$, $L_1$-$R^{20}$, cycloalkyl, heterocycloalkyl, aryl, and heteroaryl, and wherein cycloalkyl and heterocycloalkyl, as $R^4$ or as a substituent of $C_1$-$C_6$ alkyl, $C_2$-$C_6$ alkenyl, or $C_2$-$C_6$ alkynyl, are optionally substituted with one or more substituents independently selected from the group consisting of $R^{19}$, =O, =NR$^{21}$, =NOR$^{21}$, $L_1$-$R^{20}$, and $R^{23}$, and wherein aryl and heteroaryl, as $R^4$ or as a substituent of $C_1$-$C_6$ alkyl, $C_2$-$C_6$ alkenyl, or $C_2$-$C_6$ alkynyl, are optionally substituted with one or more substituents independently selected from the group consisting of $R^{19}$, $L_1$-$R^{20}$, and $R^{23}$;

$R^3$ is selected from the group consisting of $R^{24}$, $L_3$-$R^{20}$, —OR$^{25}$, —SR$^{25}$, methyl, $C_2$-$C_6$ alkyl, $C_2$-$C_6$ alkenyl, $C_2$-$C_6$ alkynyl, cycloalkyl, heterocycloalkyl, aryl, and heteroaryl, wherein methyl is substituted with one or more substituents independently selected from the group consisting of $R^{19}$, $L_1$-$R^{20}$, cycloalkyl, heterocycloalkyl, aryl, and heteroaryl, and wherein $C_2$-$C_6$ alkyl, $C_2$-$C_6$ alkenyl, and $C_2$-$C_6$ alkynyl are optionally substituted with one or more substituents independently selected from the group consisting of $R^{19}$, $L_1$-$R^{20}$, cycloalkyl, heterocycloalkyl, aryl, and heteroaryl, and wherein cycloalkyl and heterocycloalkyl, as $R^3$ or as a substituent of methyl, $C_2$-$C_6$ alkyl, $C_2$-$C_6$ alkenyl, or $C_2$-$C_6$ alkynyl, are optionally substituted with one or more substituents independently selected from the group consisting of $R^{19}$, =O, =NR$^{21}$, =NOR$^{21}$, $L_1$-$R^{20}$, and $R^{23}$, and wherein aryl and heteroaryl, as $R^3$ or as a substituent of methyl, $C_2$-$C_6$ alkyl, $C_2$-$C_6$ alkenyl, or $C_2$-$C_6$ alkynyl, are optionally substituted with one or more substituents independently selected from the group consisting of $R^{19}$, $L_1$-$R^{20}$, and $R^{23}$; and m, $L_1$, $L_3$, $R^{15}$, $R^{16}$, $R^{17}$, $R^{18}$, $R^{19}$, $R^{20}$, $R^{21}$, $R^{23}$, $R^{24}$, and $R^{25}$, are as defined for Formula I.

In some embodiments of a compound of Formula I:

$R^1$ is —OR$^9$, —SR$^{10}$, or —NR$^{12}$R$^{13}$;

$R^9$ and $R^{10}$ are independently selected from the group consisting of $C_1$-$C_6$ alkyl optionally substituted with one or more substituents $R^{14}$, $C_{3-8}$ cycloalkyl optionally substituted with one or more substituents $R^{15}$, 4-7 membered heterocycloalkyl optionally substituted with one or more substituents $R^{16}$, phenyl optionally substituted with one or more substituents $R^{17}$, and 5 or 6 membered heteroaryl optionally substituted with one or more substituents $R^{18}$;

$R^{12}$ is hydrogen or $C_1$-$C_6$ alkyl;

$R^{13}$ is selected from the group consisting of $C_1$-$C_6$ alkyl optionally substituted with one or more substituents $R^{14}$, $C_{3-8}$ cycloalkyl optionally substituted with one or more substituents $R^{15}$, and 4-7 membered heterocycloalkyl optionally substituted with one or more substituents $R^{16}$;

or $R^{12}$ and $R^{13}$, together with the nitrogen to which they are attached, form a 5-7 membered heterocycloalkyl optionally substituted with one or more substituents $R^{16}$;

$R^{14}$ at each occurrence is independently selected from the group consisting of halogen, —OH, $C_1$-$C_6$ alkoxy, —SH, —S(=O)$_m$—$C_1$-$C_6$ alkyl, —NH$_2$, $C_1$-$C_6$ alkylamino, $C_1$-$C_6$ dialkylamino, $C_{3-8}$ cycloalkyl optionally substituted with one or more substituents $R^{15}$, 4-7 membered heterocycloalkyl optionally substituted with one or more substituents $R^{16}$, phenyl optionally substituted with one or more substituents $R^{17}$, and 5 or 6 membered heteroaryl optionally substituted with one or more substituents $R^{18}$, wherein the alkyl chain of $C_1$-$C_6$ alkoxy, —S(=O)$_m$— $C_1$-$C_6$ alkyl, $C_1$-$C_6$ alkylamino, or $C_1$-$C_6$ dialkylamino is optionally substituted with one or more substituents independently selected from the group consisting of halogen, —OH, $C_1$-$C_6$ alkoxy, $C_1$-$C_6$ haloalkoxy, —SH, —S(=O)$_m$—$C_1$-$C_6$ alkyl, —S(=O)$_m$—$C_1$-$C_6$ haloalkyl, —NH$_2$, $C_1$-$C_6$ alkylamino, $C_1$-$C_6$ dialkylamino, and N-linked-heterocycloalkyl;

$R^2$ is selected from the group consisting of $R^{19}$, $L_1$-$R^{20}$, $C_{2-6}$ alkynyl, 4-7 membered heterocycloalkyl, and 5 or 6 membered heteroaryl, wherein $C_2$-$C_6$ alkynyl is optionally substituted with one or more substituents independently selected from the group consisting of $R^{19}$ and $L_1$-$R^{20}$, and wherein 4-7 membered heterocycloalkyl is optionally substituted with one or more substituents independently selected from the group consisting of $R^{19}$, =O, =NR$^{21}$, =NOR$^{21}$, $L_1$-$R^{20}$, and $R^{23}$, and wherein 5 or 6 membered heteroaryl is optionally substituted with one or more substituents independently selected from the group consisting of $R^{19}$, $L_1$-$R^{20}$, and $R^{23}$;

$R^4$ is selected from the group consisting of hydrogen, $R^{19}$, $L_1$-$R^{20}$, $C_1$-$C_6$ alkyl, $C_2$-$C_6$ alkenyl, $C_2$-$C_6$ alkynyl, cycloalkyl, heterocycloalkyl, aryl, and heteroaryl, wherein $C_1$-$C_6$ alkyl, $C_2$-$C_6$ alkenyl, and $C_2$-$C_6$ alkynyl are optionally substituted with one or more substituents independently selected from the group consisting of $R^{19}$, $L_1$-$R^{20}$, cycloalkyl, heterocycloalkyl, aryl, and heteroaryl, and wherein cycloalkyl and heterocycloalkyl, as $R^4$ or as a substituent of $C_1$-$C_6$ alkyl, $C_2$-$C_6$ alkenyl, or $C_2$-$C_6$ alkynyl, are optionally substituted with one or more substituents independently selected from the group consisting of $R^{19}$, =O, =$NR^{21}$, =$NOR^{21}$, $L_1$-$R^{20}$, and $R^{23}$, and wherein aryl and heteroaryl, as $R^4$ or as a substituent of $C_1$-$C_6$ alkyl, $C_2$-$C_6$ alkenyl, or $C_2$-$C_6$ alkynyl, are optionally substituted with one or more substituents independently selected from the group consisting of $R^{19}$, $L_1$-$R^{20}$, and $R^{23}$;

$R^3$ is selected from the group consisting of $R^{24}$, $L_3$-$R^{20}$, —$OR^{25}$, —$SR^{25}$, methyl, $C_2$-$C_6$ alkyl, $C_2$-$C_6$ alkenyl, $C_2$-$C_6$ alkynyl, cycloalkyl, heterocycloalkyl, aryl, and heteroaryl, wherein methyl is substituted with one or more substituents independently selected from the group consisting of $R^{19}$, $L_1$-$R^{20}$, cycloalkyl, heterocycloalkyl, aryl, and heteroaryl, and wherein $C_2$-$C_6$ alkyl, $C_2$-$C_6$ alkenyl, and $C_2$-$C_6$ alkynyl are optionally substituted with one or more substituents independently selected from the group consisting of $R^{19}$, $L_1$-$R^{20}$, cycloalkyl, heterocycloalkyl, aryl, and heteroaryl, and wherein cycloalkyl and heterocycloalkyl, as $R^3$ or as a substituent of methyl, $C_2$-$C_6$ alkyl, $C_2$-$C_6$ alkenyl, or $C_2$-$C_6$ alkynyl, are optionally substituted with one or more substituents independently selected from the group consisting of $R^{19}$, =O, =$NR^{21}$, =$NOR^{21}$, $L_1$-$R^{20}$, and $R^{23}$, and wherein aryl and heteroaryl, as $R^3$ or as a substituent of methyl, $C_2$-$C_6$ alkyl, $C_2$-$C_6$ alkenyl, or $C_2$-$C_6$ alkynyl, are optionally substituted with one or more substituents independently selected from the group consisting of $R^{19}$, $L_1$-$R^{20}$, and $R^{23}$; and m, $L_1$, $L_3$, $R^{15}$, $R^{16}$, $R^{17}$, $R^{18}$, $R^{19}$, $R^{20}$, $R^{21}$, $R^{23}$, $R^{24}$, and $R^{25}$, are as defined for Formula I.

In some embodiments of a compound of Formula I:
$R^1$ is —$NR^{12}R^{13}$;
$R^{12}$ is hydrogen or $C_1$-$C_6$ alkyl;
$R^{13}$ is selected from the group consisting of $C_1$-$C_6$ alkyl optionally substituted with one or more substituents $R^{14}$, $C_{3-8}$ cycloalkyl optionally substituted with one or more substituents $R^{15}$, and 4-7 membered heterocycloalkyl optionally substituted with one or more substituents $R^{16}$;
or $R^{12}$ and $R^{13}$, together with the nitrogen to which they are attached, form a 5-7 membered heterocycloalkyl optionally substituted with one or more substituents $R^{16}$;
$R^{14}$ at each occurrence is independently selected from the group consisting of halogen, —OH, $C_1$-$C_6$ alkoxy, —SH, —S(=O)$_m$—$C_1$-$C_6$ alkyl, —$NH_2$, $C_1$-$C_6$ alkylamino, $C_1$-$C_6$ dialkylamino, $C_{3-8}$ cycloalkyl optionally substituted with one or more substituents $R^{15}$, 4-7 membered heterocycloalkyl optionally substituted with one or more substituents $R^{16}$, phenyl optionally substituted with one or more substituents $R^{17}$, and 5 or 6 membered heteroaryl optionally substituted with one or more substituents $R^{18}$, wherein the alkyl chain of $C_1$-$C_6$ alkoxy, —S(=O)$_m$—$C_1$-$C_6$ alkyl, $C_1$-$C_6$ alkylamino, or $C_1$-$C_6$ dialkylamino is optionally substituted with one or more substituents independently selected from the group consisting of halogen, —OH, $C_1$-$C_6$ alkoxy, $C_1$-$C_6$ haloalkoxy, —SH, —S(=O)$_m$—$C_1$-$C_6$ alkyl, —S(=O)$_m$—$C_1$-$C_6$ haloalkyl, —$NH_2$, $C_1$-$C_6$ alkylamino, $C_1$-$C_6$ dialkylamino, and N-linked-heterocycloalkyl;
$R^2$ is selected from the group consisting of $R^{19}$, $L_1$-$R^{20}$, $C_{2-6}$ alkynyl, 4-7 membered heterocycloalkyl, and 5 or 6 membered heteroaryl, wherein $C_2$-$C_6$ alkynyl is optionally substituted with one or more substituents independently selected from the group consisting of $R^{19}$ and $L_1$-$R^{20}$, and wherein 4-7 membered heterocycloalkyl is optionally substituted with one or more substituents independently selected from the group consisting of $R^{19}$, =O, =$NR^{21}$, =$NOR^{21}$, $L_1$-$R^{20}$, and $R^{23}$, and wherein 5 or 6 membered heteroaryl is optionally substituted with one or more substituents independently selected from the group consisting of $R^{19}$, $L_1$-$R^{20}$, and $R^{23}$;

$R^4$ is selected from the group consisting of hydrogen, $R^{19}$, $L_1$-$R^{20}$, $C_1$-$C_6$ alkyl, $C_2$-$C_6$ alkenyl, $C_2$-$C_6$ alkynyl, cycloalkyl, heterocycloalkyl, aryl, and heteroaryl, wherein $C_1$-$C_6$ alkyl, $C_2$-$C_6$ alkenyl, and $C_2$-$C_6$ alkynyl are optionally substituted with one or more substituents independently selected from the group consisting of $R^{19}$, $L_1$-$R^{20}$, cycloalkyl, heterocycloalkyl, aryl, and heteroaryl, and wherein cycloalkyl and heterocycloalkyl, as $R^4$ or as a substituent of $C_1$-$C_6$ alkyl, $C_2$-$C_6$ alkenyl, or $C_2$-$C_6$ alkynyl, are optionally substituted with one or more substituents independently selected from the group consisting of $R^{19}$, =O, =$NR^{21}$, =$NOR^{21}$, $L_1$-$R^{20}$, and $R^{23}$, and wherein aryl and heteroaryl, as $R^4$ or as a substituent of $C_1$-$C_6$ alkyl, $C_2$-$C_6$ alkenyl, or $C_2$-$C_6$ alkynyl, are optionally substituted with one or more substituents independently selected from the group consisting of $R^{19}$, $L_1$-$R^{20}$, and $R^{23}$;

$R^3$ is selected from the group consisting of $R^{24}$, $L_3$-$R^{20}$, —$OR^{25}$, —$SR^{25}$, methyl, $C_2$-$C_6$ alkyl, $C_2$-$C_6$ alkenyl, $C_2$-$C_6$ alkynyl, cycloalkyl, heterocycloalkyl, aryl, and heteroaryl, wherein methyl is substituted with one or more substituents independently selected from the group consisting of $R^{19}$, $L_1$-$R^{20}$, cycloalkyl, heterocycloalkyl, aryl, and heteroaryl, and wherein $C_2$-$C_6$ alkyl, $C_2$-$C_6$ alkenyl, and $C_2$-$C_6$ alkynyl are optionally substituted with one or more substituents independently selected from the group consisting of $R^{19}$, $L_1$-$R^{20}$, cycloalkyl, heterocycloalkyl, aryl, and heteroaryl, and wherein cycloalkyl and heterocycloalkyl, as $R^3$ or as a substituent of methyl, $C_2$-$C_6$ alkyl, $C_2$-$C_6$ alkenyl, or $C_2$-$C_6$ alkynyl, are optionally substituted with one or more substituents independently selected from the group consisting of $R^{19}$, =O, =$NR^{21}$, =$NOR^{21}$, $L_1$-$R^{20}$, and $R^{23}$, and wherein aryl and heteroaryl, as $R^3$ or as a substituent of methyl, $C_2$-$C_6$ alkyl, $C_2$-$C_6$ alkenyl, or $C_2$-$C_6$ alkynyl, are optionally substituted with one or more substituents independently selected from the group consisting of $R^{19}$, $L_1$-$R^{20}$, and $R^{23}$; and m, $L_1$, $L_3$, $R^{15}$, $R^{16}$, $R^{17}$, $R^{18}$, $R^{19}$, $R^{20}$, $R^{21}$, $R^{23}$, $R^{24}$, and $R^{25}$, are as defined for Formula I.

In some embodiments of a compound of Formula I, further to any of the above embodiments of Formula I, $R^2$ is selected from the group consisting of —I, —Cl, —$CH_3$, —CH=CH, —CN, —C(=O)$NH_2$, —C(=O)$NHCH_3$, imidazole, triazole, thiazole, oxazole, pyridine, and pyrimidin-4(3H)-one. In one embodiment, $R^2$ is —CN, —C(=O)$NH_2$, —C(=O)$NHCH_3$, imidazole, 1,2,4-triazole, or pyrimidin-4(3H)-one. In one embodiment, $R^2$ is —CN, —C(=O)$NH_2$, —C(=O)$NHCH_3$,

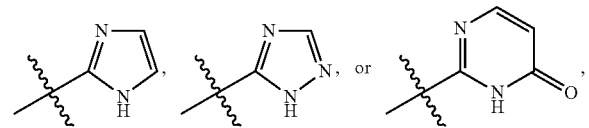 [SMILES: *c1ncc[nH]1 ; *c1ncn[nH]1 ; *c1nccc(=O)[nH]1]

wherein

indicates the point of attachment to the cinnoline 3 position. In one embodiment, $R^2$ is —C(=O)NH$_2$, or

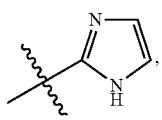

wherein

indicates the point of attachment to the cinnoline 3 position. In one embodiment, $R^2$ is —C(=O)NH$_2$.

In some embodiments of a compound of Formula I, further to any of the above embodiments of Formula I, $R^1$ is selected from the group consisting of —SR$^{10}$, or —NR$^{12}$R$^{13}$, R$^{12}$ is H and R$^{10}$ and R$^{13}$ are independently selected from the group consisting of C$_3$-C$_{10}$ cycloalkyl, 4-7 membered heterocycloalkyl optionally substituted with one C$_1$-C$_6$ alkyl, and C$_1$-C$_6$ alkyl optionally substituted with one substituent selected from the group consisting of —OH, C$_3$-C$_8$ cycloalkyl, 4-7 membered heterocycloalkyl, phenyl and pyridyl. In one embodiment, $R^1$ is —NR$^{12}$R$^{13}$, R$^{12}$ is H and R$^{13}$ is selected from the group consisting of C$_3$-C$_{10}$ cycloalkyl, 4-7 membered heterocycloalkyl optionally substituted with one C$_1$-C$_6$ alkyl, and C$_1$-C$_6$ alkyl optionally substituted with one substituent selected from the group consisting of —OH, C$_3$-C$_8$ cycloalkyl, 4-7 membered heterocycloalkyl, phenyl and pyridyl.

In some embodiments of a compound of Formula I, further to any of the above embodiments of Formula I, $R^1$ is selected from the group consisting of

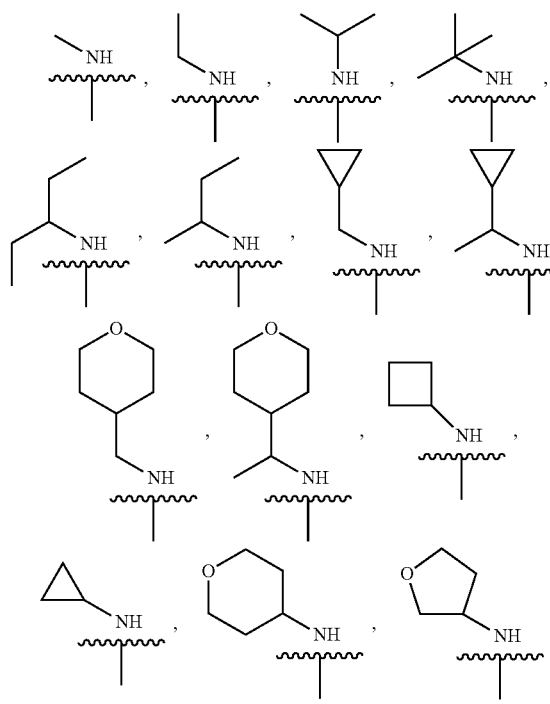

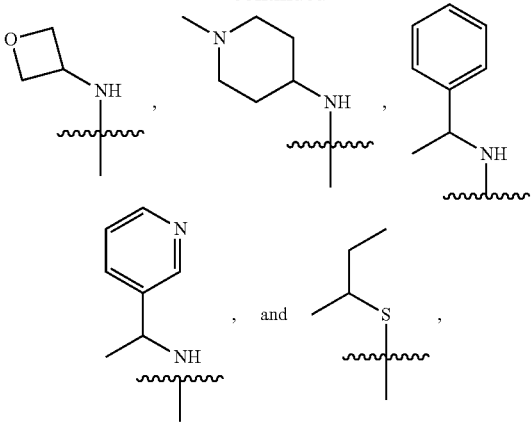

wherein indicates the point of attachment of $R^1$ to the cinnoline 4 position. In one embodiment, $R^1$ is selected from the group consisting of

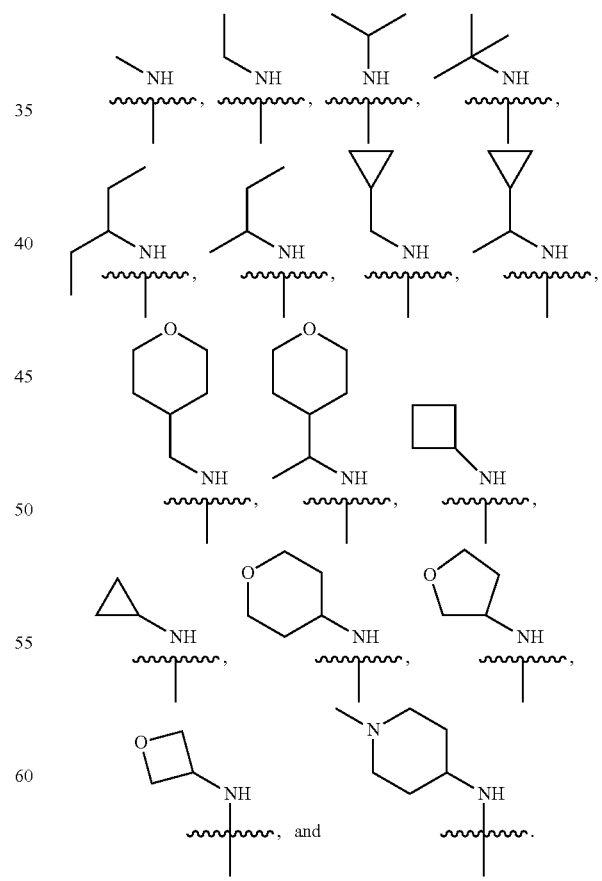

In one embodiment, $R^1$ is selected from the group consisting of

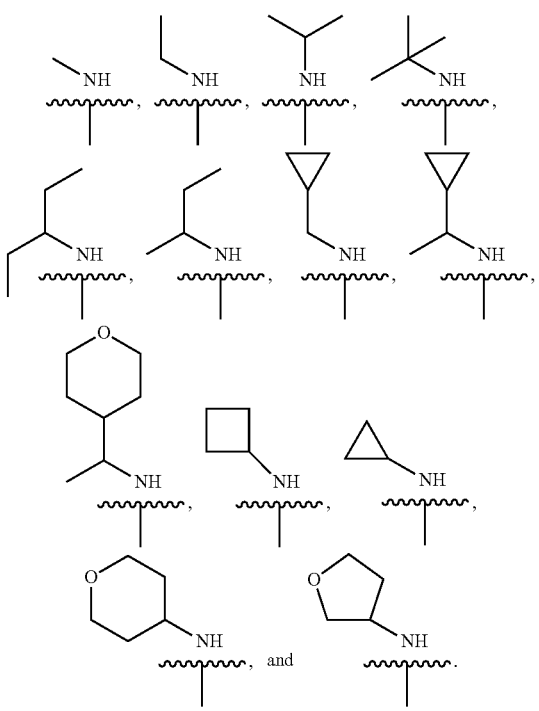

In one embodiment, $R^1$ is selected from the group consisting of

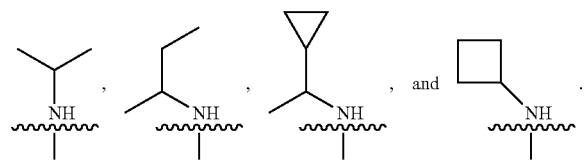

In some embodiments of a compound of Formula I, further to any of the above embodiments of Formula I, one of $R^3$ and $R^4$ is H and the other of $R^3$ and $R^4$ is selected from the group consisting of —$NHR^{25}$, —$OR^{25}$, —$SR^{25}$, $C_2$-$C_4$ alkyl, $C_2$-$C_3$ alkenyl, $C_3$-$C_6$ cycloalkyl, phenyl, heteroaryl, and heterocycloalkyl selected from the group consisting of piperazine, morpholine, pyrrolidine, oxazolidine, dihydropyridine, and indoline, wherein $C_2$-$C_4$ alkyl is optionally substituted with one OH, and wherein heterocycloalkyl is optionally substituted with one or more =O or $C_1$-$C_6$ alkyl, and wherein phenyl and heteroaryl are optionally substituted with one or more substituents independently selected from the group consisting of halogen, —$OR^{20}$, —$S(=O)R^{20}$, —$NR^{21}R^{20}$, —$C(=O)NR^{21}R^{20}$, $C_1$-$C_6$ alkyl optionally substituted with one or more $C_1$-$C_6$ alkoxy, piperazine optionally substituted with one or more =O or $C_1$-$C_6$ alkyl, morpholine optionally substituted with one or more =O or $C_1$-$C_6$ alkyl, pyrrolidine optionally substituted with one or more =O or $C_1$-$C_6$ alkyl, oxazolidine optionally substituted with one or more =O or $C_1$-$C_6$ alkyl, phenyl optionally substituted with one or more substituents selected from the group consisting of halogen, $C_1$-$C_6$ alkoxy, morpholine optionally substituted with one or more =O or $C_1$-$C_6$ alkyl, and oxazolidine optionally substituted with one or more =O or $C_1$-$C_6$ alkyl, and heteroaryl optionally substituted with one or more substituents selected from the group consisting of halogen, $C_1$-$C_6$ alkyl, or $C_1$-$C_6$ alkoxy; $R^{25}$ is phenyl optionally substituted with one or more $C_1$-$C_3$ alkoxy or $C_1$-$C_3$ haloalkoxy, or pyridine optionally substituted with one or more $C_1$-$C_3$ alkoxy or $C_1$-$C_3$ haloalkoxy; $R^{20}$ at each occurrence is independently $C_1$-$C_6$ alkyl optionally substituted with one $C_3$-$C_6$ cycloalkyl or with one or more fluoro; and $R^{21}$ at each occurrence is independently hydrogen or $C_1$-$C_6$ alkyl.

In some embodiments of a compound of Formula I, further to any of the above embodiments of Formula I, one of $R^3$ and $R^4$ is H and the other of $R^3$ and $R^4$ is selected from the group consisting of —$NHR^{25}$, —$OR^{25}$, —$SR^{25}$, $C_2$-$C_4$ alkyl optionally substituted with one OH, $C_2$-$C_3$ alkenyl, $C_3$-$C_6$ cycloalkyl, 4-methyl-piperazine, 1-methylpyridin-2(1H)-one, indolin-2-one, pyrrolidin-2-one, morpholine, phenyl, pyridine, pyrimidine, isoquinoline, pyrazole optionally substituted with one methyl, and thiazole, wherein phenyl is optionally substituted with one or more substituents independently selected from the group consisting of halogen, —$OR^{20}$, —$S(=O)_2R^{20}$, —$NR^{21}R^{20}$, —$C(=O)NR^{21}R^{20}$, morpholin-3-one, oxazolidin-2-one, pyridine optionally substituted with one fluoro, pyrazine optionally substituted with one methoxy, imidazole optionally substituted with one methyl, pyrazole optionally substituted with one methyl, and phenyl optionally substituted with one or more substituents selected from the group consisting of halogen, $C_1$-$C_3$ alkoxy, morpholin-3-one, and oxazolidin-2-one; $R^{25}$ is phenyl optionally substituted with one $C_1$-$C_3$ alkoxy, or pyridine optionally substituted with one $C_1$-$C_3$ alkoxy; $R^{20}$ at each occurrence is independently $C_1$-$C_3$ alkyl optionally substituted with one $C_3$-$C_6$ cycloalkyl; and $R^{21}$ at each occurrence is independently $C_1$-$C_3$ alkyl. In one embodiment the other of $R^3$ and $R^4$ is selected from the group consisting of —$NHR^{25}$, $C_2$-$C_3$ alkenyl, 4-methyl-piperazine, 1-methyl-pyridin-2(1H)-one, indolin-2-one, phenyl, pyridine, pyrazole optionally substituted with methyl, and thiazole, wherein phenyl is optionally substituted with one or more substituents independently selected from the group consisting of halogen, —$OR^{20}$, —$S(=O)_2$—$C_1$-$C_3$ alkyl, —$C(=O)N$—$(C_1$-$C_3$ alkyl$)_2$, morpholin-3-one, oxazolidin-2-one, pyridine optionally substituted with one fluoro, pyrazine optionally substituted with one methoxy, imidazole optionally substituted with one methyl, and pyrazole optionally substituted with one methyl; $R^{25}$ is phenyl optionally substituted with one $C_1$-$C_3$ alkoxy, or pyridine optionally substituted with one $C_1$-$C_3$ alkoxy; $R^{20}$ at each occurrence is $C_1$-$C_3$ alkyl optionally substituted with one $C_3$-$C_6$ cycloalkyl.

In some embodiments of a compound of Formula I, further to any of the above embodiments of Formula I, one of $R^3$ and $R^4$ is H and the other of $R^3$ and $R^4$ is selected from the group consisting of

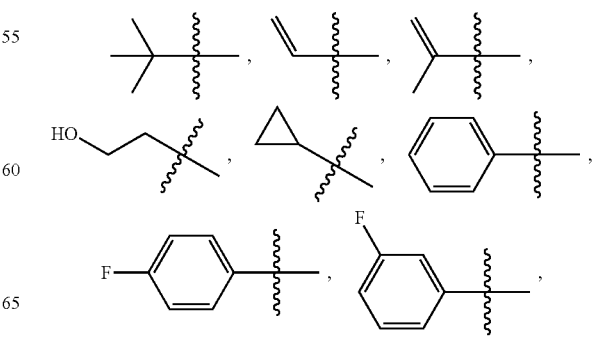

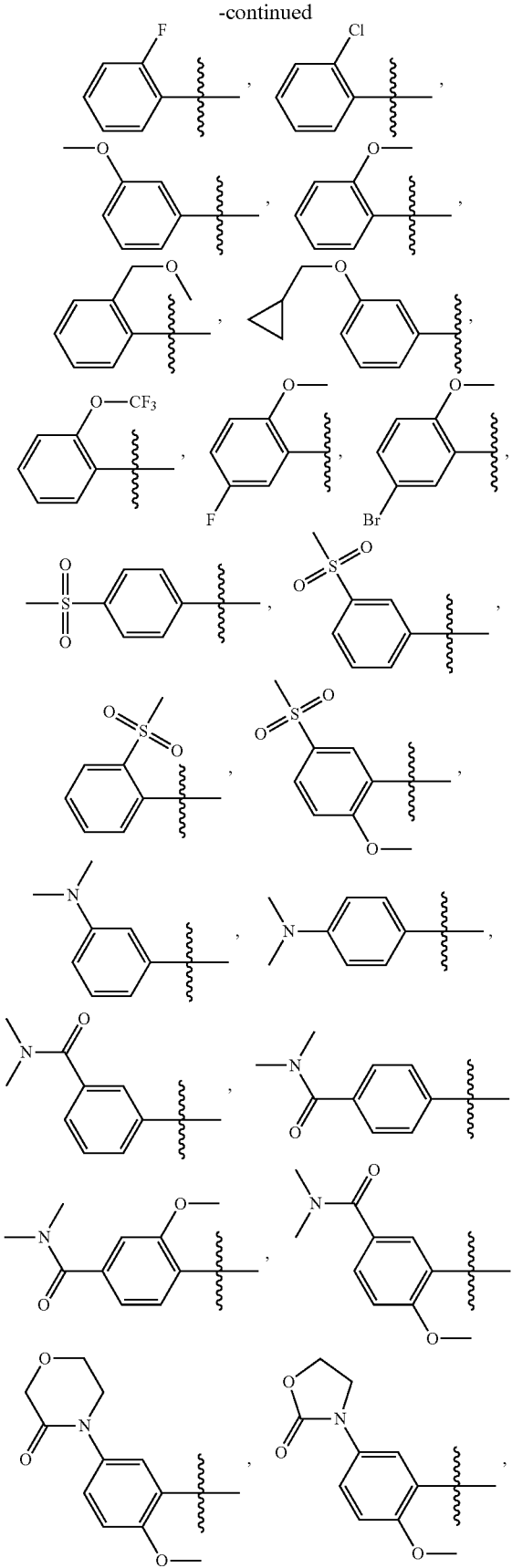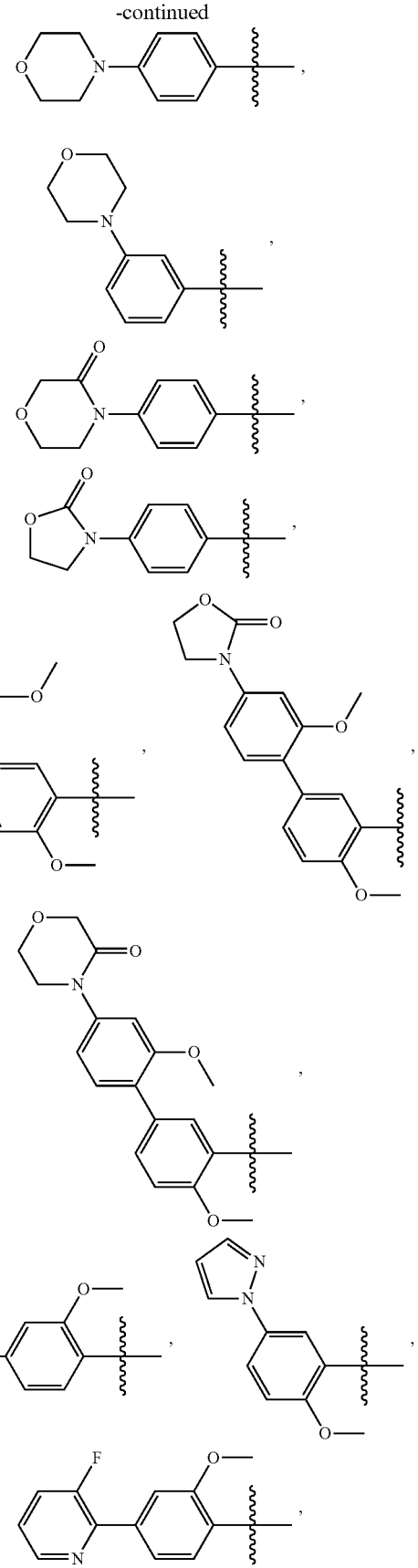

-continued
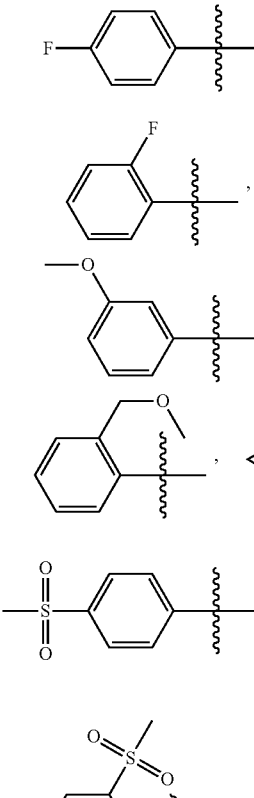
wherein
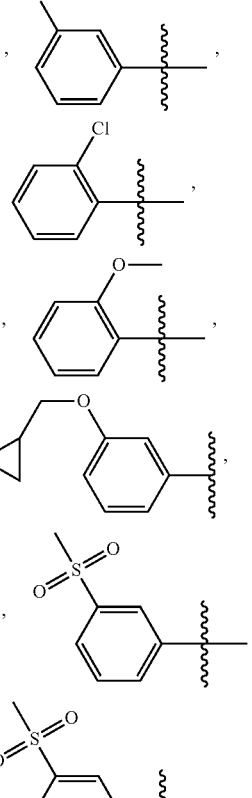
indicates the point of attachment to the cinnoline 6 or 7 position.
In some embodiments of a compound of Formula I, further to any of the above embodiments of Formula I, one of $R^3$ and $R^4$ is H and the other of $R^3$ and $R^4$ is selected from the group consisting of
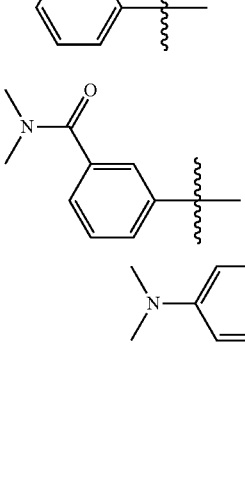

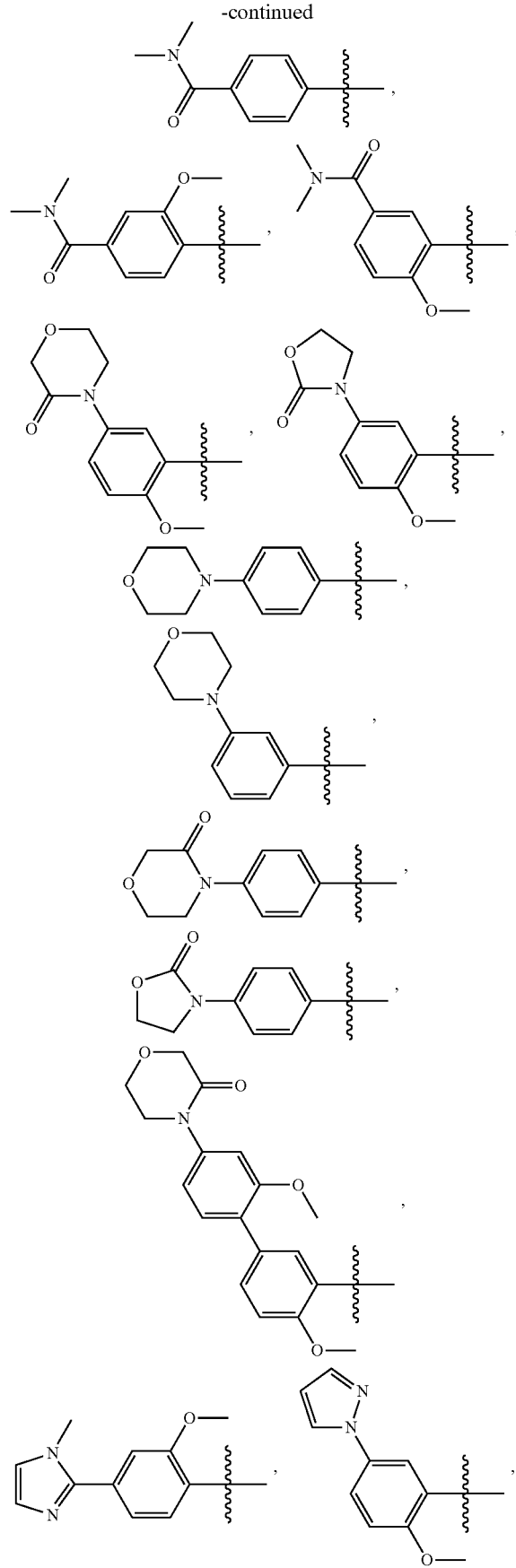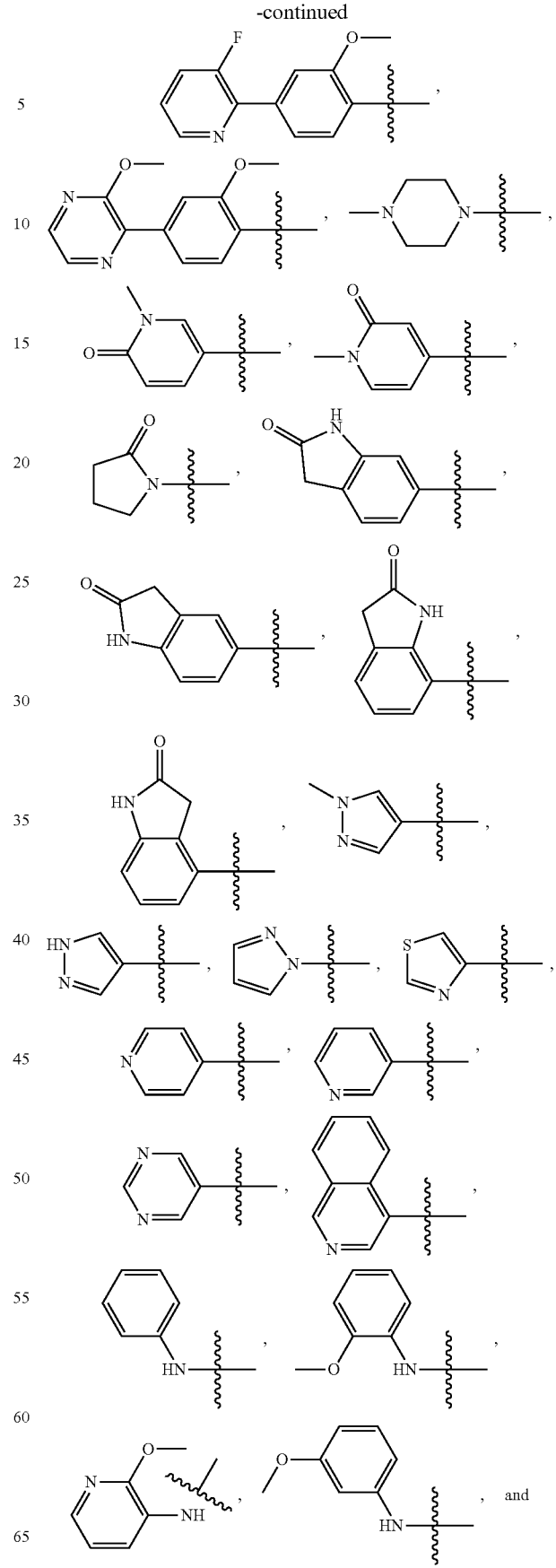

-continued
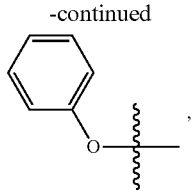
wherein
indicates the point of attachment to the cinnoline 6 or 7 position.
In some embodiments of a compound of Formula I, further to any of the above embodiments of Formula I, one of $R^3$ and $R^4$ is H and the other of $R^3$ and $R^4$ is selected from the group consisting of
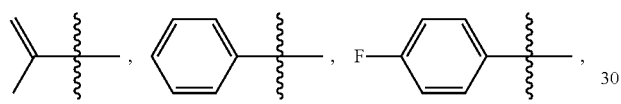
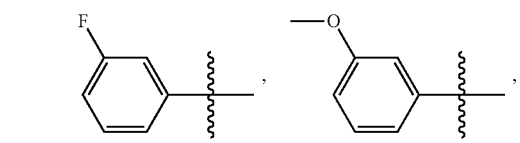
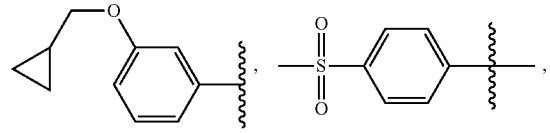
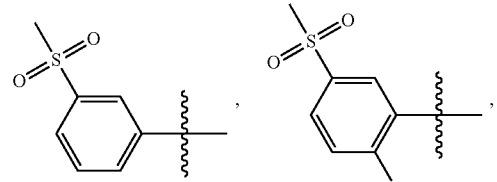
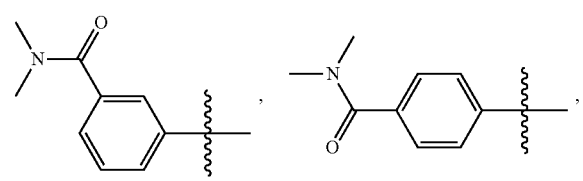
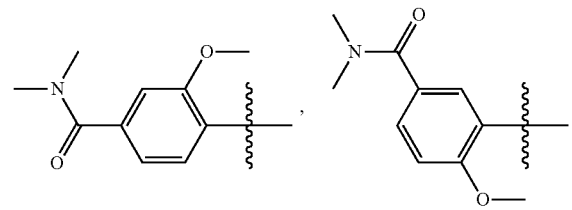
-continued
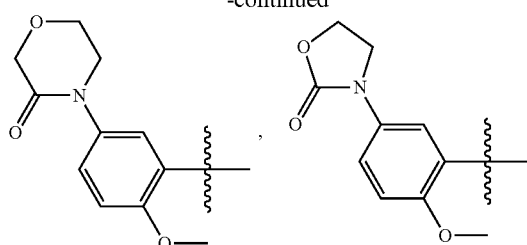
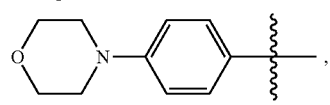
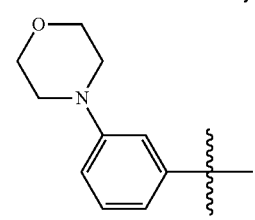
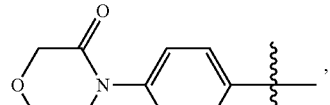
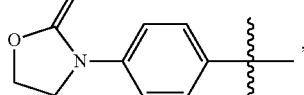
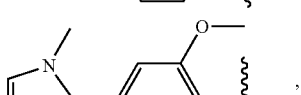
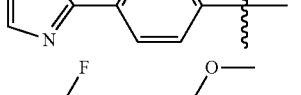
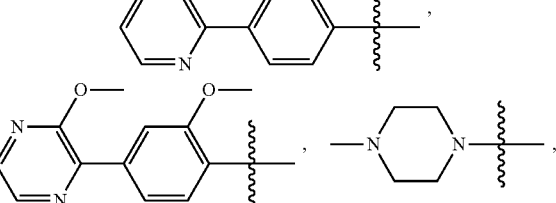
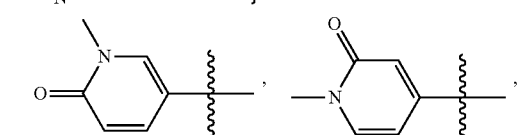
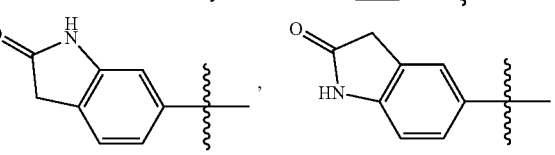
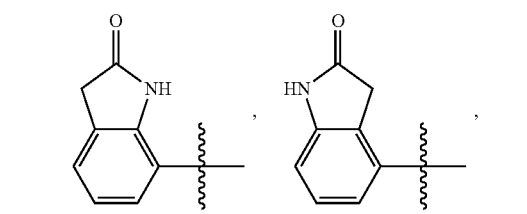

-continued

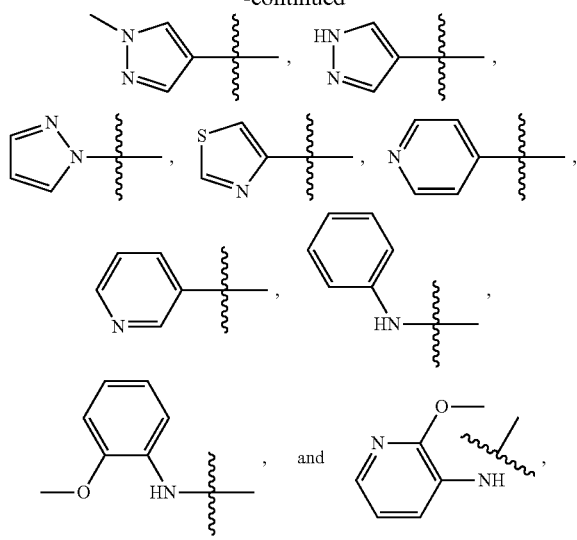

wherein

indicates the point of attachment to the cinnoline 6 or 7 position.

In some embodiments of a compound of Formula I, further to any of the above embodiments of Formula I, one of $R^3$ and $R^4$ is H and the other of $R^3$ and $R^4$ is selected from the group consisting of

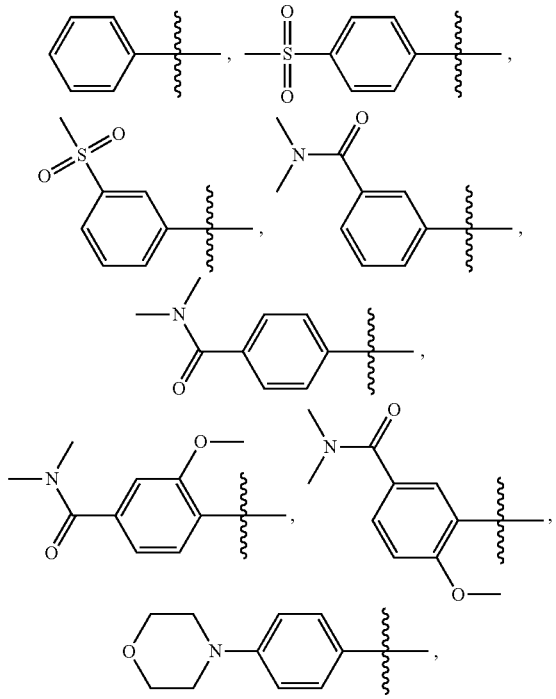

-continued

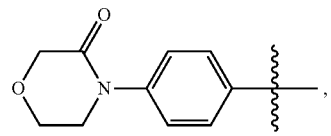

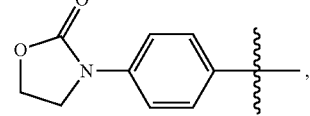

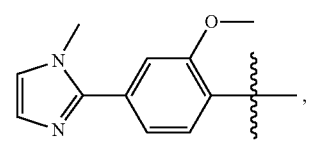

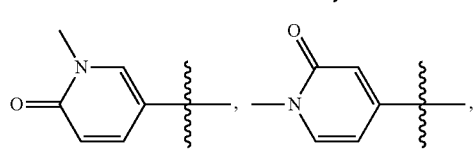

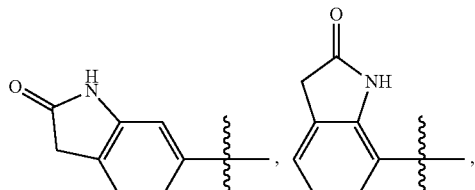

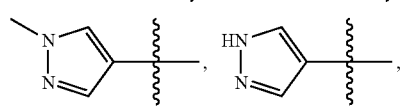

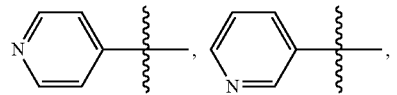

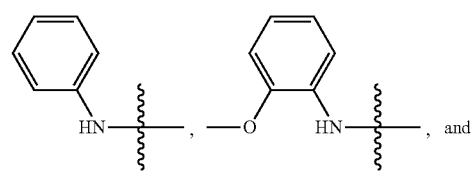

wherein

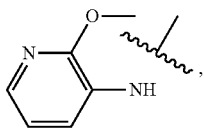

indicates the point of attachment to the cinnoline 6 or 7 position.

In some embodiments of a compound of Formula I, further to any of the above embodiments of Formula I, when $R^1$ is

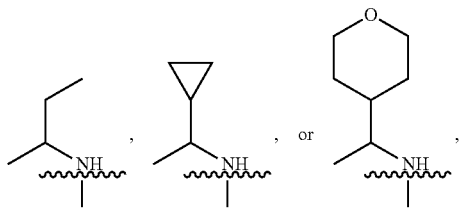

these compounds have an enantiomeric excess of the stereoisomer

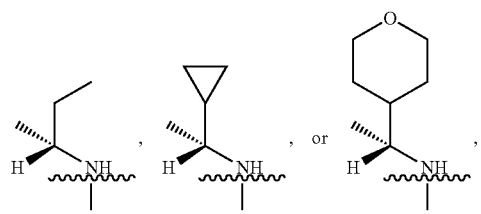

respectively.

In some embodiments of a compound of Formula I, further to any of the above embodiments of Formula I, the compound has the structure I-1,

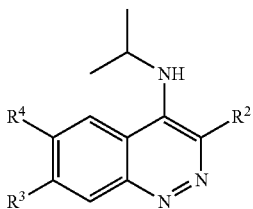

I-1 wherein $R^2$, $R^3$ and $R^4$ are as defined for any of the above embodiments of Formula I.

In some embodiments of a compound of Formula I, further to any of the above embodiments of Formula I, the compound has the structure I-2

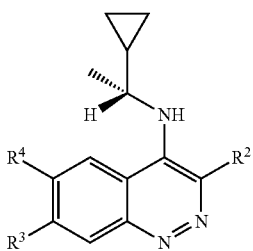

I-2 wherein $R^2$, $R^3$ and $R^4$ are as defined for any of the above embodiments of Formula I.

In some embodiments of a compound of Formula I, further to any of the above embodiments of Formula I, one of $R^3$ and $R^4$ is H. In one embodiment $R^3$ is H. In one embodiment $R^4$ is H.

In some embodiments of a compound of Formula I, further to any of the above embodiments of Formula I, $R^2$ is —C(=O)NH$_2$.

In one aspect, compounds of Formula I are provided having a structure according to Formula Ia:

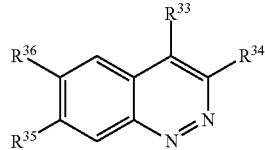

Ia or a salt thereof, wherein:

$R^{33}$ is —CR$^{37}$R$^{38}$R$^{39}$, —OR$^{40}$, —SR$^{41}$, or —NR$^{42}$R$^{43}$;

$R^{37}$ and $R^{38}$ are independently hydrogen, halogen, —OH, $C_1$-$C_6$ alkoxy, $C_1$-$C_6$ haloalkoxy, —SH, —S(=O)$_m$—$C_1$-$C_6$ alkyl, —S(=O)$_m$—$C_1$-$C_6$ haloalkyl, —NH$_2$, $C_1$-$C_6$ alkylamino, $C_1$-$C_6$ dialkylamino, or $C_1$-$C_6$ alkyl optionally substituted with one or more substituents $R^{44}$;

$R^{39}$ is halogen, —OH, $C_1$-$C_6$ alkoxy, $C_1$-$C_6$ haloalkoxy, —SH, —S(=O)$_m$—$C_1$-$C_6$ alkyl, —S(=O)$_m$—$C_1$-$C_6$ haloalkyl, —NH$_2$, $C_1$-$C_6$ alkylamino, $C_1$-$C_6$ dialkylamino, $C_1$-$C_6$ alkyl optionally substituted with one or more substituents $R^{44}$, $C_3$-$C_8$ cycloalkyl optionally substituted with one or more substituents $R^{45}$, or 4-7 membered heterocycloalkyl optionally substituted with one or more substituents $R^{46}$; or any two of $R^{37}$, $R^{38}$ and $R^{39}$ together with the carbon to which they are attached, form a 3-8 membered cycloalkyl optionally substituted with one or more substituents $R^{45}$ or a 4-7 membered heterocycloalkyl optionally substituted with one or more substituents $R^{46}$, and the other of $R^{37}$, $R^{38}$ and $R^{39}$ is hydrogen, halogen, —OH, $C_1$-$C_6$ alkoxy, $C_1$-$C_6$ haloalkoxy, —SH, —S(=O)$_m$—$C_1$-$C_6$ alkyl, —S(=O)$_m$—$C_1$-$C_6$ haloalkyl, —NH$_2$, $C_1$-$C_6$ alkylamino, $C_1$-$C_6$ dialkylamino, or $C_1$-$C_6$ alkyl optionally substituted with one or more substituents $R^{44}$;

$R^{40}$ and $R^{41}$ are independently $C_1$-$C_6$ alkyl optionally substituted with one or more substituents $R^{44}$, $C_3$-$C_8$ cycloalkyl optionally substituted with one or more substituents $R^{45}$, or 4-7 membered heterocycloalkyl optionally substituted with one or more substituents $R^{46}$;

$R^{42}$ is hydrogen or $C_1$-$C_6$ alkyl;

$R^{43}$ is hydrogen, $C_1$-$C_6$ alkyl optionally substituted with one or more substituents $R^{44}$, $C_3$-$C_8$ cycloalkyl optionally substituted with one or more substituents $R^{45}$, 4-7 membered heterocycloalkyl optionally substituted with one or more substituents $R^{46}$;

or $R^{42}$ and $R^{43}$, together with the nitrogen to which they are attached, form a 5-7 membered heterocycloalkyl optionally substituted with one or more substituents $R^{46}$;

$R^{34}$ is selected from the group consisting of halogen, —CN, —C≡CH, —C(=O)NH$_2$, $L_6$-$R^{47}$, 4-7 membered heterocycloalkyl optionally substituted with one or more substituents $R^{48}$, or 5 or 6 membered heteroaryl optionally substituted with one or more substituents $R^{49}$;

one of $R^{35}$ and $R^{36}$ is selected from the group consisting of hydrogen, $R^{50}$, $L_7$-$R^{51}$, $C_1$-$C_6$ alkyl, $C_2$-$C_6$ alkenyl, $C_2$-$C_6$ alkynyl, cycloalkyl, heterocycloalkyl, aryl, and heteroaryl, wherein $C_1$-$C_6$ alkyl, $C_2$-$C_6$ alkenyl, and $C_2$-$C_6$ alkynyl are optionally substituted with one or more substituents independently selected from the group consisting of $R^{50}$, $L_7$-$R^{51}$, cycloalkyl, heterocycloalkyl, aryl, and heteroaryl, and wherein cycloalkyl and heterocycloalkyl, as $R^{35}$ or $R^{36}$ or as a substituent of $C_1$-$C_6$ alkyl, $C_2$-$C_6$ alkenyl, or $C_2$-$C_6$ alkynyl, are optionally substituted with one or more substituents independently selected from the group consisting of $R^{50}$, =O, =NR$^{52}$, =NOR$^{52}$, $L_7$-$R^{51}$, and $R^{53}$, and wherein aryl and heteroaryl, as $R^{35}$ or $R^{36}$ or as a substituent of $C_1$-$C_6$ alkyl, $C_2$-$C_6$ alkenyl, or $C_2$-$C_6$ alkynyl, are optionally substituted with one or more substituents independently selected from the group consisting of $R^{50}$, $L_7$-$R^{51}$, and $R^{53}$;

the other of $R^{35}$ and $R^{36}$ is selected from the group consisting of $R^{54}$, $L_8$-$R^{51}$, —OR$^{55}$, —SR$^{55}$, methyl, $C_2$-$C_6$ alkyl, $C_2$-$C_6$ alkenyl, $C_2$-$C_6$ alkynyl, cycloalkyl, heterocycloalkyl, aryl, and heteroaryl, wherein methyl is substituted with one or more substituents independently selected from the group consisting of $R^{50}$, $L_7$-$R^{51}$, cycloalkyl, heterocycloalkyl, aryl, and heteroaryl, and wherein $C_2$-$C_6$ alkyl, $C_2$-$C_6$ alkenyl, and $C_2$-$C_6$ alkynyl are optionally substituted with one or more substituents independently selected from the group consisting of $R^{50}$, $L_7$-$R^{51}$, cycloalkyl, heterocycloalkyl, aryl, and heteroaryl, and wherein cycloalkyl and heterocycloalkyl, as $R^{35}$ or $R^{36}$ or as a substituent of methyl, $C_2$-$C_6$ alkyl, $C_2$-$C_6$ alkenyl, or $C_2$-$C_6$ alkynyl, are optionally substituted with one or more substituents independently selected from the group consisting of $R^{50}$, =O, =NR$^{52}$, =NOR$^{52}$, $L_7$-$R^{51}$, and $R^{53}$, and wherein aryl and heteroaryl, as $R^{35}$ or $R^{36}$ or as a substituent of methyl, $C_2$-$C_6$ alkyl, $C_2$-$C_6$ alkenyl, or $C_2$-$C_6$ alkynyl, are optionally substituted with one or more substituents independently selected from the group consisting of $R^{50}$, $L_7$-$R^{51}$, and $R^{53}$;

$R^{44}$ at each occurrence is independently selected from the group consisting of halogen, —OH, $C_1$-$C_6$ alkoxy, $C_1$-$C_6$ haloalkoxy, —SH, —S(=O)$_m$—$C_1$-$C_6$ alkyl, —S(=O)$_m$—$C_1$-$C_6$ haloalkyl, —NH$_2$, $C_1$-$C_6$ alkylamino, $C_1$-$C_6$ dialkylamino, $C_3$-$C_8$ cycloalkyl optionally substituted with one or more substituents $R^{45}$, and 4-7 membered heterocycloalkyl optionally substituted with one or more substituents $R^{46}$;

$R^{45}$ at each occurrence is independently selected from the group consisting of halogen, $C_1$-$C_6$ alkyl, $C_1$-$C_6$ haloalkyl, —OH, =O, $C_1$-$C_6$ alkoxy, $C_1$-$C_6$ haloalkoxy, —SH, —S(=O)$_m$—$C_1$-$C_6$ alkyl, —S(=O)$_m$—$C_1$-$C_6$ haloalkyl, —NH$_2$, $C_1$-$C_6$ alkylamino, $C_1$-$C_6$ dialkylamino, and N-linked-heterocycloalkyl;

$R^{46}$ at each occurrence is independently selected from the group consisting of halogen, $C_1$-$C_6$ alkyl, $C_1$-$C_6$ haloalkyl, —OH, =O, $C_1$-$C_6$ alkoxy, $C_1$-$C_6$ haloalkoxy, —SH, —S(=O)$_m$—$C_1$-$C_6$ alkyl, —S(=O)$_m$—$C_1$-$C_6$ haloalkyl, —NH$_2$, $C_1$-$C_6$ alkylamino, $C_1$-$C_6$ dialkylamino, and N-linked-heterocycloalkyl;

$R^{48}$ at each occurrence, are independently selected from the group consisting of $R^{50}$, =O, =NR$^{52}$, =NOR$^{52}$, $L_7$-$R^{51}$, $C_1$-$C_6$ alkyl, $C_2$-$C_6$ alkenyl, $C_2$-$C_6$ alkynyl, cycloalkyl, heterocycloalkyl, aryl, and heteroaryl, wherein $C_1$-$C_6$ alkyl, $C_2$-$C_6$ alkenyl, and $C_2$-$C_6$ alkynyl are optionally substituted with one or more substituents independently selected from the group consisting of $R^{50}$, $L_9$-$R^{56}$, cycloalkyl, heterocycloalkyl, aryl, and heteroaryl, and wherein cycloalkyl and heterocycloalkyl, as $R^{48}$ or as a substituent of $C_1$-$C_6$ alkyl, $C_2$-$C_6$ alkenyl, or $C_2$-$C_6$ alkynyl, are optionally substituted with one or more substituents independently selected from the group consisting of $R^{50}$, =O, =NR$^{52}$, =NOR$^{52}$, -$L_9$-$R^{56}$, and $R^{56}$, and wherein aryl and heteroaryl, as $R^{48}$ as a substituent of $C_1$-$C_6$ alkyl, $C_2$-$C_6$ alkenyl, or $C_2$-$C_6$ alkynyl, are optionally substituted with one or more substituents independently selected from the group consisting of $R^{50}$, -$L_9$-$R^{56}$, and $R^{56}$;

$R^{49}$ at each occurrence, are independently selected from the group consisting of $R^{50}$, $L_7$-$R^{51}$, $C_1$-$C_6$ alkyl, $C_2$-$C_6$ alkenyl, $C_2$-$C_6$ alkynyl, cycloalkyl, heterocycloalkyl, aryl, and heteroaryl, wherein $C_1$-$C_6$ alkyl, $C_2$-$C_6$ alkenyl, and $C_2$-$C_6$ alkynyl are optionally substituted with one or more substituents independently selected from the group consisting of $R^{50}$, $L_9$-$R^{56}$, cycloalkyl, heterocycloalkyl, aryl, and heteroaryl, and wherein cycloalkyl and heterocycloalkyl, as $R^{49}$ or as a substituent of $C_1$-$C_6$ alkyl, $C_2$-$C_6$ alkenyl, or $C_2$-$C_6$ alkynyl, are optionally substituted with one or more substituents independently selected from the group consisting of $R^{50}$, =O, =NR$^{52}$, =NOR$^{52}$, $L_9$-$R^{56}$, and $R^{56}$, and wherein aryl and heteroaryl, as $R^{49}$ or as a substituent of $C_1$-$C_6$ alkyl, $C_2$-$C_6$ alkenyl, or $C_2$-$C_6$ alkynyl, are optionally substituted with one or more substituents independently selected from the group consisting of $R^{50}$, $L_9$-$R^{56}$, and $R^{56}$;

$R^{50}$ at each occurrence is independently selected from the group consisting of halogen, —CN, —NO$_2$, —OH, —SH, —NH$_2$, —NHOH, —C(=X)OH, —C(=X)NH$_2$, —C(=X)NHOH, —OC(=X)NH$_2$, —NHC(=X)NH$_2$, —NHC(=X)OH, —S(=O)$_2$NH$_2$, —S(=O)$_2$NHOH, —NHS(=O)$_2$NH$_2$, and —NHC(NH$_2$)=NH;

$R^{54}$ at each occurrence is independently selected from the group consisting of —CN, —NH$_2$, —NHOH, —C(=X)OH, —C(=X)NH$_2$, —C(=X)NHOH, —OC(=X)NH$_2$, —NHC(=X)NH$_2$, —NHC(=X)OH, —S(=O)$_2$NH$_2$, —S(=O)$_2$NHOH, —NHS(=O)$_2$NH$_2$, and —NHC(NH$_2$)=NH;

$R^{47}$, $R^{51}$, and $R^{53}$, at each occurrence, are independently selected from the group consisting of $C_1$-$C_6$ alkyl, $C_2$-$C_6$ alkenyl, $C_2$-$C_6$ alkynyl, cycloalkyl, heterocycloalkyl, aryl, and heteroaryl, wherein $C_1$-$C_6$ alkyl, $C_2$-$C_6$ alkenyl, and $C_2$-$C_6$ alkynyl are optionally substituted with one or more substituents independently selected from the group consisting of $R^{50}$, $L_9$-$R^{56}$, cycloalkyl, heterocycloalkyl, aryl, and heteroaryl, and wherein cycloalkyl and heterocycloalkyl as $R^{47}$, $R^{51}$, or $R^{53}$, or as a substituent of $C_1$-$C_6$ alkyl, $C_2$-$C_6$ alkenyl, or $C_2$-$C_6$ alkynyl, are optionally substituted with one or more substituents independently selected from the group consisting of $R^{50}$, =O, =NR$^{52}$, =NOR$^{52}$, $L_9$-$R^{56}$, and $R^{56}$, and wherein aryl and heteroaryl, as $R^{47}$, $R^{51}$, or $R^{53}$, or as a substituent of $C_1$-$C_6$ alkyl, $C_2$-$C_6$ alkenyl, or $C_2$-$C_6$ alkynyl, are optionally substituted with one or more substituents independently selected from the group consisting of $R^{50}$, $L_9$-$R^{56}$, and $R^{56}$;

$R^{55}$ at each occurrence is independently selected from the group consisting of methyl, $C_2$-$C_6$ alkyl, $C_2$-$C_6$ alkenyl, $C_2$-$C_6$ alkynyl, cycloalkyl, heterocycloalkyl, aryl, and heteroaryl, wherein methyl is substituted with one or more substituents independently selected from the group consisting of $R^{50}$, $L_9$-$R^{56}$, cycloalkyl, heterocycloalkyl, aryl, and heteroaryl, and wherein $C_2$-$C_6$ alkyl, $C_2$-$C_6$ alkenyl, and $C_2$-$C_6$ alkynyl are optionally substituted with one or more substituents independently selected from the group consisting of $R^{50}$, $L_9$-$R^{56}$, cycloalkyl, heterocycloalkyl, aryl, and heteroaryl, and wherein cycloalkyl and heterocycloalkyl as $R^{55}$ or as a substituent of methyl, $C_2$-$C_6$ alkyl, $C_2$-$C_6$ alkenyl, or $C_2$-$C_6$ alkynyl, are optionally substituted with one or more substituents independently selected from the group consisting of $R^{50}$, =O, =NR$^{52}$, =NOR$^{52}$, $L_9$-$R^{56}$, and $R^{56}$, and wherein aryl and heteroaryl, as $R^{55}$ or as a substituent of methyl, $C_2$-$C_6$ alkyl, $C_2$-$C_6$ alkenyl, or $C_2$-$C_6$ alkynyl, are optionally substituted with one or more substituents independently selected from the group consisting of $R^{50}$, $L_9$-$R^{56}$, and $R^{56}$;

$L_6$ at each occurrence is independently selected from the group consisting of —O—, —S—, —NR$^{52}$—, —NR$^{52}$O—, —C(=X)—, —C(=X)NR$^{52}$—, —C(=X)NR$^{52}$O—, —NR$^{52}$C(=X)—, —OC(=X)NR$^{52}$—, —NR$^{52}$C(=X)NR$^{52}$—, —NR$^{52}$C(=X)O—, —S(=O)—, —S(=O)$_2$—, —S(=O)$_2$NR$^{52}$—, —S(=O)$_2$NR$^{52}$O—, —NR$^{52}$S(=O)$_2$—, —NR$^{52}$S(=O)$_2$NR$^{52}$—, —NR$^{52}$C(=NR$^{52}$)NR$^{52}$—, and —NR$^{52}$C(NR$^{52}$R$^{52}$)=N—;

$L_7$ and $L_9$ at each occurrence, are independently selected from the group consisting of —O—, —S—, —NR$^{52}$—, —NR$^{52}$—O, —C(=X)—, —C(=X)O—, —OC(=X)—, —C(=X)NR$^{52}$—, —C(=X)NR$^{52}$O—, —NR$^{52}$C(=X)—, —OC(=X)NR$^{52}$—, —NR$^{52}$C(=X)NR$^{52}$—, —NR$^{52}$C(=X)O—, —S(=O)—, —S(=O)$_2$—, —S(=O)$_2$NR$^{52}$—, —S(=O)$_2$NR$^{52}$O—, —NR$^{52}$S(=O)$_2$—, —NR$^{52}$S(=O)$_2$NR$^{52}$—, —NR$^{52}$C(=NR)NR$^{52}$—, and —NR$^{52}$C(NR$^{52}$R$^{52}$)=N—;

$L_8$ at each occurrence is independently selected from the group consisting of —NR$^{52}$—, —NR$^{52}$O—, —C(=X)—, —C(=X)O—, —OC(=X)—, —C(=X)NR$^{52}$—, —C(=X)NR$^{52}$O—, —NR$^{52}$C(=X)—, —OC(=X)NR$^{52}$—, —NR$^{52}$C(=X)NR$^{52}$—, —NR$^{52}$C(=X)O—, —S(=O)—, —S(=O)$_2$—, —S(=O)$_2$NR$^{52}$—, —S(=O)$_2$NR$^{52}$O—, —NR$^{52}$S(=O)$_2$—, —NR$^{52}$S(=O)$_2$NR$^{52}$—, —NR$^{52}$C(=NR$^{52}$)NR$^{52}$—, and —NR$^{52}$C(NR$^{52}$R$^{52}$)=N—;

X is O or S;

$R^{52}$ at each occurrence is independently selected from the group consisting of hydrogen, $C_1$-$C_6$ alkyl, $C_2$-$C_6$ alkenyl, $C_2$-$C_6$ alkynyl, cycloalkyl, heterocycloalkyl, aryl, and heteroaryl, wherein $C_1$-$C_6$ alkyl, $C_2$-$C_6$ alkenyl, and $C_2$-$C_6$ alkynyl are optionally substituted with one or more substituents $R^{57}$, and wherein cycloalkyl and heterocycloalkyl are optionally substituted with one or more substituents $R^{58}$, and wherein aryl and heteroaryl are optionally substituted with one or more substituents $R^{59}$;

$R^{56}$ at each occurrence is independently selected from the group consisting of $C_1$-$C_6$ alkyl, $C_2$-$C_6$ alkenyl, $C_2$-$C_6$ alkynyl, cycloalkyl, heterocycloalkyl, aryl, and heteroaryl, wherein $C_1$-$C_6$ alkyl, $C_2$-$C_6$ alkenyl, and $C_2$-$C_6$ alkynyl are optionally substituted with one or more substituents $R^{57}$, and wherein cycloalkyl and heterocycloalkyl are optionally substituted with one or more substituents $R^{58}$, and wherein aryl and heteroaryl are optionally substituted with one or more substituents $R^{59}$;

$R^{57}$ at each occurrence is independently selected from the group consisting of halogen, —OH, $C_1$-$C_6$ alkoxy, —SH, —S(=O)$_m$—$C_1$-$C_6$ alkyl, —NH$_2$, $C_1$-$C_6$ alkylamino, $C_1$-$C_6$ dialkylamino, cycloalkyl, heterocycloalkyl, aryl, and heteroaryl, wherein the alkyl chain of $C_1$-$C_6$ alkoxy, —S(=O)$_m$—$C_1$-$C_6$ alkyl, $C_1$-$C_6$ alkylamino, or $C_1$-$C_6$ dialkylamino is optionally substituted with one or more substituents selected from the group consisting of halogen, —OH, $C_1$-$C_6$ alkoxy, $C_1$-$C_6$ haloalkoxy, —SH, —S(=O)$_m$—$C_1$-$C_6$ alkyl, —S(=O)$_m$—$C_1$-$C_6$ haloalkyl, —NH$_2$, $C_1$-$C_6$ alkylamino, $C_1$-$C_6$ dialkylamino, and N-linked-heterocycloalkyl, and wherein cycloalkyl and heterocycloalkyl are optionally substituted with one or more substituents $R^{58}$, and aryl and heteroaryl are optionally substituted with one or more substituents $R^{59}$;

$R^{58}$ at each occurrence is independently selected from the group consisting of halogen, $C_1$-$C_6$ alkyl, —OH, =O, $C_1$-$C_6$ alkoxy, —SH, —S(=O)$_m$—$C_1$-$C_6$ alkyl, —NH$_2$, $C_1$-$C_6$ alkylamino, $C_1$-$C_6$ dialkylamino, and N-linked-heterocycloalkyl, wherein the alkyl chain of $C_1$-$C_6$ alkyl, $C_1$-$C_6$ alkoxy, —S(=O)$_m$—$C_1$-$C_6$ alkyl, $C_1$-$C_6$ alkylamino, or $C_1$-$C_6$ dialkylamino is optionally substituted with one or more substituents selected from the group consisting of halogen, —OH, $C_1$-$C_6$ alkoxy, $C_1$-$C_6$ haloalkoxy, —SH, —S(=O)$_m$—$C_1$-$C_6$ alkyl, —S(=O)$_m$—$C_1$-$C_6$ haloalkyl, —NH$_2$, $C_1$-$C_6$ alkylamino, $C_1$-$C_6$ dialkylamino, and N-linked-heterocycloalkyl;

$R^{59}$ at each occurrence is independently selected from the group consisting of halogen, $C_1$-$C_6$ alkyl, —OH, —CN, $C_1$-$C_6$ alkoxy, —SH, —S(=O)$_m$—$C_1$-$C_6$ alkyl, —NH$_2$, $C_1$-$C_6$ alkylamino, $C_1$-$C_6$ dialkylamino, and N-linked-heterocycloalkyl, wherein the alkyl chain of $C_1$-$C_6$ alkyl, $C_1$-$C_6$ alkoxy, —S(=O)$_m$—$C_1$-$C_6$ alkyl, $C_1$-$C_6$ alkylamino, or $C_1$-$C_6$ dialkylamino is optionally substituted with one or more substituents selected from the group consisting of halogen, —OH, $C_1$-$C_6$ alkoxy, $C_1$-$C_6$ haloalkoxy, —SH, —S(=O)$_m$—$C_1$-$C_6$ alkyl, —S(=O)$_m$—$C_1$-$C_6$ haloalkyl, —NH$_2$, $C_1$-$C_6$ alkylamino, $C_1$-$C_6$ dialkylamino, and N-linked-heterocycloalkyl, and provided, however, that when $R^{34}$ is —C(=O)NH$_2$, $R^{36}$ is halogen, $R^{35}$ is N-linked-heterocycloalkyl or $L_7$-$R^{51}$ wherein $L_7$ is —NR$^{52}$— and $R^{51}$ is pyridine, or phenyl optionally substituted with methyl, or $L_7$ is —O— and $R^{51}$ is $C_1$-$C_6$ alkyl optionally substituted with methoxy, $R^{33}$ is —NR$^{42}$R$^{43}$, and $R^{42}$ is hydrogen, $R^{43}$ is selected from the group consisting of $C_1$-$C_6$ alkyl optionally substituted with one or more substituents $R^{44}$, $C_3$-$C_8$ cycloalkyl optionally substituted with one or more substituents $R^{45}$, or 4-7 membered heterocycloalkyl optionally substituted with one or more substituents $R^{46}$; or when $R^{34}$ is $L_6$-$R^{47}$, $L_6$ is —C(=X)— or —C(=X)NR$^{52}$—, one of $R^{35}$ and $R^{36}$ is hydrogen, the other of $R^{35}$ and $R^{36}$ is unsubstituted $C_1$-$C_6$ alkyl, $R^{33}$ is —NR$^{42}$R$^{43}$, and $R^{42}$ is hydrogen, $R^{43}$ is selected from the group consisting of $C_1$-$C_6$ alkyl optionally substituted with one or more substituents $R^{44}$, $C_3$-$C_8$ cycloalkyl optionally substituted with one or more substituents $R^{45}$, or 4-7 membered heterocycloalkyl optionally substituted with one or more substituents $R^{46}$; and provided that the compound does not have the structure of

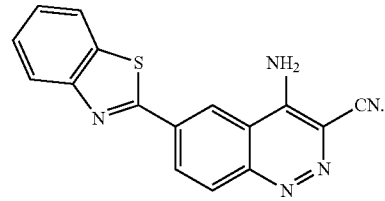 [SMILES: N#Cc1nnc2ccc(-c3nc4ccccc4s3)cc2c1N]

In some embodiments of a compound of Formula Ia:
$R^{33}$ is —CR$^{37}$R$^{38}$R$^{39}$, —OR$^{40}$, —SR$^{41}$, or —NR$^{42}$R$^{43}$;
$R^{42}$ is hydrogen or $C_1$-$C_6$ alkyl;
$R^{43}$ is $C_1$-$C_6$ alkyl optionally substituted with one or more substituents $R^{44}$, $C_3$-$C_8$ cycloalkyl optionally substituted with one or more substituents $R^{45}$, 4-7 membered heterocycloalkyl optionally substituted with one or more substituents $R^{46}$;
or $R^{42}$ and $R^{43}$, together with the nitrogen to which they are attached, form a 5-7 membered heterocycloalkyl optionally substituted with one or more substituents $R^{46}$;
wherein $R^{34}$, $R^{35}$, $R^{36}$, $R^{37}$, $R^{38}$, $R^{39}$, $R^{40}$, $R^{41}$, $R^{44}$, $R^{45}$, and $R^{46}$ are as defined for Formula Ia.

In some embodiments of a compound of Formula Ia:
$R^{33}$ is —OR$^{40}$, —SR$^{41}$, or —NR$^{42}$R$^{43}$;
$R^{42}$ is hydrogen or $C_1$-$C_6$ alkyl;

$R^{43}$ is $C_1$-$C_6$ alkyl optionally substituted with one or more substituents $R^{44}$, $C_3$-$C_8$ cycloalkyl optionally substituted with one or more substituents $R^{45}$, 4-7 membered heterocycloalkyl optionally substituted with one or more substituents $R^{46}$;

or $R^{42}$ and $R^{43}$, together with the nitrogen to which they are attached, form a 5-7 membered heterocycloalkyl optionally substituted with one or more substituents $R^{46}$;

wherein $R^{34}$, $R^{35}$, $R^{36}$, $R^{40}$, $R^{41}$, $R^{44}$, $R^{45}$, and $R^{46}$ are as defined for Formula Ia.

In some embodiments of a compound of Formula Ia:
$R^{33}$ is —$NR^{42}R^{43}$;
$R^{42}$ is hydrogen or $C_1$-$C_6$ alkyl;
$R^{43}$ is $C_1$-$C_6$ alkyl optionally substituted with one or more substituents $R^{44}$, $C_3$-$C_8$ cycloalkyl optionally substituted with one or more substituents $R^{45}$, 4-7 membered heterocycloalkyl optionally substituted with one or more substituents $R^{46}$;

or $R^{42}$ and $R^{43}$, together with the nitrogen to which they are attached, form a 5-7 membered heterocycloalkyl optionally substituted with one or more substituents $R^{46}$; and wherein $R^{34}$, $R^{35}$, $R^{36}$, $R^{44}$, $R^{45}$, and $R^{46}$ are as defined for Formula Ia.

In some embodiments of a compound of Formula Ia:
$R^{33}$ is —$CR^{37}R^{38}R^{39}$, —$OR^{40}$, —$SR^{41}$, or —$NR^{42}R^{43}$;
$R^{42}$ is hydrogen or $C_1$-$C_6$ alkyl;
$R^{43}$ is $C_1$-$C_6$ alkyl optionally substituted with one or more substituents $R^4$, $C_3$-$C_8$ cycloalkyl optionally substituted with one or more substituents $R^{45}$, 4-7 membered heterocycloalkyl optionally substituted with one or more substituents $R^{46}$;

or $R^{42}$ and $R^{43}$, together with the nitrogen to which they are attached, form a 5-7 membered heterocycloalkyl optionally substituted with one or more substituents $R^{46}$;

$R^{36}$ is selected from the group consisting of hydrogen, $R^{50}$, $L_7$-$R^{51}$, $C_1$-$C_6$ alkyl, $C_2$-$C_6$ alkenyl, $C_2$-$C_6$ alkynyl, cycloalkyl, heterocycloalkyl, aryl, and heteroaryl, wherein $C_1$-$C_6$ alkyl, $C_2$-$C_6$ alkenyl, and $C_2$-$C_6$ alkynyl are optionally substituted with one or more substituents independently selected from the group consisting of $R^{50}$, $L_7$-$R^{51}$, cycloalkyl, heterocycloalkyl, aryl, and heteroaryl, and wherein cycloalkyl and heterocycloalkyl, as $R^{36}$ or as a substituent of $C_1$-$C_6$ alkyl, $C_2$-$C_6$ alkenyl, or $C_2$-$C_6$ alkynyl, are optionally substituted with one or more substituents independently selected from the group consisting of $R^{50}$, =O, =$NR^{52}$, =$NOR^{52}$, $L_7$-$R^{51}$, and $R^{53}$, and wherein aryl and heteroaryl, as $R^{36}$ or as a substituent of $C_1$-$C_6$ alkyl, $C_2$-$C_6$ alkenyl, or $C_2$-$C_6$ alkynyl, are optionally substituted with one or more substituents independently selected from the group consisting of $R^{50}$, $L_7$-$R^{51}$, and $R^{53}$;

$R^{35}$ is selected from the group consisting of $R^{54}$, $L_8$-$R^{51}$, —$OR^{55}$, —$SR^{55}$, methyl, $C_2$-$C_6$ alkyl, $C_2$-$C_6$ alkenyl, $C_2$-$C_6$ alkynyl, cycloalkyl, heterocycloalkyl, aryl, and heteroaryl, wherein methyl is substituted with one or more substituents independently selected from the group consisting of $R^{50}$, $L_7$-$R^{51}$, cycloalkyl, heterocycloalkyl, aryl, and heteroaryl, and wherein $C_2$-$C_6$ alkyl, $C_2$-$C_6$ alkenyl, and $C_2$-$C_6$ alkynyl are optionally substituted with one or more substituents independently selected from the group consisting of $R^{50}$, $L_7$-$R^{51}$, cycloalkyl, heterocycloalkyl, aryl, and heteroaryl, and wherein cycloalkyl and heterocycloalkyl, as $R^{35}$ or as a substituent of methyl, $C_2$-$C_6$ alkyl, $C_2$-$C_6$ alkenyl, or $C_2$-$C_6$ alkynyl, are optionally substituted with one or more substituents independently selected from the group consisting of $R^{50}$, =O, =$NR^{52}$, =$NOR^{52}$, $L_7$-$R^{51}$, and $R^{53}$, and wherein aryl and heteroaryl, as $R^{35}$ or as a substituent of methyl, $C_2$-$C_6$ alkyl, $C_2$-$C_6$ alkenyl, or $C_2$-$C_6$ alkynyl, are optionally substituted with one or more substituents independently selected from the group consisting of $R^{50}$, $L_7$-$R^{51}$, and $R^{53}$; and wherein $R^{34}$, $R^{37}$, $R^{38}$, $R^{39}$, $R^{40}$, $R^{41}$, $R^{44}$, $R^{45}$, $R^{46}$, $R^{50}$, $R^{51}$, $R^{52}$, $R^{53}$, $R^{54}$, $R^{55}$, $L_7$, and $L_8$, are as defined for Formula Ia.

In some embodiments of a compound of Formula Ia:
$R^{33}$ is —$OR^{40}$, —$SR^{41}$, or —$NR^{42}R^{43}$;
$R^{42}$ is hydrogen or $C_1$-$C_6$ alkyl;
$R^{43}$ is $C_1$-$C_6$ alkyl optionally substituted with one or more substituents $R^{44}$, $C_3$-$C_8$ cycloalkyl optionally substituted with one or more substituents $R^{45}$, 4-7 membered heterocycloalkyl optionally substituted with one or more substituents $R^{46}$;

or $R^{42}$ and $R^{43}$, together with the nitrogen to which they are attached, form a 5-7 membered heterocycloalkyl optionally substituted with one or more substituents $R^{46}$;

$R^{36}$ is selected from the group consisting of hydrogen, $R^{50}$, $L_7$-$R^{51}$, $C_1$-$C_6$ alkyl, $C_2$-$C_6$ alkenyl, $C_2$-$C_6$ alkynyl, cycloalkyl, heterocycloalkyl, aryl, and heteroaryl, wherein $C_1$-$C_6$ alkyl, $C_2$-$C_6$ alkenyl, and $C_2$-$C_6$ alkynyl are optionally substituted with one or more substituents independently selected from the group consisting of $R^{50}$, $L_7$-$R^{51}$, cycloalkyl, heterocycloalkyl, aryl, and heteroaryl, and wherein cycloalkyl and heterocycloalkyl, as $R^{36}$ or as a substituent of $C_1$-$C_6$ alkyl, $C_2$-$C_6$ alkenyl, or $C_2$-$C_6$ alkynyl, are optionally substituted with one or more substituents independently selected from the group consisting of $R^{50}$, =O, =$NR^{52}$, =$NOR^{52}$, $L_7$-$R^{51}$, and $R^{53}$, and wherein aryl and heteroaryl, as $R^{36}$ or as a substituent of $C_1$-$C_6$ alkyl, $C_2$-$C_6$ alkenyl, or $C_2$-$C_6$ alkynyl, are optionally substituted with one or more substituents independently selected from the group consisting of $R^{50}$, $L_7$-$R^{51}$, and $R^{53}$;

$R^{35}$ is selected from the group consisting of $R^{54}$, $L_8$-$R^{51}$, —$OR^{55}$, —$SR^{55}$, methyl, $C_2$-$C_6$ alkyl, $C_2$-$C_6$ alkenyl, $C_2$-$C_6$ alkynyl, cycloalkyl, heterocycloalkyl, aryl, and heteroaryl, wherein methyl is substituted with one or more substituents independently selected from the group consisting of $R^{50}$, $L_7$-$R^{51}$, cycloalkyl, heterocycloalkyl, aryl, and heteroaryl, and wherein $C_2$-$C_6$ alkyl, $C_2$-$C_6$ alkenyl, and $C_2$-$C_6$ alkynyl are optionally substituted with one or more substituents independently selected from the group consisting of $R^{50}$, $L_7$-$R^{51}$, cycloalkyl, heterocycloalkyl, aryl, and heteroaryl, and wherein cycloalkyl and heterocycloalkyl, as $R^{35}$ or as a substituent of methyl, $C_2$-$C_6$ alkyl, $C_2$-$C_6$ alkenyl, or $C_2$-$C_6$ alkynyl, are optionally substituted with one or more substituents independently selected from the group consisting of $R^{50}$, =O, =$NR^{52}$, =$NOR^{52}$, $L_7$-$R^{51}$, and $R^{53}$, and wherein aryl and heteroaryl, as $R^{35}$ or as a substituent of methyl, $C_2$-$C_6$ alkyl, $C_2$-$C_6$ alkenyl, or $C_2$-$C_6$ alkynyl, are optionally substituted with one or more substituents independently selected from the group consisting of $R^{50}$, $L_7$-$R^{51}$, and $R^{53}$; and wherein $R^{34}$, $R^{40}$, $R^{41}$, $R^{44}$, $R^{45}$, $R^{46}$, $R^{50}$, $R^{51}$, $R^{52}$, $R^{53}$, $R^{54}$, $R^{55}$, $L_7$, and $L_8$, are as defined for Formula Ia.

In some embodiments of a compound of Formula Ia:
$R^{33}$ is —$NR^{42}R^{43}$;
$R^{42}$ is hydrogen or $C_1$-$C_6$ alkyl;
$R^{43}$ is $C_1$-$C_6$ alkyl optionally substituted with one or more substituents $R^{44}$, $C_3$-$C_8$ cycloalkyl optionally substituted with one or more substituents $R^{45}$, 4-7 membered heterocycloalkyl optionally substituted with one or more substituents $R^{46}$;

or $R^{42}$ and $R^{43}$, together with the nitrogen to which they are attached, form a 5-7 membered heterocycloalkyl optionally substituted with one or more substituents $R^{46}$;

$R^{36}$ is selected from the group consisting of hydrogen, $R^{50}$, $L_7$-$R^{51}$, $C_1$-$C_6$ alkyl, $C_2$-$C_6$ alkenyl, $C_2$-$C_6$ alkynyl, cycloalkyl, heterocycloalkyl, aryl, and heteroaryl, wherein $C_1$-$C_6$ alkyl, $C_2$-$C_6$ alkenyl, and $C_2$-$C_6$ alkynyl are optionally substituted with one or more substituents independently selected from the group consisting of $R^{50}$, $L_7$-$R^{51}$, cycloalkyl, heterocycloalkyl, aryl, and heteroaryl, and wherein cycloalkyl and heterocycloalkyl, as $R^{36}$ or as a substituent of $C_1$-$C_6$ alkyl, $C_2$-$C_6$ alkenyl, or $C_2$-$C_6$ alkynyl, are optionally substituted with one or more substituents independently selected from the group consisting of $R^{50}$, =O, =$NR^2$, =$NOR^{52}$, $L_7$-$R^{51}$, and $R^{53}$, and wherein aryl and heteroaryl, as $R^{36}$ or as a substituent of $C_1$-$C_6$ alkyl, $C_2$-$C_6$ alkenyl, or $C_2$-$C_6$ alkynyl, are optionally substituted with one or more substituents independently selected from the group consisting of $R^{50}$, $L_7$-$R^{51}$, and $R^{53}$;

$R^{35}$ is selected from the group consisting of $R^{54}$, $L_8$-$R^{51}$, —$OR^{55}$, —$SR^{55}$, methyl, $C_2$-$C_6$ alkyl, $C_2$-$C_6$ alkenyl, $C_2$-$C_6$ alkynyl, cycloalkyl, heterocycloalkyl, aryl, and heteroaryl, wherein methyl is substituted with one or more substituents independently selected from the group consisting of $R^{50}$, $L_7$-$R^{51}$, cycloalkyl, heterocycloalkyl, aryl, and heteroaryl, and wherein $C_2$-$C_6$ alkyl, $C_2$-$C_6$ alkenyl, and $C_2$-$C_6$ alkynyl are optionally substituted with one or more substituents independently selected from the group consisting of $R^{50}$, $L_7$-$R^{51}$, cycloalkyl, heterocycloalkyl, aryl, and heteroaryl, and wherein cycloalkyl and heterocycloalkyl, as $R^{35}$ or as a substituent of methyl, $C_2$-$C_6$ alkyl, $C_2$-$C_6$ alkenyl, or $C_2$-$C_6$ alkynyl, are optionally substituted with one or more substituents independently selected from the group consisting of $R^{50}$, =O, =$NR^{52}$, =$NOR^{52}$, $L_7$-$R^{51}$, and $R^{53}$, and wherein aryl and heteroaryl, as $R^{35}$ or as a substituent of methyl, $C_2$-$C_6$ alkyl, $C_2$-$C_6$ alkenyl, or $C_2$-$C_6$ alkynyl, are optionally substituted with one or more substituents independently selected from the group consisting of $R^{50}$, $L_7$-$R^{51}$, and $R^{53}$; and wherein $R^{34}$, $R^{44}$, $R^{45}$, $R^{46}$, $R^{50}$, $R^{51}$, $R^{52}$, $R^{53}$, $R^{54}$, $R^{55}$, $L_7$, and $L_8$, are as defined for Formula Ia.

In some embodiments of a compound of Formula Ia, further to any of the above embodiments of Formula Ia, $R^{34}$ is selected from the group consisting of —I, —Cl, —$CH_3$, —CH=CH, —CN, —C(=O)$NH_2$, —C(=O)$NHCH_3$, imidazole, triazole, thiazole, oxazole, pyridine, and pyrimidin-4(3H)-one. In one embodiment, $R^{34}$ is —CN, —C(=O)$NH_2$, —C(=O)$NHCH_3$, imidazole, 1,2,4-triazole, or pyrimidin-4(3H)-one. In one embodiment, $R^{34}$ is —CN, —C(=O)$NH_2$, —C(=O)$NHCH_3$,

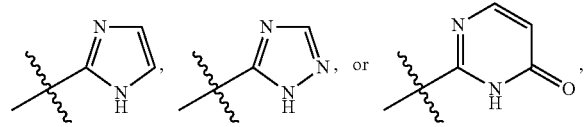 [SMILES: *c1ncc[nH]1 ; *c1ncn[nH]1 ; *c1nccc(=O)[nH]1]

wherein

indicates the point of attachment to the cinnoline 3 position. In one embodiment, $R^{34}$ is —C(=O)$NH_2$, or

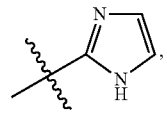

wherein

indicates the point of attachment to the cinnoline 3 position. In one embodiment, $R^{34}$ is —C(=O)$NH_2$.

In some embodiments of a compound of Formula Ia, further to any of the above embodiments of Formula Ia, $R^{33}$ is selected from the group consisting of —$SR^{41}$, or —$NR^{42}R^{43}$, $R^{42}$ is H and $R^{41}$ and $R^{43}$ are independently selected from the group consisting of $C_3$-$C_{10}$ cycloalkyl, 4-7 membered heterocycloalkyl optionally substituted with one $C_1$-$C_6$ alkyl, and $C_1$-$C_6$ alkyl optionally substituted with one substituent selected from the group consisting of —OH, $C_3$-$C_8$ cycloalkyl, 4-7 membered heterocycloalkyl, phenyl and pyridyl. In one embodiment, $R^1$ is —$NR^{42}R^{43}$, $R^{42}$ is H and $R^{43}$ is selected from the group consisting of $C_3$-$C_{10}$ cycloalkyl, 4-7 membered heterocycloalkyl optionally substituted with one $C_1$-$C_6$ alkyl, and $C_1$-$C_6$ alkyl optionally substituted with one substituent selected from the group consisting of —OH, $C_3$-$C_8$ cycloalkyl, 4-7 membered heterocycloalkyl, phenyl and pyridyl.

In some embodiments of a compound of Formula Ia, further to any of the above embodiments of Formula Ia, $R^{33}$ is selected from the group consisting of

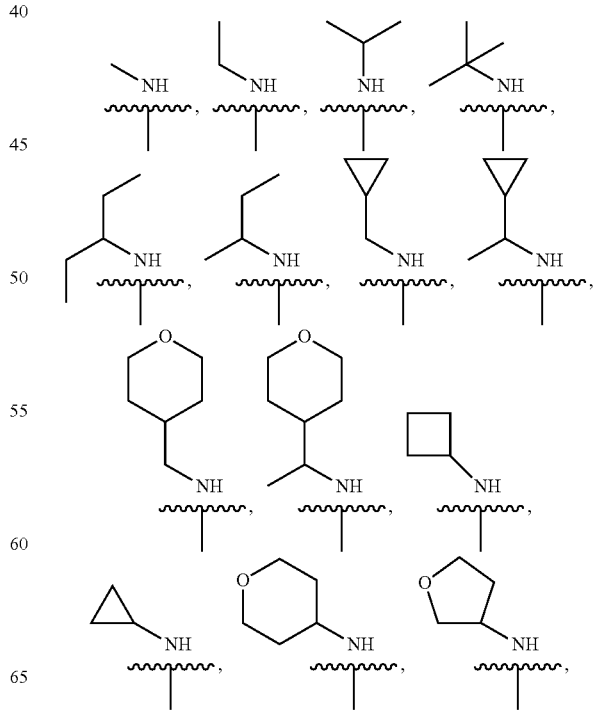

-continued

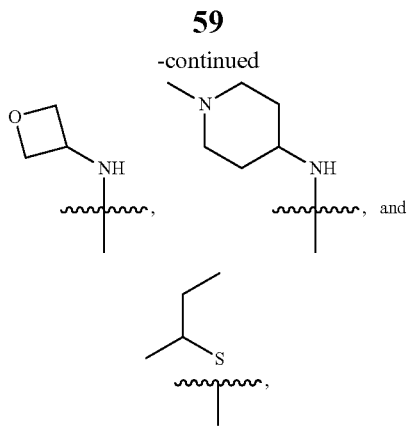

wherein

indicates the point of attachment of $R^{33}$ to the cinnoline 4 position. In one embodiment, $R^{33}$ is selected from the group consisting of

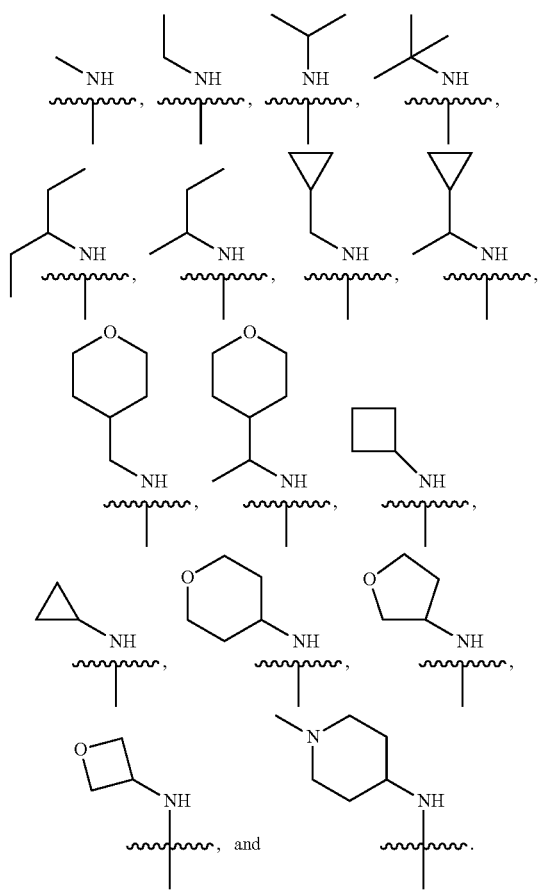

In one embodiment, $R^{33}$ is selected from the group consisting of

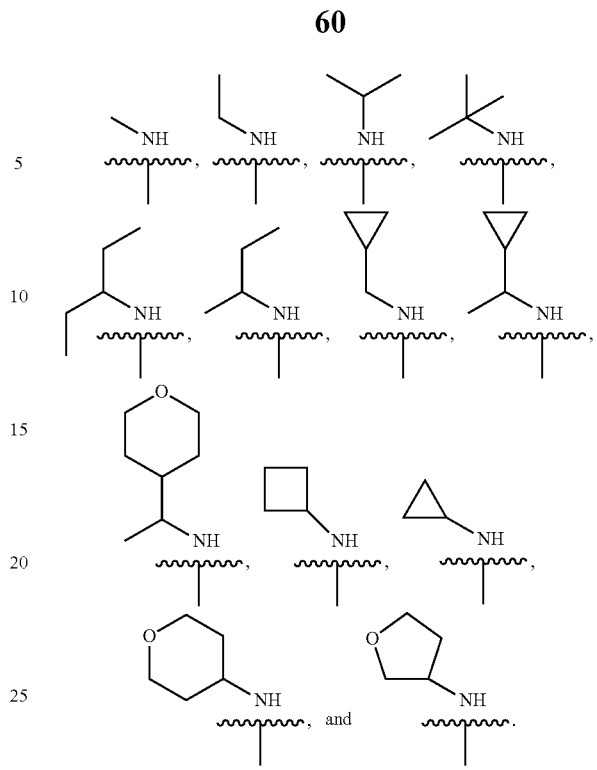

In one embodiment, $R^{33}$ is selected from the group consisting of

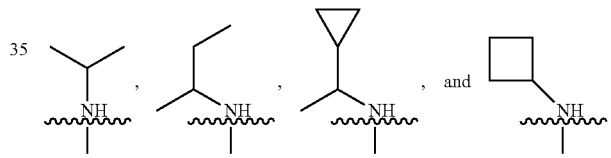

In some embodiments of a compound of Formula Ia, further to any of the above embodiments of Formula Ia, one of $R^{35}$ and $R^{36}$ is H and the other of $R^{35}$ and $R^{36}$ is selected from the group consisting of —NHR$^{55}$, —OR$^{55}$, —SR$^{55}$, $C_2$-$C_4$ alkyl, $C_2$-$C_3$ alkenyl, $C_3$-$C_6$ cycloalkyl, phenyl, heteroaryl, and heterocycloalkyl selected from the group consisting of piperazine, morpholine, pyrrolidine, oxazolidine, dihydropyridine, and indoline, wherein $C_2$-$C_4$ alkyl is optionally substituted with one OH, and wherein heterocycloalkyl is optionally substituted with one or more =O or $C_1$-$C_6$ alkyl, and wherein phenyl and heteroaryl are optionally substituted with one or more substituents independently selected from the group consisting of halogen, —OR$^{51}$, —S(=O)$_2$R$^{51}$, —NR$^{52}$R$^{51}$, —C(=O)NR$^{52}$R$^{51}$, $C_1$-$C_6$ alkyl optionally substituted with one or more $C_1$-$C_6$ alkoxy, piperazine optionally substituted with one or more =O or $C_1$-$C_6$ alkyl, morpholine optionally substituted with one or more =O or $C_1$-$C_6$ alkyl, pyrrolidine optionally substituted with one or more =O or $C_1$-$C_6$ alkyl, oxazolidine optionally substituted with one or more =O or $C_1$-$C_6$ alkyl, phenyl optionally substituted with one or more substituents selected from the group consisting of halogen, $C_1$-$C_6$ alkoxy, morpholine optionally substituted with one or more =O or $C_1$-$C_6$ alkyl, and oxazolidine optionally substituted with one or more =O or $C_1$-$C_6$ alkyl, and heteroaryl optionally substituted with one or more substituents selected from the group consisting of halogen, $C_1$-$C_6$ alkyl, or $C_1$-$C_6$ alkoxy;

$R^{55}$ is phenyl optionally substituted with one or more $C_1$-$C_3$ alkoxy or $C_1$-$C_3$ haloalkoxy, or pyridine optionally substituted with one or more $C_1$-$C_3$ alkoxy or $C_1$-$C_3$ haloalkoxy; $R^{51}$ at each occurrence is independently $C_1$-$C_6$ alkyl optionally substituted with one $C_3$-$C_6$ cycloalkyl or with one or more fluoro; and $R^{52}$ at each occurrence is independently hydrogen or $C_1$-$C_6$ alkyl.

In some embodiments of a compound of Formula Ia, further to any of the above embodiments of Formula Ia, one of $R^{35}$ and $R^{36}$ is H and the other of $R^{35}$ and $R^{36}$ is selected from the group consisting of —$NHR^{55}$, —$OR^{55}$, —$SR^{55}$, $C_2$-$C_4$ alkyl optionally substituted with one OH, $C_2$-$C_3$ alkenyl, $C_3$-$C_6$ cycloalkyl, 4-methyl-piperazine, 1-methyl-pyridin-2(1H)-one, indolin-2-one, pyrrolidin-2-one, morpholine, phenyl, pyridine, pyrimidine, isoquinoline, pyrazole optionally substituted with one methyl, and thiazole, wherein phenyl is optionally substituted with one or more substituents independently selected from the group consisting of halogen, —$OR^{51}$, —$S(=O)_2R^{51}$, —$NR^{52}R^{51}$, —$C(=O)NR^{52}R^{51}$, morpholin-3-one, oxazolidin-2-one, pyridine optionally substituted with one fluoro, pyrazine optionally substituted with one methoxy, imidazole optionally substituted with one methyl, pyrazole optionally substituted with one methyl, and phenyl optionally substituted with one or more substituents selected from the group consisting of halogen, $C_1$-$C_3$ alkoxy, morpholin-3-one, and oxazolidin-2-one; $R^{55}$ is phenyl optionally substituted with one $C_1$-$C_3$ alkoxy, or pyridine optionally substituted with one $C_1$-$C_3$ alkoxy; $R^{51}$ at each occurrence is independently $C_1$-$C_3$ alkyl optionally substituted with one $C_3$-$C_6$ cycloalkyl; and $R^{52}$ at each occurrence is independently $C_1$-$C_3$ alkyl. In one embodiment the other of $R^{35}$ and $R^{36}$ is selected from the group consisting of —$NHR^{55}$, $C_2$-$C_3$ alkenyl, 4-methyl-piperazine, 1-methylpyridin-2(1H)-one, indolin-2-one, phenyl, pyridine, pyrazole optionally substituted with one methyl, and thiazole, wherein phenyl is optionally substituted with one or more substituents independently selected from the group consisting of halogen, —$OR^{51}$, —$S(=O)_2$—$C_1$-$C_3$ alkyl, —$C(=O)N$—$(C_1$-$C_3$ alkyl$)_2$, morpholin-3-one, oxazolidin-2-one, pyridine optionally substituted with one fluoro, pyrazine optionally substituted with one methoxy, imidazole optionally substituted with one methyl, and pyrazole optionally substituted with one methyl; $R^{55}$ is phenyl optionally substituted with one $C_1$-$C_3$ alkoxy, or pyridine optionally substituted with one $C_1$-$C_3$ alkoxy; $R^{51}$ at each occurrence is independently $C_1$-$C_3$ alkyl optionally substituted with one $C_3$-$C_6$ cycloalkyl.

In some embodiments of a compound of Formula Ia, further to any of the above embodiments of Formula Ia, one of $R^{35}$ and $R^{36}$ is H and the other of $R^{35}$ and $R^{36}$ is selected from the group consisting of

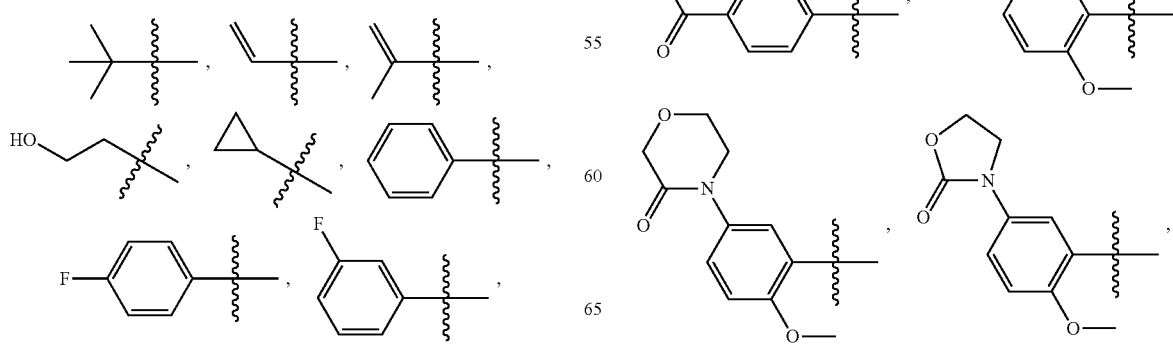

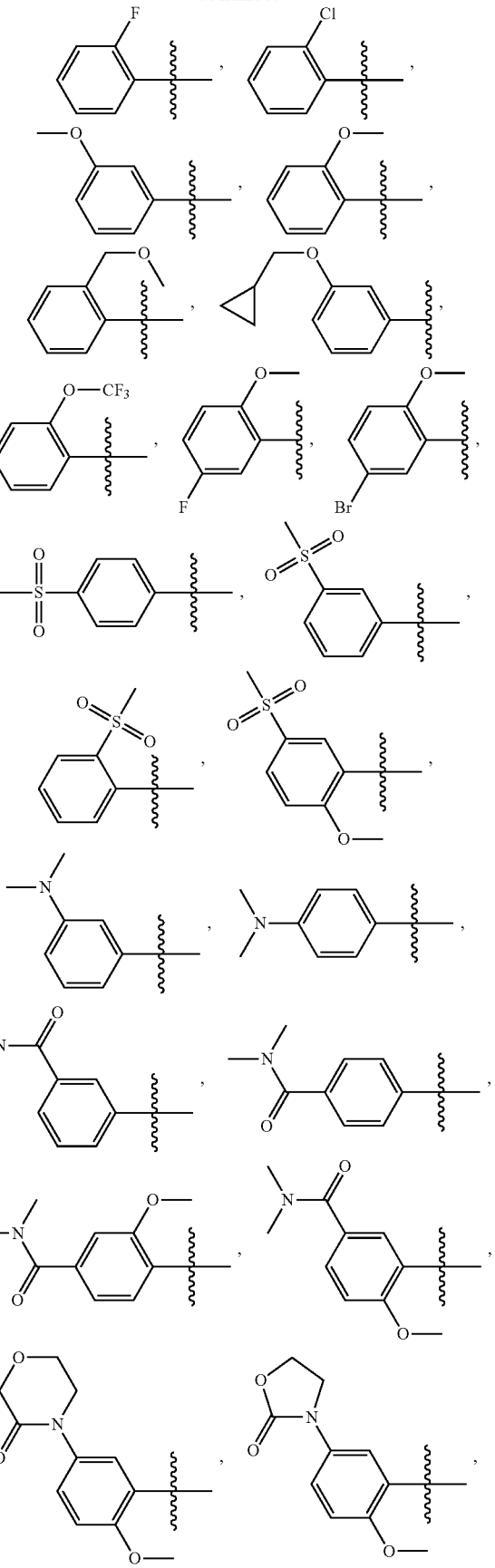

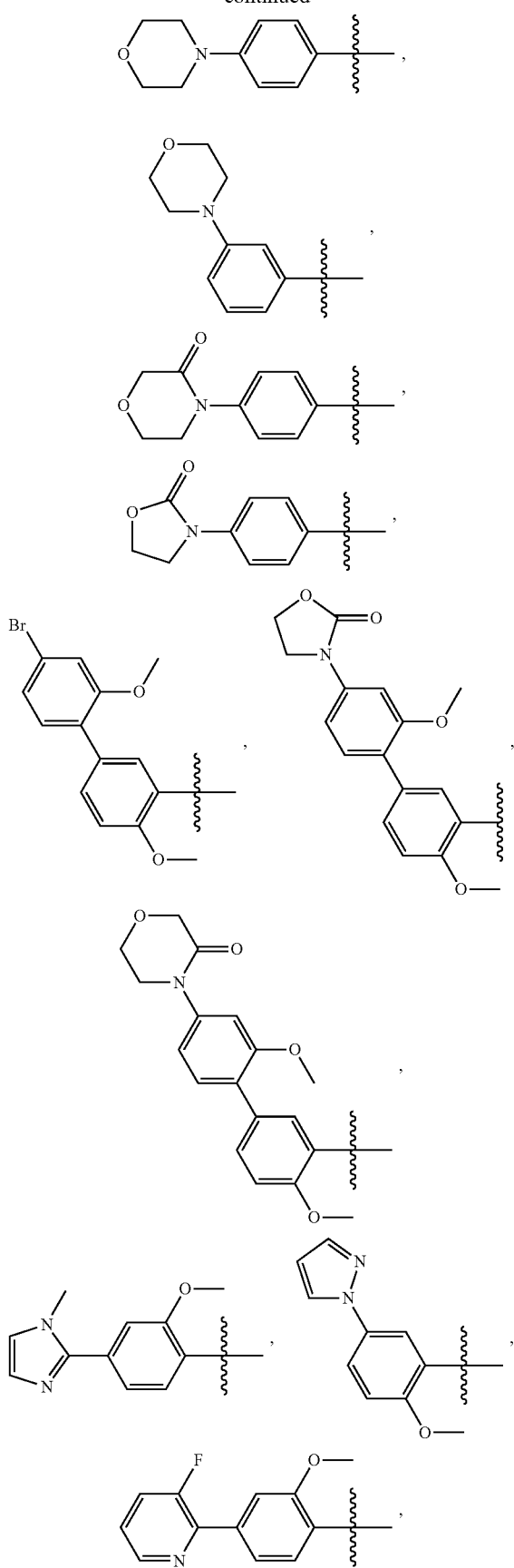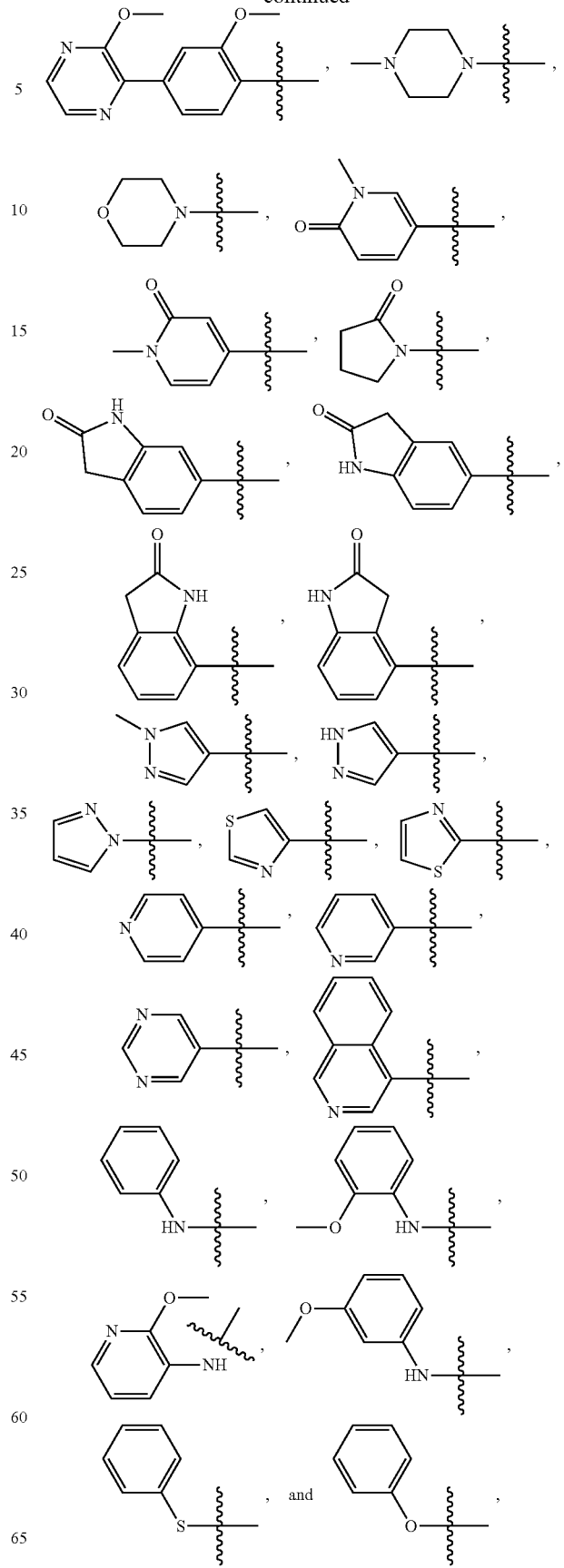

wherein
indicates the point of attachment to the cinnoline 6 or 7 position.
In some embodiments of a compound of Formula Ia, further to any of the above embodiments of Formula Ia, one of $R^{35}$ and $R^{36}$ is H and the other of $R^{35}$ an $R^{36}$ is selected from the group consisting of
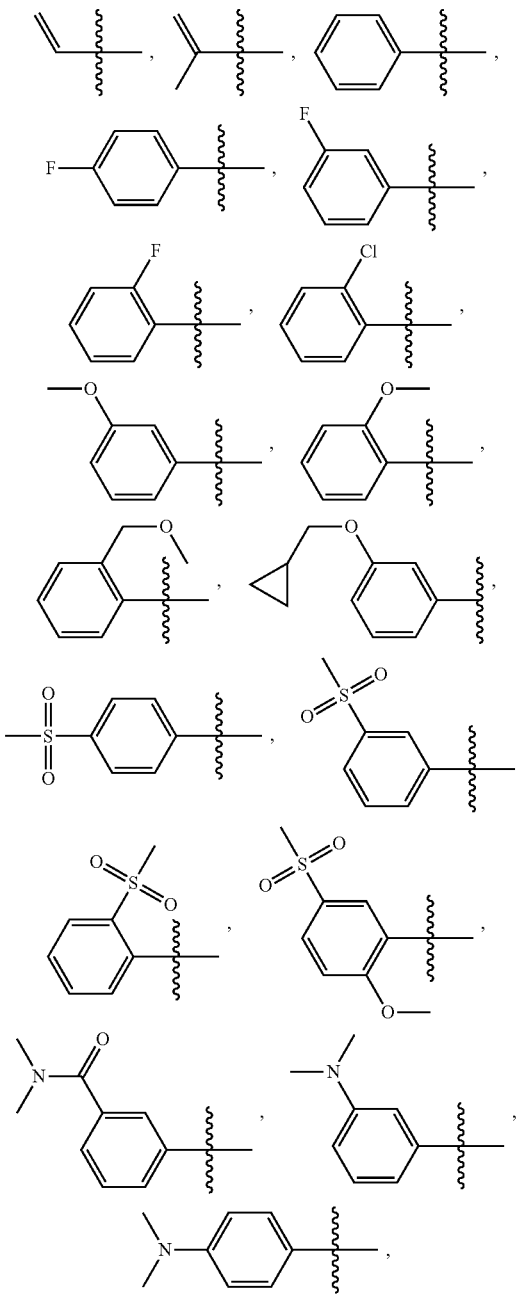
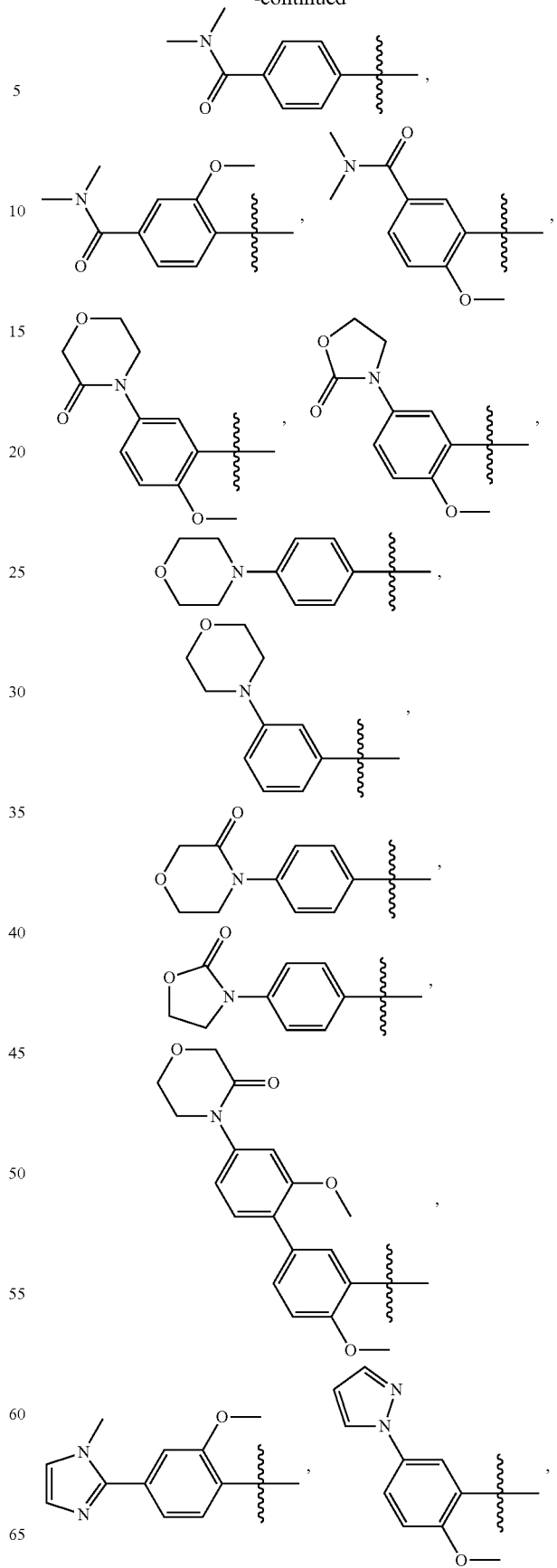

-continued
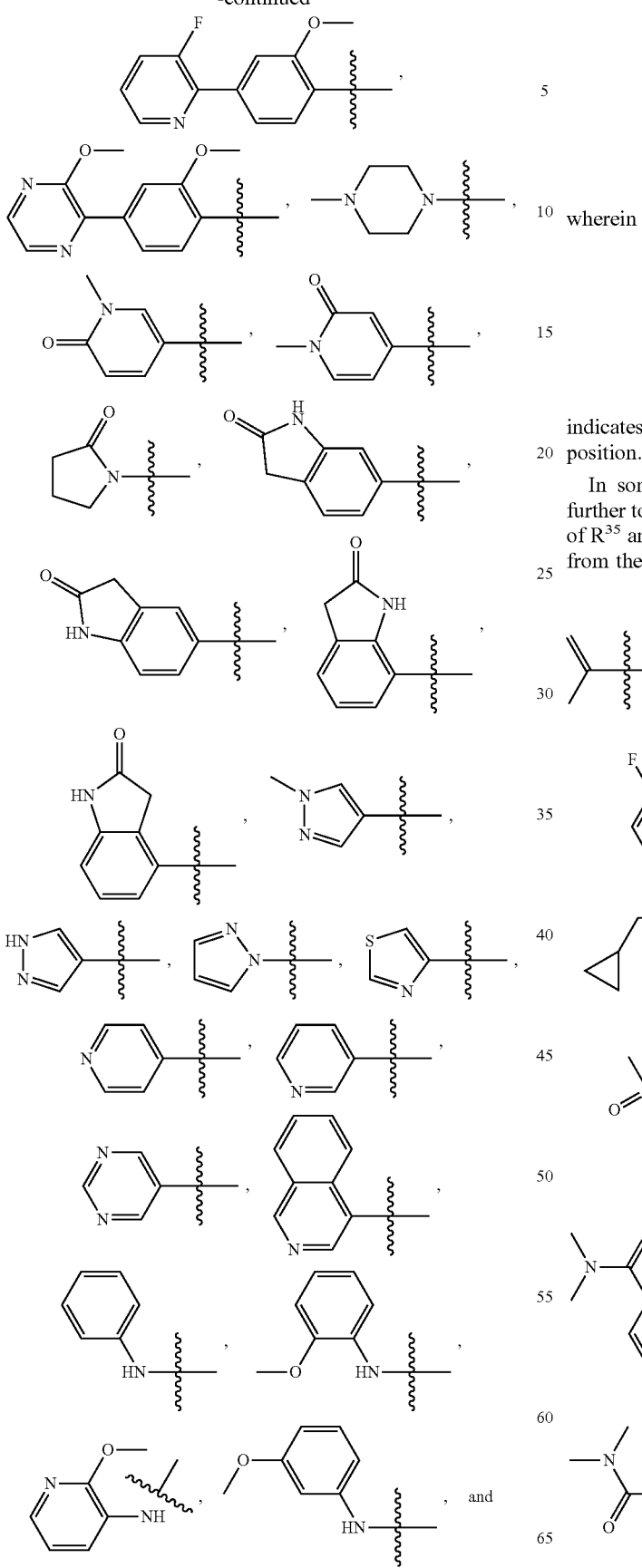
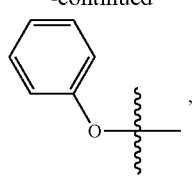
wherein
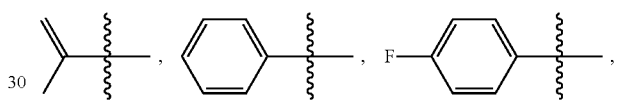
indicates the point of attachment to the cinnoline 6 or 7 position.
In some embodiments of a compound of Formula Ia, further to any of the above embodiments of Formula Ia, one of $R^{35}$ and $R^{36}$ is H and the other of $R^{35}$ and $R^{36}$ is selected from the group consisting of
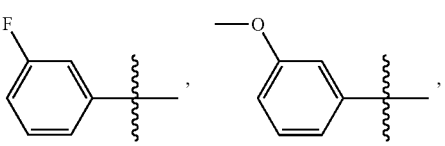
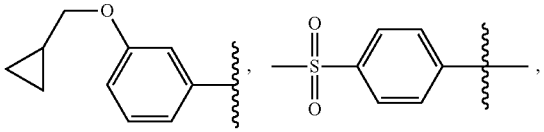
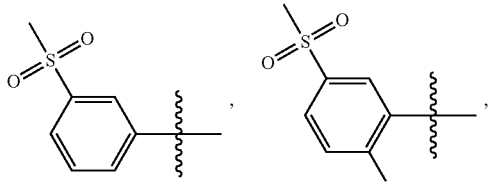
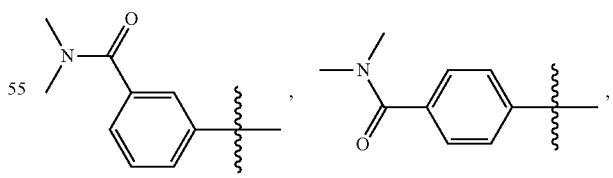
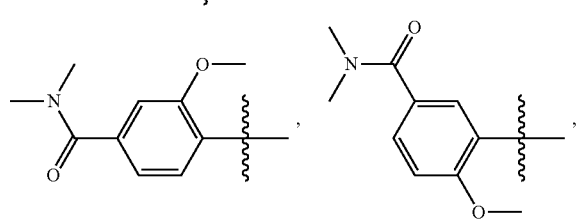

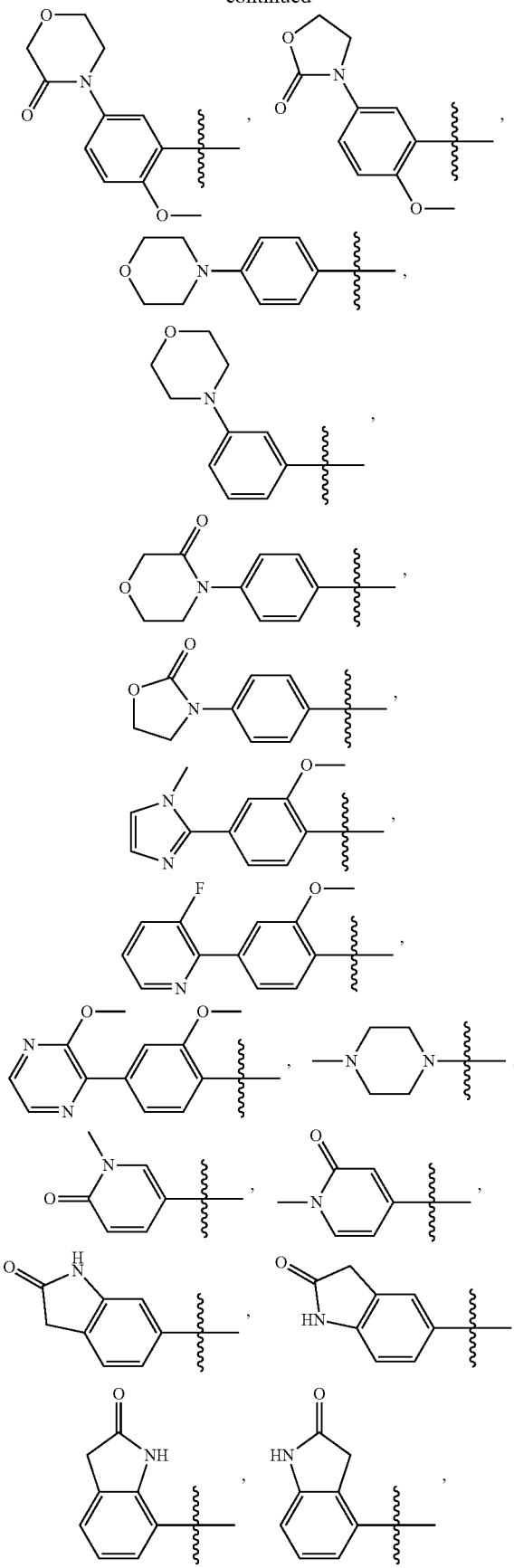
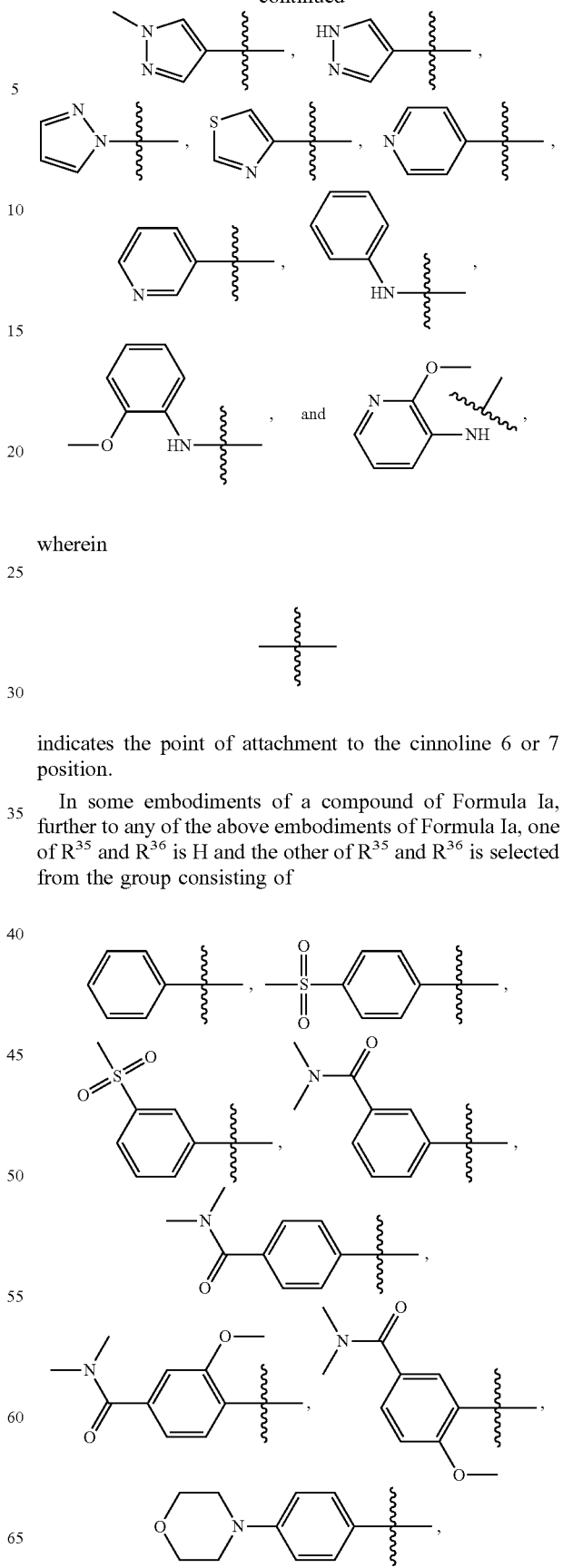
wherein
indicates the point of attachment to the cinnoline 6 or 7 position.
In some embodiments of a compound of Formula Ia, further to any of the above embodiments of Formula Ia, one of $R^{35}$ and $R^{36}$ is H and the other of $R^{35}$ and $R^{36}$ is selected from the group consisting of
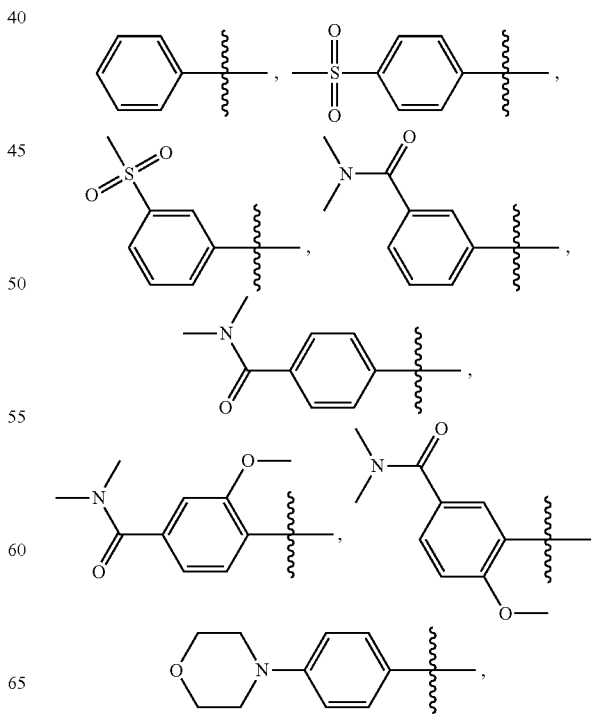

indicates the point of attachment to the cinnoline 6 or 7 position.

In some embodiments of a compound of Formula Ia, further to any of the above embodiments of Formula Ia, when $R^{33}$ is these compounds have an enantiomeric excess of the stereoisomer respectively.

In some embodiments of a compound of Formula Ia, further to any of the above embodiments of Formula Ia, the compound has the structure Ia-1, Ia-1 wherein $R^{34}$, $R^{35}$ and $R^{36}$ are as defined for any of the above embodiments of Formula I.

In some embodiments of a compound of Formula Ia, further to any of the above embodiments of Formula Ia, the compound has the structure Ia-2, Ia-2 wherein $R^{34}$, $R^{35}$ and $R^{36}$ are as defined for any of the above embodiments of Formula I.

In some embodiments of a compound of Formula I, further to any of the above embodiments of Formula I, one of $R^{35}$ and $R^{36}$ is H. In one embodiment $R^{35}$ is H. In one embodiment $R^{36}$ is H.

In some embodiments of a compound of Formula Ia, further to any of the above embodiments of Formula Ia, $R^{34}$ is —C(=O)NH$_2$.

In one aspect, compounds of Formula I are provided having a structure according to Formula Ib:

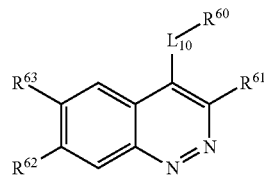

or a salt thereof, wherein:
$L_{10}$ is —O—, —S—, or —NH—;
$R^{60}$ is $C_1$-$C_6$ alkyl optionally substituted with one or more substituents $R^{64}$, $C_3$-$C_{10}$ cycloalkyl, or 4-7 membered heterocycloalkyl optionally substituted with one $C_1$-$C_6$ alkyl;
$R^{61}$ is selected from the group consisting of halogen, —CN, $C_1$-$C_6$ alkyl, $C_2$-$C_6$ alkenyl, $C_2$-$C_6$ alkynyl, —C(=O)NHR$^{65}$, pyrimidinone, or 5 or 6 membered heteroaryl;
one of $R^{62}$ and $R^{63}$ is hydrogen;
the other of $R^{62}$ and $R^{63}$ is selected from the group consisting of —NHR$^{66}$, —OR$^{66}$, —SR$^{66}$, $C_2$-$C_6$ alkyl optionally substituted with one OH, $C_2$-$C_6$ alkenyl, $C_3$-$C_6$ cycloalkyl, heterocycloalkyl optionally substituted with one or more =O or $C_1$-$C_6$ alkyl, phenyl, and heteroaryl, wherein phenyl and heteroaryl are optionally substituted with one or more substituents independently selected from the group consisting of halogen, —OR$^{67}$, —S(=O)$_2$R$^{68}$, —NR$^{69}$R$^{70}$, —C(=O)NR$^{69}$R$^{70}$, $C_1$-$C_6$ alkyl optionally substituted with one or more R$^{71}$, heterocycloalkyl optionally substituted with one or more =O or $C_1$-$C_6$ alkyl, phenyl optionally substituted with one or more R$^{72}$, and heteroaryl optionally substituted with one or more R$^{73}$;
$R^{64}$ at each occurrence is independently selected from the group consisting of —OH, $C_3$-$C_8$ cycloalkyl, 4-7 membered heterocycloalkyl, phenyl and pyridyl;
$R^{65}$ is hydrogen or $C_1$-$C_6$ alkyl;
$R^{66}$ is phenyl optionally substituted with one or more R$^{70}$, or 5 or 6 membered heteroaryl optionally substituted with one or more R$^{71}$;
$R^{67}$, $R^{68}$ and $R^{69}$ are independently $C_1$-$C_6$ alkyl optionally substituted with one or more R$^{71}$;
$R^{70}$ is hydrogen or $C_1$-$C_6$ alkyl optionally substituted with one or more R$^{71}$;
$R^{71}$ is halogen, $C_1$-$C_6$ alkoxy, $C_1$-$C_6$ haloalkoxy, or $C_3$-$C_6$ cycloalkyl;
$R^{72}$ is halogen, $C_1$-$C_6$ alkyl, $C_1$-$C_6$ haloalkyl, $C_1$-$C_6$ alkoxy, $C_1$-$C_6$ haloalkoxy, or 4-7 membered heterocycloalkyl optionally substituted with one or more =O or $C_1$-$C_6$ alkyl; and
$R^{73}$ is halogen, $C_1$-$C_6$ alkyl, $C_1$-$C_6$ haloalkyl, $C_1$-$C_6$ alkoxy, $C_1$-$C_6$ haloalkoxy, or 4-7 membered heterocycloalkyl optionally substituted with one or more =O or $C_1$-$C_6$ alkyl.

In some embodiments of a compound of Formula Ib, $R^{61}$ is selected from the group consisting of —I, —Cl, —CH$_3$, —CH=CH, —CN, —C(=O)NH$_2$, —C(=O)NHCH$_3$, imidazole, triazole, thiazole, oxazole, pyridine, and pyrimidin-4(3H)-one. In some embodiments, $R^{61}$ is —CN, —C(=O)NH$_2$, —C(=O)NHCH$_3$, imidazole, 1,2,4-triazole, or pyrimidin-4(3H)-one, in one instance —CN, —C(=O)NH$_2$, —C(=O)NHCH$_3$,

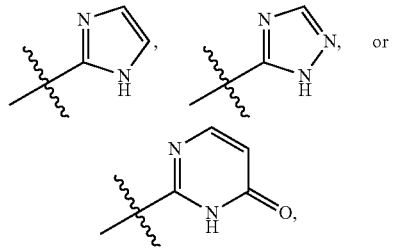

wherein

indicates the point of attachment to the cinnoline 3 position. In some embodiments, $R^{61}$ is —C(=O)NH$_2$, or

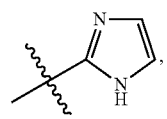

wherein

indicates the point of attachment to the cinnoline 3 position.

In some embodiments of a compound of Formula Ib, further to any of the above embodiments of Formula Ib, $L_{10}$ is —S—, or —NH— and $R^{60}$ is selected from the group consisting of $C_3$-$C_{10}$ cycloalkyl, 4-7 membered heterocycloalkyl optionally substituted with one $C_1$-$C_6$ alkyl, and $C_1$-$C_6$ alkyl optionally substituted with one substituent selected from the group consisting of —OH, $C_3$-$C_8$ cycloalkyl, 4-7 membered heterocycloalkyl, phenyl and pyridyl. In one embodiment, $L_{10}$ is —NH— and $R^{60}$ is selected from the group consisting of $C_3$-$C_{10}$ cycloalkyl, 4-7 membered heterocycloalkyl optionally substituted with one $C_1$-$C_6$ alkyl, and $C_1$-$C_6$ alkyl optionally substituted with one substituent selected from the group consisting of —OH, $C_3$-$C_8$ cycloalkyl, 4-7 membered heterocycloalkyl, phenyl and pyridyl.

In some embodiments of a compound of Formula Ib, further to any of the above embodiments of Formula Ib, one of $R^{62}$ and $R^{63}$ is hydrogen and the other of $R^{62}$ and $R^{63}$ is selected from the group consisting of —NHR$^{66}$, —OR$^{66}$, —SR$^{66}$, $C_2$-$C_4$ alkyl, $C_2$-$C_3$ alkenyl, $C_3$-$C_6$ cycloalkyl, phenyl, heteroaryl, and heterocycloalkyl selected from the group consisting of piperazine, morpholine, pyrrolidine, oxazolidine, dihydropyridine, and indoline, wherein $C_2$-$C_4$ alkyl is optionally substituted with one OH, and wherein heterocycloalkyl is optionally substituted with one or more =O or $C_1$-$C_6$ alkyl, and wherein phenyl and heteroaryl are optionally substituted with one or more substituents independently selected from the group consisting of halogen, —OR$^{67}$, —S(=O)$_2$R$^{68}$, —NR$^{69}$R$^{70}$, —C(=O)NR$^{69}$R$^{70}$, $C_1$-$C_6$ alkyl optionally substituted with one or more $C_1$-$C_6$ alkoxy, piperazine optionally substituted with one or more =O or $C_1$-$C_6$ alkyl, morpholine optionally substituted with one or more =O or $C_1$-$C_6$ alkyl, pyrrolidine optionally substituted with one or more =O or $C_1$-$C_6$ alkyl, oxazolidine optionally substituted with one or more =O or $C_1$-$C_6$ alkyl, phenyl optionally substituted with one or more $R^{72}$, and heteroaryl optionally substituted with one or more $R^{73}$; $R^{66}$ is phenyl optionally substituted with one or more $C_1$-$C_3$ alkoxy or $C_1$-$C_3$ haloalkoxy, or pyridine optionally substituted with one or more $C_1$-$C_3$ alkoxy or $C_1$-$C_3$ haloalkoxy; $R^{67}$ at each occurrence is independently $C_1$-$C_6$ alkyl optionally substituted with one $C_3$-$C_6$ cycloalkyl or with one or more fluoro; $R^{68}$ and $R^{69}$ at each occurrence are independently $C_1$-$C_6$ alkyl; $R^{70}$ at each occurrence is independently hydrogen or $C_1$-$C_6$ alkyl; $R^{72}$ at each occurrence is independently halogen, $C_1$-$C_6$ alkoxy, morpholine optionally substituted with one or more =O or $C_1$-$C_6$ alkyl, or oxazolidine optionally substituted with one or more =O or $C_1$-$C_6$ alkyl; and $R^{73}$ at each occurrence is independently halogen, $C_1$-$C_6$ alkyl, or $C_1$-$C_6$ alkoxy.

In some embodiments of a compound of Formula Ib, further to any of the above embodiments of Formula Ib, one of $R^{62}$ and $R^{63}$ is hydrogen; the other of $R^{62}$ and $R^{63}$ is selected from the group consisting of —$NHR^{66}$, —OR, —$SR^{66}$, $C_2$-$C_4$ alkyl optionally substituted with one OH, $C_2$-$C_3$ alkenyl, $C_3$-$C_6$ cycloalkyl, 4-methyl-piperazine, 1-methylpyridin-2(1H)-one, indolin-2-one, pyrrolidin-2-one, morpholine, phenyl, pyridine, pyrimidine, isoquinoline, pyrazole optionally substituted with one methyl, and thiazole, wherein phenyl is optionally substituted with one or more substituents independently selected from the group consisting of halogen, —$OR^{67}$, —S(=O)$_2R^{68}$, —$NR^{69}R^{70}$, —C(=O)$NR^{69}R^{70}$, morpholin-3-one, oxazolidin-2-one, pyridine optionally substituted with one fluoro, pyrazine optionally substituted with one methoxy, imidazole optionally substituted with one methyl, pyrazole optionally substituted with one methyl, and phenyl optionally substituted with one or more halogen, $C_1$-$C_3$ alkoxy, morpholin-3-one, or oxazolidin-2-one; $R^{66}$ is phenyl optionally substituted with one $C_1$-$C_3$ alkoxy, or pyridine optionally substituted with one $C_1$-$C_3$ alkoxy; $R^{67}$ at each occurrence is independently $C_1$-$C_3$ alkyl optionally substituted with one $C_3$-$C_6$ cycloalkyl; and $R^{68}$, $R^{69}$, and $R^{70}$ at each occurrence are independently $C_1$-$C_3$ alkyl. In some embodiments one of $R^{62}$ and $R^{63}$ is hydrogen; the other of $R^{62}$ and $R^{63}$ is selected from the group consisting of —$NHR^{66}$, $C_2$-$C_3$ alkenyl, 4-methyl-piperazine, 1-methylpyridin-2(1H)-one, indolin-2-one, phenyl, pyridine, pyrazole optionally substituted with one methyl, and thiazole, wherein phenyl is optionally substituted with one or more substituents independently selected from the group consisting of halogen, —$OR^{67}$, —S(=O)$_2R^{68}$, —C(O)$NR^{69}R^{70}$, morpholin-3-one, oxazolidin-2-one, pyridine optionally substituted with one fluoro, pyrazine optionally substituted with one methoxy, imidazole optionally substituted with methyl, and pyrazole optionally substituted with methyl; $R^{66}$ is phenyl optionally substituted with one $C_1$-$C_3$ alkoxy, or pyridine optionally substituted with one $C_1$-$C_3$ alkoxy; $R^{67}$ at each occurrence is independently $C_1$-$C_6$ alkyl optionally substituted with one $C_3$-$C_6$ cycloalkyl; and $R^{68}$, $R^{69}$, and $R^{70}$ at each occurrence are independently $C_1$-$C_3$ alkyl.

In some embodiments of a compound of Formula Ib, $L_{10}$-$R^{60}$ is selected from the group consisting of

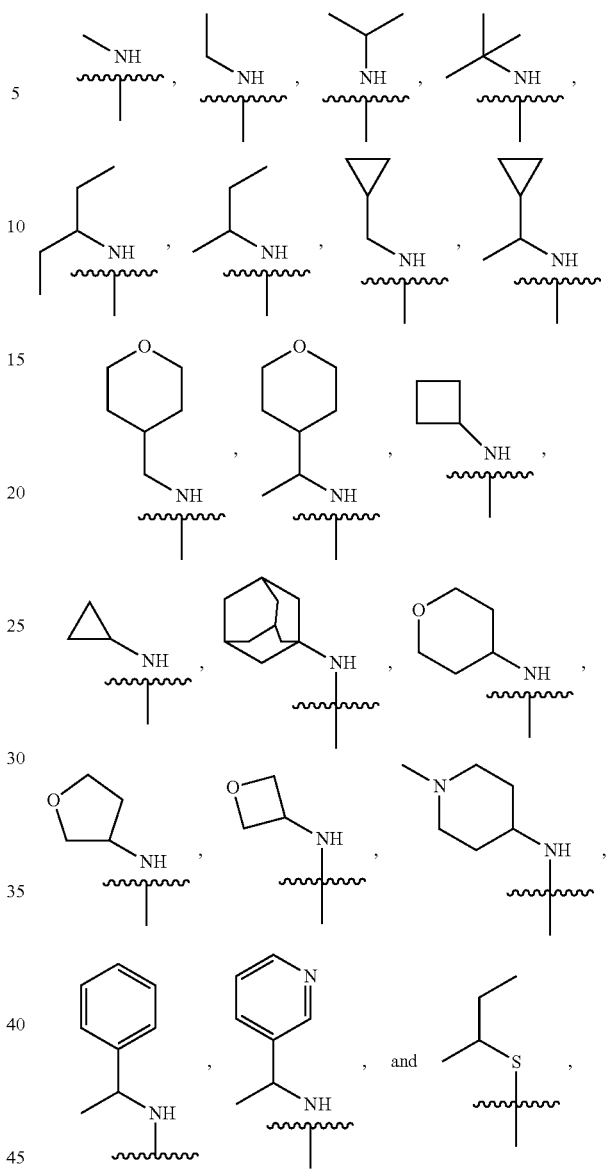

wherein

indicates the point of attachment of $L_{10}$ to the cinnoline 4 position; $R^{61}$ is selected from the group consisting of —I, —Cl, —$CH_3$, —CH≡CH, —CN, —C(=O)$NH_2$, —C(=O)$NHCH_3$,

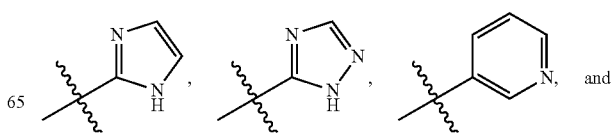

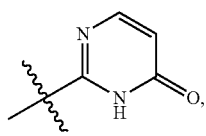
wherein
indicates the point of attachment to the cinnoline 3 position; one of R⁶² and R⁶³ is hydrogen; and the other of R⁶² and R⁶³ is selected from the group consisting of
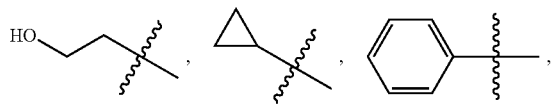
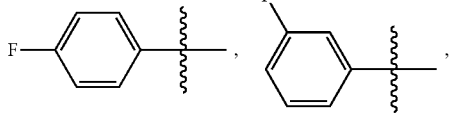
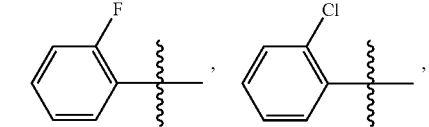
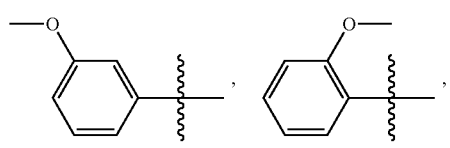
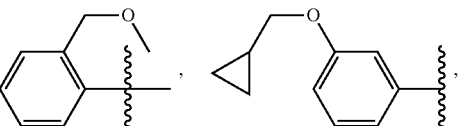
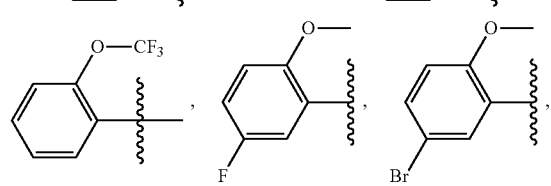
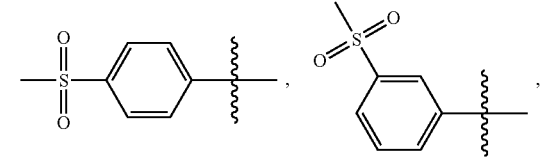
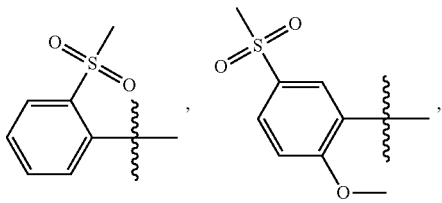
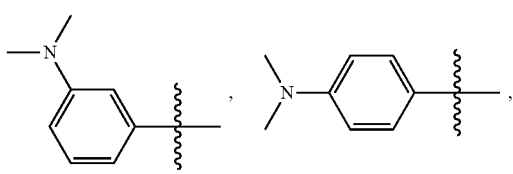
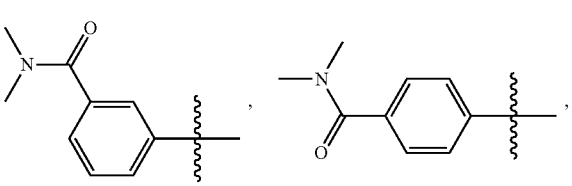
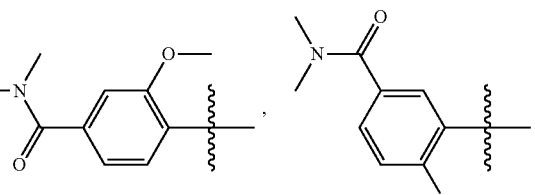
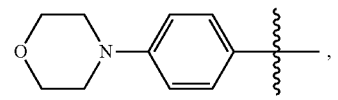
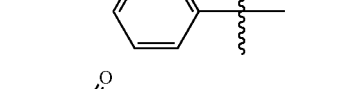
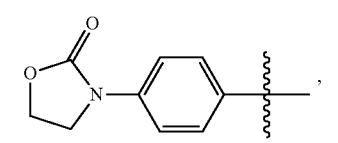

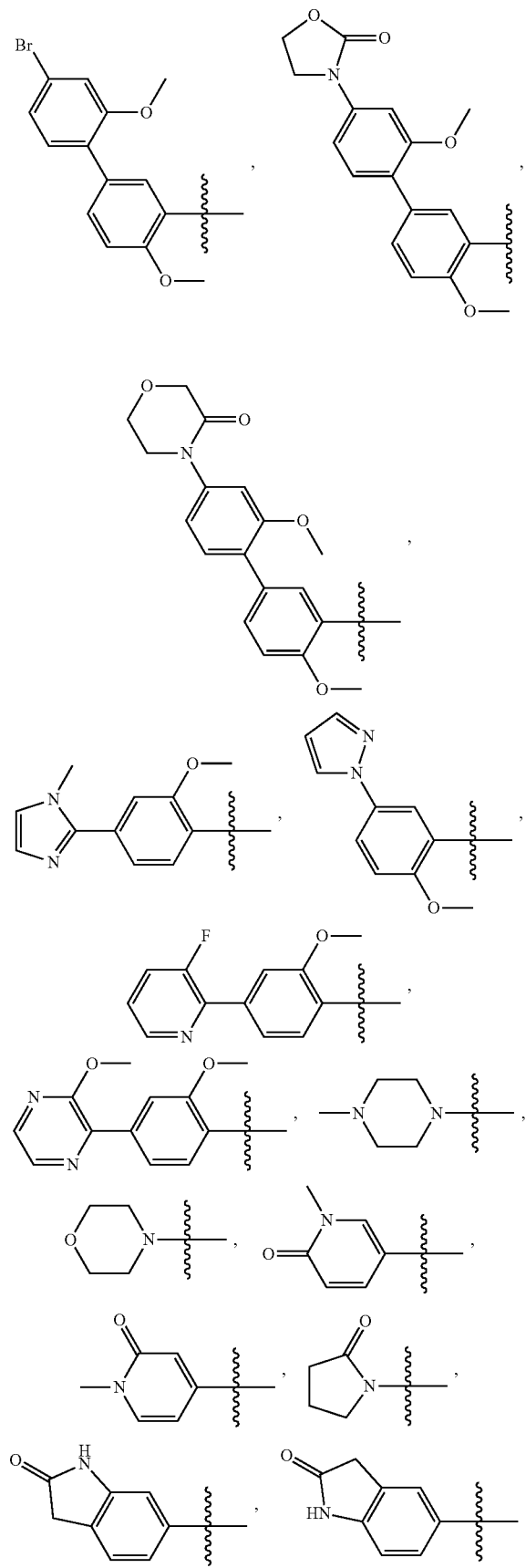
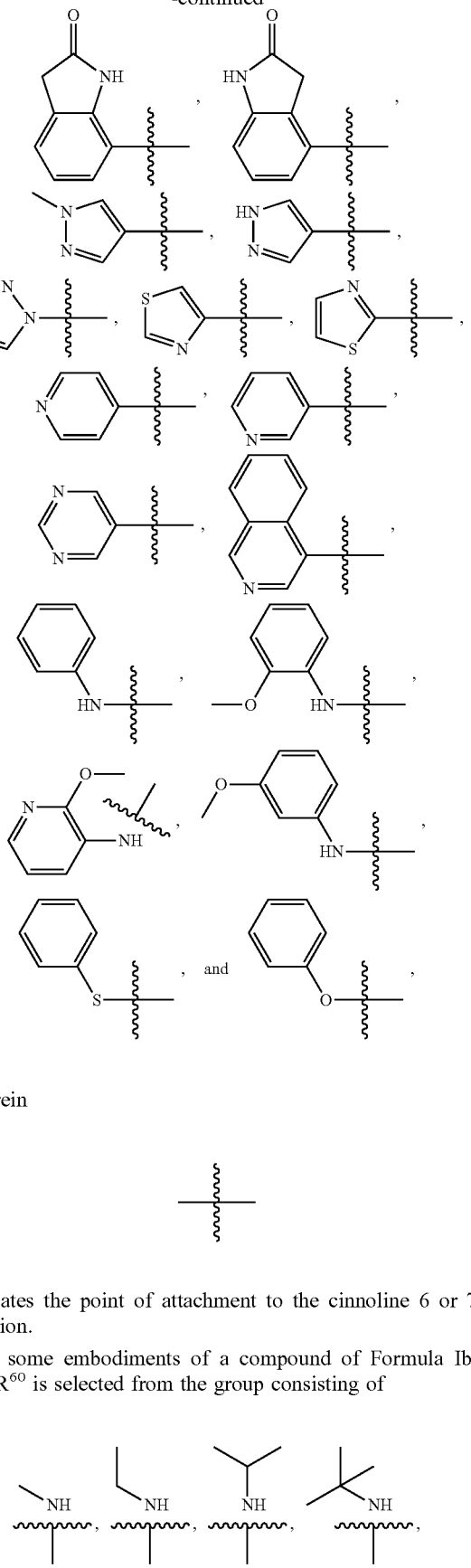
wherein
indicates the point of attachment to the cinnoline 6 or 7 position.
In some embodiments of a compound of Formula Ib, $L_{10}$-$R^{60}$ is selected from the group consisting of
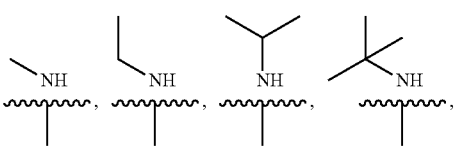

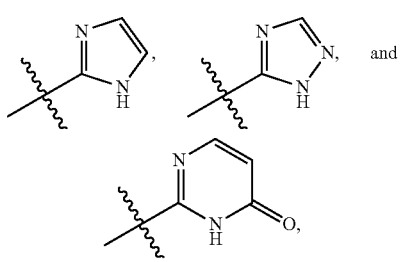
wherein
indicates the point of attachment of L$_{10}$ to the cinnoline 4 position; R$^{61}$ is selected from the group consisting of —CN, —C(=O)NH$_2$, —C(=O)NHCH$_3$,
wherein
indicates the point of attachment to the cinnoline 3 position; one of R$^{62}$ and R$^{63}$ is hydrogen; and the other of R$^{62}$ and R$^{63}$ is selected from the group consisting of
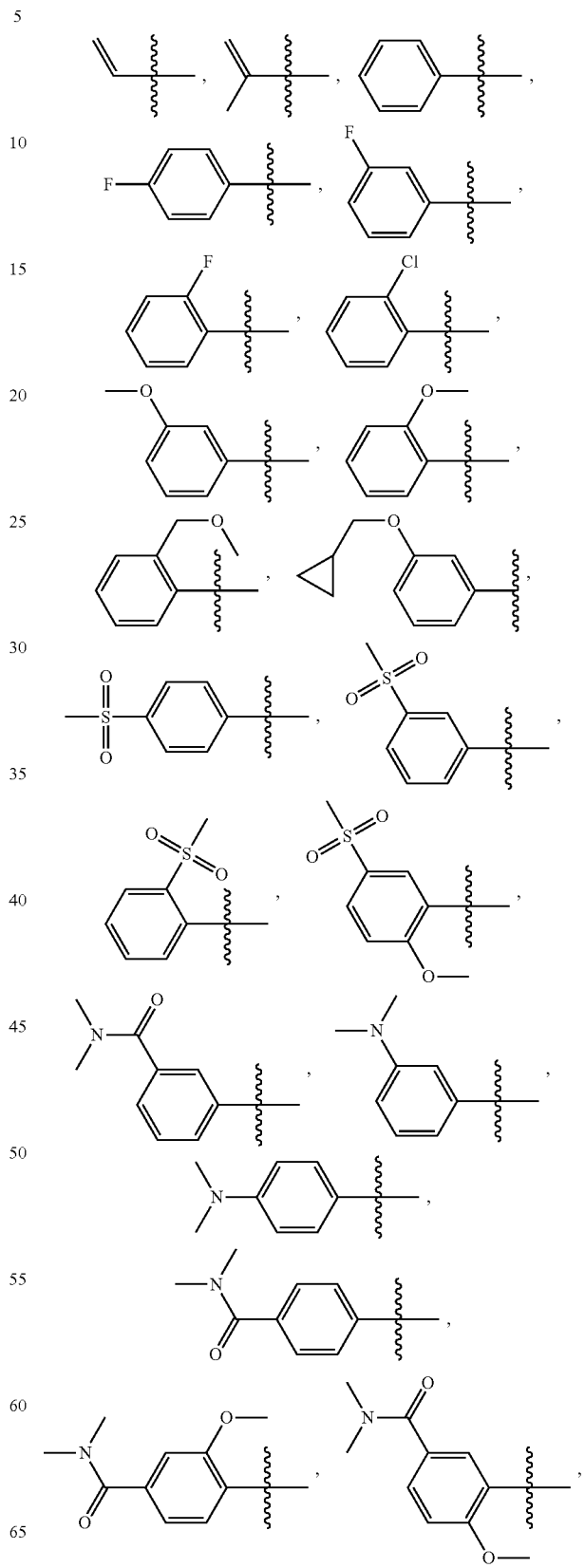

-continued
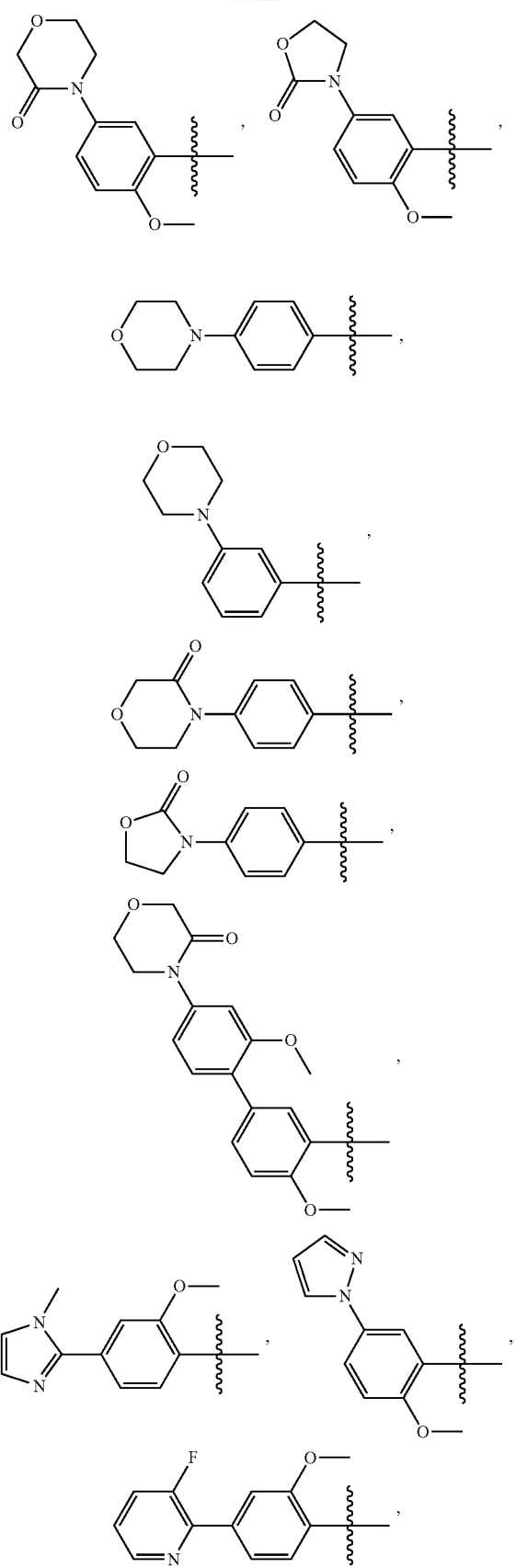
-continued
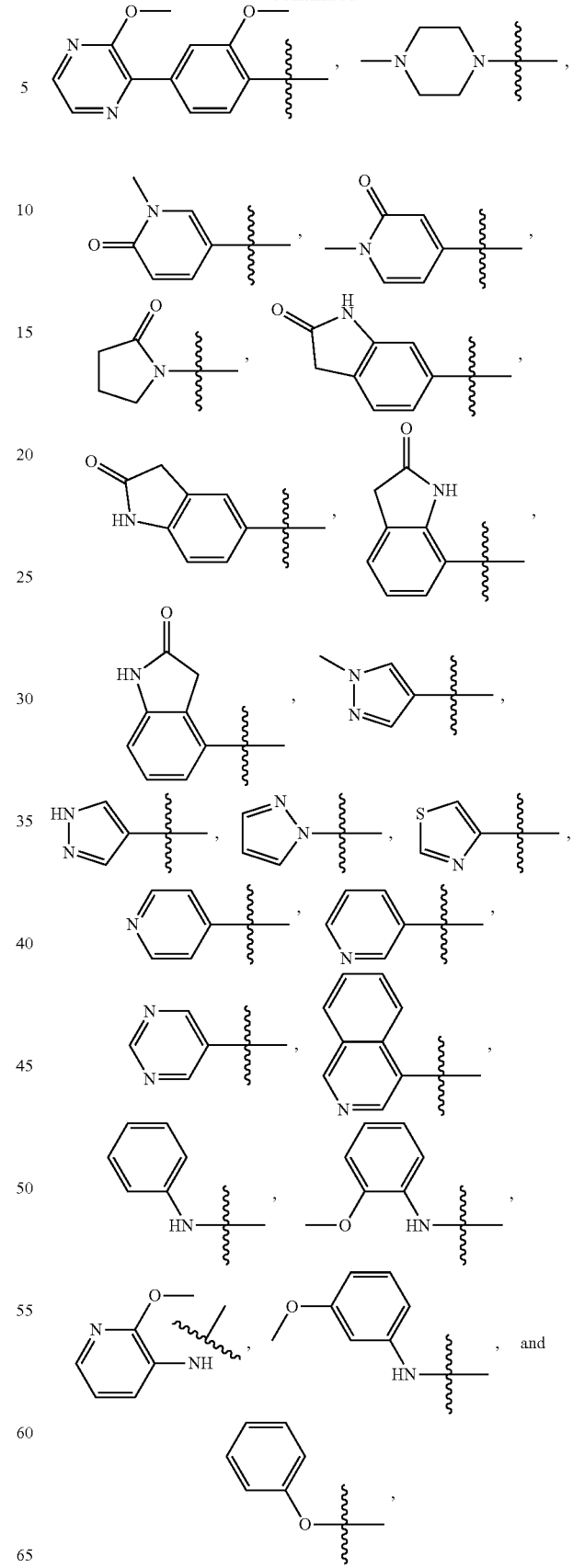

wherein

indicates the point of attachment to the cinnoline 6 or 7 position.

In some embodiments of a compound of Formula Ib, $L_{10}$-$R^{60}$ is selected from the group consisting of

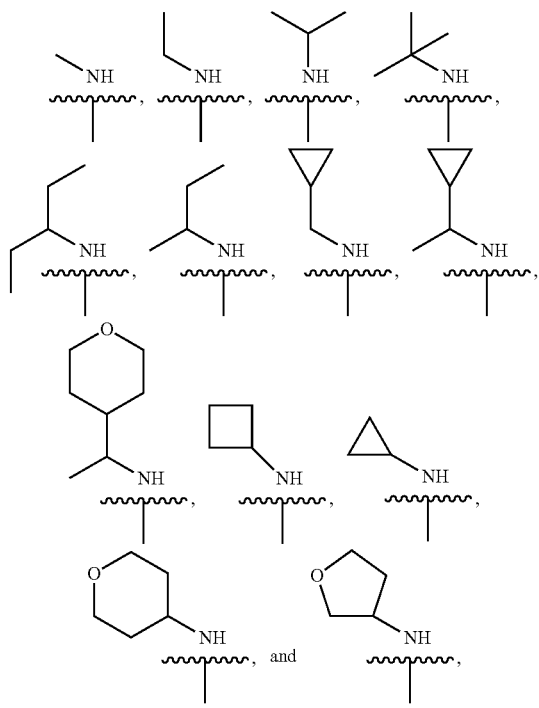

wherein

indicates the point of attachment of $L_{10}$ to the cinnoline 4 position; $R^{61}$ is —C(=O)NH$_2$ or

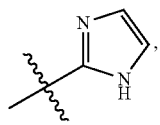 [SMILES: *c1ncc[nH]1]

wherein

indicates the point of attachment to the cinnoline 3 position; one of $R^{62}$ and $R^{63}$ is hydrogen; and the other of $R^{62}$ and $R^{63}$ is selected from the group consisting of

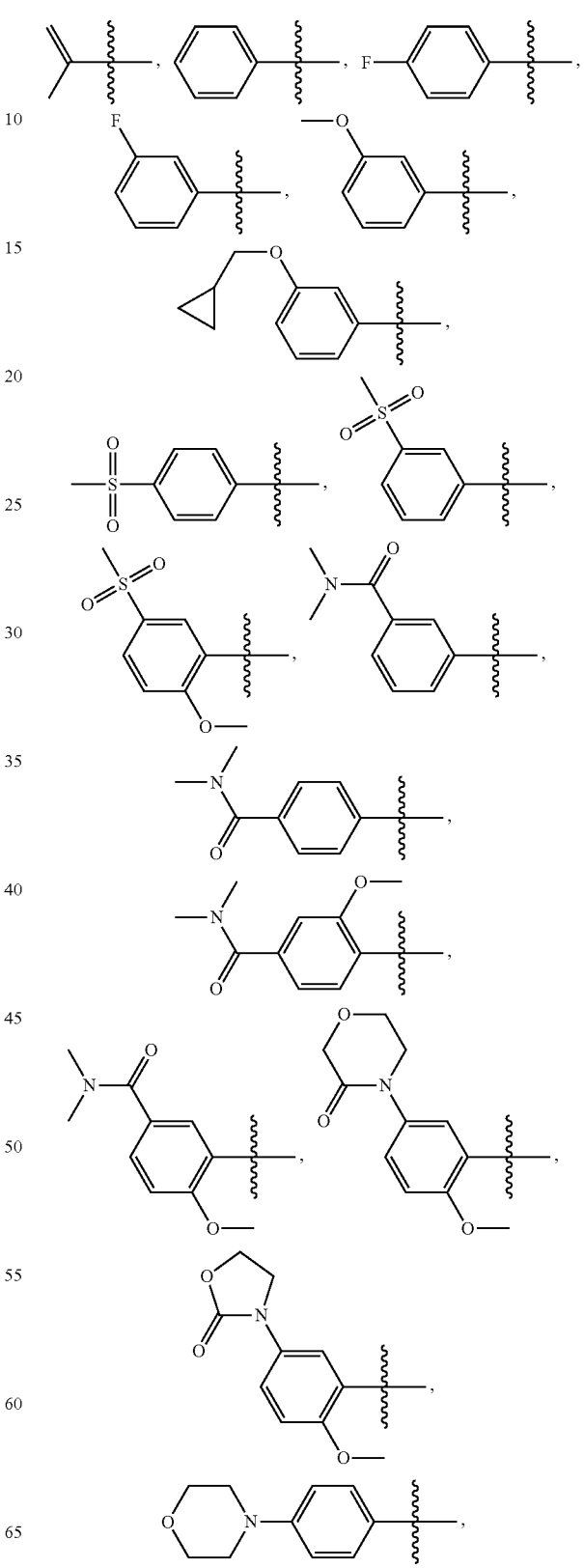

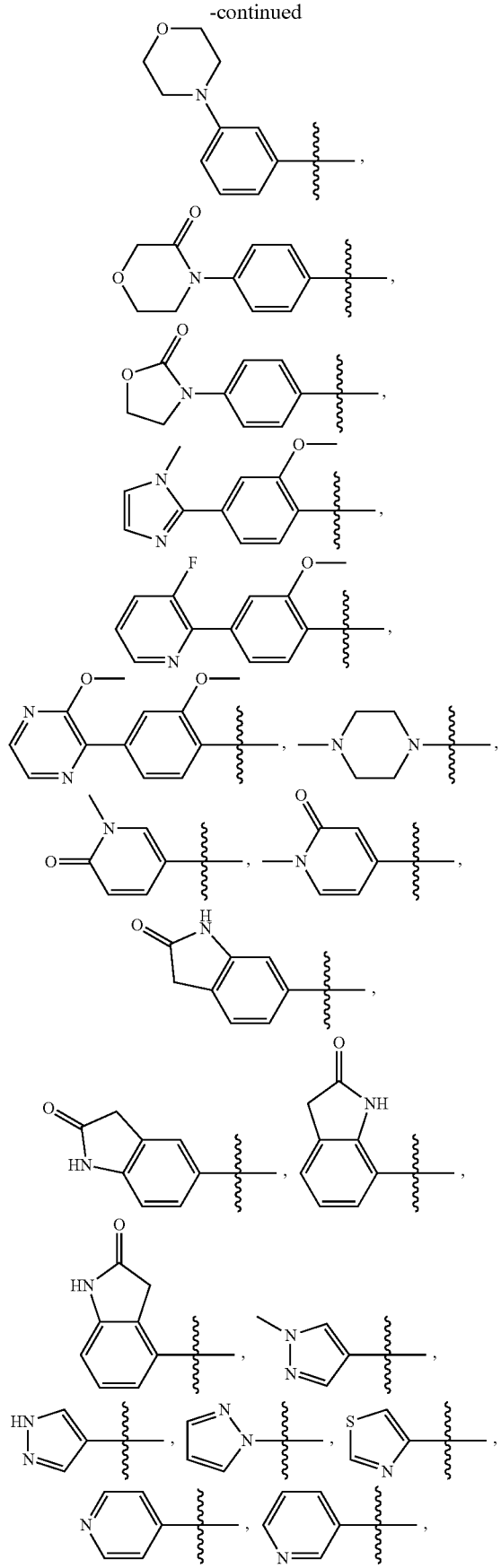
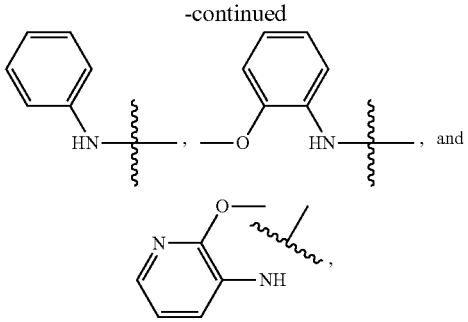
indicates the point of attachment to the cinnoline 6 or 7 position.
In some embodiments of a compound of Formula Ib, $L_{10}$-$R^{60}$ is selected from the group consisting of
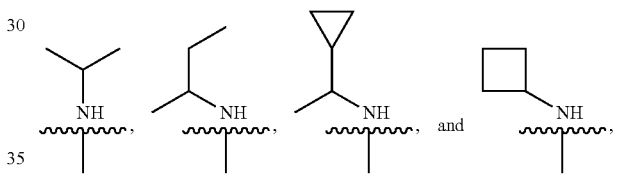
wherein
indicates the point of attachment of $L_{10}$ to the cinnoline 4 position; $R^{61}$ is —C(=O)NH$_2$; one of $R^{62}$ and $R^{63}$ is hydrogen; and the other of $R^{62}$ and $R^{63}$ is selected from the group consisting of
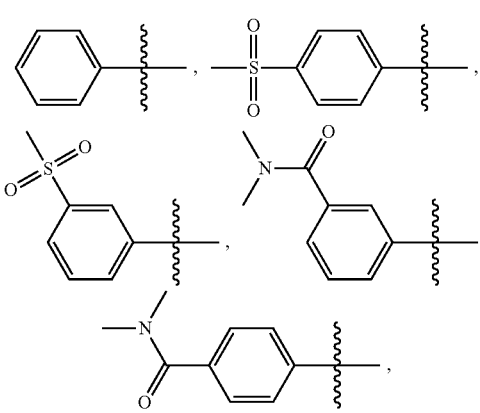

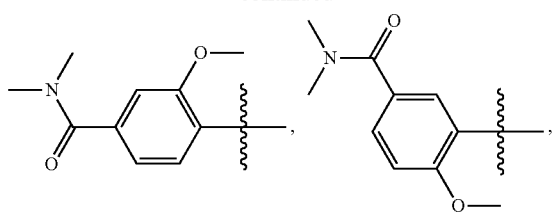,

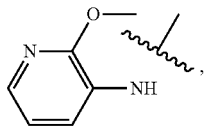, wherein

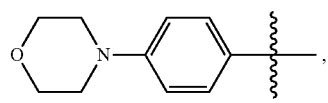,

indicates the point of attachment to the cinnoline 6 or 7 position.

In some embodiments of a compound of Formula Ib, further to any of the above embodiments of Formula Ib, $R^{63}$ is H.

In some embodiments of a compound of Formula Ib, further to any of the above embodiments of Formula Ib, $L_{10}$-$R^{60}$ is

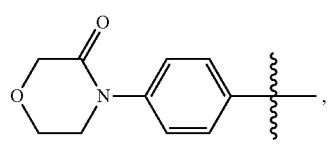,

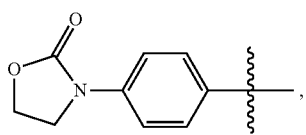,

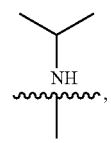

wherein

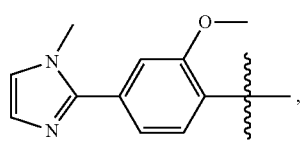,

indicates the point of attachment of $L_{10}$ to the cinnoline 4 position; $R^{61}$ is —CN or —C(=O)NH$_2$; $R^{62}$ is H; and $R^{63}$ is selected from the group consisting of

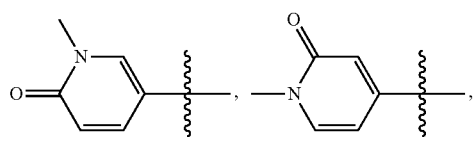,

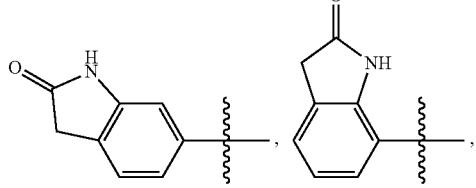,

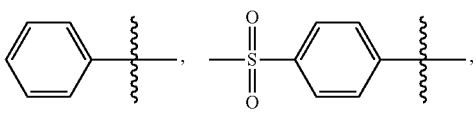,

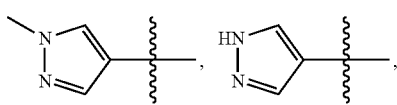, 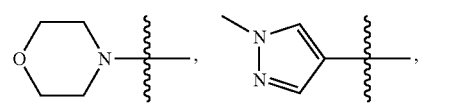

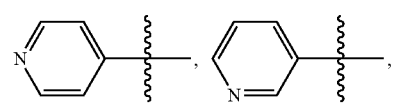, and

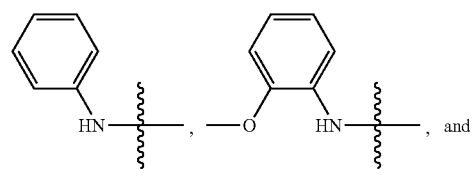, 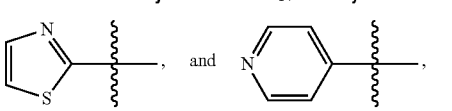

and wherein

indicates the point of attachment to the cinnoline 6 position.
In some embodiments, $L_{10}$-$R^{60}$ is

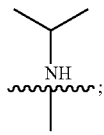

$R^{61}$ is —CN or —C(=O)NH$_2$; $R^{62}$ is H; and $R^{63}$ is selected from the group consisting of

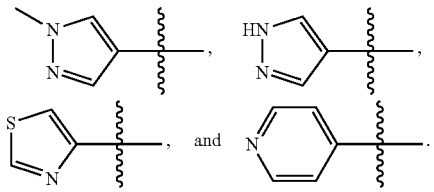

In some embodiments, $L_{10}$-$R^{60}$ is

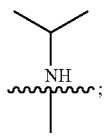

$R^{61}$ is —C(=O)NH$_2$; $R^{62}$ is H; and $R^{63}$ is

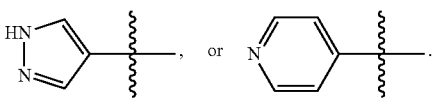 [SMILES: *c1cn[nH]c1 ; *c1ccncc1]

In some embodiments of a compound of Formula Ib, further to any of the above embodiments of Formula Ib, when $L_{10}$-$R^{60}$ is

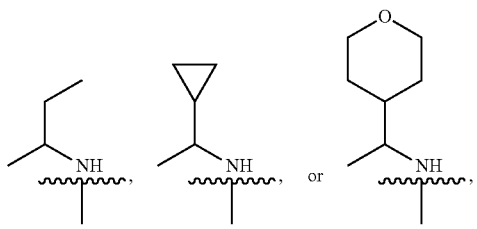

these compounds have an enantiomeric excess of the stereoisomer

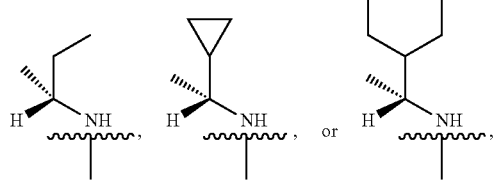

respectively.

In some embodiments of a compound of Formula Ib, further to any of the above embodiments of Formula Ib, the compound has the structure Ib-1, Ib-1

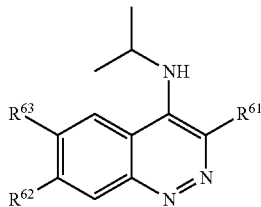

wherein $R^{61}$, $R^{62}$ and $R^{63}$ are as defined for any of the above embodiments of Formula Ib.

In some embodiments of a compound of Formula Ib, further to any of the above embodiments of Formula Ib, the compound has the structure Ib-2, Ib-2

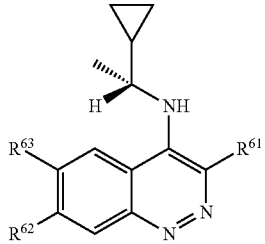

wherein $R^{61}$, $R^{62}$ and $R^{63}$ are as defined for any of the above embodiments of Formula Ib.

In some embodiments of a compound of Formula Ib, further to any of the above embodiments of Formula Ib, $R^{61}$ is —C(=O)NH$_2$.

In some embodiments of a compound of Formula I, Ia, or Ib, further to any of the above embodiments of Formula I, Ia, or Ib, $R^4$, $R^{36}$ or $R^{63}$ is H.

In some embodiments of a compound of Formula I, Ia, or Ib, further to any of the above embodiments of Formula I, Ia, or Ib, $R^3$, $R^{35}$ or $R^{62}$ is H.

In some embodiments of a compound of Formula I, Ia, or Ib, further to any of the above embodiments of Formula I, Ia, or Ib, $R^2$, $R^{34}$ or $R^{61}$ is —C(=O)NH$_2$.

In some embodiments of a compound of Formula I, Ia, or Ib, further to any of the above embodiments of Formula I, Ia, or Ib, $R^1$, $R^{33}$, or $L_{10}$-$R^{60}$ is selected from the group consisting of

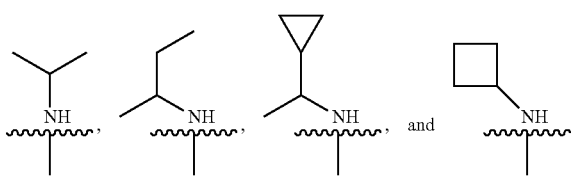

wherein

indicates the point of attachment of $R^1$, $R^3$, or $L_{10}$ to the cinnoline 4 position. In one embodiment, $R^1$, $R^{33}$, or $L_{10}$-$R^{60}$ is

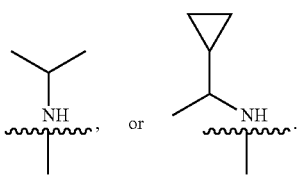

In one embodiment, $R^1$, $R^{33}$, or $L_{10}$-$R^{60}$ is

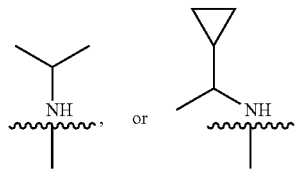

having an enantiomeric excess of the stereoisomer

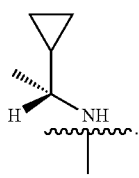

In one embodiment, $R^1$, $R^{33}$, or $L_{10}$-$R^{60}$ is

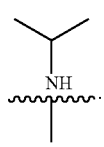

In one embodiment, $R^1$, $R^{33}$, or $L_{10}$-$R^{60}$ is

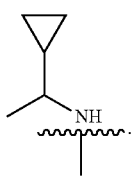

In one embodiment, $R^1$, $R^3$, or $L_{10}$-$R^{60}$ is

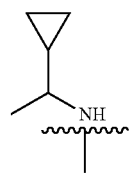

having an enantiomeric excess of the stereoisomer

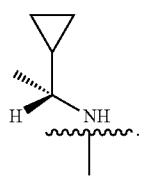

In some embodiments, the compound is any one or more compounds, or a salt thereof, as described in the Examples herein. In one embodiment the compound is any one or more compounds, or a salt thereof, selected from the group consisting of:
4-amino-7-(4-(methylsulfonyl)phenyl)cinnoline-3-carboxamide,
4-amino-7-(3-morpholinophenyl)cinnoline-3-carboxamide,
4-amino-7-(4-(dimethylamino)phenyl)cinnoline-3-carboxamide,
4-amino-7-(3-(dimethylamino)phenyl)cinnoline-3-carboxamide,
4-amino-7-(4-morpholinophenyl)cinnoline-3-carboxamide,
4-(isopropylamino)-7-(4-(methylsulfonyl)phenyl)cinnoline-3-carboxamide,
4-(isopropylamino)-7-(4-(methylsulfonyl)phenyl)cinnoline-3-carbonitrile,
4-(cyclobutylamino)-7-(4-(methylsulfonyl)phenyl)cinnoline-3-carboxamide,
4-(cyclobutylamino)-7-(4-(methylsulfonyl)phenyl)cinnoline-3-carbonitrile,
4-(1-methylpiperidin-4-ylamino)-7-(4-(methylsulfonyl)phenyl)cinnoline-3-carboxamide,
4-(1-methylpiperidin-4-ylamino)-7-(4-(methylsulfonyl)phenyl)cinnoline-3-carbonitrile,
7-(4-(methylsulfonyl)phenyl)-4-(tetrahydrofuran-3-ylamino)cinnoline-3-carboxamide,
7-(4-(methylsulfonyl)phenyl)-4-(tetrahydrofuran-3-ylamino)cinnoline-3-carbonitrile,
7-(4-(methylsulfonyl)phenyl)-4-(tetrahydro-2H-pyran-4-ylamino)cinnoline-3-carboxamide,
7-(4-(methylsulfonyl)phenyl)-4-(tetrahydro-2H-pyran-4-ylamino)cinnoline-3-carbonitrile,
7-(4-(methylsulfonyl)phenyl)-4-(oxetan-3-ylamino)cinnoline-3-carboxamide, 7-(4-(methyl sulfonyl)phenyl)-4-(oxetan-3-ylamino)cinnoline-3-carbonitrile,
4-(cyclopropylamino)-7-(4-(methylsulfonyl)phenyl)cinnoline-3-carboxamide,
4-(cyclopropylamino)-7-(4-(methylsulfonyl)phenyl)cinnoline-3-carbonitrile,
(R)-4-(sec-butylamino)-7-(4-(methylsulfonyl)phenyl)cinnoline-3-carboxamide,
(R)-4-(sec-butylamino)-7-(4-(methylsulfonyl)phenyl)cinnoline-3-carbonitrile,
(R)-7-(4-(methylsulfonyl)phenyl)-4-(1-phenylethylamino)cinnoline-3-carboxamide,
(R)-7-(4-(methylsulfonyl)phenyl)-4-(1-phenylethylamino)cinnoline-3-carbonitrile,
(R)-4-(1-cyclopropylethylamino)-7-(4-(methylsulfonyl)phenyl)cinnoline-3-carboxamide,
(R)-4-(1-cyclopropylethylamino)-7-(4-(methylsulfonyl)phenyl)cinnoline-3-carbonitrile,
4-(isopropylamino)-7-(pyridin-4-yl)cinnoline-3-carboxamide,
4-(isopropylamino)-7-(pyridin-4-yl)cinnoline-3-carbonitrile,
4-(isopropylamino)-7-(pyrimidin-5-yl)cinnoline-3-carboxamide,
4-(isopropylamino)-7-(pyrimidin-5-yl)cinnoline-3-carbonitrile,
4-(isopropylamino)-7-(1-methyl-1H-pyrazol-4-yl)cinnoline-3-carboxamide,
4-(isopropylamino)-7-(1-methyl-1H-pyrazol-4-yl)cinnoline-3-carbonitrile,
7-(4-fluorophenyl)-4-(isopropylamino)cinnoline-3-carboxamide,
7-(4-fluorophenyl)-4-(isopropylamino)cinnoline-3-carbonitrile,
7-(3-fluorophenyl)-4-(isopropylamino)cinnoline-3-carboxamide,
7-(3-fluorophenyl)-4-(isopropylamino)cinnoline-3-carbonitrile,
7-(2-fluorophenyl)-4-(isopropylamino)cinnoline-3-carboxamide,
7-(2-fluorophenyl)-4-(isopropylamino)cinnoline-3-carbonitrile,
4-(isopropylamino)-7-(4-morpholinophenyl)cinnoline-3-carboxamide,
4-(isopropylamino)-7-(4-morpholinophenyl)cinnoline-3-carbonitrile,
4-(isopropylamino)-7-(3-morpholinophenyl)cinnoline-3-carboxamide,
4-(isopropylamino)-7-(3-morpholinophenyl)cinnoline-3-carbonitrile,
4-(isopropylamino)-7-(1H-pyrazol-4-yl)cinnoline-3-carboxamide,
4-(isopropylamino)-7-(1H-pyrazol-4-yl)cinnoline-3-carbonitrile,
4-(isopropylamino)-7-(pyridin-3-yl)cinnoline-3-carboxamide,
4-(isopropylamino)-7-(pyridin-3-yl)cinnoline-3-carbonitrile,
N-isopropyl-7-(4-(methylsulfonyl)phenyl)-3-(thiazol-4-yl)cinnolin-4-amine,
3-iodo-N-isopropyl-7-(4-(methylsulfonyl)phenyl)cinnolin-4-amine,
N-isopropyl-7-(4-(methylsulfonyl)phenyl)-3-(oxazol-2-yl)cinnolin-4-amine,
N-isopropyl-7-(4-(methylsulfonyl)phenyl)-3-(pyridin-3-yl)cinnolin-4-amine,
4-(isopropylamino)-7-phenoxycinnoline-3-carboxamide,
4-(isopropylamino)-7-phenoxycinnoline-3-carbonitrile,
4-(isopropylamino)-7-(phenylthio)cinnoline-3-carboxamide,
4-(isopropylamino)-7-(phenylthio)cinnoline-3-carbonitrile,
4-(isopropylamino)-7-(phenylamino)cinnoline-3-carboxamide,
4-(isopropylamino)-7-phenylamino)cinnoline-3-carbonitrile,
4-(isopropylamino)-7-(1H-pyrazol-1-yl)cinnoline-3-carboxamide,
4-(isopropylamino)-7-(1H-pyrazol-1-yl)cinnoline-3-carbonitrile,
4-(isopropylamino)-7-(thiazol-4-yl)cinnoline-3-carboxamide,
4-(isopropylamino)-7-(thiazol-4-yl)cinnoline-3-carbonitrile,
N-isopropyl-3-methyl-7-(4-(methylsulfonyl)phenyl)cinnolin-4-amine,
3-chloro-N-isopropyl-7-(4-(methylsulfonyl)phenyl)cinnolin-4-amine,
4-(isopropylamino)-7-(2-oxopyrrolidin-1-yl)cinnoline-3-carboxamide,
4-(isopropylamino)-7-(2-oxopyrrolidin-1-yl)cinnoline-3-carbonitrile, and
3-ethynyl-N-isopropyl-7-(4-(methylsulfonyl)phenyl)cinnolin-4-amine,
(R)-4-(1-cyclopropylethylamino)-7-(pyridin-4-yl)cinnoline-3-carboxamide,
(R)-4-(1-cyclopropylethylamino)-7-(pyridin-4-yl)cinnoline-3-carbonitrile,
4-(isopropylamino)-7-(4-methylpiperazin-1-yl)cinnoline-3-carboxamide,
4-(isopropylamino)-7-(4-methylpiperazin-1-yl)cinnoline-3-carbonitrile,
4-(isopropylamino)-7-vinylcinnoline-3-carboxamide,
4-(isopropylamino)-7-vinylcinnoline-3-carbonitrile,
7-(2-hydroxyethyl)-4-(isopropylamino)cinnoline-3-carboxamide,
7-(2-hydroxyethyl)-4-(isopropylamino)cinnoline-3-carbonitrile,
(R)-4-(1-cyclopropylethylamino)-7-(1-methyl-1H-pyrazol-4-yl)cinnoline-3-carboxamide,
(R)-4-(1-cyclopropylethylamino)-7-(1-methyl-1H-pyrazol-4-yl)cinnoline-3-carbonitrile,
4-(isopropylamino)-7-(2-methoxyphenylamino)cinnoline-3-carboxamide,
4-(isopropylamino)-7-(2-methoxyphenylamino)cinnoline-3-carbonitrile,
4-(isopropylamino)-6-phenylcinnoline-3-carboxamide,
4-(isopropylamino)-6-phenylcinnoline-3-carbonitrile,
4-(isopropylamino)-6-(4-(methylsulfonyl)phenyl)cinnoline-3-carboxamide,
4-(isopropylamino)-6-(4-(methylsulfonyl)phenyl)cinnoline-3-carbonitrile,
4-(isopropylamino)-6-(pyridin-4-yl)cinnoline-3-carboxamide,
4-(isopropylamino)-6-(pyridin-4-yl)cinnoline-3-carbonitrile,
4-(isopropylamino)-6-(1H-pyrazol-4-yl)cinnoline-3-carboxamide,
4-(isopropylamino)-6-(1H-pyrazol-4-yl)cinnoline-3-carbonitrile,
4-(isopropylamino)-6-(1-methyl-1H-pyrazol-4-yl)cinnoline-3-carboxamide,
4-(isopropylamino)-6-(1-methyl-1H-pyrazol-4-yl)cinnoline-3-carbonitrile, 4-(isopropylamino)-6-(thiazol-2-yl)cinnoline-3-carboxamide,
4-(isopropylamino)-6-(thiazol-2-yl)cinnoline-3-carbonitrile,
4-(isopropylamino)-6-(thiazol-5-yl)cinnoline-3-carboxamide,
4-(isopropylamino)-6-(thiazol-5-yl)cinnoline-3-carbonitrile,
(R)-4-(1-phenylethylamino)-7-(pyridin-4-yl)cinnoline-3-carboxamide,
(R)-4-(1-phenylethylamino)-7-(pyridin-4-yl)cinnoline-3-carbonitrile,
(S)-4-(1-phenylethylamino)-7-(pyridin-4-yl)cinnoline-3-carboxamide,
(S)-4-(1-phenylethylamino)-7-(pyridin-4-yl)cinnoline-3-carbonitrile,
4-(pentan-3-ylamino)-7-(pyridin-4-yl)cinnoline-3-carboxamide,
4-(pentan-3-ylamino)-7-(pyridin-4-yl)cinnoline-3-carbonitrile,
4-(1-(pyridin-3-yl)ethylamino)-7-(pyridin-4-yl)cinnoline-3-carboxamide,
4-(1-(pyridin-3-yl)ethylamino)-7-(pyridin-4-yl)cinnoline-3-carbonitrile,
N-isopropyl-7-(4-(methylsulfonyl)phenyl)-3-(1H-1,2,4-triazol-3-yl)cinnolin-4-amine,
4-(isopropylamino)-7-(2-methoxypyridin-3-ylamino)cinnoline-3-carboxamide,
4-(isopropylamino)-7-(2-methoxypyridin-3-ylamino)cinnoline-3-carbonitrile,
2-(4-(isopropylamino)-7-(4-(methylsulfonyl)phenyl)cinnolin-3-yl)pyrimidin-4(3H)-one,
4-(isopropylamino)-6-morpholinocinnoline-3-carboxamide,
4-(isopropylamino)-6-morpholinocinnoline-3-carbonitrile,
4-(3-hydroxypropylamino)-7-(pyridin-4-yl)cinnoline-3-carboxamide,
4-(3-hydroxypropylamino)-7-(pyridin-4-yl)cinnoline-3-carbonitrile,
4-(2-hydroxyethylamino)-7-(pyridin-4-yl)cinnoline-3-carboxamide,
4-(2-hydroxyethylamino)-7-(pyridin-4-yl)cinnoline-3-carbonitrile,
4-(isopropylamino)-7-(3-methoxyphenylamino)cinnoline-3-carboxamide,
4-(isopropylamino)-7-(3-methoxyphenylamino)cinnoline-3-carbonitrile,
4-(isopropylamino)-7-(2-methoxyphenyl)cinnoline-3-carboxamide,
4-(isopropylamino)-7-(2-methoxyphenyl)cinnoline-3-carbonitrile,
4-(isopropylamino)-7-(3-methoxyphenyl)cinnoline-3-carboxamide,
4-(isopropylamino)-7-(3-methoxyphenyl)cinnoline-3-carbonitrile,
7-(5-fluoro-2-methoxyphenyl)-4-(isopropylamino)cinnoline-3-carboxamide,
7-(5-fluoro-2-methoxyphenyl)-4-(isopropylamino)cinnoline-3-carbonitrile,
4-(tert-butylamino)-7-(4-(methylsulfonyl)phenyl)cinnoline-3-carboxamide,
4-(tert-butylamino)-7-(4-(methylsulfonyl)phenyl)cinnoline-3-carbonitrile,
4-(sec-butylthio)-7-(4-(methylsulfonyl)phenyl)cinnoline-3-carboxamide,
4-(sec-butylthio)-7-(4-(methylsulfonyl)phenyl)cinnoline-3-carbonitrile,
4-(1-adamantylamino)-7-(4-(methylsulfonyl)phenyl)cinnolin-3-carboxamide,
4-(1-adamantylamino)-7-(4-(methylsulfonyl)phenyl)cinnoline-3-carbonitrile,
7-(4-(methylsulfonyl)phenyl)-4-((tetrahydro-2H-pyran-4-yl)methylamino)cinnoline-3-carboxamide,
7-(4-(methylsulfonyl)phenyl)-4-((tetrahydro-2H-pyran-4yl)methylamino)cinnoline-3-carbonitrile,
4-(isopropylamino)-7-(prop-1-en-2-yl)cinnoline-3-carboxamide,
4-(isopropylamino)-7-(prop-1-en-2-yl)cinnoline-3-carbonitrile,
(R)-4-(1-cyclopropylethylamino)-7-(3-(dimethylcarbamoyl)phenyl)cinnoline-3-carboxamide,
(R)-4-(1-cyclopropylethylamino)-7-(3-(dimethylcarbamoyl)phenyl)cinnoline-3-carbonitrile,
(R)-4-(1-cyclopropylethylamino)-7-(2-methoxyphenyl)cinnoline-3-carboxamide,
(R)-4-(1-cyclopropylethylamino)-7-(2-methoxyphenyl)cinnoline-3-carbonitrile,
(R)-4-(1-cyclopropylethylamino)-7-(2-(methoxymethyl)phenyl)cinnoline-3-carboxamide,
(R)-4-(1-cyclopropylethylamino)-7-(2-(methoxymethyl)phenyl)cinnoline-3-carbonitrile,
(R)-4-(1-cyclopropylethylamino)-7-(isoquinolin-4-yl)cinnoline-3-carboxamide,
(R)-4-(1-cyclopropylethylamino)-7-(isoquinolin-4-yl)cinnoline-3-carbonitrile,
4-amino-6-tert-butylcinnoline-3-carboxamide,
4-amino-6-tert-butylcinnoline-3-carbonitrile,
(R)-4-(1-cyclopropylethylamino)-7-(2-methoxy-5-(1H-pyrazol-1-yl)phenyl)cinnoline-3-carboxamide,
(R)-4-(1-cyclopropylethylamino)-7-(2-methoxy-5-(1H-pyrazol-1-yl)phenyl)cinnoline-3-carbonitrile,
(R)-7-(4-(methylsulfonyl)phenyl)-4-(1-(tetrahydro-2H-pyran-4-yl)ethylamino)cinnoline-3-carboxamide,
(R)-7-(4-(methylsulfonyl)phenyl)-4-(1-(tetrahydro-2H-pyran-4-yl)ethylamino)cinnoline-3-carbonitrile,
(R)-4-(1-cyclopropylethylamino)-7-(2-oxoindolin-5-yl)cinnoline-3-carboxamide,
(R)-4-(1-cyclopropylethylamino)-7-(2-oxoindolin-5-yl)cinnoline-3-carbonitrile,
(R)-4-(1-cyclopropylethylamino)-7-(5-(dimethylcarbamoyl)-2-methoxyphenyl)cinnoline-3-carboxamide,
(R)-4-(1-cyclopropylethylamino)-7-(5-(dimethylcarbamoyl)-2-methoxyphenyl)cinnoline-3-carbonitrile,
(R)-4-(1-cyclopropylethylamino)-7-(2-methoxy-5-(2-oxooxazolidin-3-yl)phenyl)cinnoline-3-carboxamide,
(R)-4-(1-cyclopropylethylamino)-7-(2-methoxy-5-(2-oxooxazolidin-3-yl)phenyl)cinnoline-3-carbonitrile,
(R)-4-(1-cyclopropylethylamino)-7-(2',4-dimethoxy-4'-(2-oxooxazolidin-3-yl)biphenyl-3-yl)cinnoline-3-carboxamide,
(R)-4-(1-cyclopropylethylamino)-7-(2',4-dimethoxy-4'-(2-oxooxazolidin-3-yl)biphenyl-3-yl)cinnoline-3-carbonitrile,
(R)-4-(1-cyclopropylethylamino)-7-(2-(trifluoromethoxy)phenyl)cinnoline-3-carboxamide,
(R)-4-(1-cyclopropylethylamino)-7-(2-(trifluoromethoxy)phenyl)cinnoline-3-carbonitrile,
(R)-7-(5-bromo-2-methoxyphenyl)-4-(1-cyclopropylethylamino)cinnoline-3-carboxamide,
(R)-7-(5-bromo-2-methoxyphenyl)-4-(1-cyclopropylethylamino)cinnoline-3-carbonitrile,
(R)-7-(4'-bromo-2',4-dimethoxybiphenyl-3-yl)-4-(1-cyclopropylethylamino)cinnoline-3-carboxamide, (R)-7-(4'-bromo-2',4-dimethoxybiphenyl-3-yl)-4-(1-cyclopropylethylamino)cinnoline-3-carbonitrile,
(R)-4-(1-cyclopropylethylamino)-7-(2-methoxy-5-(3-oxomorpholino)phenyl)cinnoline-3-carboxamide,
(R)-4-(1-cyclopropylethylamino)-7-(2-methoxy-5-(3-oxomorpholino)phenyl)cinnoline-3-carbonitrile,
(R)-4-(1-cyclopropylethylamino)-7-(2',4-dimethoxy-4'-(3-oxomorpholino)biphenyl-3-yl)cinnoline-3-carboxamide,
(R)-4-(1-cyclopropylethylamino)-7-(2',4-dimethoxy-4'-(3-oxomorpholino)biphenyl-3-yl)cinnoline-3-carbonitrile,
(R)-4-(1-cyclopropylethylamino)-7-phenylcinnoline-3-carboxamide,
(R)-4-(1-cyclopropylethylamino)-7-phenylcinnoline-3-carbonitrile,
(R)-4-(1-cyclopropylethylamino)-7-(3-(methylsulfonyl)phenyl)cinnoline-3-carboxamide,
(R)-4-(1-cyclopropylethylamino)-7-(3-(methylsulfonyl)phenyl)cinnoline-3-carbonitrile,
(R)-4-(1-cyclopropylethylamino)-7-(1-methyl-6-oxo-1,6-dihydropyridin-3-yl)cinnoline-3-carboxamide,
(R)-4-(1-cyclopropylethylamino)-7-(1-methyl-6-oxo-1,6-dihydropyridin-3-yl)cinnoline-3-carbonitrile,
(R)-4-(1-cyclopropylethylamino)-7-(3-(cyclopropylmethoxy)phenyl)cinnoline-3-carboxamide,
(R)-4-(1-cyclopropylethylamino)-7-(3-(cyclopropylmethoxy)phenyl)cinnoline-3-carbonitrile,
(R)-4-(1-cyclopropylethylamino)-7-(4-(dimethylcarbamoyl)phenyl)cinnoline-3-carboxamide,
(R)-4-(1-cyclopropylethylamino)-7-(4-(dimethylcarbamoyl)phenyl)cinnoline-3-carbonitrile,
(R)-4-(1-cyclopropylethylamino)-7-(2-methoxy-5-(methylsulfonyl)phenyl)cinnoline-3-carboxamide,
(R)-4-(1-cyclopropylethylamino)-7-(2-methoxy-5-(methylsulfonyl)phenyl)cinnoline-3-carbonitrile,
(R)-4-(1-cyclopropylethylamino)-7-(4-(3-oxomorpholino)phenyl)cinnoline-3-carboxamide,
(R)-4-(1-cyclopropylethylamino)-7-(4-(3-oxomorpholino)phenyl)cinnoline-3-carbonitrile,
(R)-4-(1-cyclopropylethylamino)-7-(4-(2-oxooxazolidin-3-yl)phenyl)cinnoline-3-carboxamide,
(R)-4-(1-cyclopropylethylamino)-7-(4-(2-oxooxazolidin-3yl)phenyl)cinnoline-3-carbonitrile,
(R)-7-(2-chlorophenyl)-4-(1-cyclopropylethylamino)cinnoline-3-carboxamide,
(R)-7-(2-chlorophenyl)-4-(1-cyclopropylethylamino)cinnoline-3-carbonitrile,
(R)-4-(1-cyclopropylethylamino)-7-(4-(dimethylcarbamoyl)-2-methoxyphenyl)cinnoline-3-carboxamide,
(R)-4-(1-cyclopropylethylamino)-7-(4-(dimethylcarbamoyl)-2-methoxyphenyl)cinnoline-3-carbonitrile,
(R)-4-(1-cyclopropylethylamino)-7-(2-oxoindolin-4-yl)cinnoline-3-carboxamide,
(R)-4-(1-cyclopropylethylamino)-7-(2-oxoindolin-4-yl)cinnoline-3-carbonitrile,
(R)-4-(1-cyclopropylethylamino)-7-(2-oxoindolin-6-yl)cinnoline-3-carboxamide,
(R)-4-(1-cyclopropylethylamino)-7-(2-oxoindolin-6-yl)cinnoline-3-carbonitrile,
(R)-4-(1-cyclopropylethylamino)-7-(2-oxoindolin-7-yl)cinnoline-3-carboxamide,
(R)-4-(1-cyclopropylethylamino)-7-(2-oxoindolin-7-yl)cinnoline-3-carbonitrile,
(R)-4-(1-cyclopropylethylamino)-7-(1-methyl-2-oxo-1,2-dihydropyridin-4-yl)cinnoline-3-carboxamide,
(R)-4-(1-cyclopropylethylamino)-7-(1-methyl-2-oxo-1,2-dihydropyridin-4-yl)cinnoline-3-carbonitrile,
(R)-4-(1-cyclopropylethylamino)-7-(2-(methylsulfonyl)phenyl)cinnoline-3-carboxamide,
(R)-4-(1-cyclopropylethylamino)-7-(2-(methylsulfonyl)phenyl)cinnoline-3-carbonitrile,
4-(cyclopropylmethylamino)-7-(4-(methylsulfonyl)phenyl)cinnoline-3-carboxamide,
4-(cyclopropylmethylamino)-7-(4-(methylsulfonyl)phenyl)cinnoline-3-carbonitrile,
4-(ethylamino)-7-(4-(methylsulfonyl)phenyl)cinnoline-3-carboxamide,
4-(ethylamino)-7-(4-(methylsulfonyl)phenyl)cinnoline-3-carbonitrile,
4-(methylamino)-7-(4-(methylsulfonyl)phenyl)cinnoline-3-carboxamide,
4-(methylamino)-7-(4-(methylsulfonyl)phenyl)cinnoline-3-carbonitrile,
(R)-4-(1-cyclopropylethylamino)-7-(4-(3-fluoropyridin-2-yl)-2-methoxyphenyl)cinnoline-3-carboxamide,
(R)-4-(1-cyclopropylethylamino)-7-(4-(3-fluoropyridin-2-yl)-2-methoxyphenyl)cinnoline-3-carbonitrile,
(R)-7-(4-bromo-2-methoxyphenyl)-4-(1-cyclopropylethylamino)cinnoline-3-carboxamide,
(R)-7-(4-bromo-2-methoxyphenyl)-4-(1-cyclopropylethylamino)cinnoline-3-carbonitrile,
(R)-4-(1-cyclopropylethylamino)-7-(2-methoxy-4-(3-methoxypyrazin-2-yl)phenyl)cinnoline-3-carboxamide,
(R)-4-(1-cyclopropylethylamino)-7-(2-methoxy-4-(3-methoxypyrazin-2-yl)phenyl)cinnoline-3-carbonitrile,
(R)-4-(1-cyclopropylethylamino)-7-(2-methoxy-4-(1-methyl-1H-imidazol-2-yl)phenyl)cinnoline-3-carboxamide,
(R)-4-(1-cyclopropylethylamino)-7-(2-methoxy-4-(1-methyl-1H-imidazol-2-yl)phenyl)cinnoline-3-carbonitrile,
N-methyl-4-(methylamino)-7-(4-(methylsulfonyl)phenyl)cinnoline-3-carboxamide,
4-(isopropylamino)-N-methyl-7-(4-(methylsulfonyl)phenyl)cinnoline-3-carboxamide,
3-(1H-imidazol-2-yl)-N-isopropyl-7-(4-(methylsulfonyl)phenyl)cinnolin-4-amine,
(R)-4-(1-cyclopropylethylamino)-N-methyl-7-(prop-1-en-2-yl)cinnoline-3-carboxamide,
(R)-4-(1-cyclopropylethylamino)-N-methyl-7-(4-(methylsulfonyl)phenyl)cinnoline-3-carboxamide, and
(R)-7-cyclopropyl-4-(1-cyclopropylethylamino)-N-methylcinnoline-3-carboxamide.

Exemplary compounds as described herein, e.g. compounds of Formula I, and their in vitro biological activities are listed in the table of Example A.

In some embodiments, the compounds as described herein, e.g. compounds of Formula I are inhibitors of LRRK2 kinase activity, including LRRK2 mutant kinase activity, also LRRK2 mutant G2019S kinase activity, with an $IC_{50}$ of less than about 50 µM, less than about 40 µM, less than about 30 µM, less than about 20 µM or less than about 10 µM. In one embodiment, the compounds of Formula I exhibit inhibitory activity against LRRK2 kinase activity, including LRRK2 mutant kinase activity, also LRRK2 mutant G2019S kinase activity, with an $IC_{50}$ of less than about 9 µM, less than about 8 µM, less than about 7 µM, less than about 6 µM, less than about 5 µM, less than about 4 µM, less than about 3 µM, less than about 2 µM, or less than about 1 µM. In one embodiment, the compounds of Formula I exhibit inhibitory activity against LRRK2 kinase activity, including LRRK2 mutant kinase activity, also LRRK2 mutant G2019S kinase activity, with an $IC_{50}$ of less than about 0.9 µM, less than about 0.8 µM, less than about 0.7

µM, less than about 0.6 µM, less than about 0.5 µM, less than about 0.4 µM, less than about 0.3 µM, less than about 0.2 µM. In one embodiment, the compounds of Formula I exhibit inhibitory activity against LRRK2 kinase activity, including LRRK2 mutant kinase activity, also LRRK2 mutant G2019S kinase activity, with an $IC_{50}$ of less than about 0.1 µM (100 nM). In one embodiment, the compounds of Formula I exhibit inhibitory activity against LRRK2 kinase, including LRRK2 kinase mutant kinase activity, also LRRK2 mutant G2019S kinase activity, with an $IC_{50}$ of less than about 90 nM, less than about 80 nM, less than about 70 nM, less than about 60 nM, less than about 50 nM, less than about 40 nM, less than about 30 nM or less than about 20 nM. In one embodiment, the compounds of Formula I exhibit inhibitory activity against LRRK2 kinase activity, including LRRK2 mutant kinase activity, also LRRK2 mutant G2019S kinase activity, with an $IC_{50}$ of less than about 10 nM.

In some embodiments, compounds as described herein, e.g. compounds of Formula I, inhibit LRRK2 kinase activity, including LRRK2 mutant kinase activity, also LRRK2 mutant G2019S kinase activity, and are selective compared to LRRK1 kinase activity. In one embodiment, compounds of Formula I inhibit LRRK2 mutant G2019S kinase activity, and are selective compared to LRRK1 kinase activity and wild-type LRRK2 kinase activity. For the purpose of this application the selectivity of the instant compounds for LRRK2, including LRRK2 mutant G2019S, over LRRK1; or LRRK2 mutant G2019S over wild-type LRRK2 is expressed in a ratio of $IC_{50}$ values. Those can be determined using assays known in the art or those described herein (see e.g., Example A).

In some embodiments, compounds as described herein, e.g. compounds of Formula I, inhibit LRRK2 kinase activity, including LRRK2 mutant kinase activity, also LRRK2 mutant G2019S kinase activity, and are selective as compared to other kinases. Particularly, compounds of Formula I inhibit LRRK2 kinase activity, including LRRK2 mutant kinase activity, also LRRK2 mutant G2019S kinase activity, and are selective compared to one or more kinases selected from the group consisting of AKT1, AurA, BRAF, CAMK2A, CDK1, CDK2, CDK5, CLK1, FAK2, LCK, MARK2, MLK1, MST2/STK3, PKA, PKC beta, PLK1, PLK2, PLK3, and RET. In one embodiment, compounds are selective as compared to other kinases, such as one or more kinases selected from the group consisting of AKT1, AurA, BRAF, CAMK2A, CDK1, CDK2, CDK5, CLK1, FAK2, LCK, MARK2, MLK1, MST2/STK3, PKA, PKC beta, PLK1, PLK2, PLK3, and RET, and are selective compared to LRRK1 kinase activity. In some instances, compounds of Formula I inhibit LRRK2 mutant G2019S kinase activity, and are selective compared to one or more kinases selected from the group consisting of AKT1, AurA, BRAF, CAMK2A, CDK1, CDK2, CDK5, CLK1, FAK2, LCK, MARK2, MLK1, MST2/STK3, PKA, PKC beta, PLK1, PLK2, PLK3, and RET, and are selective compared to LRRK1 kinase activity and wild-type LRRK2 kinase activity. For the purpose of this application the selectivity of the instant compounds for the inhibition of LRRK2 kinase activity over other kinases is expressed in a ratio of $IC_{50}$ values, or in some instances as a ratio of % inhibition at a given concentration of compound, such as at 10 µM, which can be determined using assays known in the art or those described herein (see e.g., Example A).

In one aspect, any tautomer, stereoisomer, prodrug, derivative, conjugate, polymorph, isotopically enhanced form, pharmaceutically acceptable salt or pharmaceutically acceptable solvate of a compound of Formula I is provided. In one embodiment, any tautomer of a compound of Formula I is provided. In one embodiment, any stereoisomer of a compound of Formula I is provided. In one embodiment, any prodrug of a compound of Formula I is provided. In one embodiment, any derivative of a compound of Formula I is provided. In one embodiment, any conjugate of a compound of Formula I is provided. In one embodiment, any polymorph of a compound of Formula I is provided. In one embodiment, any isotopically enhanced form of a compound of Formula I is provided. In one embodiment, any pharmaceutically acceptable salt of a compound of Formula I is provided. In one embodiment, any polymorph of any pharmaceutically acceptable salt of a compound of Formula I is provided. In one embodiment, any pharmaceutically acceptable solvate of a compound of Formula I is provided. In one embodiment, any polymorph of any pharmaceutically acceptable solvate of a compound of Formula I is provided.

In one aspect, a pharmaceutical composition comprising a compound as described herein, e.g. a compound of Formula I, and a pharmaceutically acceptable carrier is provided. In one embodiment, a pharmaceutical composition comprising any tautomer of a compound of Formula I and a pharmaceutically acceptable carrier is provided. In one embodiment, a pharmaceutical composition comprising any stereoisomer of a compound of Formula I and a pharmaceutically acceptable carrier is provided. In one embodiment, a pharmaceutical composition comprising any prodrug of a compound of Formula I and a pharmaceutically acceptable carrier is provided. In one embodiment, a pharmaceutical composition comprising any derivative of a compound of Formula I and a pharmaceutically acceptable carrier is provided. In one embodiment, a pharmaceutical composition comprising any conjugate of a compound of Formula I and a pharmaceutically acceptable carrier is provided. In one embodiment, a pharmaceutical composition comprising any polymorph of a compound of Formula I and a pharmaceutically acceptable carrier is provided. In one embodiment, a pharmaceutical composition comprising any isotopically enhanced form of a compound of Formula I and a pharmaceutically acceptable carrier is provided. In one embodiment, a pharmaceutical composition comprising any pharmaceutically acceptable salt of a compound of Formula I and a pharmaceutically acceptable carrier is provided. In one embodiment, a pharmaceutical composition comprising any polymorph of any pharmaceutically acceptable salt of a compound of Formula I and a pharmaceutically acceptable carrier is provided. In one embodiment, a pharmaceutical composition comprising any pharmaceutically acceptable solvate of a compound of Formula I and a pharmaceutically acceptable carrier is provided. In one embodiment, a pharmaceutical composition comprising any polymorph of any pharmaceutically acceptable solvate of a compound of Formula I and a pharmaceutically acceptable carrier is provided.

In one aspect, a kit is provided that includes a compound or composition thereof as described herein, e.g. a compound of Formula I, or a pharmaceutically acceptable salt or solvate thereof, or a composition comprising such a compound or pharmaceutically acceptable salt or solvate thereof. In some embodiments, the compound or composition thereof is packaged, e.g., in a vial, bottle or similar container, which may be further packaged, e.g., within a box, envelope, or similar container. In some embodiments, the compound or composition thereof is approved by the U.S. Food and Drug Administration or similar regulatory agency for administration to a mammal, e.g., a human. In some embodiments the compound or composition thereof is approved for administration to a mammal, e.g., a human, for a LRRK2 mediated disease or condition, including a LRRK2 mutant mediated condition. In one embodiment, such a kit includes written instructions for use and/or other indication that the compound or composition is suitable or approved for administration to a mammal, e.g., a human, for a suitable disease or condition. In some embodiments, the compound or composition is packaged in unit dose or single dose form, e.g., single dose pills, capsules, or the like.

In one aspect, a method is provided for treating a disease. The method includes administering to a mammalian subject (e.g., human) in need thereof a therapeutically effective amount of a compound of Formula I, or a salt or solvate thereof, or a composition comprising such compounds or salt or solvate thereof. In one embodiment, a method of treating a disease is provided comprising administering to a mammalian subject in need thereof a therapeutically effective amount of a compound of Formula I, or a salt or solvate thereof, or a composition comprising such compounds or salt or solvate thereof, wherein the disease is selected from the group consisting of Parkinson's disease, Parkinson disease with dementia, Parkinson's disease at risk syndrome, dementia with Lewy bodies, Lewy body variant of Alzheimer's disease, combined Parkinson's disease and Alzheimer's disease, multiple system atrophy, striatonigral degeneration, olivopontocerebellar atrophy, Shy-Drager syndrome, Hallervorden-Spatz syndrome, fronto-temporal dementia, Sandhoff disease, progressive supranuclear palsy, corticobasal degeneration, postural hypotension, orthostatic hypotension, cerebellar dysfunctions, ataxia, movement disorders, cognitive deterioration, sleep disorders, hearing disorders, tremors, rigidity, bradykinesia, akinesia, postural instability, melanoma, acute myelogenous leukemia, breast carcinoma, lung adenocarincoma, prostate adenocarcinoma, renal cell carcinoma, papillary thyroid carcinoma, Crohn's disease, ulcerative colitis, and leprosy.

In one embodiment, a method of treating a neurological disease is provided comprising administering to a mammalian subject in need thereof a therapeutically effective amount of a compound of Formula I, or a salt or solvate thereof, or a composition comprising such compounds or salt or solvate thereof, wherein the neurological disease is selected from the group consisting of Parkinson's disease, Parkinson disease with dementia, Parkinson's disease at risk syndrome, dementia with Lewy bodies, Lewy body variant of Alzheimer's disease, combined Parkinson's disease and Alzheimer's disease, multiple system atrophy, striatonigral degeneration, olivopontocerebellar atrophy, Shy-Drager syndrome, Hallervorden-Spatz syndrome, fronto-temporal dementia, Sandhoff disease, progressive supranuclear palsy, corticobasal degeneration, postural hypotension, orthostatic hypotension, cerebellar dysfunctions, ataxia, movement disorders, cognitive deterioration, sleep disorders, hearing disorders, tremors, rigidity, bradykinesia, akinesia, and postural instability.

In one embodiment, a method of treating a neurological disease is provided comprising administering to a mammalian subject in need thereof a therapeutically effective amount of a compound of Formula I, or a salt or solvate thereof, or a composition comprising such compounds or salt or solvate thereof, wherein the neurological disease is selected from the group consisting of Parkinson's disease, Parkinson disease with dementia, Parkinson's disease at risk syndrome, dementia with Lewy bodies, Lewy body variant of Alzheimer's disease, combined Parkinson's disease and Alzheimer's disease, multiple system atrophy, striatonigral degeneration, olivopontocerebellar atrophy, and Shy-Drager syndrome.

In one embodiment, a method of treating Parkinson's disease is provided comprising administering to a mammalian subject in need thereof a therapeutically effective amount of a compound of Formula I, or a salt or solvate thereof, or a composition comprising such compounds or salt or solvate thereof.

In one embodiment, a method of treating a cancer is provided comprising administering to a mammalian subject in need thereof a therapeutically effective amount of a compound of Formula I, or a salt or solvate thereof, or a composition comprising such compounds or salt or solvate thereof, wherein the cancer is selected from the group consisting of melanoma, acute myelogenous leukemia, breast carcinoma, lung adenocarincoma, prostate adenocarcinoma, renal cell carcinoma, and papillary thyroid carcinoma.

In one embodiment, a method of treating an autoimmune disease is provided comprising administering to a mammalian subject in need thereof a therapeutically effective amount of a compound of Formula I, or a salt or solvate thereof, or a composition comprising such compounds or salt or solvate thereof, wherein the autoimmune disease is selected from the group consisting of Crohn's disease and ulcerative colitis.

In one embodiment, a method of treating leprosy is provided comprising administering to a mammalian subject in need thereof a therapeutically effective amount of a compound of Formula I, or a salt or solvate thereof, or a composition comprising such compounds or salt or solvate thereof.

Compound Forms and Derivatives

In one aspect, various forms or derivatives of compounds as described herein are provided. In one embodiment, a compound of Formula I may exist in a number of different forms or derivatives, for example, tautomers, isomers, racemic mixtures, prodrugs, active metabolites, pharmaceutically acceptable salts, pharmaceutically acceptable solvates, isotopically enhanced forms, conjugates, and other solid forms thereof, including different crystal forms, polymorphs or amorphous solids.

A compound as described herein, e.g. a compound of Formula I, can exist in particular geometric, conformational or stereoisomeric forms. The compound of Formula I includes all such isomeric forms, including cis- and trans-isomers, atropisomers, (−)- and (+)-enantiomers, diastereomers, (D)-isomers, (L)-isomers, the racemic mixtures thereof, and other mixtures thereof, such as enantiomerically or diastereomerically enriched mixtures. Such regioisomers and stereoisomers may be isolated in enriched form by standard separation methods known to those skilled in the art. Additional asymmetric carbon atoms can be present in a substituent such as an alkyl group. When the compounds described herein contain olefinic double bonds or other centers of geometric asymmetry, and unless specified otherwise, it is intended that the compounds include both E and Z geometric isomers. Compounds may also include regions that are sterically constrained such that atropisomers may be isolated by standard separation methods known to those skilled in the art. Likewise, all tautomeric forms and mixtures of tautomers are included.

Optically active (R)- and (S)-isomers and d and l isomers can be prepared using chiral synthons or chiral reagents, or resolved using conventional techniques. Resolution of the racemates can be accomplished, for example, by conventional methods such as crystallization in the presence of a resolving agent; chromatography, using, for example a chiral HPLC column; or derivatizing the racemic mixture with a resolving reagent to generate diastereomers, separating the diastereomers via chromatography, and removing the resolving agent to generate the original compound in enantiomerically enriched form. Any of the above procedures can be repeated to increase the enantiomeric purity of a compound. If, for instance, a particular enantiomer of a compound as described herein is desired, it can be prepared by asymmetric synthesis, or by derivatization with a chiral auxiliary, where the resulting diastereomeric mixture is separated and the auxiliary group cleaved to provide the desired enantiomers. Alternatively, where the molecule contains a basic functional group, such as an amino group, or an acidic functional group, such as a carboxyl group, diastereomeric salts can be formed with an appropriate optically active acid or base, followed by resolution of the diastereomers thus formed by fractional crystallization or chromatographic means known in the art, and subsequent recovery of the enantiomers in enriched form. In addition, separation of enantiomers and diastereomers is frequently accomplished using chromatography employing chiral, stationary phases, optionally in combination with chemical derivatization (e.g., formation of carbamates from amines).

A compound as described herein, e.g. a compound of Formula I, can exist in a prodrug form. A prodrug of a compound as described herein is a pharmaceutically acceptable derivative of a compound of Formula I that readily undergoes chemical changes under physiological conditions to provide the compound as described herein (e.g. a compound of Formula I). It is understood that such prodrugs are effectively equivalent to a compound of Formula I, i.e. when such a prodrug is administered into a subject, such administration effectively encompasses the use of a compound of Formula I. Non-limiting examples of a pharmaceutically acceptable derivative or prodrug include pharmaceutically acceptable esters, phosphate esters or sulfonate esters thereof as well as other derivatives of a compound as described herein which, upon administration to a recipient, is capable of providing, either directly or indirectly, a compound as described herein (e.g. a compound of Formula I). Particularly favored derivatives or prodrugs are those that increase the bioavailability of a compound as described herein when such compound is administered to a mammal (e.g., by allowing an orally administered compound to be more readily absorbed into the blood stream) or which enhance delivery of the parent compound to a biological compartment (e.g., the brain or lymphatic system) relative to the parent species.

Prodrugs include a variety of esters (e.g. carboxylic acid ester) or protected amines (e.g. acylated amine groups). Ester groups that are suitable as prodrug groups are generally known in the art and include benzyloxy, di($C_1$-$C_6$ alkyl)aminoethyloxy, acetoxymethyl, pivaloyloxymethyl, phthalidoyl, ethoxycarbonyloxyethyl, 5-methyl-2-oxo-1,3-dioxol-4-yl methyl, and $C_1$-$C_6$ alkoxy esters, optionally substituted by N-morpholino and amide-forming groups such as di($C_1$-$C_6$ alkyl)amino. Exemplary ester prodrug groups include $C_1$-$C_6$ alkoxy esters. Those skilled in the art will recognize various synthetic methodologies that may be employed to form a pharmaceutically acceptable prodrug of the compound of Formula I (e.g., via esterification of a carboxylic acid or hydroxyl group, acylation of an amine group).

In some embodiments, the prodrug is suitable for treatment/prevention of those diseases and conditions that require the drug molecule to cross the blood brain barrier. In one embodiment, the prodrug enters the brain, where it is converted into the active form of the drug molecule. In one embodiment, a prodrug is used to enable an active drug molecule to reach the inside of the eye after topical application of the prodrug to the eye. Additionally, prodrugs can be converted to a compound as described herein (e.g. a compound of Formula I) by chemical or biochemical methods in an ex vivo environment. For example, a prodrug can be slowly converted to the compound of Formula I when placed in a transdermal patch reservoir with a suitable enzyme or chemical reagent.

A compound as described herein, e.g. a compound of Formula I, when used in vivo may form an active metabolites. Thus, such metabolites are provided as pharmacologically active compounds or compounds that further metabolize to pharmacologically active compounds that are derivatives of compounds as described herein resulting from metabolic processes in the body of a subject Such metabolites are readily identified by those of skill in the art, and may further be prepared similarly to the methods as described herein, such that a suitable metabolite can be prepared and isolated for pharmaceutical use.

A compound as described herein, e.g. a compound of Formula I, can exist in a pharmaceutically acceptable salts form. A compound of Formula I may be prepared with relatively nontoxic acids or bases, depending on the particular substituents found on the compounds described herein. Such salts and their preparation for use as pharmaceuticals are readily known to those of skill in the art. Such salts may provide improved properties, e.g. solubility or pharmacokinetic properties, such that the activity of the compound of Formula I is enhanced upon administration to a subject. It is understood that such salts are effectively equivalent to a compound of Formula I, i.e. when such a salt is administered into a subject, such administration effectively encompasses the use of a compound of Formula I. When a compound as described herein (e.g. a compound of Formula I) contain relatively acidic functionalities (e.g., —COOH group), base addition salts can be obtained by contacting the compound (e.g., neutral form of such compound) with a sufficient amount of the desired base, either neat or in a suitable inert solvent. Examples of pharmaceutically acceptable base addition salts include lithium, sodium, potassium, calcium, ammonium, organic amino (e.g. ethylenediamine, diethylamine, piperazine, ethanolamine, diethanolamine, triethanolamine, tromethamine, choline, meglumine, benzathine, 4-phenylcyclohexylamine), zinc, magnesium and aluminum salts and the like. When a compound as described herein (e.g. a compound of Formula I) contains relatively basic functionalities (e.g., amines), acid addition salts can be obtained, e.g., by contacting the compound (e.g., neutral form of such compound) with a sufficient amount of the desired acid, either neat or in a suitable inert solvent. Examples of pharmaceutically acceptable acid addition salts include those derived from inorganic acids like hydrochloric, hydrobromic, hydroiodic, nitric, carbonic, monohydrogencarbonic, phosphoric, diphosphoric, monohydrogenphosphoric, dihydrogenphosphoric, sulfuric, monohydrogensulfuric, thiocyanic, hydriodic and the like, as well as the salts derived from relatively nontoxic organic acids like formic, acetic, alginic, propionic, isobutyric, ascorbic, aspartic, gentisic, galactaric, D-glucoheptanoic, D-gluconic, D-glucoronic, D-galactunoric, malic, maleic, malonic, benzoic, succinic, suberic, fumaric, glutaric, 2-oxoglutaric, adipic, capric, caproic, caprylic, dodecylsulfuric, lactic, lactobionic, mandelic, naphthylene-1,5-disulfonic, naphthalene-2-sulfonic, 1-hydroxy-2-napthoic, orotic, oxalic, phthalic, pyroglutamic, glycerophosphoric, hippuric, benzenesulfonic, p-toluenesulfonic, camphorsulfonic, camphoric, cinnamic, citric, tartaric, methanesulfonic, nicotinic, ethanesulfonic, ethane-1,2-disulfonic, 2-hydroxyethanesulfonic, salicylic, lauric, oleic, palmitic, pamoic, sebacic, undecylenic, stearic and the like. Also included are salts of amino acids such as glutamate, lysinate, arginate and the like (see, for example, Berge et al., Journal of Pharmaceutical Science, 1977, 66: 1-19). Certain specific compounds as described herein (e.g. a compound of Formula I) contain both basic and acidic functionalities that allow the compounds to be converted into either base or acid addition salts.

The neutral forms of the compounds can be regenerated, for example, by contacting the salt with a base or acid and isolating the parent compound in the conventional manner. The parent form of the compound can differ from the various salt forms in certain physical properties, such as solubility in polar solvents, but otherwise the salts are equivalent to the parent form of the compound for the purposes of the present invention.

When a substituent includes a negatively charged oxygen atom "O$^-$", e.g., in "—COO$^-$", then the formula is meant to optionally include a proton or an organic or inorganic cationic counterion. In one example, the resulting salt form of the compound is pharmaceutically acceptable. Further, when a compound of Formula I includes an acidic group, such as a carboxylic acid group, e.g., written as the substituent "—COOH", "—CO$_2$H" or "—C(O)$_2$H", then the formula is meant to optionally include the corresponding "de-protonated" form of that acidic group, e.g., "—COO$^-$", "—CO$_2{}^-$" or "—C(O)$_2{}^-$", respectively.

A compound as described herein, e.g. a compound of Formula I, can exist in unsolvated forms as well as solvated forms, including hydrated forms. Such solvates may provide improved properties, e.g. solubility or pharmacokinetic properties, such that the activity of the compound of Formula I is enhanced upon administration to a subject. It is understood that such solvated forms are effectively equivalent to a compound of Formula I, i.e. when such a solvate is administered into a subject, such administration effectively encompasses the use of a compound of Formula I.

A compound as described herein, e.g. a compound of Formula I, can exist in multiple crystalline forms, i.e. polymorphs, or in an amorphous form, and a compound of Formula I encompasses all such forms of the compound. In general, all physical forms are of use in the methods contemplated herein. Such physical forms may provide improved properties, e.g. solubility or pharmacokinetic properties, such that the activity of the compound of Formula I is enhanced upon administration of the particular form to a subject.

A compound as described herein, e.g. a compound of Formula I, can contain natural or unnatural proportions of atomic isotopes at one or more of the atoms that constitute such compounds. For example, the compounds can be radiolabeled with radioactive isotopes, such as for example tritium ($^3$H), iodine-125 ($^{125}$I) or carbon-14 ($^{14}$C). All isotopic variations of a compound as described herein, whether radioactive or not, are effectively encompassed by a compound as described herein, e.g., a compound in which one or more of the hydrogen atoms are replaced with another stable isotope of hydrogen (i.e., deuterium) or a radioactive isotope (i.e., tritium), is expected to have similar activity as it relates to LRRK2 kinase inhibition, and is effectively equivalent to a compound of Formula I. Such an isotopically enhanced compound may be useful, for example, in detection of the compound in vivo or in biological tissue, such as a radiolabelled compound containing $^3$H or $^{14}$C to assess tissue distribution, or a positron emitting compound containing $^{11}$C, $^{15}$O, $^{13}$N, $^{18}$F or the like useful in positron emission tomography for in vivo imaging. Similarly, a deuterated compound my provide the compound with greater metabolic stability relative to the non-deuterated compound to provide improved pharmacokinetic properties. Such a compound is readily prepared by the methods as described herein, where suitable isotopically enhanced reagents may be used in place of non enhanced reagents. For example, alkyl groups may include isotopic variants of hydrogen and carbon, such that methyl, for example, includes —CH$_3$, or may include the analogous structure in which any atoms can include any isotopes thereof, for example —CD$_3$, —$^{14}$CH$_3$, and the like.

Pharmaceutical Compositions:

Pharmaceutical compositions are provided, including a compound as described herein, e.g. compounds of Formula I, or any salts or solvates thereof, and at least one pharmaceutically acceptable carrier. The term "pharmaceutically acceptable carrier" means all pharmaceutically acceptable ingredients known to those of skill in the art, which are typically considered non-active ingredients. The term "pharmaceutically acceptable carrier" includes solvents, solid or liquid diluents, vehicles, adjuvants, excipients, glidants, binders, granulating agents, dispersing agents, suspending agents, wetting agents, lubricating agents, disintegrants, solubilizers, stabilizers, emulsifiers, fillers, preservatives (e.g., anti-oxidants), flavoring agents, sweetening agents, thickening agents, buffering agents, coloring agents and the like, as well as any mixtures thereof. Exemplary carriers (i.e., excipients) are described in, e.g., *Handbook of Pharmaceutical Manufacturing Formulations*, Volumes 1-6, Niazi, Sarfaraz K., Taylor & Francis Group 2005, which is incorporated herein by reference in its entirety. A pharmaceutical composition may include one or more compounds of Formula I or any salt or solvate thereof, in association with one or more pharmaceutically acceptable carrier and optionally other active ingredients.

The compounds of Formula I may be administered orally, topically, parenterally, by inhalation or spray or rectally in dosage unit formulations containing at least one pharmaceutically acceptable carrier. The term "parenteral" as used herein includes percutaneous, subcutaneous, intravascular (e.g., intravenous), intramuscular, or intrathecal injection or infusion techniques and the like. The pharmaceutical compositions containing compounds of Formula I may be in a form suitable for oral use, for example, as tablets, troches, lozenges, aqueous or oily suspensions, dispersible powders or granules, emulsion, hard or soft capsules, or syrups or elixirs.

Compositions intended for oral use may be prepared according to any method known to the art for the manufacture of pharmaceutical compositions and such compositions may contain one or more agents selected from the group consisting of sweetening agents, flavoring agents, coloring agents and preservative agents in order to provide pharmaceutically elegant and palatable preparations. Tablets contain the active ingredient in admixture with non-toxic pharmaceutically acceptable excipients that are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques. In some cases such coatings may be prepared by known techniques to delay disintegration and absorption in the gastrointestinal tract and thereby provide a sustained action over a longer period. For example, a time delay material such as glyceryl monosterate or glyceryl distearate may be employed.

Formulations for oral use may also be presented as hard gelatin capsules, wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil. Formulations for oral use may also be presented as lozenges.

Aqueous suspensions contain the active materials in admixture with excipients suitable for the manufacture of aqueous suspensions. Such excipients are suspending agents, for example sodium carboxymethylcellulose, methylcellulose, hydropropyl-methylcellulose, sodium alginate, polyvinylpyrrolidone, gum tragacanth and gum acacia; dispersing or wetting agents may be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose or saccharin.

Oily suspensions may be formulated by suspending the active ingredients in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents and flavoring agents may be added to provide palatable oral preparations. These compositions may be preserved by the addition of an antioxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents or suspending agents are exemplified by those already mentioned above. Additional excipients, for example sweetening, flavoring and coloring agents, may also be present.

Pharmaceutical compositions of compounds of Formula I, or any salts or solvates thereof, may also be in the form of oil-in-water emulsions. The oily phase may be a vegetable oil or a mineral oil or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol, anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol, glucose or sucrose. Such formulations may also contain a demulcent, a preservative, a flavoring agent or a coloring agent. The pharmaceutical compositions may be in the form of a sterile, injectable, aqueous or oleaginous suspension. This suspension may be formulated according to the known art using those suitable dispersing or wetting agents and suspending agents that have been mentioned above. The sterile injectable preparation may also be a sterile injectable solution or suspension in a non-toxic parentally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of Formula I may also be administered in the form of suppositories, e.g., for rectal administration of the drug. These compositions can be prepared by mixing the drug with a suitable non-irritating excipient that is solid at ordinary temperatures but liquid at the rectal temperature and will therefore melt in the rectum to release the drug. Such materials include cocoa butter and polyethylene glycols.

Compounds of Formula I may be administered parenterally in a sterile medium. The compound, depending on the vehicle and concentration used, can either be suspended or dissolved in the vehicle. Advantageously, adjuvants such as local anesthetics, preservatives and buffering agents can be dissolved in the vehicle.

For disorders of the eye or other external tissues, e.g., mouth and skin, the formulations are readily applied as a topical gel, spray, ointment or cream, or as a scleral suppository, containing the active ingredients in a total amount of, for example, 0.075 to 30% w/w, also 0.2 to 20% w/w and also 0.4 to 15% w/w. When formulated in an ointment, the active ingredients may be employed with either paraffinic or a water-miscible ointment base.

Alternatively, the active ingredients may be formulated in a cream with an oil-in-water cream base. If desired, the aqueous phase of the cream base may include, for example at least 30% w/w of a polyhydric alcohol such as propylene glycol, butane-1,3-diol, mannitol, sorbitol, glycerol, polyethylene glycol and mixtures thereof. The topical formulation may desirably include a compound, which enhances absorption or penetration of the active ingredient through the skin or other affected areas. Examples of such dermal penetration enhancers include dimethylsulfoxide and related analogs. The compounds of Formula I can also be administered by a transdermal device. In one example topical administration will be accomplished using a patch either of the reservoir and porous membrane type or of a solid matrix variety. In either case, the active agent is delivered continuously from the reservoir or microcapsules through a membrane into the active agent permeable adhesive, which is in contact with the skin or mucosa of the recipient. If the active agent is absorbed through the skin, a controlled and predetermined flow of the active agent is administered to the recipient. In the case of microcapsules, the encapsulating agent may also function as the membrane. The transdermal patch may include the compound in a suitable solvent system with an adhesive system, such as an acrylic emulsion, and a polyester patch. The oily phase of the emulsions may be constituted from known ingredients in a known manner. While the phase may comprise merely an emulsifier, it may comprise a mixture of at least one emulsifier with a fat or oil or with both a fat and an oil. In one example, a hydrophilic emulsifier is included together with a lipophilic emulsifier, which acts as a stabilizer. In one example, both an oil and a fat are included. Together, the emulsifier(s) with or without stabilizer(s) make-up the so-called emulsifying wax, and the wax together with the oil and fat make up the so-called emulsifying ointment base, which forms the oily, dispersed phase of the cream formulations. Emulsifiers and emulsion stabilizers suitable for use in the formulation of compounds as described herein include Tween 60, Span 80, cetostearyl alcohol, myristyl alcohol, glyceryl monostearate, and sodium lauryl sulfate, among others. The choice of suitable oils or fats for the formulation is based on achieving the desired cosmetic properties, since the solubility of the active compound in most oils likely to be used in pharmaceutical emulsion formulations is very low. Thus, an exemplary cream is a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters may be used. These may be used alone or in combination depending on the properties required. Alternatively, high melting point lipids such as white soft paraffin and/or liquid paraffin or other mineral oils can be used.

Formulations suitable for topical administration to the eye also include eye drops wherein the active ingredients are dissolved or suspended in suitable carrier, especially an aqueous solvent for the active ingredients. The anti-inflammatory active ingredients are can be present in such formulations in a concentration of 0.5 to 20%, advantageously 0.5 to 10% and particularly about 1.5% w/w. For therapeutic purposes, the active compounds, i.e. compounds of Formula I, are ordinarily combined with one or more adjuvants appropriate to the indicated route of administration. The compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets may contain a controlled-release formulation as may be provided in a dispersion of active compound in hydroxypropylmethyl cellulose. Formulations for parenteral administration may be in the form of aqueous or non-aqueous isotonic sterile injection solutions or suspensions. These solutions and suspensions may be prepared from sterile powders or granules having one or more of the carriers or diluents mentioned for use in the formulations for oral administration. The compounds may be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art.

Dosage levels of the order of from about 0.005 mg to about 100 mg per kilogram of body weight per day are useful in the treatment of the diseases and conditions described herein (e.g., about 0.35 mg to about 7 g per human patient per day, based on an average adult person weight of 70 kg). The amount of active ingredient that may be combined with the carrier materials to produce a single dosage form will vary depending upon the host treated and the particular mode of administration. Dosage unit forms will generally contain between from about 1 mg to about 500 mg of an active ingredient. The daily dose can be administered in one to four doses per day. In the case of skin conditions, it may be efficacious to apply a topical preparation of compounds of Formula I to the affected area one to four times a day.

Formulations suitable for inhalation or insufflation include solutions and suspensions in pharmaceutically acceptable aqueous or organic solvents, or mixtures thereof, and powders. The liquid or solid compositions may contain suitable pharmaceutically acceptable excipients as describe above. The compositions may be administered by oral or nasal respiratory route for local or systemic effect. Compositions may be nebulized by use of inert gases or vaporized, and breathed directly from the nebulizing/vaporizing device or the nebulizing device may be attached to a facemask tent or intermittent positive pressure-breathing machine.

It will be understood, however, that the specific dose level for any particular patient will depend upon a variety of factors including the activity of the specific compound employed, the age, body weight, general health, sex, diet, time of administration, mute of administration, and rate of excretion, drug combination and the severity of the particular disease undergoing therapy.

For administration to non-human animals, the composition may also be added to the animal feed or drinking water. It may be convenient to formulate the animal feed and drinking water compositions so that the animal takes in a therapeutically appropriate quantity of the composition along with its diet. It may also be convenient to present the composition as a premix for addition to the feed or drinking water.

Methods of Use:

Over-activation of LRRK2 kinase activity, e.g. in kinase mutant G2019S, is believed to be an important mechanism in α-synuclein related neurodegeneration, and is implicated in diseases that are characterized by the formation of Lewy bodies. Compounds as described herein exhibit inhibitory activity against LRRK2 kinase, including LRRK2 mutant kinase, including mutant G2019S. Kinase activity can be determined using a kinase assay, which typically employs a kinase substrate and a phosphate group donor, such as ATP (or a derivative thereof). Exemplary kinase assays are described in Example A. The kinase catalyzes the transfer of a phosphate group from the phosphate group donor (e.g., ATP) onto the substrate forming a covalent bond. Compounds as described herein can inhibit the activity of the kinase, slowing the above described reaction and resulting in a smaller number of phosphate groups being transferred. In one example, a method (i.e., an in vitro assay) is provided that includes: (i) contacting a compound of Formula I with a LRRK2 kinase, thereby forming a mixture. The method may further include (ii) contacting the mixture with a kinase substrate (e.g., peptide substrate) and ATP (or a derivative thereof), thereby forming an amount of phosphorylated kinase substrate. The method can further include (iii) measuring the amount of phosphorylated kinase substrate. The amount of phosphorylated substrate may be measured using a detection reagent. Suitable detection reagents can include a metal reagent, such as a lanthanoid (e.g., Eu-63), a radioactive probe, a labeled (e.g., fluorescently labelled) antibody and combinations thereof. In one example, the assay is a fluorescence resonance energy transfer (FRET) assay (e.g., TR-FRET). Examples of such assays are described in Example A. In a particular embodiment, a compound of Formula I is used as a reference standard to determine the in vitro activity of other compounds in a kinase assay as described above. Thus, in another example, the compound of Formula I is used in an in vitro assay for identifying candidate compounds that are capable of inhibiting LRRK2 kinase, including LRRK2 mutant kinase, including mutant G2019S kinase.

Compounds and compositions as described herein (i.e. Compounds of Formula I, or a salt or solvate thereof) are useful in the treatment and/or prevention of LRRK2 kinase mediated disorders, including LRRK2 kinase mutant mediated diseases, such as LRRK2 kinase mutant G2019S mediated diseases, including neurological diseases such as Parkinson's disease and other Lewy body diseases such as Parkinson disease with dementia, Parkinson's disease at risk syndrome, dementia with Lewy bodies (i.e., diffuse Lewy body disease (DLBD), Lewy body dementia, Lewy body disease, cortical Lewy body disease or senile dementia of Lewy type), Lewy body variant of Alzheimer's disease (i.e., diffuse Lewy body type of Alzheimer's disease), combined Parkinson's disease and Alzheimer's disease, as well as diseases associated with glial cortical inclusions, such as syndromes identified as multiple system atrophy, including striatonigral degeneration, olivopontocerebellar atrophy, and Shy-Drager syndrome, or other diseases associated with Parkinsonism, such as Hallervorden-Spatz syndrome (also referred to as Hallervorden-Spatz disease), fronto-temporal dementia, Sandhoff disease, progressive supranuclear palsy, corticobasal degeneration, autonomic dysfunctions (e.g., postural or orthostatic hypotension), cerebellar dysfunctions, ataxia, movement disorders, cognitive deterioration, sleep disorders, hearing disorders, tremors, rigidity (e.g., joint stiffness, increased muscle tone), bradykinesia, akinesia and postural instability (failure of postural reflexes, along other disease related factors such as orthostatic hypotension or cognitive and sensory changes, which lead to impaired balance and falls); cancers, including melanoma, acute myelogenous leukemia, breast carcinoma, lung adenocarincoma, prostate adenocarcinoma, renal cell carcinoma, and papillary thyroid carcinoma; autoimmune diseases such as Inflammatory Bowel Disease (e.g. Crohn's disease and ulcerative colitis); and leprosy. An in vivo model, which can be used to assess the potential in vivo beneficial effect of the compounds of Formula I, is described in Example C.

In addition to the compounds of Formula I, pharmaceutically acceptable derivatives or prodrugs of the compounds of Formula I may also be employed in compositions to treat or prevent the above-identified disorders.

In Vitro Activities:

Certain compounds as described herein, e.g. compounds of Formula I, exhibit various in vitro biological activities (see, e.g., Example A), such as inhibition of LRRK2 kinase activity and LRRK2 mutant G2019S kinase activity. In vitro assays for the determination of LRRK2 kinase activities are known in the art and exemplary assay formats are described herein (see e.g., Example A).

In Vivo Activities:

Certain compounds as described herein exhibit cellular biological activities, such as reduction in phosphorylation of ser910 or ser935 in HEK-293 cells transfected with either wild-type LRRK2 or LRRK2 G2019S mutant. For example, the phosphorylation of ser910 or ser935 in such HEK-293 transfected cells treated with a compound of Formula I will be less than 90%, less than 80%, less than 70%, less than 60%, less than 50%, less than 40%, less than 30%, less than 20%, less than 10%, less than 5%, or less than 1% of the phosphorylation of ser910 or ser935 control cells that are not treated with compound.

Certain compounds as described herein exhibit in vivo biological activities, such as reduction in phosphorylation of ser910 or ser935 in a mouse model. For example, following peritoneal injection of a compound of Formula I (e.g., at a dose of about 50 mg, about 100 mg, about 200 mg or about 300 mg/kg), or a vehicle control, kidney and brain tissue can be harvested and assessed for the phosphorylation of ser910 or ser935. In one example, the phosphorylation of ser910 or ser935 from the kidneys of mice treated with a compound of Formula I will be less than 90%, less than 80%, less than 70%, less than 60%, less than 50%, less than 40%, less than 30%, less than 20%, less than 10%, less than 5%, or less than 1% of the phosphorylation of ser910 or ser935 from the kidneys of control mice that are not treated with compound, and the phosphorylation of ser910 or ser935 from the brains of mice treated with a compound of Formula I will be less than 90%, less than 80%, less than 70%, less than 60%, less than 50%, less than 40%, less than 30%, less than 20%, less than 10%, less than 5%, or less than 1% of the phosphorylation of ser910 or ser935 from the brains of control mice that are not treated with compound.

Synthesis of the Compounds:

The compounds as described herein, e.g. compounds of Formula I, can be prepared using methods known in the art of organic synthesis and those described herein in the Examples. The starting materials and various intermediates may be obtained from commercial sources, prepared from commercially available compounds, and/or prepared using known synthetic methods. For example, the compounds as described herein, as well as all intermediates, can be synthesized by known processes using either solution or solid phase techniques. Exemplary procedures for preparing compounds as described herein are outlined in the following schemes.

Additionally, as will be apparent to those skilled in the art, conventional protecting groups may be necessary to prevent certain functional groups from undergoing undesired reactions. Suitable protecting groups for various functional groups as well as suitable conditions for protecting and deprotecting particular functional groups are well known in the art. For example, numerous protecting groups are described in T. W. Greene and P. G. M. Wuts, *Protecting Groups in Organic Synthesis*, Third Edition, Wiley, New York, 1999, and references cited therein.

In one example, compounds of Formula I wherein $R^1$ is $NH_2$ and $R_2$ is $C(=O)NH_2$, i.e. 4-amino-3-carboxamide cinnoline derivatives, are prepared from 3-haloanalines in three steps by methods as described in the following Scheme 1.

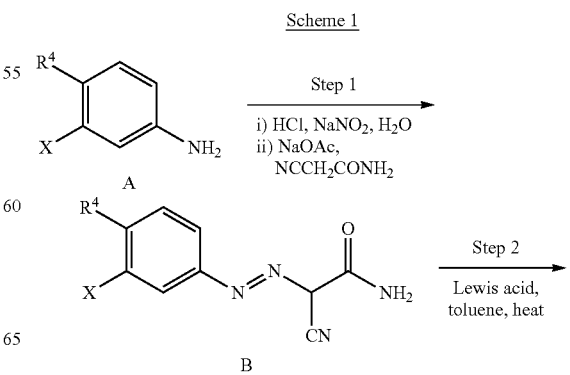

-continued

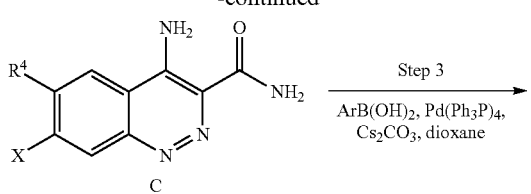

C

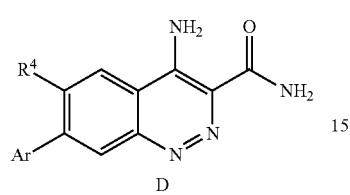

D

2-Cyano-2-(phenyldiazenyl)acetamides, B (X is a suitable leaving group, such as a halogen, $R^4$ is as defined for Formula I) is obtained by the coupling of 2-cyanoacetamide with the diazonium salts of suitably substituted 3-haloanilines. The diazonium salts of 3-haloaniline A are prepared by reaction with sodium nitrite in aqueous acid, then reacted with 2-cyanoacetamide in acetic acid to form B. Cyclization of B is accomplished by heating in the presence of a Lewis acid such as $AlCl_3$ or $TiCl_4$ to provide the optionally 6 substituted-7-halo-4-amino-cinnoline-3-carboxamide C. A coupling reaction with the halogen substituted 7 position of cinnoline C is employed to give optionally 6-substituted 7-(aryl or heteroaryl)-substituted-4-amino-cinnoline-3-carboxamide, D (Ar is aryl or heteroaryl consistent with $R^3$ of Formula I).

In one example, similar cinnolines where the 4-position amine is suitably substituted (i.e. where $R^1$ is $-NR^{12}R^{13}$ in Formula I) are prepared from compound C1, where X is e.g. iodo, in four steps, or further reacted in an additional step to the 3-nitrile substituted analogs, by methods as described in the following Scheme 2.

Scheme 2

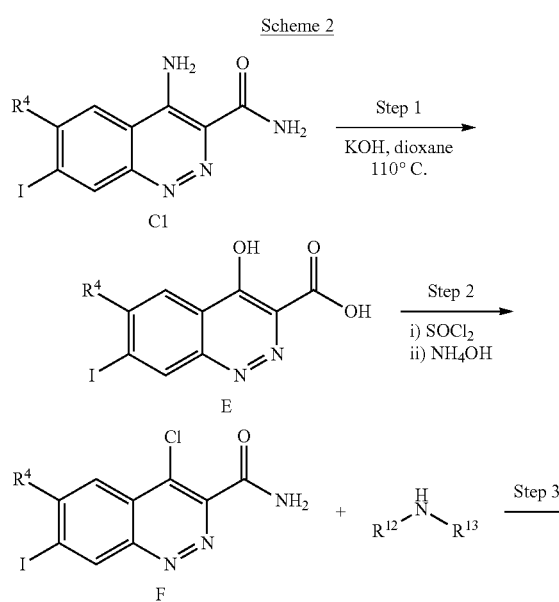

-continued 4-amino-7-iodocinnoline-3-carboxamide derivative optionally substituted at the 6 position, C1 ($R^4$ is as defined for Formula I) is reacted by heating under basic conditions, e.g. with KOH in dioxane to provide the 3-carboxylic acid-4-hydroxy cinnoline, E. Cinnoline E is then reacted with a suitable halogenating agent, such as thionyl chloride, followed by ammonium hydroxide to provide the 4-chloro-cinnoline-3-carboxamide F. Cinnoline F is then reacted with a suitable amine ($R^{12}$, $R^{13}$ are as defined for Formula I) to provide the 4-(substituted)amino-cinnoline-3-carboxamide G, which is reacted similarly to Step 3 of Scheme 1 to provide the desired optionally 6-substituted-4-(substituted) amino-7-(aryl or heteroaryl) substituted cinnoline-3-carboxamide H. Cinnoline H can be further reacted to convert the 3 position amide to nitrile, for example with $POCl_3$ and triethylamine via step 5, to provide cinnoline J. Alternatively, the amine $NHR^{12}R^{13}$ used in step 3 can be replaced with a suitable alcohol $OHR^9$ or thiol $SHR^{10}$, where $R^9$ and $R^{10}$ are as defined for Formula I, to provide the corresponding 3-carboxamide or carbonitrile compounds having $OR^9$ or $SR^{10}$ at the 4 position.

Additional 4-amino-cinnolines suitably substituted at the 6 or 7 position may be prepared from a suitably 3- or 4-substituted aniline in four (3-carboxamide substituted compounds) or five (3-nitrile substituted compounds) steps by methods as described in the following Scheme 3.

Scheme 3

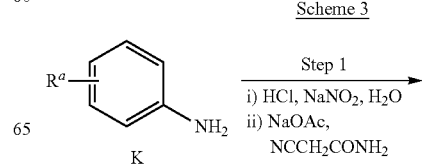

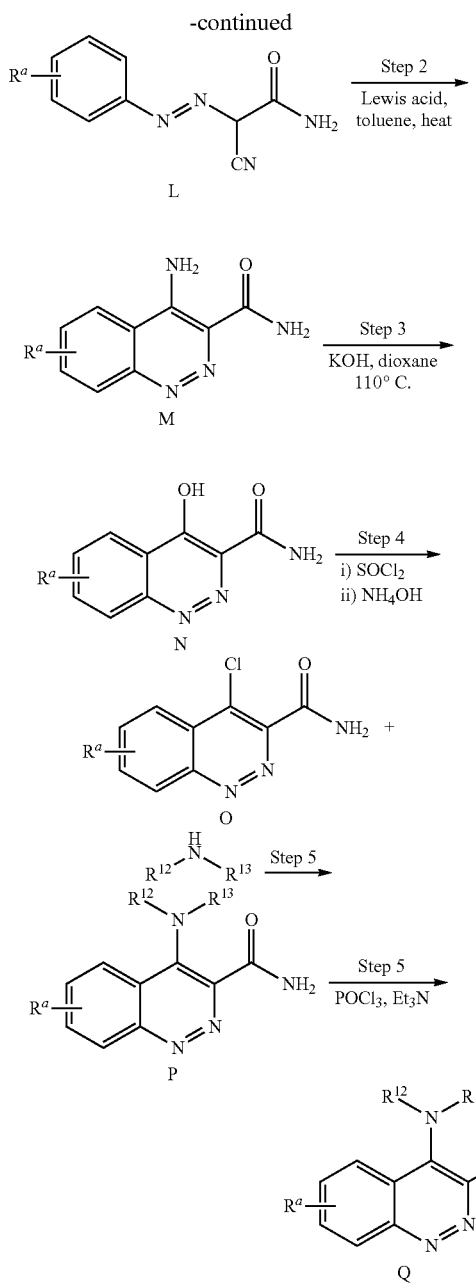

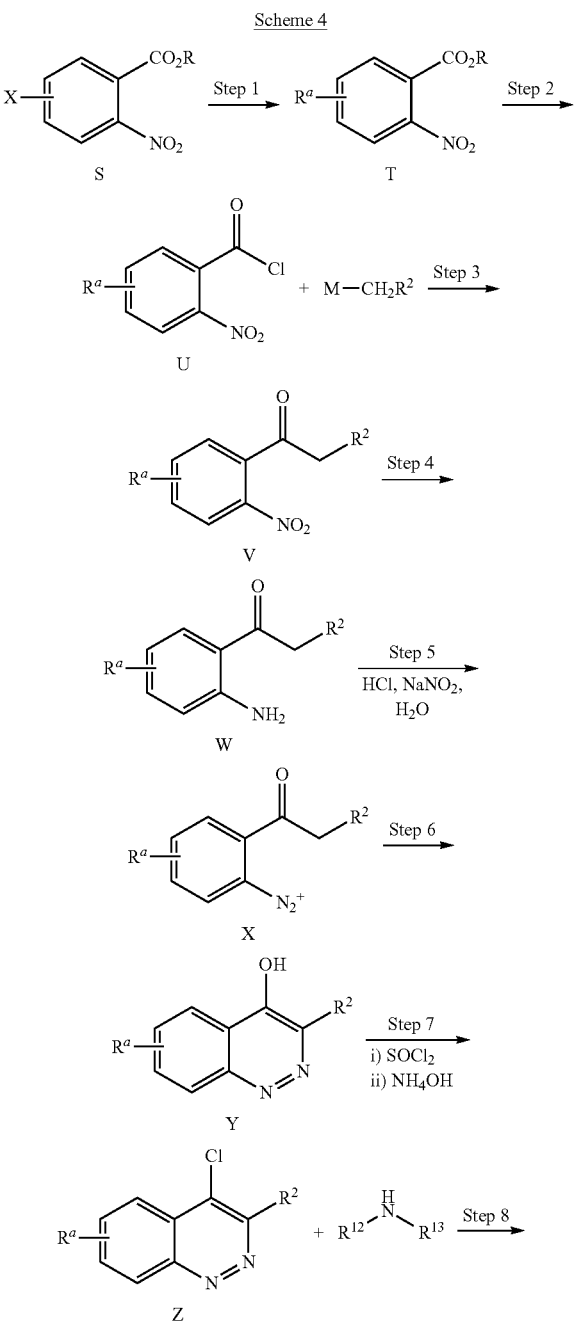

provide the 4-(substituted)amino cinnoline-3 carboxamide P which may be further reacted to convert the 3 position amide to nitrile, for example with $POCl_3$ and triethylamine via step 6, to provide cinnoline Q. Alternatively, the amine $NHR^{12}R^{13}$ used in step 5 can be replaced with a suitable alcohol $OHR^9$ or thiol $SHR^{10}$, where $R^9$ and $R^{10}$ are as defined for Formula I, to provide the corresponding 3-carboxamide or carbonitrile compounds having $OR^9$ or $SR^{10}$ at the 4 position.

Additional 4-amino-cinnolines suitably substituted at the 3 position and the 6 or 7 position may be prepared from a 4- or 5-halo substituted 2-nitrobenzoate in eight steps by methods as described in the following Scheme 4.

2-Cyano-2-(phenyldiazenyl)acetamides, L ($R^a$ at 3 or 4 position, within the description of $R^3$ and $R^4$ of Formula I) may be obtained by the coupling of 2-cyanoacetamide with the diazonium salts of 3- or 4-substituted anilines. The diazonium salts of 3- or 4-substitute aniline K are prepared by reaction with sodium nitrite in aqueous acid, then reacted with 2-cyanoacetamide in acetic acid to form L. Cyclization of L may be accomplished by heating in the presence of a Lewis acid such as $AlCl_3$ or $TiCl_4$ to give the 6- or 7-substituted 4-amino-cinnoline-3-carboxamide derivative M, which is reacted in step 3 by heating under basic conditions, e.g. with KOH in dioxane to provide the 3-carboxylic acid-4-hydroxy cinnoline, N. Cinnoline N is then reacted with a suitable halogenating agent, such as thionyl chloride, followed by ammonium hydroxide to provide the 4-chloro-carboxamide cinnoline O. Cinnoline O is then reacted with a suitable amine ($R^{12}$, $R^{13}$ are as defined for Formula I) to

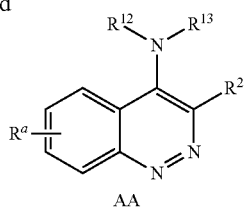

An appropriately 4- or 5-substituted 2-nitrobenzoate S (X is a suitable leaving group, such as a halogen) may be appended by any of a variety of known coupling procedures to afford 4- or 5-substituted 2-nitrobenzoate T ($R^a$ at the 4- or 5-position is within the description of $R^3$ and $R^4$ of Formula I). Elaboration of the carboxylate to the acyl chloride U and further reaction with M-$CH_2R^2$ ($R^2$ as defined for Formula I, e.g. a suitable sodium enolate, zincate, or Grignard reagent) provides an appropriately substituted ketone V. In step 4, reduction of the nitro group (e.g. using Fe/AcOH) provides aniline W. Diazotization by reaction with sodium nitrite in aqueous acid provides X, which can be cyclized, for example by reaction with sodium acetate, to the cinnoline Y, which is then reacted with a suitable halogenating agent, such as thionyl chloride, followed by ammonium hydroxide to provide the 4-Cl cinnoline Z. Cinnoline Z can be further substituted with, for example, a suitable amine to provide the 6 or 7 $R^a$ substituted-3-$R^2$ substituted-4-(substituted)amino-cinnoline AA ($R^{12}$, $R^{13}$ are as defined for Formula I). Alternatively, the amine $NHR^{12}R^{13}$ used in step 8 can be replaced with a suitable alcohol $OHR^9$ or thiol $SHR^{10}$, where $R^9$ and $R^{10}$ are as defined for Formula I, to provide the corresponding compounds having $OR^9$ or $SR^{10}$ at the 4 position.

The invention is illustrated further by the following examples, which are not to be construed as limiting the invention in scope or spirit to the specific procedures described in them. Analogous structures and alternative synthetic routes within the scope of the invention will be apparent to those skilled in the art.

EXAMPLES

General

Reagents and solvents obtained from commercial suppliers are used without further purification unless otherwise stated. Thin layer chromatography is performed on pre-coated 0.25 mm silica gel plates (E. Merck, silica gel 60, $F_{254}$). Visualization is achieved using UV illumination or staining with phosphomolybdic acid, ninhydrin or other common staining reagents. Flash chromatography is performed using either a Biotage Flash 40 system and pre-packed silica gel columns or hand packed columns (E. Merck silica gel 60, 230-400 mesh). Preparatory HPLC is performed on a Varian Prepstar high performance liquid chromatograph. $^1H$ and $^{13}C$ NMR spectra are recorded at 400 MHz Bruker Avance spectrometer, or in some instance at 500 MHz as indicated in the following examples. Chemical shifts are reported in parts per million (ppm) downfield relative to tetramethylsilane (TMS) or to proton resonances resulting from incomplete deuteration of the NMR solvent (δ scale). In some instances the synthetic examples give a racemic mixture of stereoisomers, which are readily separated by chiral HPLC.

LCMS is performed on an Agilent 1100 Series HPLC with a Series 1100 MSD with electrospray ionization using a Phenomenex Luna C18 4.6 mm i.d.×30 mm length, 3μ particle size column. Compound purity is typically determined by HPLC/MS analysis using a variety of analytical methods.

The examples are intended to be illustrative and are not limiting or restrictive to the scope of the invention. For example, where additional compounds are prepared similarly to synthetic methods of another example, or in the same manner as another example, it is understood that conditions may vary, for example, any of the solvents, reaction times, reagents, temperatures, work up conditions, or other reaction parameters may be varied employing alternate solvents, reagents, reaction times, temperatures, work up conditions, and the like, as are readily available to one skilled in the art.

Example 1

Synthesis of 4-amino-7-(4-(methylsulfonyl)phenyl)cinnoline-3-carboxamide (5)

4-Amino-7-(4-(methylsulfonyl)phenyl)cinnoline-3-carboxamide (5) was prepared from 3-chloroaniline (1) in 3 steps as follows:

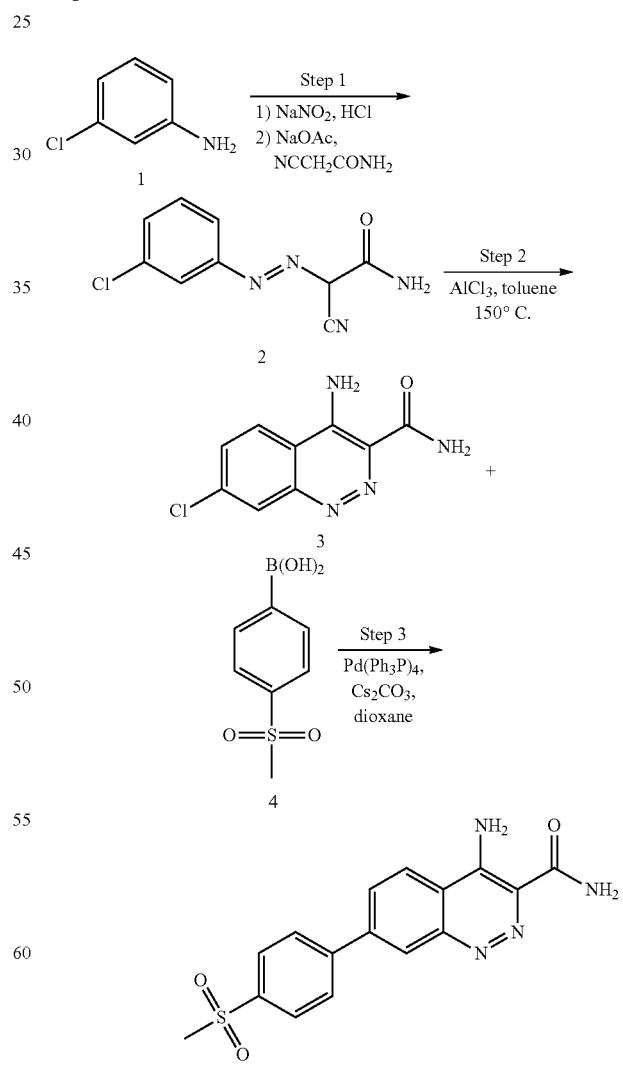

Step 1—synthesis of 2-((3-chlorophenyl)diazenyl)-2-cyanoacetamide (2): A 250 mL round-bottom flask was charged with 3-chloroaniline (1, 7.4 g, 58.1 mmol) and 15 mL of concentrated HCl was added slowly, followed by 10 mL of water, resulting in a slurry. Sodium nitrite (4.0 g in 15 mL of water, 58.1 mmol) was added at 0° C. After stirring for 15 min at 0° C., sodium acetate (19.1 g, 232 mmol) and cyanoacetamide (4.89 g, 58.1 mmol) in a solution of 85 mL of water and 60 mL of ethanol was added slowly using an addition funnel. After the addition was complete, the ice bath was removed and the suspension was slowly warmed to 23° C. and stirred for 16 h. The desired material was isolated by filtration and rinsed with water, ethanol, and $Et_2O$, then dried under vacuum to give the desired compound (2, 9.0 g, 70%).

Step 2—synthesis of 4-amino-7-chlorocinnoline-3-carboxamide (3): A 5 mL vial was charged with 2-((3-chlorophenyl)diazenyl)-2-cyanoacetamide (2, 150 mg) and suspended in 4 mL of toluene. A spatula tip of $AlCl_3$ was added and the vial was sealed under nitrogen. The heterogeneous reaction mixture was heated using microwave irradiation to 150° C. for 0.5 h, then 5 mL of 4N HCl was added to the cooled, bi-phasic reaction mixture, and solid was evolved. The solid product was recovered by filtration to give 125 mg of the desired compound 3. $^1$H NMR (400 MHz, DMSO-$d_6$) δ: 8.52 (d, J=9.1 Hz, 1H), 8.32 (bs, 1H), 8.17 (s, 1H), 7.79 (d, J=8.2 Hz, 1H), 7.58 (bs, 1H). MS: 223.0 m/z $(M+H)^+$. 4-Amino-6-chlorocinnoline-3-carboxamide is prepared similarly, using 4-chloroaniline in place of 3-chloroaniline in Step 1.

Step 3—synthesis of 4-amino-7-(4-(methylsulfonyl)phenyl)cinnoline-3-carboxamide (5): A 5 mL reaction vial was charged with 4-amino-7-chlorocinnoline-3-carboxamide (3, 125 mg, 0.56 mmol), 4-(methylsulfonyl)phenylboronic acid (4, 224 mg, 1.12 mmol), $Pd(Ph_3P)_4$ (128 mg, 0.11 mmol), $Cs_2CO_3$ (72 mg, 0.22 mmol), and 3 mL of dioxane. The heterogeneous mixture was heated to 150° C. for 0.5 h using microwave irradiation. Upon cooling to 23° C., the reaction mixture was quenched by addition of a saturated, aqueous sodium bicarbonate solution. The heterogeneous mixture was extracted with EtOAc and the organic layer was dried over $Na_2SO_4$, filtered and the filtrate concentrated under reduced pressure to give 370 mg of crude material. The crude material was further purified by HPLC to give the desired compound (5, 11.2 mg). $^1$H NMR (400 MHz, DMSO-$d_6$) δ: 8.70 (d, J=8.3 Hz, 1H), 8.54 (s, 1H), 8.38 (s, 1H), 8.24 (d, J=8.4 Hz, 1H), 8.18 (d, J=8.4 Hz, 2H), 8.12 (d, J=8.0 Hz, 2H), 7.94 (s, 1H), 3.31 (s, 3H). MS: 343.0 m/z $(M+H)^+$.

Additional compounds are prepared similarly to this method, replacing 4-(methylsulfonyl)phenylboronic acid with a suitable boronic acid in Step 3. The following compounds are prepared:
4-amino-7-(3-morpholinophenyl)cinnoline-3-carboxamide (6),
4-amino-7-(4-(dimethylamino)phenyl)cinnoline-3-carboxamide (7),
4-amino-7-(3-(dimethylamino)phenyl)cinnoline-3-carboxamide (8), and
4-amino-7-(4-morpholinophenyl)cinnoline-3-carboxamide (9).

The following table provides the compound number (column 1), boronic acid used in Step 3 (column 2) to give the compound shown in column 3. Identification data is provided in column 4.

| Comp. number | Boronic Acid | Compound structure | Identification |
|---|---|---|---|
| 6 | 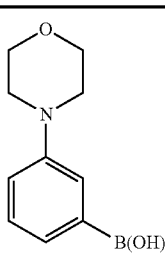 | 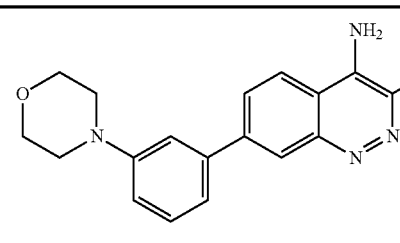 | MS: 350.1 m/z $(M + H)^+$ $^1$H-NMR (400 MHz, DMSO-d6) δ: 8.65 (d, J = 8.8 Hz, 1H), 8.52 (s, 1H), 8.22 (m, 2H), 7.97 (bs, 1H), 7.42 (m, 2H), 7.30 (d, J = 7.8 Hz, 1H), 7.11 (dd, J = 8.0, 1.8 Hz, 1H), 4.34 (m, 4H), 3.25 (m, 4H). |
| 7 | 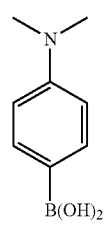 | 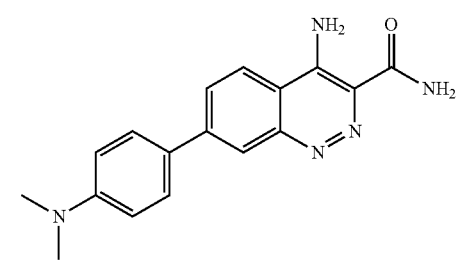 [SMILES: CN(C)c1ccc(-c2ccc3c(N)c(C(N)=O)nnc3c2)cc1] | MS: 308.1 m/z $(M + H)^+$ $^1$H-NMR (400 MHz, $CDCl_3$) δ: 8.38 (d, J = 8.8 Hz, 1H), 8.26 (s, 1H), 7.98 (d, J = 8.8 Hz 1H), 7.77 (d, J = 8.7 Hz, 2H), 7.33 (d, J = 8.8 Hz, 2H), 3.28 (s, 6H). |

-continued

| Comp. number | Boronic Acid | Compound structure | Identification |
|---|---|---|---|
| 8 | 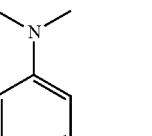 | 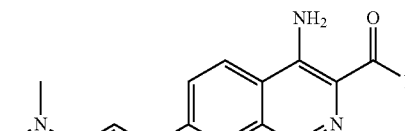 | MS: 308.1 m/z (M + H)+<br>¹H-NMR (400 MHz, CDCl₃) δ: 8.29 (d, J = 8.8 Hz, 1H), 8.16 (s, 1H), 7.91 (d, J = 8.8 Hz 1H), 6.92 (m, 2H), 6.74 (d. J = 8.2 Hz, 1H), 3.19(s, 6H). |
| 9 | 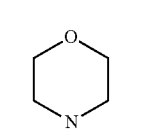 | 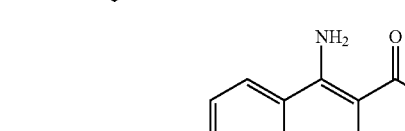 | MS: 350.2 m/z (M + H)+<br>¹H-NMR (400 MHz, CD₃OD) δ: 8.03 (m, 2H), 7.56 (m, 1H), 7.35 (d, J = 8.8 Hz, 2H), 7.15 (d, J = 8.8 Hz, 2H), 3.85 (m, 2H), 3.27 (m, 2H). |

4-amino-6-tert-butylcinnoline-3-carboxamide (186)

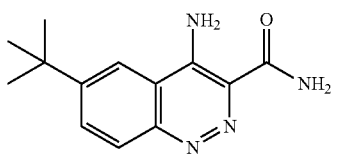 [SMILES: CC(C)(C)c1ccc2nnc(C(N)=O)c(N)c2c1]

is prepared similarly to this method, replacing 3-chloroaniline 1 with 4-tert-butylaniline in Step 1. ¹H NMR (500 MHz, DMSO-d₆) δ: 10.54 (bs, 1H), 10.22 (bs, 1H), 8.55 (s, 1H), 8.50 (s, 1H), 8.24 (d, J=9.0 Hz, 1H), 8.06 (s, 1H), 8.00 (d, J=9.0 Hz, 1H), 1.41 (s, 9H). MS: 245.2 m/z (M+H)+.

Example 2

Synthesis of 4-(isopropylamino)-7-(4-(methylsulfonyl)phenyl)cinnoline-3-carboxamide (17) and 4-(isopropylamino)-7-(4-(methylsulfonyl)phenyl)cinnoline-3-carbonitrile (18)

4-(isopropylamino)-7-(4-(methylsulfonyl)phenyl)cinnoline-3-carboxamide (17) and 4-(isopropylamino)-7-(4-(methylsulfonyl)phenyl)cinnoline-3-carboxamide (18) were prepared from 3-iodoaniline (10) in 6 or 7 steps as follows:

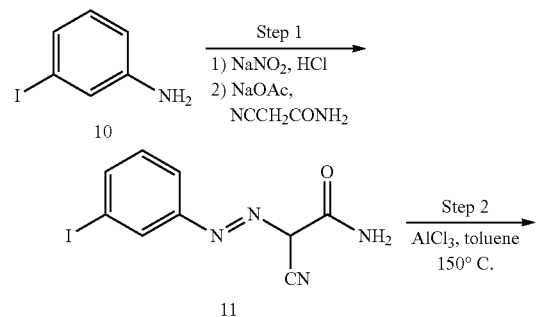

-continued

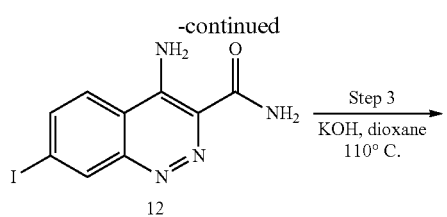

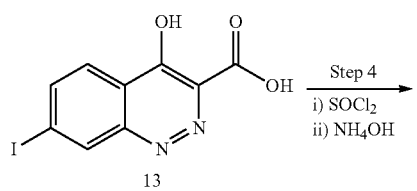

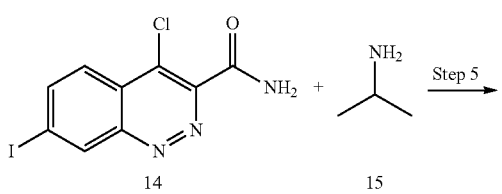

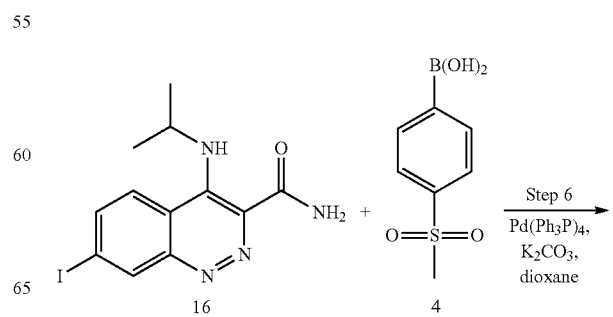

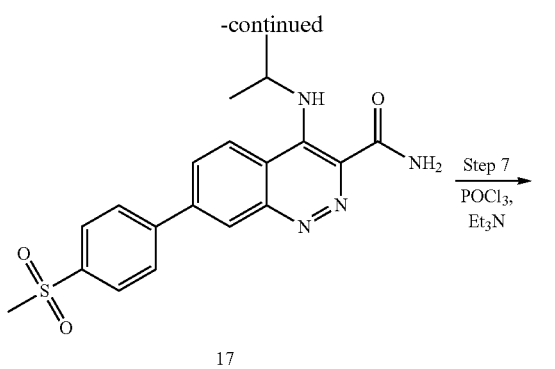

17

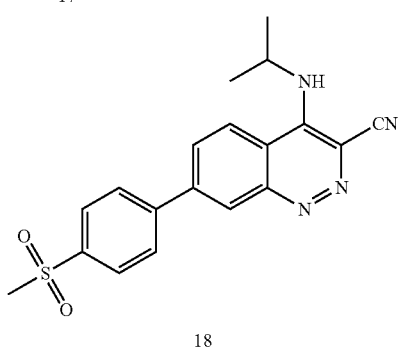

18

Step 1—synthesis of 2-cyano-2-((3-iodophenyl)diazenyl) acetamide (11): A 250 mL round-bottom flask was charged with 3-iodoaniline (10, 12.7 g, 58.1 mmol) and reacted similarly to Step 1 of Example 1 to give the desired compound (11, 70%).

Step 2—synthesis of 4-amino-7-iodocinnoline-3-carboxamide (12): A 20 mL reaction vial was charged with 2-cyano-2-((3-iodophenyl)diazenyl)acetamide (11, 1 g, 3.2 mmol) and suspended in 13 mL of toluene. Five spatula tips of $AlCl_3$ were added and the vial was sealed under nitrogen. The heterogeneous reaction mixture was heated using microwave irradiation to 150° C. for 20 min, then cooled and the reaction was added to 2 mL of cold 4N HCl. The resulting green solid was evolved and recovered by filtration to provide the desired compound (12, 0.95 g, 95% yield). $^1$H-NMR (400 MHz, DMSO-$d_6$, 60° C.) δ: 8.47(s, 1H), 8.42 (d, J=1 Hz, 1H), 8.27 (d, J=9 Hz, 1H), 8.07 (dd, J=9, 1 Hz, 1H), 7.87 (bs, 1H). MS: 314.9 m/z $(M+H)^+$.

Step 3—synthesis of 4-hydroxy-7-iodocinnoline-3-carboxylic acid (13): A 30 mL reaction vial was charged with 4-amino-7-iodocinnoline-3-carboxamide (12, 520 mg, 1.7 mmol) and suspended in 5 mL of dioxane, then 10 mL of 3N KOH solution was added and the reaction vial was sealed. The biphasic mix was heated to 110° C. for 16 h in an oil bath. After cooling to 23° C., the reaction mixture was quenched by the addition of 10 mL of glacial acetic acid. The resulting solid material was collected by filtration and dried under vacuum to provide the desired compound (13, 240 mg).

Step 4—synthesis of 4-chloro-7-iodocinnoline-3-carboxamide (14): The 4-hydroxy-7-iodocinnoline-3-carboxylic acid (13, 240 mg) was transferred to a 30 mL reaction vial, and 5 mL of thionyl chloride was added. The vial was sealed and heated to 110° C. for 4 h. After cooling to 23° C., excess thionyl chloride was blown off using a stream of nitrogen to assure a dry acid chloride material. This was further dried under vacuum, and the resulting dark crust was suspended in 5 mL of dry acetone and chilled to 0° C. before 2 mL of $NH_4OH$ was added using a syringe. The reaction mix was stirred for 0.5 h at 0° C. and the resulting solid was collected by filtration to give the desired compound (14, 120 mg).

Step 5—synthesis of 7-iodo-4-(isopropylamino)cinnoline-3-carboxamide (16): 4-chloro-7-iodocinnoline-3-carboxamide (14, 20 mg) was charged to a 3 mL microwave vessel and suspended in 0.4 mL of EtOH. Isopropylamine (15, 2 drops) was added, and the vial was sealed and heated to 140° C. using microwave irradiation for 0.5 h. The resulting material was purified by HPLC to give the desired compound (16, 10 mg). $^1$H NMR (400 MHz, CDCl$_3$) δ: 8.70 (s, 1H), 7.87 (s, 2H), 4.41 (quint, J=8.4 Hz, 1H), 3.37 (s,1H), 2.71 (m, 6H). MS: 357.0 m/z $(M+H)^+$.

Step 6—synthesis of 4-(isopropylamino)-7-(4-(methylsulfonyl)phenyl)cinnoline-3-carboxamide (17): A 5 mL reaction vial was charged with 7-iodo-4-(isopropylamino)cinnoline-3-carboxamide (16, 50 mg, 0.14 mmol), 4-(methylsulfonyl)phenylboronic acid 4 (56 mg, 0.28 mmol), Pd(Ph$_3$P)$_4$ (33 mg, 0.028 mmol), 2N K$_2$CO$_3$ (0.15 mL, 0.28 mmol), and 1.5 mL of dioxane. The heterogeneous mixture was heated to 130° C. for 0.5 h using microwave irradiation. Upon cooling to 23° C., the reaction mixture was quenched by addition of a saturated, aqueous NaHCO$_3$ solution. The heterogeneous mixture was extracted with EtOAc and the organic layer was dried over Na$_2$SO$_4$, filtered and the filtrate concentrated under reduced pressure to give crude material, which was further purified by HPLC to give the desired compound (17, 38 mg, 71%). $^1$H-NMR (400 MHz, CDCl$_3$) δ: 8.56 (s, 1H), 8.29 (d, J=12.0 Hz, 1H), 8.01 (d, J=11.1 2H), 7.89 (m, 3H), 4.54 (m, 1H), 3.24 (m, 1H), 3.04 (d, J=6.8 Hz, 3H), 1.49 (d, J=8.3 Hz, 6H). MS: 385.1 m/z $(M+H)^+$.

Step 7—synthesis of 4-(isopropylamino)-7-(4-(methylsulfonyl)phenyl)cinnoline-3-carbonitrile (18)

A solution of 4-(isopropylamino)-7-(4-(methylsulfonyl) phenyl)cinnoline-3-carboxamide (17, 68 mg, 0.18 mmol) and triethylamine (178 mL, 1.76 mmol) in 2.0 mL of dichloromethane was stirred at 0° C. as POCl$_3$ (81 mg, 0.53 mmol) was added dropwise. After 1 hour the reaction mixture was diluted with dichloromethane and washed with saturated aqueous NaHCO$_3$. The organic solution was dried over Na$_2$SO$_4$, filtered, and the filtrate concentrated using rotary evaporation. The crude material was purified by HPLC to give the desired compound (18, 13 mg, 20%). $^1$H NMR (400 MHz, DMSO-$d_6$) δ: 8.71 (d, J=8.5 Hz, 1H), 8.64 (s, 1H), 8.22-8.27 (m, 3H), 8.09 (d, J=7.9 Hz, 1H), 7.95 (d, J=7.8 Hz, 1H), 4.74-4.76 (m, 1H), 3.30 (s, 3H), 1.41 (d, J=6.0 Hz, 6H). MS: 367.1 m/z $(M+H)^+$.

Additional compounds are prepared similarly to this method, replacing isopropylamine 15 with a suitable amine, alcohol or thioalcohol in Step 5, isolating the carboxamide after Step 6, or reacting through Step 7 to provide the carbonitrile. The following compounds are prepared:

4-(cyclobutylamino)-7-(4-(methylsulfonyl)phenyl)cinnoline-3-carboxamide (19), 4-(1-methylpiperidin-4-ylamino)-7-(4-(methylsulfonyl)phenyl)cinnoline-3-carboxamide (21), 7-(4-(methylsulfonyl)phenyl)-4-(tetrahydrofuran-3-ylamino)cinnoline-3-carboxamide (23), 7-(4-(methylsulfonyl)phenyl)-4-(tetrahydro-2H-pyran-4-ylamino)cinnoline-3-carboxamide (25), 7-(4-(methylsulfonyl)phenyl)-4-(oxetan-3-ylamino)cinnoline-3-carboxamide (27), 4-(cyclopropylamino)-7-(4-(methylsulfonyl)phenyl)cinnoline-3-carboxamide (29), (R)-(sec-butylamino)-7-(4-(methylsulfonyl)phenyl)cinnoline-3-carboxamide (37), (R)-4-(sec-butylamino)-7-(4-(methylsulfonyl)phenyl)cinnoline-3-carbonitrile (38),
(R)-7-(4-(methylsulfonyl)phenyl)-4-(1-phenylethylamino)cinnoline-3-carboxamide (39),
(R)-4-(1-cyclopropylethylamino)-7-(4-(methylsulfonyl)phenyl)cinnoline-3-carboxamide (41),
(R)-4-(1-cyclopropylethylamino)-7-(4-(methylsulfonyl)phenyl)cinnoline-3-carbonitrile (42),
4-(1-adamantylamino)-7-(4-(methylsulfonyl)phenyl)cinnoline-3-carboxamide (88),
7-(4-(methylsulfonyl)phenyl)-4-((tetrahydro-2H-pyran-4-yl)methylamino)cinnoline-3-carboxamide (89)
(R)-7-(4-(methylsulfonyl)phenyl)-4-(1-(tetrahydro-2H-pyran-4-yl)ethylamino)cinnoline-3-carboxamide (90),
4-(tert-butylamino)-7-(4-(methylsulfonyl)phenyl)cinnoline-3-carboxamide (91),
4-cyclopropylmethylamino)-7-(4-(methylsulfonyl)phenyl)cinnoline-3-carboxamide (92),
4-(ethylamino)-7-(4-(methylsulfonyl)phenyl)cinnoline-3-carboxamide (93),
4-(methylamino)-7-(4-(methylsulfonyl)phenyl)cinnoline-3-carboxamide (94), and
4-(sec-butylthio)-7-(4-(methylsulfonyl)phenyl)cinnoline-3-carboxamide (243).

The following table provides the compound number (column 1), amine used in Step 5 (column 2) to give the compound shown in column 3. Identification data is provided in column 4.

| Comp. No. | Amine | Compound structure | Identification |
|---|---|---|---|
| 19 | cyclobutylamine | (structure) | MS: 397.1 m/z (M + H)⁺<br>$^1$H-NMR (400 MHz, DMSO-d6) δ: 8.67 (s, 1H), 8.38 (d, J = 9.2 Hz, 1H), 8.32 (s, 1H), 8.10-8.12 (m, 5H), 4.79-4.81 (m, 1H), 3.29 (s, 3H), 2.19-2.60 (m, 2H), 2.15-2.17 (m, 2H), 1.53-1.91 (m, 2H). |
| 21 | 1-methylpiperidin-4-amine | (structure) | MS: 440.2 m/z (M + H)⁺<br>$^1$H-NMR (400 MHz, DMSO-d6) δ: 9.47 (s, 1H), 8.74 (s, 1H), 8.55 (s, 1H), 8.42 (d, J = 8.7 Hz, 1H), 8.07-8.20 (m, 4H), 7.62-7.96 (m, 1H), 4.40-4.45 (m, 1H), 3.53-3.56 (m, 2H), 3.31 (s, 3H), 3.13-3.22 (m, 2H), 2.82 (s, 3H), 2.36-2.39 (m, 2H), 1.79-1.83 (m, 2H). |
| 23 | tetrahydrofuran-3-amine | (structure) | MS: 413.1 m/z (M + H)⁺<br>$^1$H-NMR (400 MHz, DMSO-d6) δ: 11.9 (s, 1H), 8.71 (s, 1H), 8.57 (d, J = 8.2 Hz, 1H), 8.37 (s, 1H), 8.12-8.18 (m, 5H), 5.10 (s, 1H), 3.31 (s, 3H), 2.86-3.99 (m, 4H), 2.52-2.58 (m, 1H), 2.08-2.10 (m, 1H). |

-continued
| Comp. No. | Amine | Compound structure | Identification |
|---|---|---|---|
| 25 | 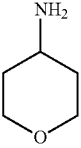 | 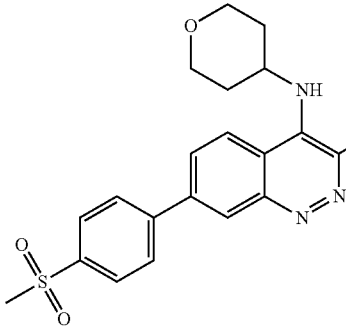 | MS: 427.1 m/z (M + H)+<br>$^1$H-NMR (400 MHz, DMSO-d6) δ: 8.71 (s, 1H), 8.50 (d, J = 10.1 Hz, 1H), 8.37 (s, 1H), 8.12-8.18 (m, 5H), 4.60 (s, 1H), 3.89-3.91 (m, 2H), 3.59-3.62 (m, 2H), 3.31 (s, 3H), 2.11-2.14 (m, 2H), 1.69-1.72 (m, 2H). |
| 27 | 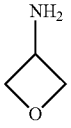 | 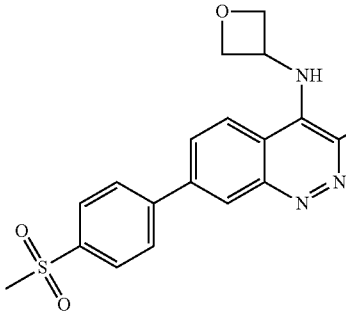 | MS: 399.1 m/z (M + H)+<br>$^1$H-NMR (400 MHz, CD$_3$OD) δ: 8.27 (s, 1H), 8.10-8.19 (m, 6H), 5.62-5.64 (m, 1H), 5.25 (dd, J = 7.0, 6.9 Hz, 2H), 4.82 (dd, J = 6.9, 5.8 Hz, 2H), 3.21 (s, 3H). |
| 29 |  | 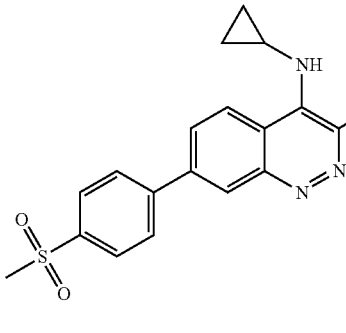 | MS: 383.1 m/z (M + H)+<br>$^1$H-NMR (400 MHz, DMSO-d6) δ: 11.6 (s, 1H), 8.71 (s, 1H), 9.15 (d, J = 9.0 Hz, 1H), 8.66 (s, 1H), 8.37 (s, 1H), 8.04-8.17 (m, 6H), 3.49 (s, 1H), 3.30 (s, 3H), 1.12-1.14 (m, 2H), 0.85 (s, 2H). |
| 37 | 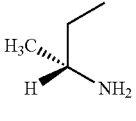 | 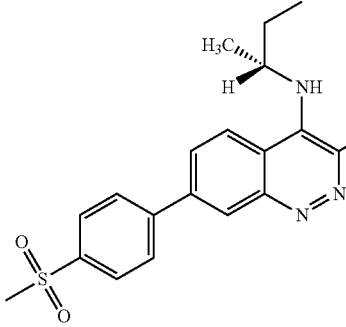 | MS: 399.1 m/z (M + H)+<br>$^1$H-NMR (400 MHz, CDCl$_3$) δ: 9.08 (d, J = 2.3 Hz, 1H), 8.35 (d, J = 12.1 Hz, 1H), 8.13 (m, 2H), 7.98 (m, 3H), 7.96 (d, J = 2.3 Hz, 1H), 5.74 (m, 1H), 4.39 (m, 1H), 3.12 (s, 3H), 1.91 (m, 2H), 1.61 (d, J = 6.3 Hz, 3H), 1.12 (t, J = 9.8 Hz, 3H). |

-continued
| Comp. No. | Amine | Compound structure | Identification |
|---|---|---|---|
| 38* | 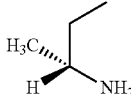 | 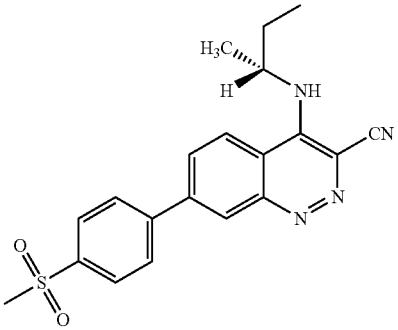 [SMILES: CC[C@@H](C)Nc1c(C#N)nnc2cc(-c3ccc(S(C)(=O)=O)cc3)ccc12] | MS: 381.1 m/z (M + H)+<br>1H-NMR (400 MHz, CDCl3) δ: 8.59 (m, 1H), 8.20 (d, J = 8.7 Hz, 1H), 8.08 (d, J = 7.5 Hz, 2H), 7.94 (d, J = 8.4 Hz, 1H), 7.88 (d, J = 7.5 Hz, 2H), 6.66 (brs, 1H), 4.70 (m, 1H), 3.12 (s, 3H), 1.81 (m, 2H), 1.51 (d, J = 5.9 Hz, 3H), 1.08 (J = 7.1 Hz, 3H) |
| 39 | 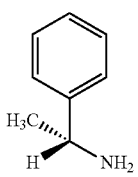 | 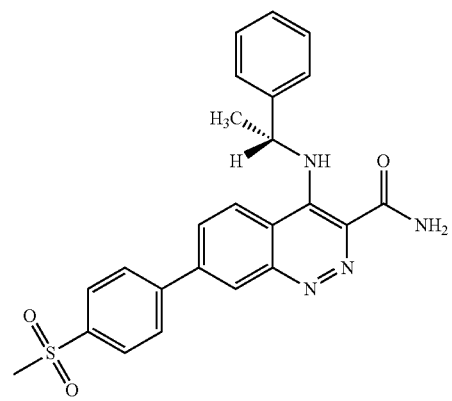 [SMILES: C[C@@H](Nc1c(C(N)=O)nnc2cc(-c3ccc(S(C)(=O)=O)cc3)ccc12)c1ccccc1] | MS: 447.2 m/z (M + H)+<br>1H-NMR (400 MHz, CDCl3) δ: 8.99 (brs, 1H), 8.20 (m, 1H), 8.08 (m, 3H), 7.93 (m, 1H), 7.44 (m, 4H), 7.37 (m, 1H), 5.77 (s, 1H), 5.47 (m, 1H), 3.10 (s, 3H), 1.87 (d, J = 5.9 Hz, 3H). |
| 41 | 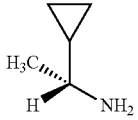 | 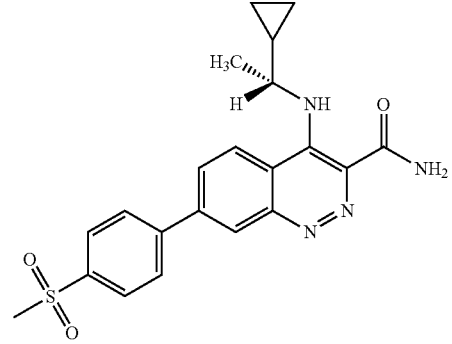 [SMILES: C[C@@H](Nc1c(C(N)=O)nnc2cc(-c3ccc(S(C)(=O)=O)cc3)ccc12)C1CC1] | MS: 411.2 m/z (M + H)+<br>1H-NMR (400 MHz, CDCl3) δ: 9.07 (d, J = 2.2 Hz, 1H), 8.35 (d, J = 12.1 Hz, 1H), 8.12 (m, 2H), 7.95 (m, 3H), 5.74 (m, 1H), 4.07 (m, 1H), 3.12 (s, 3H), 1.63 (d, J = 8.5 Hz, 3H), 1.32 (m, 1H), 0.75 (m, 2H), 0.43 (m, 2H). |
| 42 | 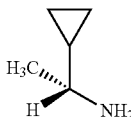 | 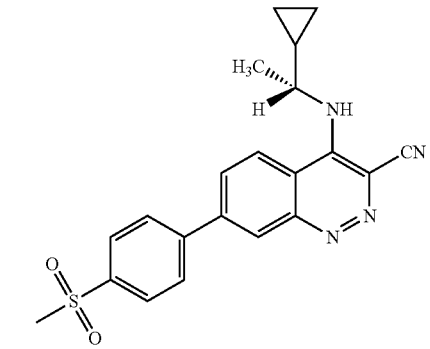 [SMILES: C[C@@H](Nc1c(C#N)nnc2cc(-c3ccc(S(C)(=O)=O)cc3)ccc12)C1CC1] | MS: 393.1 m/z (M + H)+<br>1H-NMR (400 MHz, CDCl3) δ: 8.67 (b s, 1H), 8.26-8.21 (m, 1H), 8.15-8.08 (m, 2H), 8.06-8.00 (m, 1H), 7.98-7.91 (m, 2H), 4.26-4.12 (m, 1H), 3.67-3.41 (m, 1H), 3.26 (s, 3H), 1.57 (d, J = 6.36 Hz, 3H), 1.25-1.18 (m, 1H), 0.80-0.63 (m, 2H), 0.56-0.46 (m, 2H). |

-continued
| Comp. No. | Amine | Compound structure | Identification |
|---|---|---|---|
| 88 | 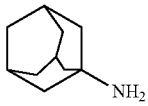 | 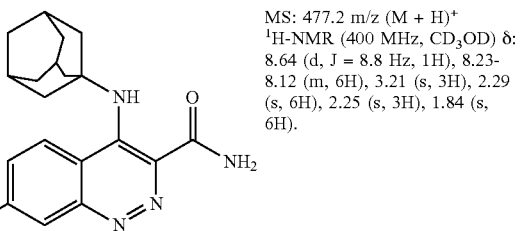 | MS: 477.2 m/z (M + H)$^+$<br>$^1$H-NMR (400 MHz, CD$_3$OD) δ: 8.64 (d, J = 8.8 Hz, 1H), 8.23-8.12 (m, 6H), 3.21 (s, 3H), 2.29 (s, 6H), 2.25 (s, 3H), 1.84 (s, 6H). |
| 89 | 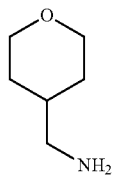 | 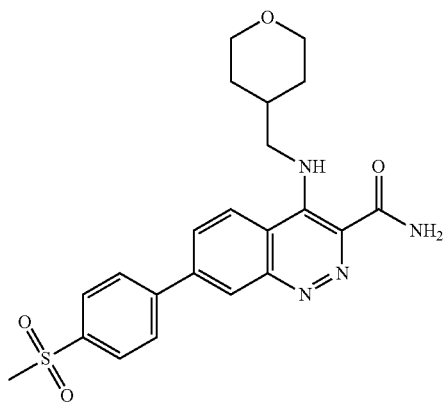 [SMILES: CS(=O)(=O)c1ccc(-c2ccc3c(NCC4CCOCC4)c(C(N)=O)nnc3c2)cc1] | MS: 441.1 m/z (M + H)$^+$<br>$^1$H-NMR (400 MHz, CD$_3$OD) δ: 8.75 (d, J = 9.2 Hz, 1H), 8.21 (d, J = 1.6 Hz, 1H), 8.13 (m, 5H), 4.05 (m, 4H), 3.51 (m, 2H), 3.19 (s, 3H), 2.17 (m, 1H), 1.91 (m, 2H), 1.54 (m, 2H). |
| 90 | 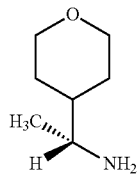 | 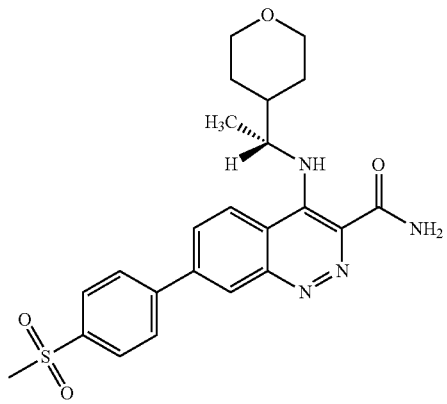 [SMILES: C[C@@H](Nc1c(C(N)=O)nnc2cc(-c3ccc(S(C)(=O)=O)cc3)ccc12)C1CCOCC1] | MS: 455.2 m/z (M + H)$^+$<br>$^1$H-NMR (400 MHz, CD$_3$OD) δ: 8.63 (d, J = 8.8 Hz, 1H), 8.23 (s, 2H), 8.15 (m, 5H), 4.51 (m, 1H), 4.03 (m, 2H), 3.47 (m, 2H), 3.20 (s, 1H), 2.05 (m, 1H), 1.84 (m, 2H), 1.58 (m, 5H). |
| 91 | 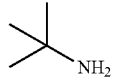 | 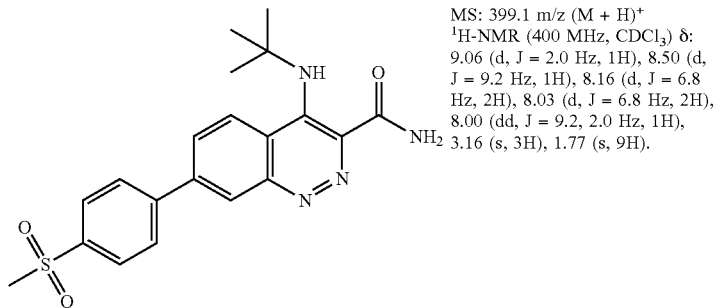 | MS: 399.1 m/z (M + H)$^+$<br>$^1$H-NMR (400 MHz, CDCl$_3$) δ: 9.06 (d, J = 2.0 Hz, 1H), 8.50 (d, J = 9.2 Hz, 1H), 8.16 (d, J = 6.8 Hz, 2H), 8.03 (d, J = 6.8 Hz, 2H), 8.00 (dd, J = 9.2, 2.0 Hz, 1H), 3.16 (s, 3H), 1.77 (s, 9H). |

-continued

| Comp. No. | Amine | Compound structure | Identification |
|---|---|---|---|
| 92 | 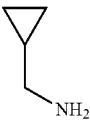 | 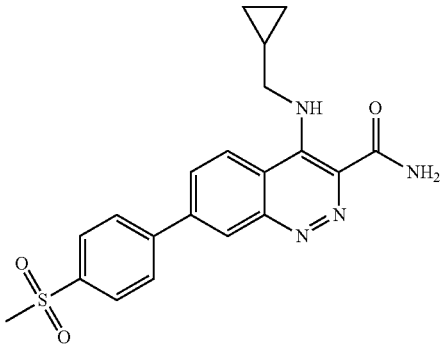 [SMILES: CS(=O)(=O)c1ccc(-c2ccc3c(NCC4CC4)c(C(N)=O)nnc3c2)cc1] | MS: 397 m/z (M + H)+<br>$^1$H-NMR (400 MHz, DMSO-d6)<br>δ: 8.67 (broad s, 1H), 8.58 (d, J = 9.2 Hz, 1H), 8.30 (broad s, 1H), 8.13 (s, 4H), 8.07 (dd, J = 9.2, 1.6 Hz, 1H), 3.91 (t, J = 6.0 Hz, 2H), 3.30 (s, 3H), 1.30 (m, 1H) 0.65 (m, 2H), 0.44 (m, 2H). |
| 93 |  | 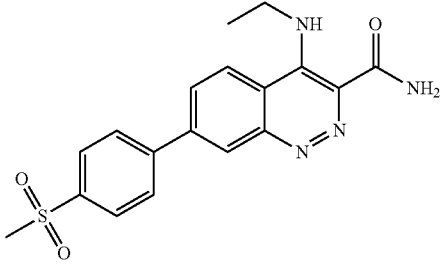 [SMILES: CCNc1c(C(N)=O)nnc2cc(-c3ccc(S(C)(=O)=O)cc3)ccc12] | MS: 371 m/z (M + H)+<br>$^1$H-NMR (400 MHz, DMSO-d6)<br>δ: 8.65 (broad s, 1H), 8.62 (d, J = 8.8 Hz, 1H), 8.32 (d, J = 1.6 Hz, 1H), 8.12 (m, 6H), 4.01 (m, 2H), 3.30 (s, 3H), 1.41 (t, J = 7.2 Hz, 3H). |
| 94 |  | 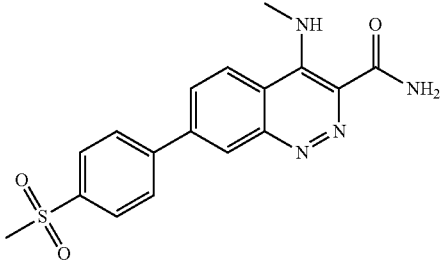 [SMILES: CNc1c(C(N)=O)nnc2cc(-c3ccc(S(C)(=O)=O)cc3)ccc12] | MS: 357 m/z (M + H)+<br>$^1$H-NMR (400 MHz, DMSO-d6)<br>δ: 8.73 (d, J = 8.8 Hz, 1H), 8.60 (broad s, 1H), 8.30 (broad s, 1H), 8.12 (m, 5H), 3.58 (broad s, 3H), 3.30 (s, 3H). |
| 243 |  | 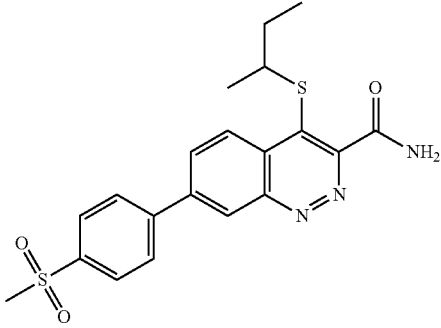 [SMILES: CCC(C)Sc1c(C(N)=O)nnc2cc(-c3ccc(S(C)(=O)=O)cc3)ccc12] | MS: 416 m/z (M + H)+<br>$^1$H-NMR (400 MHz, CD$_3$OD) δ: 8.82 (d, J = 1.6 Hz, 1H), 8.75 (d, J = 8.8 Hz, 1H), 8.37 (dd, J = 8.8, 1.6 Hz, 1H), 8.16 (m, 4H), 3.62 (m, 1H), 3.20 (s, 3H), 1.63 (m, 2H), 1.25 (d, J = 6.8 Hz, 3H), 1.20 (t, J = 7.6 Hz, 3H). |

*trifluoroacetic anhydride was used in place of POCl$_3$ for step 7.

Additional compounds are prepared similarly to this method, replacing 4-(methylsulfonyl)phenylboronic acid 4 with a suitable boronic acid in Step 6, an and isolating the carboxamide after Step 6. The following compounds are prepared:

4-(isopropylamino)-7-(pyridin-4-yl)cinnoline-3-carboxamide (31), 4-(isopropylamino)-7-(pyrimidin-5-yl)cinnoline-3-carboxamide (33), 4-(isopropylamino)-7-(1-methyl-1H-pyrazol-4-yl)cinnoline-3-carboxamide (35), 7-(4-fluorophenyl)-4-(isopropylamino)cinnoline-3-carboxamide (43), 7-(3-fluorophenyl)-4-(isopropylamino)cinnoline-3-carboxamide (45), 7-(2-fluorophenyl)-4-(isopropylamino)cinnoline-3-carboxamide (47), 4-(isopropylamino)-7-(4-morpholinophenyl)cinnoline-3-carboxamide (49), 4-(isopropylamino)-7-(3-morpholinophenyl)cinnoline-3-carboxamide (51), 4-(isopropylamino)-7-(1H-pyrazol-4-yl)cinnoline-3-carboxamide (53), and 4-(isopropylamino)-7-(pyridin-3-yl)cinnoline-3-carboxamide (57), 4-(isopropylamino)-7-vinylcinnoline-3-carboxamide (95), 4-(isopropylamino)-7-(2-methoxyphenyl)cinnoline-3-carboxamide (96), 4-(isopropylamino)-7-(3-methoxyphenyl)cinnoline-3-carboxamide (97), 7-(5-fluoro-2-methoxyphenyl)-4-(isopropylamino)cinnoline-3-carboxamide (98), and 4-(isopropylamino)-7-(prop-1-en-2-yl)cinnoline-3-carboxamide (99).

The following table provides the compound number (column 1), boronic acid used in Step 6 (column 2) to give the compound shown in column 3. Identification data is provided in column 4.

| Comp. No. | Boronic acid | Compound structure | Identification |
|---|---|---|---|
| 31 | 4-pyridinylboronic acid | 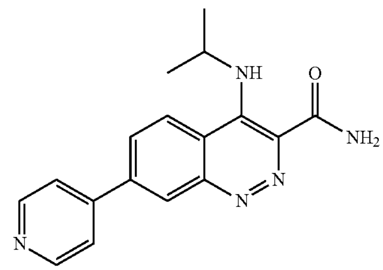 [SMILES: CC(C)Nc1c(C(N)=O)nnc2cc(-c3ccncc3)ccc12] | MS: 308.1 m/z (M + H)$^+$ $^1$H-NMR (400 MHz, CD$_3$OD) δ: 8.14 (s, 2H), 8.66 (d, J = 9.0 Hz, 1H), 8.31 (s, 1H), 8.19 (d, J = 8.9 Hz, 1H), 8.01 (d, J = 4.5 Hz, 2H), 4.80-4.86 (m, 1H), 1.58 (d, J = 6.0 Hz, 6H). |
| 33 | 5-pyrimidinylboronic acid | 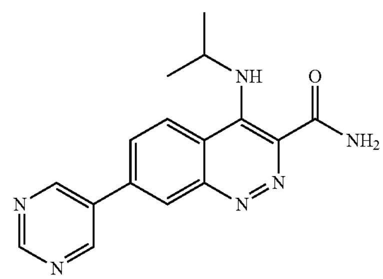 [SMILES: CC(C)Nc1c(C(N)=O)nnc2cc(-c3cncnc3)ccc12] | MS: 309.1 m/z (M + H)$^+$ $^1$H-NMR (400 MHz, CD$_3$OD) δ: 9.29-9.31 (3H), 8.66 (d, J = 8.9 Hz, 1H), 8.25 (s, 1H), 8.17 (d, J = 8.9 Hz, 1H), 4.80-4.83 (m, 1H), 1.58 (d, J = 6.0 Hz, 6H). |
| 35 | 1-methyl-1H-pyrazol-4-ylboronic acid | 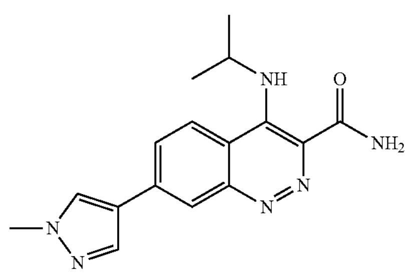 [SMILES: CC(C)Nc1c(C(N)=O)nnc2cc(-c3cnn(C)c3)ccc12] | MS: 311.2 m/z (M + H)$^+$ $^1$H-NMR (400 MHz, DMSO-d6) δ: 11.8 (s, 1H), 8.61 (s, 1H), 8.49 (s, 1H), 8.39 (d, J = 8.8 Hz, 1H), 8.13 (s, 1H), 8.03 (s, 1H), 7.98 (d, J = 8.8 Hz, 1H), 4.62-4.64 (m, 1H), 3.94 (s, 3H), 1.43 (d, J = 5.8 Hz, 6H). |
| 43 | 4-fluorophenylboronic acid | 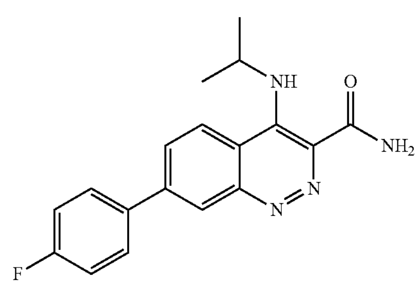 [SMILES: CC(C)Nc1c(C(N)=O)nnc2cc(-c3ccc(F)cc3)ccc12] | MS: 325.1 m/z (M + H)$^+$ $^1$H-NMR (400 MHz, CDCl$_3$) δ: 8.92 (d, J = 2.4 Hz, 1H), 8.32 (d, J = 12.2 Hz, 1H), 8.02 (s, 1H), 7.95 (dd, J = 12.1, 2.5 Hz, 1H), 7.82 (m, 2H), 5.68 (s, 1H), 4.62 (m, 1H), 1.61 (d, J = 8.4 Hz, 6H). |

-continued

| Comp. No. | Boronic acid | Compound structure | Identification |
|---|---|---|---|
| 45 | 3-fluorophenylboronic acid | 7-(3-fluorophenyl)-4-(isopropylamino)cinnoline-3-carboxamide | MS: 325.1 m/z (M + H)+<br>1H-NMR (400 MHz, CDCl3) δ: 8.91 (d, J = 2.4 Hz, 1H), 8.34 (d, J = 12.2 Hz, 1H), 8.00 (s, 1H), 7.94 (dd, J = 12.1, 2.5 Hz, 1H), 7.57 (m, 1H), 7.52 (m, 1H), 7.45 (m, 1H), 7.19 (m, 1H), 5.70(s, 1H), 4.60 (m, 1H), 1.61 (d, J = 8.4 Hz, 6H). |
| 47 | 2-fluorophenylboronic acid | 7-(2-fluorophenyl)-4-(isopropylamino)cinnoline-3-carboxamide | MS: 325.1 m/z (M + H)+<br>1H-NMR (400 MHz, CDCl3) δ: 8.78 (d, J = 2.4 Hz, 1H), 8.31 (d, J = 12.2 Hz, 1H), 8.03 (s, 1H), 7.97 (dt, J = 12.0, 2.8 Hz, 1H), 7.69 (m, 1H), 7.46 (m, 1H), 7.35 (m, 1H), 7.20(m, 1H), 5.72 (s, 1H), 4.61 (m, 1H), 1.61(d, J = 8.4 Hz, 6H) |
| 49 | 4-morpholinophenylboronic acid | 4-(isopropylamino)-7-(4-morpholinophenyl)cinnoline-3-carboxamide | MS: 392.1 m/z (M + H)+<br>1H-NMR (400 MHz, CDCl3) δ: 8.84 (s, 1H), 8.25 (d, J = 12.2 Hz, 1H), 7.99 (m, 2H), 7.81 (d, J = 11.8 Hz, 2H), 7.05 (d, J = 11.8 Hz, 2H), 5.65 (m, 1H), 4.60 (m, 2H) 3.89 (m, 4H), 3.30 (m, 4H), 1.6 (d, J = 8.5 Hz, 3H) |
| 51 | 3-morpholinophenylboronic acid | 4-(isopropylamino)-7-(3-morpholinophenyl)cinnoline-3-carboxamide | MS: 392.1 m/z (M + H)+<br>1H-NMR (400 MHz, CDCl3) δ: 9.00 (s, 1H), 8.30 (m, 1H), 8.02 (m, 2H), 7.45 (m, 1H), 7.43 (m, 1H), 7.06 (m, 1H), 5.73 (s, 1H), 4.63 (m, 1H), 3.91 (m, 4H), 3.33 (m, 4H), 1.6 (d, J = 8.5 Hz, 3H) |
| 53 | 1H-pyrazol-4-ylboronic acid | 4-(isopropylamino)-7-(1H-pyrazol-4-yl)cinnoline-3-carboxamide | MS: 297.1 m/z (M + H)+<br>1H-NMR (400 MHz, CD3OD) δ: 8.48 (d, J = 8.7 Hz, 1H), 8.29 (s, 2H), 8.07 (d, J = 8.7 Hz, 1H), 8.00 (s, 1H), 4.74-4.77 (m, 1H), 1.55 (d, J = 5.9 Hz, 6H). |

| Comp. No. | Boronic acid | Compound structure | Identification |
|---|---|---|---|
| 57 | 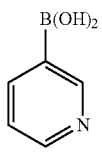 | 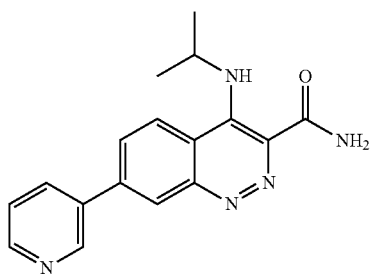 [SMILES: CC(C)Nc1c(C(N)=O)nnc2cc(-c3cccnc3)ccc12] | MS: 308.1 m/z (M + H)+ 1H-NMR (400 MHz, CD3OD) δ: 9.06 (s, 1H), 8.73 (s, 1H), 8.64 (d, J = 9.1 Hz, 1H), 8.37 (d, J = 8.5 Hz, 1H), 8.14-8.18 (m, 2H), 7.70-7.71 (m, 1H), 4.72-4.78 (m, 1H), 1.57 (d, J = 6.0, 6H). |
| 95 | 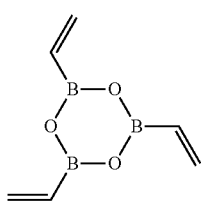 | 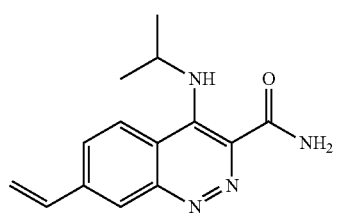 [SMILES: C=Cc1ccc2c(NC(C)C)c(C(N)=O)nnc2c1] | MS: 257.1 m/z (M + H)+ 1H-NMR (400 MHz, CD3OD) δ: 8.47 (d, J = 8.8 Hz, 1H), 7.98 (d, J = 8.8 Hz, 1H), 7.85 (s, 1H), 7.00 (dd, J = 17, 10 Hz, 1H), 6.26 (d, J = 17 Hz, 1H), 5.73 (d, J = 10 Hz, 1H), 4.74 (m, 1H), 1.55 (d, J = 6 Hz, 6H). |
| 96 | 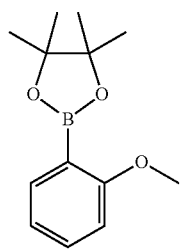 | 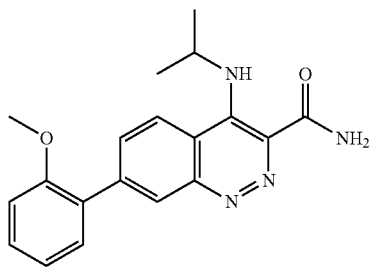 [SMILES: COc1ccccc1-c1ccc2c(NC(C)C)c(C(N)=O)nnc2c1] | MS: 337.1 m/z (M + H)+ 1H-NMR (400 MHz, CD3OD) δ: 8.52 (d, J = 9.2 Hz, 1H), 8.12 (d, J = 1.6 Hz, 1H), 8.03 (dd, J = 9.2, 2 Hz, 1H), 7.50(m, 2H), 7.19 (d, J = 8.4 Hz, 1H), 7.14 (m, 1H), 4.78 (m, 1H), 3.88 (s, 3H), 1.57 (d, J = 6.4 Hz, 6H). |
| 97 | 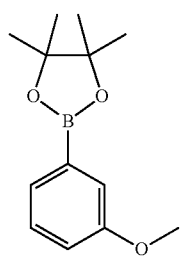 | 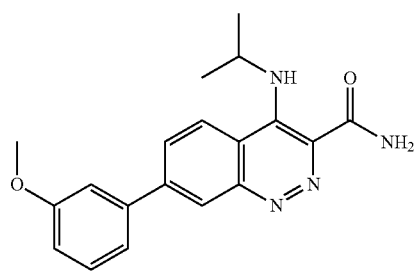 [SMILES: COc1cccc(-c2ccc3c(NC(C)C)c(C(N)=O)nnc3c2)c1] | MS: 337.1 m/z (M + H)+ 1H-NMR (400 MHz, CD3OD) δ: 8.59 (d, J = 9.6 Hz, 1H), 8.13 (m, 2H), 7.51 (m, 1H), 7.41 (m, 1H), 7.38 (m, 1H), 7.14 (m, 1H), 4.79 (m, 1H), 3.91 (s, 3H), 1.59 (d, J = 6.2 Hz, 6H). |
| 98 | 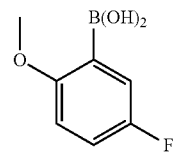 | 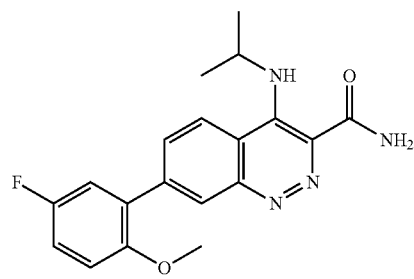 [SMILES: COc1ccc(F)cc1-c1ccc2c(NC(C)C)c(C(N)=O)nnc2c1] | MS: 355.1 m/z (M + H)+ 1H-NMR (400 MHz, CD3OD) δ: 8.56 (d, J = 9.2 Hz, 1H), 8.15 (d, J = 1.6 Hz, 1H), 8.01 (dd, 9.2, 1.6 Hz, 1H), 7.35 (dd, J = 8.8, 2.8 Hz, 1H), 7.25 (m, 2H), 4.79 (m, 1H), 3.86 (s, 3H), 1.59 (d, J = 6.4 Hz, 6H). |

| Comp. No. | Boronic acid | Compound structure | Identification |
|---|---|---|---|
| 99 | | 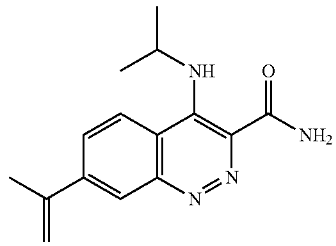 [SMILES: C=C(C)c1ccc2c(NC(C)C)c(C(N)=O)nnc2c1] | MS: 271.1 m/z (M + H)+<br>1H-NMR (400 MHz, CDCl3) δ: 12.90 (broad s, 1H), 8.69 (broad s, 1H), 8.22 (d, J = 9.2 Hz, 1H), 8.11 (broad s, 1H), 7.89 (d, J = 9.2 Hz, 1H), 8.00 (dd, J = 9.2, 2.0 Hz, 1H), 3.16 (s, 3H), 1.77 (s, 9H). |

Additional compounds are prepared similarly to this method, replacing isopropylamine 15 with (R)-1-cyclopropylethanamine in Step 5, and replacing 4-(methylsulfonyl)phenylboronic acid 4 with a suitable boronic acid in Step 6, and isolating the carboxamide after Step 6. The following compounds are prepared:

(R)-4-(1-cyclopropylethylamino)-7-(pyridin-4-yl)cinnoline-3-carboxamide (100),
(R)-4-(1-cyclopropylethylamino)-7-(1-methyl-1H-pyrazol-4-yl)cinnoline-3-carboxamide (101),
(R)-4-(1-cyclopropylethylamino)-7-(3-(dimethylcarbamoyl)phenyl)cinnoline-3-carboxamide (102),
(R)-4-(1-cyclopropylethylamino)-7-(2-methoxyphenyl)cinnoline-3-carboxamide (103),
(R)-4-(1-cyclopropylethylamino)-7-(2-(methoxymethyl)phenyl)cinnoline-3-carboxamide (104),
(R)-4-(1-cyclopropylethylamino)-7-(isoquinolin-4-yl)cinnoline-3-carboxamide (105),
(R)-4-(1-cyclopropylethylamino)-7-(2-oxoindolin-5-yl)cinnoline-3-carboxamide (106),
(R)-4-(1-cyclopropylethylamino)-7-(5-(dimethylcarbamoyl)-2-methoxyphenyl)cinnoline-3-carboxamide (107),
(R)-4-(1-cyclopropylethylamino)-7-(2-(trifluoromethoxy)phenyl)cinnoline-3-carboxamide (108),
(R)-7-(5-bromo-2-methoxyphenyl)-4-(1-cyclopropylethylamino)cinnoline-3-carboxamide (109),
(R)-4-(1-cyclopropylethylamino)-7-phenylcinnoline-3-carboxamide (110),
(R)-4-(1-cyclopropylethylamino)-7-(3-(methylsulfonyl)phenyl)cinnoline-3-carboxamide (111),
(R)-4-(1-cyclopropylethylamino)-7-(1-methyl-6-oxo-1,6-dihydropyridin-3-yl)cinnoline-3-carboxamide (112),
(R)-4-(1-cyclopropylethylamino)-7-(3-(cyclopropylmethoxy)phenyl)cinnoline-3-carboxamide (113),
(R)-4-(1-cyclopropylethylamino)-7-(4-(dimethylcarbamoyl)phenyl)cinnoline-3-carboxamide (114),
(R)-4-(1-cyclopropylethylamino)-7-(2-methoxy-5-(methylsulfonyl)phenyl)cinnoline-3-carboxamide (115),
(R)-4-(1-cyclopropylethylamino)-7-(4-(3-oxomorpholino)phenyl)cinnoline-3-carboxamide (116),
(R)-7-(2-chlorophenyl)-4-(1-cyclopropylethylamino)cinnoline-3-carboxamide (117),
(R)-4-(1-cyclopropylethylamino)-7-(4-(dimethylcarbamoyl)-2-methoxyphenyl)cinnoline-3-carboxamide (118),
(R)-4-(1-cyclopropylethylamino)-7-(2-oxoindolin-4-yl)cinnoline-3-carboxamide (119),
(R)-4-(1-cyclopropylethylamino)-7-(2-oxoindolin-6-yl)cinnoline-3-carboxamide (120),
(R)-4-(1-cyclopropylethylamino)-7-(2-oxoindolin-7-yl)cinnoline-3-carboxamide (121),
(R)-4-(1-cyclopropylethylamino)-7-(1-methyl-2-oxo-1,2-dihydropyridin-4-yl)cinnoline-3-carboxamide (122),
(R)-4-(1-cyclopropylethylamino)-7-(2-(methylsulfonyl)phenyl)cinnoline-3-carboxamide (123),
(R)-7-(4-bromophenyl)-4-(1-cyclopropylethylamino)cinnoline-3-carboxamide (211), and
(R)-7-(4-bromo-2-methoxyphenyl)-4-(1-cyclopropylethylamino)cinnoline-3-carboxamide (215).

The following table provides the compound number (column 1), boronic acid used in Step 6 (column 2) to give the compound shown in column 3. Identification data is provided in column 4.

| Comp. No. | Boronic acid | Compound structure | Identification |
|---|---|---|---|
| 100 | B(OH)2 (4-pyridyl) | 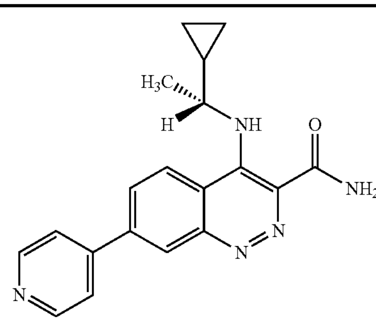 | MS: 334.1 m/z (M + H)+<br>1H NMR (400 MHz, CD3OD) δ: 8.87 (m, 2H), 8.66 (m, 1H), 8.33 (s, 1H), 8.13 (m, 2H), 4.27 (m, 1H), 1.61 (d, J = 6 Hz, 3H), 1.37 (m, 1H), 0.73 (m, 2H), 0.50 (m, 2H). |

-continued

| Comp. No. | Boronic acid | Compound structure | Identification |
|---|---|---|---|
| 101 | | 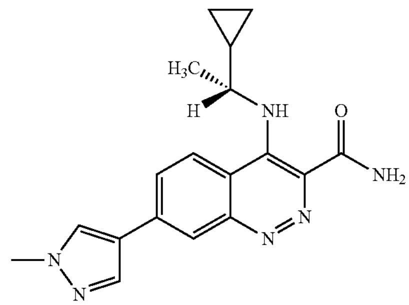 [SMILES: C[C@@H](Nc1c(C(N)=O)nnc2cc(-c3cnn(C)c3)ccc12)C1CC1] | MS: 337.1 m/z (M + H)+<br>1H NMR (400 MHz, CD3OD) δ: 8.45 (d, J = 8.8 Hz, 1H), 8.32 (s, 1H), 8.09 (s, 1H), 8.01 (d, J = 9.2 Hz, 1H), 7.96 (s, 1H), 4.21 (m, 1H), 3.99 (s, 3H), 1.58 (d, J = 6.4 Hz, 3H), 1.32 (m, 1H), 0.70 (m, 2H), 0.49 (m, 2H). |
| 102 | | 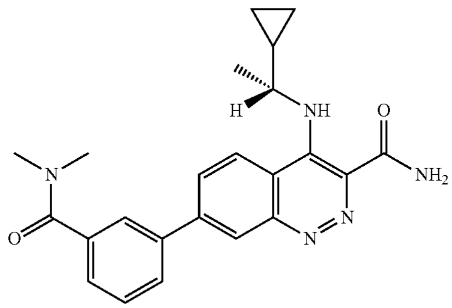 [SMILES: C[C@@H](Nc1c(C(N)=O)nnc2cc(-c3cccc(C(=O)N(C)C)c3)ccc12)C1CC1] | MS: 404.2 m/z (M + H)+<br>1H NMR (400 MHz, CD3OD) δ: 8.58 (d, J = 8.8 Hz, 1H), 8.13 (m, 2H), 7.96 (m, 1H), 7.90 (m, 1H), 7.68 (m, 1H), 7.59 (m, 1H), 4.26 (m, 1H), 3.15 (s, 3H), 3.10 (s, 3H), 1.60 (d, J = 6.4 Hz, 3H), 1.32 (m, 1H), 0.73 (m, 2H), 0.49 (m, 2h). |
| 103 | | 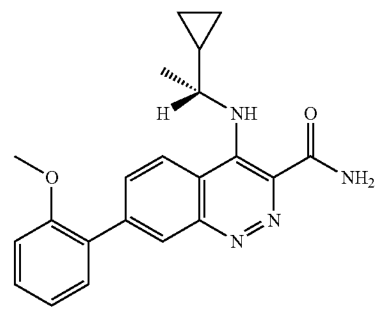 [SMILES: COc1ccccc1-c1ccc2c(N[C@H](C)C3CC3)c(C(N)=O)nnc2c1] | MS: 363.2 m/z (M + H)+<br>1H-NMR (400 MHz, CDCl3) δ: 11.87 (m, 1H), 8.68 (s, 1H), 8.18 (d, J = 9.2 Hz, 1H), 8.05 (br s, 1H), 7.94 (d, J = 9.2 Hz, 1H), 7.48 (m, 2H), 7.10 (m, 1H), 7.03 (m, 1H), 5.68 (m, 1H), 4.07 (m, 1H), 3.86 (s, 3H), 1.58 (d, J = 6 Hz, 3H), 1.27 (m, 1H), 0.73 (m, 2H), 0.42 (m, 2H). |
| 104 | | 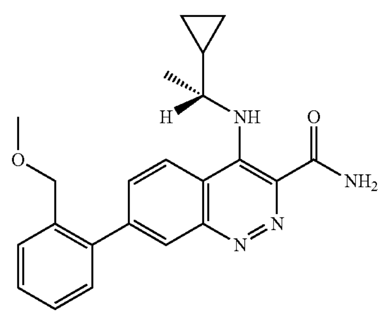 [SMILES: COCc1ccccc1-c1ccc2c(N[C@H](C)C3CC3)c(C(N)=O)nnc2c1] | MS: 377.2 m/z (M + H)+<br>1H-NMR (400 MHz, CDCl3) δ: 11.89 (m, 1H), 8.51 (s, 1H), 8.23 (d, J = 9.2 Hz, 1H), 8.06 (br s, 1H), 7.80 (d, J = 9.2 Hz, 1H), 7.54 (m, 1H), 7.46 (m, 1H), 7.36 (m, 1H), 5.68 (br s, 1H), 4.37 (s, 2H), 4.07 (m, 1H), 3.32 (s, 3H), 1.58 (d, J = 6.4 Hz, 3H), 1.28 (m, 1H), 0.73 (m, 2H), 0.42 (m, 2H). |
| 105 | | 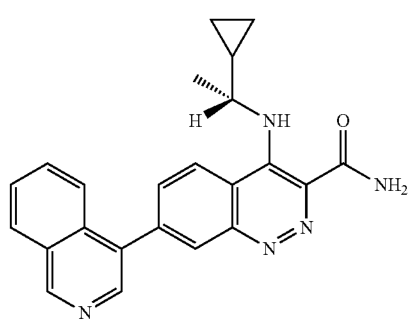 [SMILES: C[C@@H](Nc1c(C(N)=O)nnc2cc(-c3cncc4ccccc34)ccc12)C1CC1] | MS: 384.2 m/z (M + H)+<br>1H NMR (400 MHz, CD3OD) δ: 9.31 (m, 1H), 8.46 (m, 2H), 8.18 (m, 2H), 7.85 (m, 2H), 7.77 (m, 2H), 4.12 (m, 2H), 1.58 (d, J = 6.4 Hz, 3H), 1.29 (m, 1H), 1.25 (m, 1H), 0.69 (m, 2H), 0.41 (m, 2H). |

-continued

| Comp. No. | Boronic acid | Compound structure | Identification |
|---|---|---|---|
| 106 | | 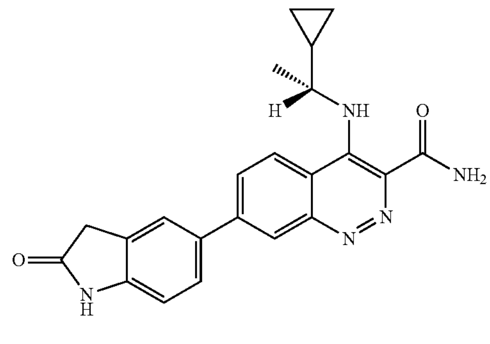 [SMILES: C[C@@H](Nc1c(C(N)=O)nnc2cc(-c3ccc4c(c3)CC(=O)N4)ccc12)C1CC1] | MS: 388.2 mix (M + H)+<br>1H NMR (400 MHz, CD3OD) δ: 8.32 (m, 1H), 8.15 (m, 1H), 7.90 (m, 1H), 7.63 (m, 1H), 7.02 (m, 2H), 4.05 (m, 2H), 1.52 (d, J = 6.4 Hz, 3H), 1.21 (m, 2H), 0.66 (m, 2H), 0.40 (m, 2H). |
| 107 | | 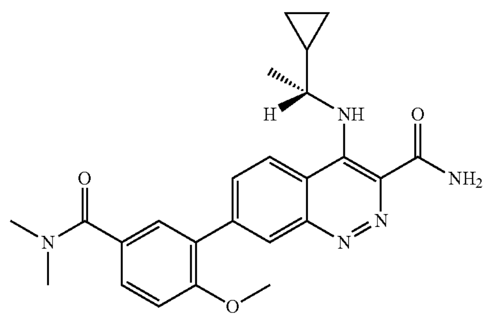 [SMILES: COc1ccc(C(=O)N(C)C)cc1-c1ccc2c(N[C@H](C)C3CC3)c(C(N)=O)nnc2c1] | MS: 434.2 m/z (M + H)+<br>1H NMR (400 MHz, CD3OD) δ: 8.53 (d, J = 8.8 Hz, 1H), 8.12 (s, 1H), 8.02 (dd, J = 9.2 Hz, 1.6 Hz, 1H), 7.63 (m, 2H), 7.29 (m, 1H), 4.26 (m, 1H), 3.94(s, 3H), 3.12 (m, 6H), 1.59 (d, J = 6.4 Hz, 3H), 1.35 (m, 1H), 0.69 (m, 2H), 0.48 (m, 2H). |
| 108 | | 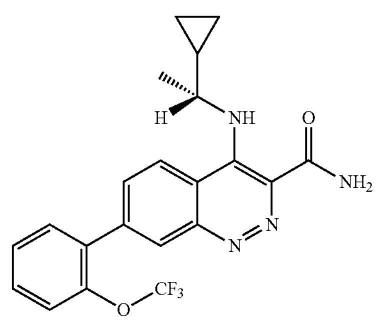 [SMILES: C[C@@H](Nc1c(C(N)=O)nnc2cc(-c3ccccc3OC(F)(F)F)ccc12)C1CC1] | MS: 417.1 m/z (M + H)+<br>1H NMR (400 MHz, CD3OD) δ: 8.59 (d, J = 8.8 Hz, 1H), 8.05 (d, J = 1.6 Hz, 1H), 7.94 (dd, J = 9.2, 2 Hz, 1H), 7.70-7.56 (m, 4H), 4.25 (m, 1H), 1.60 (d, J = 6 Hz, 3H), 1.35 (m, 1H), 0.68 (m, 2H), 0.47 (m, 2H). |
| 109 | | 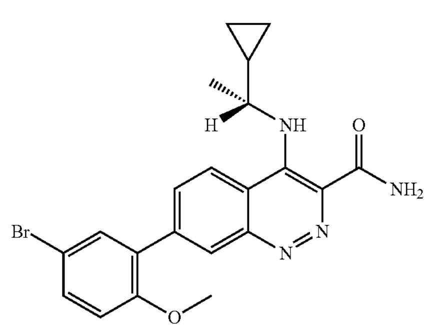 [SMILES: COc1ccc(Br)cc1-c1ccc2c(N[C@H](C)C3CC3)c(C(N)=O)nnc2c1] | MS: 443.1 m/z (M + H)+<br>1H NMR (400 MHz, CD3OD) δ: 8.51 (d, J = 8.8 Hz, 1H), 8.07 (d, J = 1.6 Hz, 1H), 7.97 (dd, J = 9.2, 2 Hz, 1H), 7.63 (m, 2H), 7.14 (d, J = 8.8 Hz, 1H), 4.23 (m, 1H), 3.87 (s, 3H), 1.60 (d, J = 6.4 Hz, 3H), 1.35 (m, 1H), 0.68 (m, 2H), 0.47 (m, 2H). |

| Comp. No. | Boronic acid | Compound structure | Identification |
|---|---|---|---|
| 110 | (pinacol boronate of phenyl) | 4-[((S)-1-cyclopropylethyl)amino]-7-phenylcinnoline-3-carboxamide | MS: 333.1 m/z (M + H)+<br>1H NMR (400 MHz, CD3OD) δ: 8.58 (d, J = 9.2 Hz, 1H), 8.11 (m, 2H), 7.87 (m, 2H), 7.57 (m, 3H), 4.26 (m, 1H), 1.61 (d, J = 6.4 Hz, 3H), 1.37 (m, 1H), 0.74 (m, 2H), 0.51 (m, 2H). |
| 111 | 3-(methylsulfonyl)phenylboronic acid | 4-[((S)-1-cyclopropylethyl)amino]-7-(3-(methylsulfonyl)phenyl)cinnoline-3-carboxamide | MS: 411.1 m/z (M + H)+<br>1H NMR (400 MHz, CD3OD) δ: 8.63 (d, J = 9.2 Hz, 1H), 8.41 (m, 1H), 8.18 (m, 4H), 7.88 (m, 1H), 4.29 (m, 1H), 3.25 (s, 3H), 1.60 (d, J = 6.4 Hz, 3H), 1.34 (m, 1H), 0.74 (m, 2H), 0.53 (m, 2H). |
| 112 | 1-methyl-5-(pinacolboronate)pyridin-2(1H)-one | 4-[((S)-1-cyclopropylethyl)amino]-7-(1-methyl-6-oxo-1,6-dihydropyridin-3-yl)cinnoline-3-carboxamide | MS: 364 m/z (M + H)+<br>1H NMR (400 MHz, CD3OD) δ: 8.42 (d, J = 9.2 Hz, 1H), 8.29 (d, J = 2.8 Hz, 1H), 7.99 (dd, J = 9.2, 2.8 Hz, 1H), 7.93 (dd, J = 8.8, 2.0 Hz, 1H), 7.91 (d, J = 2.0 Hz, 1H), 6.65 (d, J = 9.2 Hz, 1H), 4.16 (m, 1H), 3.62 (s, 3H), 1.49 (d, J = 6.4 Hz, 3H), 1.25 (m, 1H) 0.64 (m, 2H), 0.44 (m, 2H). |
| 113 | 3-(cyclopropylmethoxy)phenylboronic acid | 4-[((S)-1-cyclopropylethyl)amino]-7-(3-(cyclopropylmethoxy)phenyl)cinnoline-3-carboxamide | MS: 403.2 m/z (M + H)+<br>1H NMR (400 MHz, CD3OD) δ: 8.56 (d, J = 10 Hz, 1H), 8.10 (m, 2H), 7.48 (m, 1H), 7.38 (m, 2H), 7.11 (m, 1H), 4.25 (m, 1H), 3.94 (d, J = 6.8 Hz, 2H), 1.59 (d, J = 6.4 Hz, 1H), 1.35 (m, 2H), 0.74 (m, 4H), 0.51 (m, 2H), 0.38 (m, 2H). |

| Comp. No. | Boronic acid | Compound structure | Identification |
|---|---|---|---|
| 114 | | 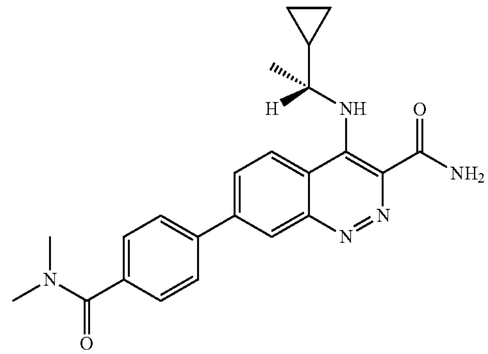 [SMILES: C[C@@H](Nc1c(C(N)=O)nnc2cc(-c3ccc(C(=O)N(C)C)cc3)ccc12)C1CC1] | MS: 404.2 m/z (M + H)$^+$<br>$^1$H NMR (400 MHz, CD$_3$OD) δ: 8.59 (d, J = 8.8 Hz, 1H), 8.15(m, 2H), 7.96 (m, 2H), 7.66 (m, 2H), 4.26 (m, 1H), 3.15 (s, 3H), 3.06 (s, 3H), 1.61 (d, J = 6.4 Hz, 3H), 1.36 (m, 1H), 0.74 (m, 2H), 0.49 (m, 2H). |
| 115 | | 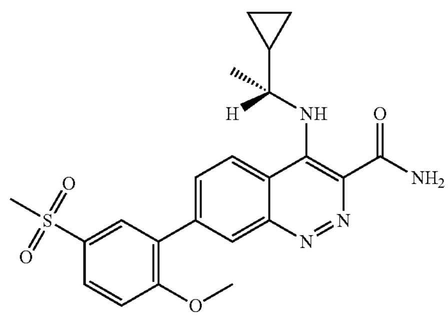 [SMILES: COc1ccc(S(C)(=O)=O)cc1-c1ccc2c(N[C@H](C)C3CC3)c(C(N)=O)nnc2c1] | MS: 441.1 m/z (M + H)$^+$<br>$^1$H NMR (400 MHz, CD$_3$OD) δ: 8.54 (d, J = 9.2 Hz), 8.12-7.99 (m, 4H), 7.45 (d, J = 8.4 Hz, 1H), 4.26 (m, 1H), 3.99 (s, 3H), 3.16 (s, 3H), 1.60 (d, J = 6.4 Hz, 3H), 1.36 (m, 1H), 0.75 (m, 2H), 0.50 (m, 2H). |
| 116 | | 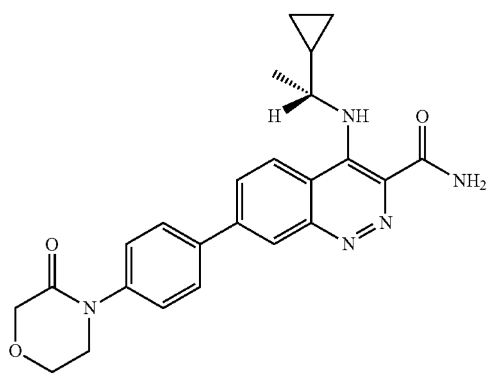 [SMILES: C[C@@H](Nc1c(C(N)=O)nnc2cc(-c3ccc(N4CCOCC4=O)cc3)ccc12)C1CC1] | MS: 432.2 m/z (M + H)$^+$<br>$^1$H NMR (400 MHz, CD$_3$OD) δ: 8.58 (m, 1H), 8.11 (m, 1H), 7.94 (m, 2H), 7.64 (m, 2H), 4.33 (s, 2H), 4.25 (m, 1H), 4.09 (m, 2H), 3.87 (m, 2H), 1.61 (d, J = 6.4 Hz, 3H), 1.33 (m, 1H), 0.74 (m, 2H), 0.49 (m, 2H). |
| 117 | | 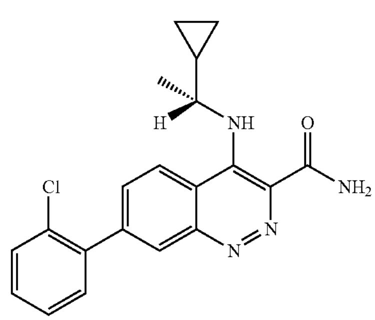 [SMILES: C[C@@H](Nc1c(C(N)=O)nnc2cc(-c3ccccc3Cl)ccc12)C1CC1] | MS: 367.1 m/z (M + H)$^+$<br>$^1$H NMR (400 MHz, CD$_3$OD) δ: 8.57 (d, J = 8.8 Hz, 1H), 7.99 (d, J = 1.6 Hz, 1H), 7.90 (dd, J = 9.2, 2.0 Hz, 1H), 7.63 (m, 1H), 7.53 (m, 3H), 4.26 (m, 1H), 1.61 (d, J = 6.4 Hz, 3H), 1.33 (m, 1H), 0.72 (m, 2H), 0.48 (m, 2H). |

| Comp. No. | Boronic acid | Compound structure | Identification |
|---|---|---|---|
| 118 | | 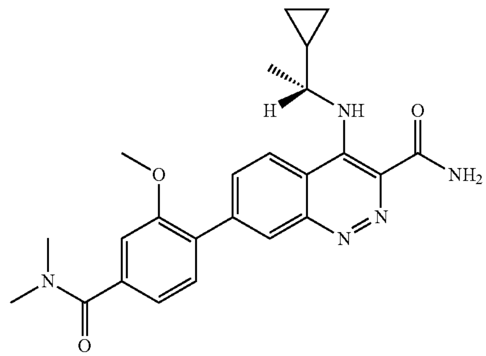 [SMILES: COc1cc(C(=O)N(C)C)ccc1-c1ccc2c(N[C@H](C)C3CC3)c(C(N)=O)nnc2c1] | MS: 434.2 m/z (M + H)+<br>$^1$H NMR (400 MHz, CD$_3$OD) δ: 8.53 (d, J = 9.2 Hz, 1H), 8.14 (s, 1H), 8.03 (dd, J = 8.8, 1.6 Hz, 1H), 7.62 (d, J = 8 Hz, 1H), 7.26 (m, 1H), 7.20 (dd, J = 7.6, 1.2 Hz, 1H), 4.26 (m, 1H), 3.93 (s, 3H), 3.15 (s, 3H), 3.08 (s, 3H), 1.62 (d, J = 6.4 Hz, 3H), 1.35 (m, 1H), 0.73 (m, 2H), 0.48 (m, 2H). |
| 119 | | 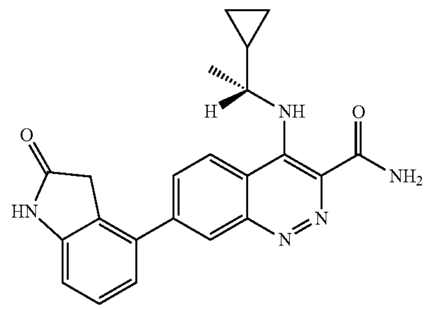 [SMILES: C[C@@H](Nc1c(C(N)=O)nnc2cc(-c3cccc4c3CC(=O)N4)ccc12)C1CC1] | MS: 388.2 m/z (M + H)+<br>$^1$H-NMR (400 MHz, CDCl$_3$/CD$_3$OD) δ: 8.40 (s, 1H), 8.23 (d, J = 9.2 Hz, 1H), 7.70 (d, J = 9.2 Hz, 1H), 7.33 (t, J = 8 Hz, 1H), 7.15 (m, 1H), 6.93 (d, J = 8 Hz, 1H), 4.00 (dq, J = 6.4, J = 6.4 Hz, 1H), 3.61 (s, 1H), 3.32 (m, 1H), 1.52 (d, J = 6.4 Hz, 3H), 1.22 (m, 1H), 0.66 (m, 2H), 0.36 (m, 2H). |
| 120 | | 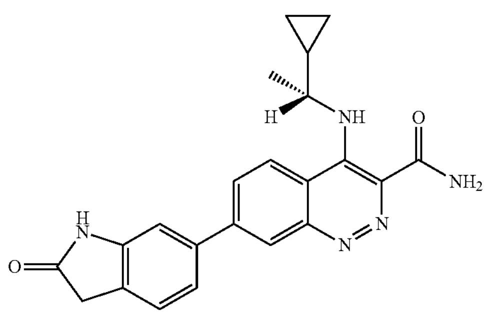 [SMILES: C[C@@H](Nc1c(C(N)=O)nnc2cc(-c3ccc4c(c3)NC(=O)C4)ccc12)C1CC1] | MS: 388.1 m/z (M + H)+<br>$^1$H-NMR (400 MHz, CDCl$_3$/CD$_3$OD) δ: 8.66 (s, 1H), 8.30 (d, J = 8.8 Hz, 1H), 7.96 (d, J = 8.8 Hz, 1H), 7.43 (m, 2H), 7.36 (m, 1H), 4.07 (dq, J = 6.0, J = 6.0 Hz, 1H), 3.37 (m, 2H), 1.58 (d, J = 6.0 Hz, 3H), 1.28 (m, 1H), 0.72 (m, 2H), 0.42 (m, 2H). |
| 121 | | 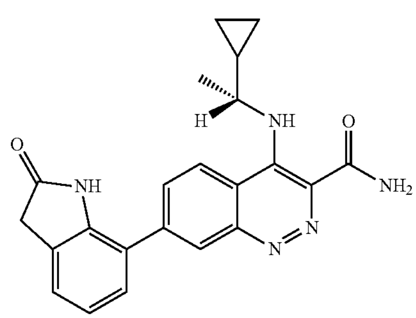 [SMILES: C[C@@H](Nc1c(C(N)=O)nnc2cc(-c3cccc4c3NC(=O)C4)ccc12)C1CC1] | MS: 388.1 m/z (M + H)+<br>$^1$H-NMR (400 MHz, CD$_3$OD) δ: 8.59 (d, J = 8.8 Hz, 1H), 8.02 (m, 1H), 7.94 (dd, J = 8.8 Hz, J = 1.8 Hz, 1H), 7.44 (m, 2H), 7.24 (t, J = 7.6 Hz, 1H), 4.29 (dq, J = 6.4, J = 6.4 Hz, 1H), 3.70 (m, 2H), 1.64 (d, J = 6.4 Hz, 3H), 1.38 (m, 1H), 0.76 (m, 2H), 0.55 (m, 2H). |

-continued

| Comp. No. | Boronic acid | Compound structure | Identification |
|---|---|---|---|
| 122 | | 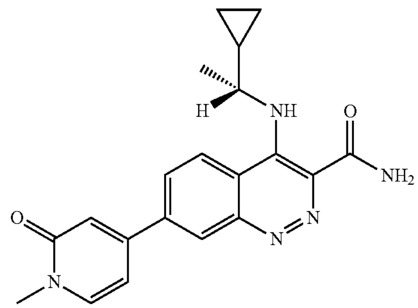 [SMILES: C[C@@H](Nc1c(C(N)=O)nnc2cc(-c3ccn(C)c(=O)c3)ccc12)C1CC1] | MS: 364 m/z (M + H)⁺<br>$^1$H-NMR (400 MHz, CD$_3$OD) δ: 8.47 (d, J = 8.8 Hz, 1H), 8.12 (d, J = 1.6 Hz, 1H), 7.94 (dd, J = 8.8 and 1.6 Hz, 1H), 7.78 (d, J = 7.2 Hz, 1H), 6.88 (d, J = 2.0 Hz, 1H), 6.74 (dd, J = 7.2, 2.0 Hz, 1H), 4.12 (m, 1H), 3.57 (s, 3H), 1.48 (d, J = 6.0 Hz, 3H), 1.23 (m, 1H) 0.62 (m, 2H), 0.40 (m, 2H). |
| 123 | | 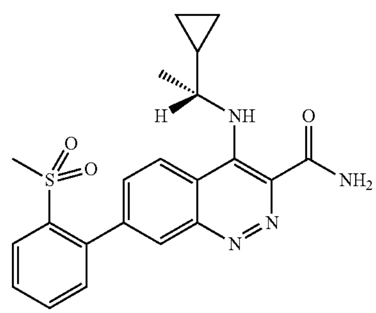 [SMILES: C[C@@H](Nc1c(C(N)=O)nnc2cc(-c3ccccc3S(C)(=O)=O)ccc12)C1CC1] | MS: 411.2 m/z (M + H)⁺<br>$^1$H-NMR (400 MHz, CD$_3$OD) δ: 8.54 (m, 1H), 8.25 (m, 1H), 7.99 (m, 1H), 7.84 (m, 3H), 7.51 (m, 1H), 4.27 (m, 1H), 3.30 (s, 3H), 2.97 (s, 3H), 1.60 (d, J = 6.4 Hz, 3H), 1.36 (m, 1H), 0.74 (m, 2H), 0.52 (m, 2H). |
| 211 | | 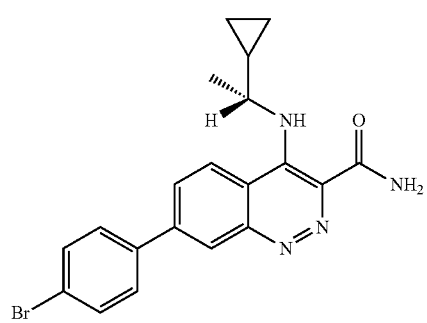 [SMILES: C[C@@H](Nc1c(C(N)=O)nnc2cc(-c3ccc(Br)cc3)ccc12)C1CC1] | |
| 215 | | 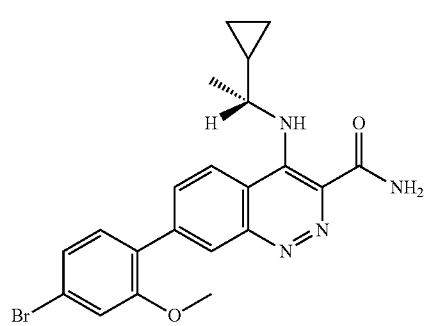 [SMILES: COc1cc(Br)ccc1-c1ccc2c(N[C@H](C)C3CC3)c(C(N)=O)nnc2c1] | |

(R)-7-(4'-bromo-2',4-dimethoxybiphenyl-3-yl)-4-(1-cyclopropylethylamino)cinnoline-3-carboxamide (203) was prepared similarly via Step 6a as follows:

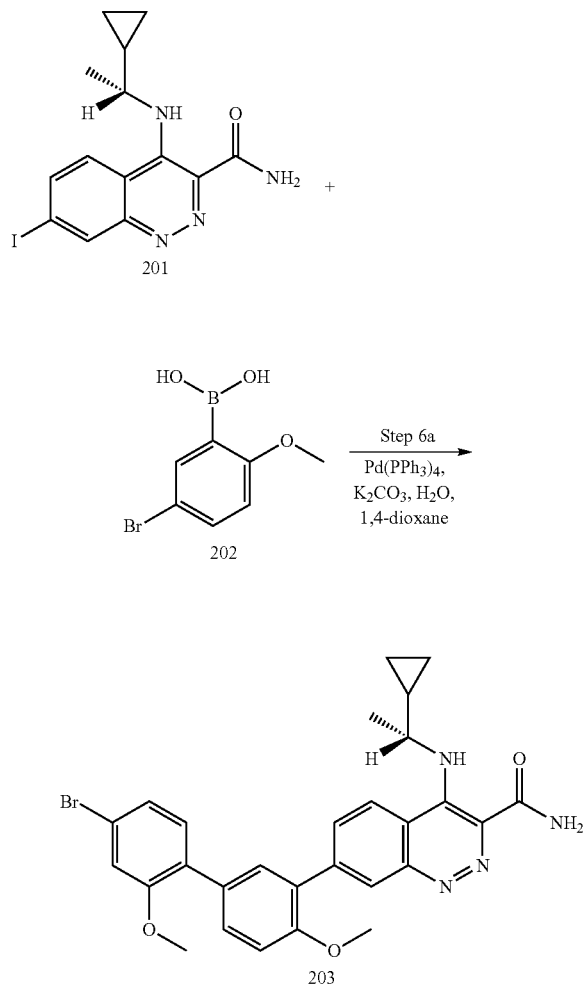

Step 6a—synthesis of (R)-7-(4'-bromo-2',4-dimethoxybiphenyl-3-yl)-4-(1-cyclopropylethylamino)cinnoline-3-carboxamide (203): The (R)-4-(1-cyclopropylethylamino)-7-iodocinnoline-3-carboxamide (201, 0.48 g, 1.26 mmol, prepared via Step 5 replacing isopropylamine 15 with (R)-1-cyclopropylethanamine) was suspended in 2 mL of 1,4-dioxane and 5-bromo-2-methoxyphenylboronic acid (202, 0.36 g, 1.58 mmol), Pd(PPh$_3$)$_4$ (0.036 g, 0.031 mmol), K$_2$CO$_3$ (0.35 g, 2.53 mmol), and 0.5 mL of water were added. The reaction mixture was heated in the microwave for 25 minutes at 140° C., then diluted with CH$_2$Cl$_2$ and water. The organic layer was separated and dried with Na$_2$SO$_4$, filtered, and the filtrate concentrated under vacuum. The resulting residue was purified by preparative HPLC to afford 8 mg (1%) of the desired compound 203. $^1$H NMR (CD$_3$OD, 400 MHz) δ: 8.52 (d, J=8.8 Hz, 1H), 8.15 (d, J=1.6 Hz, 1H), 8.05 (dd, J=9.2, 2 Hz, 1H), 7.64 (m, 2H), 7.45 (m, 2H), 7.27 (d, J=9.2 Hz, 1H), 7.05 (d, J=8.8 Hz, 1H), 4.27 (m, 1H), 3.94 (s, 3H), 3.82 (s, 3H), 1.62 (d, J=6.4 Hz, 3H), 1.35 (m, 1H), 0.68 (m, 2H), 0.47 (m, 2H). MS: 547.1 m/z (M+H)$^+$.

Analogs of the above compounds that are substituted at the 6 position instead of the 7-position can be readily prepared by replacing 3-iodoaniline (10) in step 1 with 4-iodoaniline, with Step 2 resulting in the analog 4-amino-6-iodocinnoline-3-carboxamide (12a, $^1$H NMR (400 MHz, CD$_3$OD) δ: 9.01 (s, 1H), 8.41 (d, J=9.0 Hz, 1H), 7.80 (d, J=9.0 Hz, 1H. MS: 314.9 m/z (M+H)$^+$), Step 4 resulting in the analog 4-chloro-6-iodocinnoline-3-carboxamide (14a), and Step 5 resulting in the analog 6-iodo-4-(isopropylamino)cinnoline-3-carboxamide (16a, $^1$H NMR (500 MHz, CD$_3$OD) δ: 8.58 (d, J=2.0 Hz, 1H), 8.03 (dd, J=1.5, 9.0 Hz, 1H), 7.79 (d, J=9.0 Hz, 1H), 4.34-4.30 (m, 1H), 1.33 (d, J=6.0 Hz, 6H). MS: 357.0 m/z (M+H)$^+$). Similarly, 4-bromoaniline can be used in Step 1 to give 6-bromo-4-(isopropylamino)cinnoline-3-carboxamide (16b, $^1$H NMR (400 MHz, CD$_3$OD) δ: 11.28 (bs, 1H), 8.65 (s, 1H), 8.50 (s, 1H), 8.17-8.15 (m, 1H), 8.09 (s, 1H), 8.02-8.00 (m, 1H), 4.58-4.52 (m, 1H), 1.39 (d, J=6.0 Hz, 6H). MS: 309.1/311.1 m/z (M+H)$^+$). Step 5 can also be used to provide other amine substituted compounds by replacing isopropylamine with a suitable amine, and compounds can be carried through with an appropriate boronic acid in step 6 to give the 6 position ring substituted analogs.

The 6-iodo analogs to compounds 12 and 16, 4-amino-6-iodocinnoline-3-carboxamide and 6-iodo-4-(isopropylamino)cinnoline-3-carboxamide are prepared similarly, using 4-iodoaniline in place of 3-iodoaniline in Step 1. 4-Amino-6-iodocinnoline-3-carboxamide $^1$H NMR (400 MHz, CD$_3$OD) δ: 9.01 (s, 1H), 8.41 (d, J=9.0 Hz, 1H), 7.80 (d, J=9.0 Hz, 1H). MS: 314.9 m/z (M+H)$^+$. 6-Iodo-4-(isopropylamino)cinnoline-3-carboxamide $^1$H NMR (500 MHz, CD$_3$OD) δ: 8.58 (d, J=2.0 Hz, 1H), 8.03 (dd, J=1.5, 9.0 Hz, 1H), 7.79 (d, J=9.0 Hz, 1H), 4.34-4.30 (m, 1H), 1.33 (d, J=6.0 Hz, 6H). MS: 357.0 m/z (M+H)$^+$.

Additional compounds are prepared similarly to this method, reacting 6-iodo-4-(isopropylamino)cinnoline-3-carboxamide (16a) with 4-(methylsulfonyl)phenylboronic acid 4 or other suitable boronic acid in Step 6, and isolating the carboxamide after Step 6, or reacting further to the carbonitrile via Step 7. The following compounds are prepared:

4-(isopropylamino)-6-phenylcinnoline-3-carboxamide (124), 4-(isopropylamino)-6-(4-(methylsulfonyl)phenyl)cinnoline-3-carboxamide (125), 4-(isopropylamino)-6-(pyridin-4-yl)cinnoline-3-carboxamide (126), 4-(isopropylamino)-6-(1H-pyrazol-4-yl)cinnoline-3-carboxamide (127), 4-(isopropylamino)-6-(1H-pyrazol-4-yl)cinnoline-3-carbonitrile (128), 4-(isopropylamino)-6-(1-methyl-1H-pyrazol-4-yl)cinnoline-3-carboxamide (129), 4-(isopropylamino)-6-(thiazol-2-yl)cinnoline-3-carboxamide (130), and 4-(isopropylamino)-6-(thiazol-5-yl)cinnoline-3-carboxamide (131).

The following table provides the compound number (column 1), boronic acid used in Step 6 (column 2) to give the compound shown in column 3. Identification data is provided in column 4.

| Comp. No. | Boronic acid | Compound structure | Identification |
|---|---|---|---|
| 124 | (pinacol boronate of phenyl) | 6-phenyl-4-(isopropylamino)cinnoline-3-carboxamide | MS: 307.2 m/z (M + H)⁺<br>¹H-NMR (500 MHz, DMSO-d6) δ: 10.34 (d, J = 7.0 Hz, 1H), 8.60 (bs, 1H), 8.42 (s, 1H), 8.28 (d, J = 8.5 Hz, 1H), 8.19-8.18 (m, 1H), 7.83 (d, J = 7.5 Hz, 2H), 7.73 (s, 1H), 7.58-7.56 (m, 2H), 7.48-7.47 (m, 1H), 4.56-4.52 (m, 1H), 1.38 (d, J = 6.0 Hz, 6H). |
| 125 | 4-(methylsulfonyl)phenylboronic acid | 6-(4-(methylsulfonyl)phenyl)-4-(isopropylamino)cinnoline-3-carboxamide | MS: 385.1 m/z (M + H)⁺<br>¹H-NMR (500 MHz, DMSO-d6) δ: 8.68 (s, 1H), 8.57 (s, 1H), 8.42 (d, J = 8.5 Hz, 1H), 8.18-8.09 (m, 6H), 4.74 (bs, 1H), 3.31 (s, 3H), 1.46 (d, J = 6.0 Hz, 6H). |
| 126 | pyridin-4-ylboronic acid | 6-(pyridin-4-yl)-4-(isopropylamino)cinnoline-3-carboxamide | MS: 308.2 m/z (M + H)⁺<br>¹H-NMR (500 MHz, DMSO-d6) δ: 10.45 (s, 1H), 8.73 (d, J = 5.5 Hz, 2H), 8.61 (s, 1H), 8.55 (s, 1H), 8.33-8.27 (m, 2H), 7.86 (d, J = 5.5 Hz, 2H), 7.76 (s, 1H), 4.60-4.56 (m, 1H), 1.39 (d, J = 6.0 Hz, 6H). |
| 127 | 1H-pyrazol-4-yl pinacol boronate | 6-(1H-pyrazol-4-yl)-4-(isopropylamino)cinnoline-3-carboxamide | MS: 297.2 m/z (M + H)⁺<br>¹H-NMR (500 MHz, DMSO-d6) δ: 10.18 (bs, 1H), 8.57 (s, 1H), 8.33 (s, 1H), 8.29-8.27 (m, 2H), 8.19-8.14 (m, 2H), 7.69 (s, 1H), 4.58-4.52 (m, 1H), 1.36 (d, J = 6.0 Hz, 6H). |
| 128 | 1H-pyrazol-4-yl pinacol boronate | 6-(1H-pyrazol-4-yl)-4-(isopropylamino)cinnoline-3-carbonitrile | MS: 279.1 m/z (M + H)⁺<br>¹H-NMR (500 MHz, CD₃OD) δ: 8.58 (d, J = 1.5 Hz, 1H), 8.19-8.16 (m, 3H), 8.06 (d, J = 8.5 Hz, 1H), 4.89 (p, J = 6.0 Hz, 1H), 1.63 (d, J = 6.0 Hz, 6H). |

| Comp. No. | Boronic acid | Compound structure | Identification |
|---|---|---|---|
| 129 | (1-methylpyrazole-4-boronic acid pinacol ester) | (4-(isopropylamino)-6-(1-methyl-1H-pyrazol-4-yl)cinnoline-3-carboxamide) | MS: 311.1 m/z (M + H)⁺<br>¹H-NMR (500 MHz, DMSO-d6) δ: 8.63 (s, 1H), 8.42-8.39 (m, 2H), 8.31 (d, J = 7.5 Hz, 1H), 8.19 (s, 1H), 8.11 (s, 1H), 8.01 (d, J = 7.5 Hz, 1H), 4.77 (bs, 1H), 3.93 (s, 3H), 1.47 (d, J = 6.0 Hz, 6H). |
| 130 | (thiazole-2-boronic acid pinacol ester) | (4-(isopropylamino)-6-(thiazol-2-yl)cinnoline-3-carboxamide) | MS: 314.2 m/z (M + H)⁺<br>¹H-NMR (500 MHz, DMSO-d6) δ: 8.89 (s, 1H), 8.67 (s, 1H), 8.52 (d, J = 9.5 Hz, 1H), 8.17 (d, J = 9.5 Hz, 1H), 8.09-8.07 (m, 2H), 7.98 (s, 1H), 4.61 (bs, 1H), 1.48 (d, J = 6.0 Hz, 6H). |
| 131 | (thiazole-5-boronic acid pinacol ester) | (4-(isopropylamino)-6-(thiazol-5-yl)cinnoline-3-carboxamide) | MS: 314.2 m/z (M + H)⁺<br>¹H-NMR (500 MHz, CD₃OD) δ: 9.16 (s, 1H), 8.59 (s, 1H), 8.47-8.45 (m, 2H), 8.07 (d, J = 9.0 Hz, 1H), 4.85-4.81 (m, 1H), 1.63 (d, J = 6.0 Hz, 6H). |

Additional compounds are prepared similarly to this method, replacing 4-(methylsulfonyl)phenylboronic acid 4 with pyridin-4-ylboronic acid in Step 6, and replacing isopropylamine 15 with a suitable amine in Step 5, and isolating the carboxamide after Step 6. The following compounds are prepared:

(R)-4-(1-phenylethylamino)-7-(pyridin-4-yl)cinnoline-3-carboxamide (132),
(S)-4-(1-phenylethylamino)-7-(pyridin-4-yl)cinnoline-3-carboxamide (133),
4-(pentan-3-ylamino)-7-(pyridin-4-yl)cinnoline-3-carboxamide (134),
4-(1-(pyridin-3-yl)ethylamino)-7-(pyridin-4-yl)cinnoline-3-carboxamide (135),
4-(3-hydroxypropylamino)-7-(pyridin-4-yl)cinnoline-3-carboxamide (136), and
4-(2-hydroxyethylamino)-7-(pyridin-4-yl)cinnoline-3-carboxamide (137).

The following table provides the compound number (column 1), amine used in Step 5 (column 2), to give the compound shown in column 3. Identification data is provided in column 4.

| Comp. No. | Amine | Compound structure | Identification |
|---|---|---|---|
| 132 | (R)-1-phenylethylamine | (R)-4-(1-phenylethylamino)-7-(pyridin-4-yl)cinnoline-3-carboxamide | MS: 370.2 m/z (M + H)⁺<br>¹H-NMR (500 MHz, DMSO-d6) δ: 11.05 (d, J = 7.7 Hz, 1H), 8.74 (s, 1H), 8.70 (m, 2H), 8.58 (d, J = 1.9 Hz, 1H), 8.30 (d, J = 9.1 Hz, 1H), 7.92 (m, 2H), 7.86 (s, 1H), 7.46 (d, J = 7.4 Hz, 2H), 7.36 (t, J = 7.6 Hz, 2H), 7.25 (t, J = 7.5 Hz, 1H), 5.55 (pent., J = 7.0 Hz, 1H), 1.63 (d, J = 6.6 Hz, 3H). |

-continued

| Comp. No. | Amine | Compound structure | Identification |
|---|---|---|---|
| 133 |  | 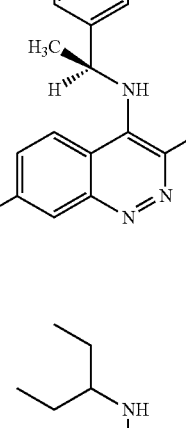 | MS: 370.2 m/z (M + H)+<br>$^1$H-NMR (500 MHz, DMSO-d6) δ: 11.05 (d, J = 7.7 Hz, 1H), 8.74 (s, 1H), 8.70 (m, 2H), 8.58 (d, J = 1.9 Hz, 1H), 8.30 (d, J = 9.1 Hz, 1H), 7.92 (m, 2H), 7.86 (s, 1H), 7.46 (d, J = 7.4 Hz, 2H), 7.36 (t, J = 7.6 Hz, 2H), 7.25 (t, J = 7.5 Hz, 1H), 5.55 (pent., J = 7.0 Hz, 1H), 1.63 (d, J = 6.6 Hz, 3H). |
| 134 |  | 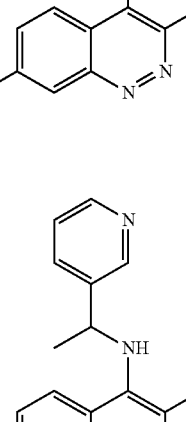 | MS: 336.2 m/z (M + H)+<br>$^1$H-NMR (500 MHz, DMSO-d6) δ: 12.20 (bs, 1H), 8.88 (m, 2H), 8.74 (s, 1H), 8.55 (d, J = 8.0 Hz, 1H), 8.44 (m, 1H), 8.23 (t, J = 9.0 Hz, 2H), 8.04 (m, 2H), 4.41 (bs, 1H), 1.88-1.72 (m, 4H), 1.00 (t, J = 7.4 Hz, 6H). |
| 135 |  | 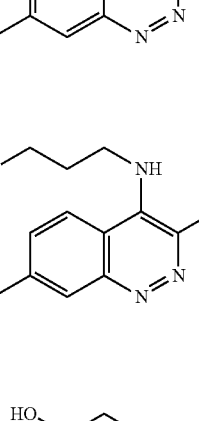 | MS: 371.2 m/z (M + H)+<br>$^1$H-NMR (500 MHz, DMSO-d6) δ: 12.03 (bs, 1H), 8.90 (d, J = 2.0 Hz, 1H), 8.88 (m, 2H), 8.81 (s, 1H), 8.65 (dd, J = 5.1, 1.3 Hz, 1H), 8.58 (d, J = 1.9 Hz, 1H), 8.34 (d, J = 9.2 Hz, 1H), 8.19 (m, 2H), 8.12 (d, J = 6.3 Hz, 2H), 8.09 (dd, J = 9.2, 2.0 Hz, 1H), 7.63 (dd, J = 8.1, 5.0 Hz, 1H), 5.86 (pent., J = 6.7 Hz, 1H), 1.77 (d, J = 6.6 Hz, 3H). |
| 136 |  | 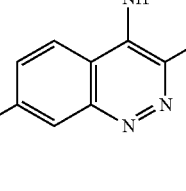 | MS: 324.2 m/z (M + H)+<br>$^1$H-NMR (500 MHz, CD$_3$OD) δ: 8.73 (m, 2H), 8.65 (d, J = 8.9 Hz, 1H), 8.48 (d, J = 1.9 Hz, 1H), 8.02 (dd, J = 8.9, 1.9 Hz, 1H), 7.93 (m, 2H), 4.07 (t, J = 6.8 Hz, 2H), 3.81 (t, J = 6.0 Hz, 2H), 2.06 (pent., J = 6.4 Hz, 2H). |
| 137 |  | 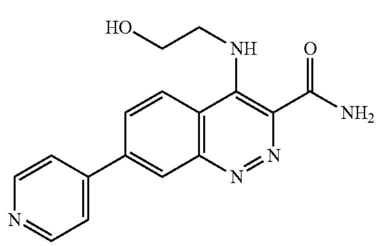 [SMILES: NC(=O)c1nnc2cc(-c3ccncc3)ccc2c1NCCO] | MS: 310.2 m/z (M + H)+<br>$^1$H-NMR (500 MHz, DMSO-d6) δ: 10.57 (s, 1H), 8.74 (d, J = 5.2 Hz, 2H), 8.59 (s, 1H), 8.55 (d, J = 8.5 Hz, 2H), 8.03 (d, J = 8.8 Hz, 1H), 7.96 (d, J = 5.2 Hz, 2H), 7.68 (s, 1H), 5.10 (m, 1H), 3.93 (m, 2H), 3.72 (m, 2H). |

The carboxamides above are further reacted through Step 7 to provide the corresponding carbonitrile. The following compounds are prepared:

4-(cyclobutylamino)-7-(4-(methylsulfonyl)phenyl)cinnoline-3-carbonitrile (20),
4-(1-methylpiperidin-4-ylamino)-7-(4-(methylsulfonyl)phenyl)cinnoline-3-carbonitrile (22),
7-(4-(methylsulfonyl)phenyl)-4-(tetrahydrofuran-3-ylamino)cinnoline-3-carbonitrile (24),
7-(4-(methylsulfonyl)phenyl)-4-(tetrahydro-2H-pyran-4-ylamino)cinnoline-3-carbonitrile (26),
7-(4-(methylsulfonyl)phenyl)-4-(oxetan-3-ylamino)cinnoline-3-carbonitrile (28),
4-(cyclopropylamino)-7-(4-(methylsulfonyl)phenyl)cinnoline-3-carbonitrile (30),
(R)-7-(4-(methylsulfonyl)phenyl)phenyl)-4-(1-phenylethylamino) cinnoline-3-carbonitrile (40), (41),
4-(isopropylamino)-7-(pyridin-4-yl)cinnoline-3-carbonitrile (32),
4-(isopropylamino)-7-(pyrimidin-5-yl)cinnoline-3-carbonitrile (34),
4-(isopropylamino)-7-(1-methyl-1H-pyrazol-4-yl)cinnoline-3-carbonitrile (36),
7-(4-fluorophenyl)-4-(isopropylamino)cinnoline-3-carbonitrile (44),
7-(3-fluorophenyl)-4-(isopropylamino)cinnoline-3-carbonitrile (46),
7-(2-fluorophenyl)-4-(isopropylamino)cinnoline-3-carbonitrile (48),
4-(isopropylamino)-7-(4-morpholinophenyl)cinnoline-3-carbonitrile (50),
4-(isopropylamino)-7-(3-morpholinophenyl)cinnoline-3-carbonitrile (52),
4-(isopropylamino)-7-(1H-pyrazol-4-yl)cinnoline-3-carbonitrile (54),
4-(isopropylamino)-7-(pyridin-3-yl)cinnoline-3-carbonitrile (58),
4-(1-adamantylamino)-7-((methylsulfonyl)phenyl)cinnoline-3-carbonitrile (138)
7-(4-(methylsulfonyl)phenyl)-4-((tetrahydro-2H-pyran-4-yl)methylamino)cinnoline-3-carbonitrile (139),
(R)-7-(4-(methylsulfonyl)phenyl)-4-(1-(tetrahydro-2H-pyran-4-yl)ethylamino)cinnoline-3-carbonitrile (140),
4-(tert-butylamino)-7-(4-(methylsulfonyl)phenyl)cinnoline-3-carbonitrile (141),
4-(cyclopropylmethylamino)-7-(4-(methylsulfonyl)phenyl)cinnoline-3-carbonitrile (142),
4-(ethylamino)-7-(4-(methylsulfonyl)phenyl)cinnoline-3-carbonitrile (143),
4-(methylamino)-7-(4-(methylsulfonyl)phenyl)cinnoline-3-carbonitrile (144),
4-(isopropylamino)-7-vinylcinnoline-3-carbonitrile (145),
4-(isopropylamino)-7-(2-methoxyphenyl)cinnoline-3-carbonitrile (146),
4-(isopropylamino)-7-(3-methoxyphenyl)cinnoline-3-carbonitrile (147),
7-(5-fluoro-2-methoxyphenyl)-4-(isopropylamino)cinnoline-3-carbonitrile (148),
4-(isopropylamino)-7-(prop-1-en-2-yl)cinnoline-3-carbonitrile (149),
(R)-4-(1-cyclopropylethylamino)-7-(pyridin-4-yl)cinnoline-3-carbonitrile (150),
(R)-4-(1-cyclopropylethylamino)-7-(1-methyl-1H-pyrazol-4-yl)cinnoline-3-carbonitrile (151),
(R)-4-(1-cyclopropylethylamino)-7-(3-(dimethylcarbamoyl)phenyl) cinnoline-3-carbonitrile (152),
(R)-4-(1-cyclopropylethylamino)-7-(2-methoxyphenyl)cinnoline-3-carbonitrile (153),
(R)-4-(1-cyclopropylethylamino)-7-(2-(methoxymethyl)phenyl)cinnoline-3-carbonitrile (154),
(R)-4-(1-cyclopropylethylamino)-7-(isoquinolin-4-yl)cinnoline-3-carbonitrile (155),
(R)-4-(1-cyclopropylethylamino)-7-(2-oxoindolin-5-yl)cinnoline-3-carbonitrile (156),
(R)-4-(1-cyclopropylethylamino)-7-(5-(dimethylcarbamoyl)-2-methoxyphenyl)cinnoline-3-carbonitrile (157),
(R)-4-(1-cyclopropylethylamino)-7-(2-(trifluoromethoxy)phenyl)cinnoline-3-carbonitrile (158),
(R)-7-(5-bromo-2-methoxyphenyl)-4-(1-cyclopropylethylamino)cinnoline-3-carbonitrile (159),
(R)-4-(1-cyclopropylethylamino)-7-phenylcinnoline-3-carbonitrile (160),
(R)-4-(1-cyclopropylethylamino)-7-(3-(methylsulfonyl)phenyl)cinnoline-3-carbonitrile (161),
(R)-4-(1-cyclopropylethylamino)-7-(1-methyl-6-oxo-1,6-dihydropyridin-3-yl)cinnoline-3-carbonitrile (162),
(R)-4-(1-cyclopropylethylamino)-7-(3-(cyclopropylmethoxy)phenyl)cinnoline-3-carbonitrile (163),
(R)-4-(1-cyclopropylethylamino)-7-(4-(dimethylcarbamoyl)phenyl)cinnoline-3-carbonitrile (164),
(R)-4-(1-cyclopropylethylamino)-7-(2-methoxy-5-(methylsulfonyl)phenyl)cinnoline-3-carbonitrile (165),
(R)-4-(1-cyclopropylethylamino)-7-(4-(3-oxomorpholino)phenyl)cinnoline-3-carbonitrile (166),
(R)-7-(2-chlorophenyl)-4-(1-cyclopropylethylamino)cinnoline-3-carbonitrile (167),
(R)-4-(1-cyclopropylethylamino)-7-(4-(dimethylcarbamoyl)-2-methoxyphenyl)cinnoline-3-carboxamide (168),
(R)-4-(1-cyclopropylethylamino)-7-(2-oxoindolin-4-yl)cinnoline-3-carbonitrile (169),
(R)-4-(1-cyclopropylethylamino)-7-(2-oxoindolin-6-yl)cinnoline-3-carbonitrile (170),
(R)-4-(1-cyclopropylethylamino)-7-(2-oxoindolin-7-yl)cinnoline-3-carbonitrile (171),
(R)-4-(1-cyclopropylethylamino)-7-(1-methyl-2-oxo-1,2-dihydropyridin-4-yl)cinnoline-3-carbonitrile (172),
(R)-4-(1-cyclopropylethylamino)-7-(2-(methylsulfonyl)phenyl)cinnoline-3-carbonitrile (173),
4-(isopropylamino)-6-phenylcinnoline-3-carbonitrile (174),
4-(isopropylamino)-6-(4-(methylsulfonyl)phenyl)cinnoline-3-carbonitrile (175),
4-(isopropylamino)-6-(pyridin-4-yl)cinnoline-3-carbonitrile (176),
4-(isopropylamino)-6-(1-methyl-1H-pyrazol-4-yl)cinnoline-3-carbonitrile (177),
4-(isopropylamino)-6-(thiazol-2-yl)cinnoline-3-carbonitrile (178),
4-(isopropylamino)-6-(thiazol-5-yl)cinnoline-3-carbonitrile (179),
(R)-4-(1-phenylethylamino)-7-(pyridin-4-yl)cinnoline-3-carbonitrile (180),
(S)-4-(1-phenylethylamino)-7-(pyridin-4-yl)cinnoline-3-carbonitrile (181),
4-(pentan-3-ylamino)-7-(pyridin-4-yl)cinnoline-3-carbonitrile (182),
4-(1-(pyridin-3-yl)ethylamino)-7-(pyridin-4-yl)cinnoline-3-carbonitrile (183),
4-(3-hydroxypropylamino)-7-(pyridin-4-yl)cinnoline-3-carbonitrile (184),
4-(2-hydroxyethylamino)-7-(pyridin-4-yl)cinnoline-3-carbonitrile (185),
(R)-7-(4'-bromo-2',4-dimethoxybiphenyl-3-yl)-4-(1-cyclopropylethylamino)cinnoline-3-carbonitrile (204), (R)-7-(4-bromophenyl)-4-(1-cyclopropylethylamino)cinnoline-3-carbonitrile (212), and (R)-7-(4-bromo-2-methoxyphenyl)-4-(1-cyclopropylethylamino)cinnoline-3-carbonitrile (216).

Reactants used in this Example, such as amines, boronic acids and the like are commercially available or readily prepared by methods known to those of skill in the art. For example boronic acids 2-methoxy-5-(methylsulfonyl)phenylboronic acid (used e.g. in the preparation of compound 115), and 4-dimethylcarbamoyl)-2-methoxyphenylboronic acid (use e.g. in the preparation of compound 118) are prepared as follows.

Synthesis of 2-methoxy-5-(methylsulfonyl)phenylboronic acid

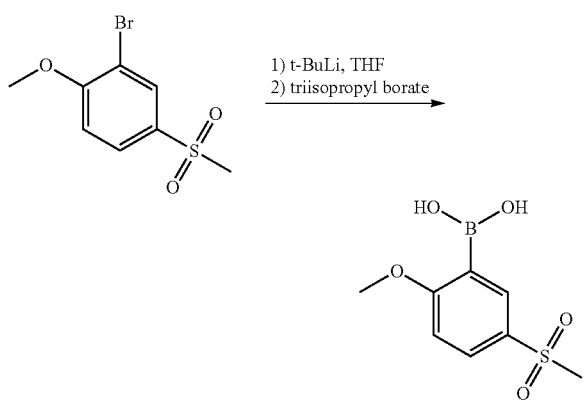

2-Bromo-1-methoxy-4-methylsulfonylbenzene (1.56 g, 5.92 mmol) was dissolved in 20 mL of THF and the temperature was decreased to −78° C. tert-Butyllithium (13.2 mL, 22 mmol; 1.7 mol/L in hexanes) was then added and the reaction mixture was stirred at −78° C. for 15 minutes, then warmed to −45° C. and stirred for 45 minutes. The temperature was decreased to −78° C. and triisopropyl borate (2.89 g, 15.39 mmol) was added. The reaction mixture was stirred for 15 minutes at −78° C., then warmed to room temperature. The reaction mixture was stirred at room temperature for 18 hours and concentrated under vacuum. The resulting residue was dissolved in water and washed with hexane. The aqueous layer was adjusted to pH 4 with 6N aqueous HCl. The aqueous layer was extracted with $CH_2Cl_2$, dried over $Na_2SO_4$, filtered, and the filtrate concentrated under vacuum. The resulting residue was triturated with $Et_2O$ and filtered to afford 2-methoxy-5-(methylsulfonyl)phenylboronic acid that was used without further purification.

Synthesis of 4-(dimethylcarbamoyl)-2-methoxyphenylboronic acid

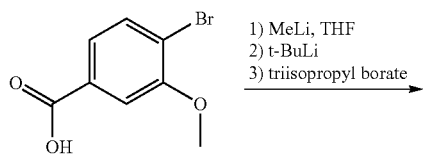

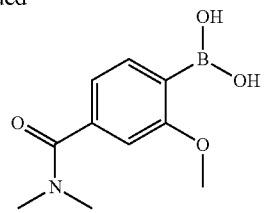

4-Bromo-3-methoxybenzoic acid (2.00 g; 8.66 mmol) was dissolved in 50 mL of THF and the temperature was decreased to −78° C. Methyllithium (6.0 mL, 9.52 mmol; 1.6 mol/L) was added slowly and the reaction mixture was stirred for 5 minutes. tert-Butyllithium (13.2 mL, 22 mmol; 1.7 mol/L in hexanes) was then added from this point the reaction was similar to that for making 2-methoxy-5-(methylsulfonyl)phenylboronic acid (for triisopropyl borate used 4.23 g, 22.5 mmol) to afford 4-(dimethylcarbamoyl)-2-methoxyphenylboronic acid that was used without further purification.

Example 3

Synthesis of N-isopropyl-7-(4-(methylsulfonyl)phenyl)-3-(thiazol-4-yl)cinnolin-4-amine (70)

N-isopropyl-7-(4-(methylsulfonyl)phenyl)-3-(thiazol-4-yl)cinnolin-4-amine (70) was prepared from 4-bromo-2-nitrobenzoic acid (59) in 10 steps as follows:

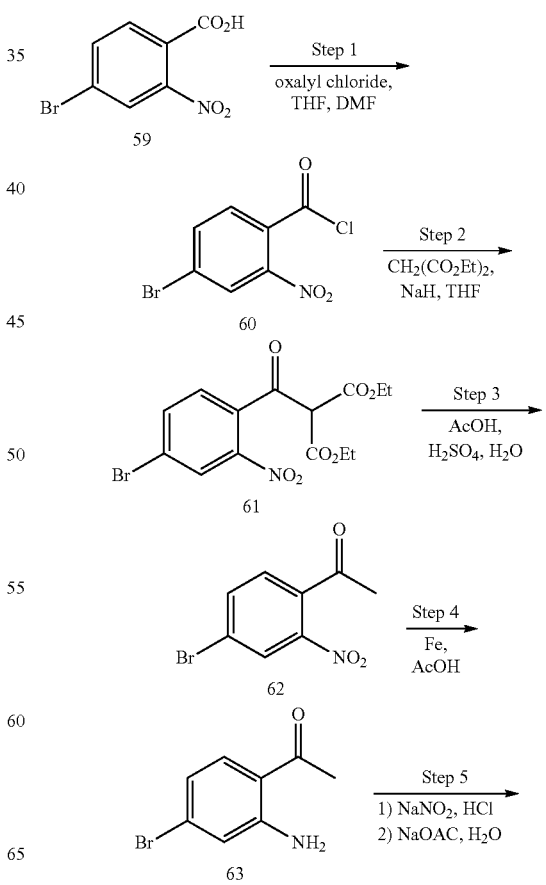

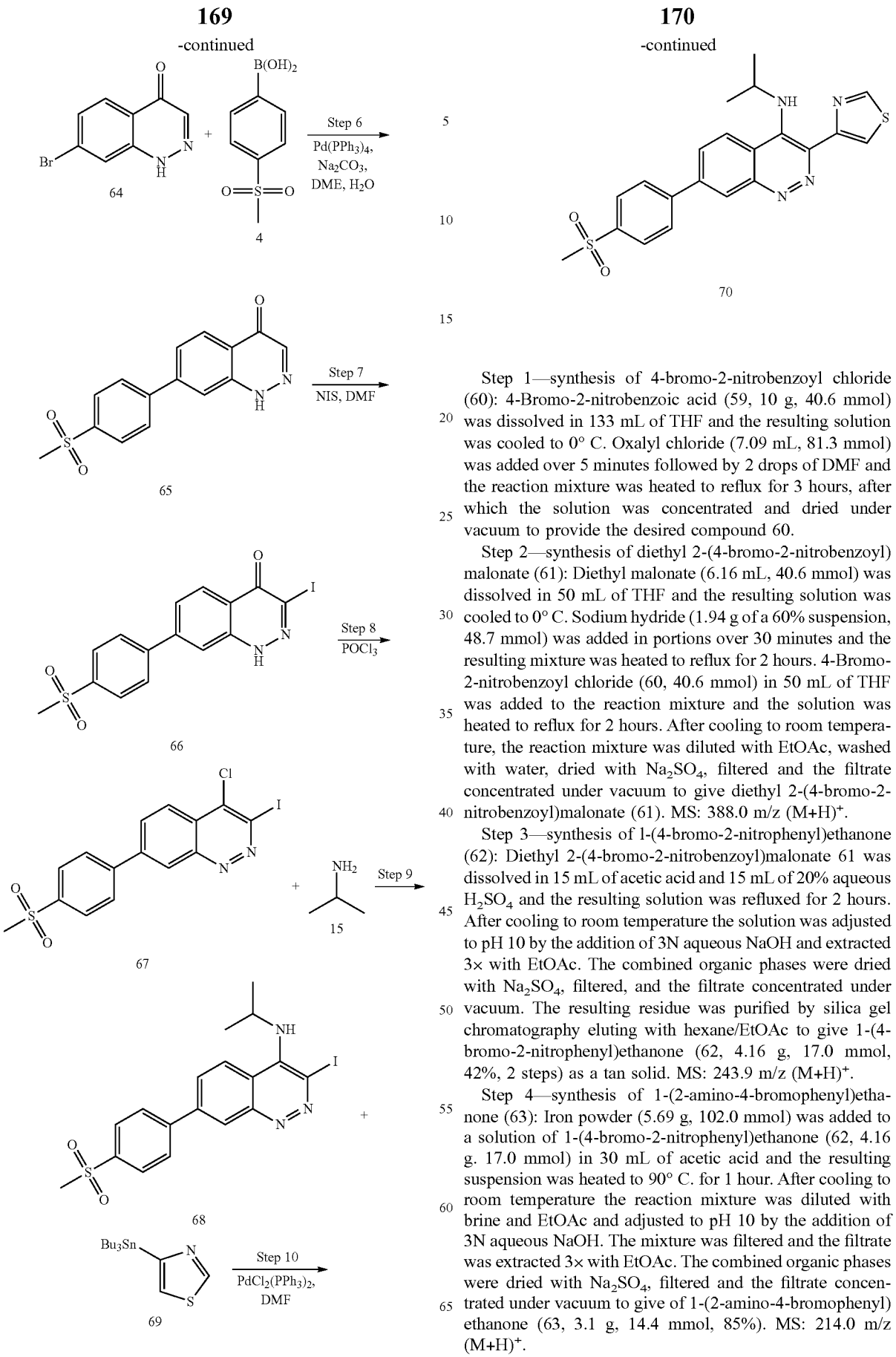

Step 1—synthesis of 4-bromo-2-nitrobenzoyl chloride (60): 4-Bromo-2-nitrobenzoic acid (59, 10 g, 40.6 mmol) was dissolved in 133 mL of THF and the resulting solution was cooled to 0° C. Oxalyl chloride (7.09 mL, 81.3 mmol) was added over 5 minutes followed by 2 drops of DMF and the reaction mixture was heated to reflux for 3 hours, after which the solution was concentrated and dried under vacuum to provide the desired compound 60.

Step 2—synthesis of diethyl 2-(4-bromo-2-nitrobenzoyl) malonate (61): Diethyl malonate (6.16 mL, 40.6 mmol) was dissolved in 50 mL of THF and the resulting solution was cooled to 0° C. Sodium hydride (1.94 g of a 60% suspension, 48.7 mmol) was added in portions over 30 minutes and the resulting mixture was heated to reflux for 2 hours. 4-Bromo-2-nitrobenzoyl chloride (60, 40.6 mmol) in 50 mL of THF was added to the reaction mixture and the solution was heated to reflux for 2 hours. After cooling to room temperature, the reaction mixture was diluted with EtOAc, washed with water, dried with $Na_2SO_4$, filtered and the filtrate concentrated under vacuum to give diethyl 2-(4-bromo-2-nitrobenzoyl)malonate (61). MS: 388.0 m/z $(M+H)^+$.

Step 3—synthesis of 1-(4-bromo-2-nitrophenyl)ethanone (62): Diethyl 2-(4-bromo-2-nitrobenzoyl)malonate 61 was dissolved in 15 mL of acetic acid and 15 mL of 20% aqueous $H_2SO_4$ and the resulting solution was refluxed for 2 hours. After cooling to room temperature the solution was adjusted to pH 10 by the addition of 3N aqueous NaOH and extracted 3× with EtOAc. The combined organic phases were dried with $Na_2SO_4$, filtered, and the filtrate concentrated under vacuum. The resulting residue was purified by silica gel chromatography eluting with hexane/EtOAc to give 1-(4-bromo-2-nitrophenyl)ethanone (62, 4.16 g, 17.0 mmol, 42%, 2 steps) as a tan solid. MS: 243.9 m/z $(M+H)^+$.

Step 4—synthesis of 1-(2-amino-4-bromophenyl)ethanone (63): Iron powder (5.69 g, 102.0 mmol) was added to a solution of 1-(4-bromo-2-nitrophenyl)ethanone (62, 4.16 g. 17.0 mmol) in 30 mL of acetic acid and the resulting suspension was heated to 90° C. for 1 hour. After cooling to room temperature the reaction mixture was diluted with brine and EtOAc and adjusted to pH 10 by the addition of 3N aqueous NaOH. The mixture was filtered and the filtrate was extracted 3× with EtOAc. The combined organic phases were dried with $Na_2SO_4$, filtered and the filtrate concentrated under vacuum to give of 1-(2-amino-4-bromophenyl) ethanone (63, 3.1 g, 14.4 mmol, 85%). MS: 214.0 m/z $(M+H)^+$.

Step 5—synthesis of 7-bromocinnolin-4(1H)-one (64): 1-(2-Amino-4-bromophenyl)ethanone (63, 1.45 g, 6.75 mmol) was dissolved in 16 mL of concentrated aqueous HCl and an aqueous solution of sodium nitrite (582 mg, 8.43 mmol in 1.68 mL $H_2O$) was added dropwise. The reaction mixture was stirred at room temperature for 3 hours and then concentrated under vacuum. The residue was dissolved in 2 mL of water and sodium acetate (2.21 g, 27.0 mmol) was added. The reaction mixture was heated to 100° C. for 2 hours, cooled to room temperature and extracted 3× with EtOAc. The combined organic phases were dried with $Na_2SO_4$, filtered, and the filtrate concentrated under vacuum. The resulting residue was purified by silica gel chromatography eluting with hexane/EtOAc (50% elution) to give 7-bromocinnolin-4(1H)-one (64, 1.07 g, 4.75 mmol, 70%). MS: 224.9 m/z $(M+H)^+$.

Step 6—synthesis of 7-(4-(methylsulfonyl)phenyl)cinnolin-4(1H)-one (65): 7-Bromocinnolin-4(1H)-one (64, 1.07 g, 4.75 mmol), 4-(methylsulfonyl)phenylboronic acid (4, 1.42 g, 7.13 mmol) and $Pd(PPh_3)_4$ (548 mg, 0.475 mmol) were placed in a screw cap vial and 15 mL of DME and 2N aqueous sodium carbonate (4.75 mL, 9.50 mmol) were added. Nitrogen was bubbled through the reaction mixture for 5 minutes and the vial was sealed and placed in a 100° C. oil bath. After 16 hours, the reaction mixture was cooled to room temperature, diluted with EtOAc, washed with water, dried with $Na_2SO_4$, filtered and the filtrate concentrated under vacuum. The resulting residue was purified by silica gel chromatography eluting with hexane/EtOAc (0-100% elution) then $CH_2Cl_2$/MeOH (0-20% elution) to give 7-(4-(methylsulfonyl)phenyl)cinnolin-4(1H)-one (65, 0.92 g, 3.06 mmol, 64%). MS: 301.0 m/z $(M+H)^+$.

Step 7—synthesis of 3-iodo-7-(4-(methylsulfonyl)phenyl)cinnolin-4(1H)-one 66): 7-(4-(Methylsulfonyl)phenyl)cinnolin-4(1H)-one (65, 0.92 g, 3.06 mmol), and N-iodosuccinimide (0.826 g, 3.67 mmol) were dissolved in 10 mL of DMF and the resulting solution was heated to 60° C. for 1 hour. The reaction mixture was diluted with EtOAc and washed with brine. A yellow solid formed in the organic phase and was isolated by filtration and purified by silica gel chromatography eluting with hexane/EtOAc (0-100% elution) then $CH_2Cl_2$/MeOH (0-20% elution) to give 3-iodo-7-(4-(methylsulfonyl)phenyl)cinnolin-4(1H)-one (66, 724 mg, 1.69 mmol, 55%). MS: 427.0 m/z $(M+H)^+$.

Step 8—synthesis of 4-chloro-3-iodo-7-(4-(methylsulfonyl)phenyl)cinnoline (67): 3-Iodo-7-(4-(methylsulfonyl)phenyl)cinnolin-4(1H)-one (66, 724 mg, 1.69 mmol) was dissolved in 3 mL of $POCl_3$ and the resulting solution was heated in a 110° C. oil bath for 30 minutes. The reaction mixture was cooled to room temperature, concentrated under vacuum and redissolved in EtOAc. The solution was washed with saturated aqueous $NaHCO_3$, the organic phases were dried with $Na_2SO_4$, filtered and the filtrated concentrated under vacuum to give 4-chloro-3-iodo-7-(4-(methylsulfonyl)phenyl)cinnoline (67, 522 mg, 1.17 mmol, 69%). MS: 444.9 m/z $(M+H)^+$.

Step 9—synthesis of 3-iodo-N-isopropyl-7-(4-(methylsulfonyl)phenyl)cinnolin-4-amine (68): 4-Chloro-3-iodo-7-(4-(methylsulfonyl)phenyl)cinnoline (67, 522 mg, 1.17 mmol) was dissolved in 5 mL of ethanol in a screw cap vial. Isopropylamine (15, 138 mg, 2.34 mmol) was added and the vial was sealed and placed in a 110° C. oil bath for 1 hour. The reaction mixture was cooled to room temperature, diluted with EtOAc, washed with saturated aqueous $NaHCO_3$ and the organic phases were dried with $Na_2SO_4$, filtered and the filtrate concentrated under vacuum. The resulting residue was purified by reverse phase HPLC to give 3-iodo-N-isopropyl-7-(4-(methylsulfonyl)phenyl)cinnolin-4-amine 68. $^1$H NMR (400 MHz, DMSO-$d_6$) δ: 8.35-8.37 (m, 2H), 8.08-8.16 (m, 5H), 4.59-4.61 (m, 1H), 3.29 (s, 3H), 1.41 (d, J=6.0 Hz, 6H). MS: 468.0 m/z $(M+H)^+$.

Step 10—synthesis of N-isopropyl-7-(4-(methylsulfonyl)phenyl)-3-(thiazol-4-yl)cinnolin-4-amine (70): 3-Iodo-N-isopropyl-7-(4-(methylsulfonyl)phenyl)cinnolin-4-amine (68, 55 mg, 0.117 mmol) was dissolved in 2 mL of DMF in a screw cap vial. 4-(tributylstannyl)thiazole (69, 88 mg, 0.235 mmol) and $PdCl_2(PPh_3)_2$ (8 mg, 0.012 mmol) were added. Nitrogen was bubbled through the reaction mixture for 5 minutes and the vial was sealed and placed in a 100° C. oil bath. After 6 hours the reaction mixture was cooled to room temperature, diluted with EtOAc, washed with brine, dried with $Na_2SO_4$, filtered and the filtrate concentrated under vacuum. The resulting residue was purified by reverse phase HPLC to give N-isopropyl-7-(4-(methylsulfonyl)phenyl)-3-(thiazol-4-yl)cinnolin-4-amine 70. $^1$H NMR (400 MHz, DMSO-$d_6$) δ: 11.8 (s, 1H), 9.50 (s, 1H), 8.64 (s, 1H), 8.58 (d, J=8.9 Hz, 1H), 8.26 (s, 1H), 8.12-8.15 (m, 5H), 4.64-4.66 (m, 1H), 3.32 (s, 3H), 1.48 (d, J=5.6 Hz, 6H). MS: 425.1 m/z $(M+H)^+$.

3-chloro-N-isopropyl-7-(4-(methylsulfonyl)phenyl) cinnolin-4-amine (84)

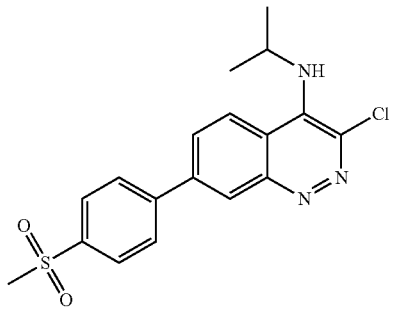

84 can be prepared similarly to the methods of Steps 7-9, where in Step 7, 7-(4-(methylsulfonyl)phenyl)cinnolin-4(1H)-one 65 is reacted with N-chlorosuccinimide in place of N-iodosuccinimide to form the corresponding 3-Cl compound. MS: 376.0 m/z $(M+H)^+$, $^1$H NMR (400 MHz, $CD_3OD$) δ: 8.55 (d, J=8.9 Hz, 1H), 8.09-8.18 (m, 6H), 4.92-4.94 (m, 1H), 3.20 (s, 3H), 1.59 (d, J=6.2 Hz, 6H).

Additional compounds are prepared similarly to this method, replacing 4-(tributylstannyl)thiazole 69 with a suitable compound in Step 10. The following compounds are prepared:

N-isopropyl-7-(4-(methylsulfonyl)phenyl)-3-(oxazol-2-yl) cinnolin-4-amine (71),

N-isopropyl-7-(4-(methylsulfonyl)phenyl)-3-(pyridin-3-yl) cinnolin-4-amine (72), and 2-(4-(isopropylamino)-7-(4-(methylsulfonyl)phenyl)cinnolin-3-yl)pyrimidin-4(3H)-one (187).

The following table provides the compound number (column 1), compound used in Step 10 (column 2) to give the compound shown in column 3. Identification data is provided in column 4.

| Comp. No. | Step 10 compound | Compound structure | Identification |
|---|---|---|---|
| 71 | 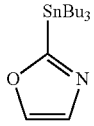 | 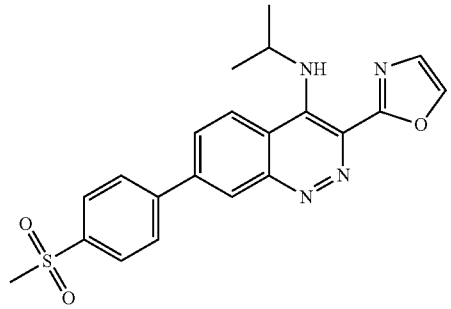 [SMILES: CC(C)Nc1c(-c2ncco2)nnc2cc(-c3ccc(S(C)(=O)=O)cc3)ccc12] | |
| 72 | 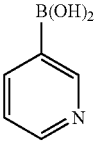 | 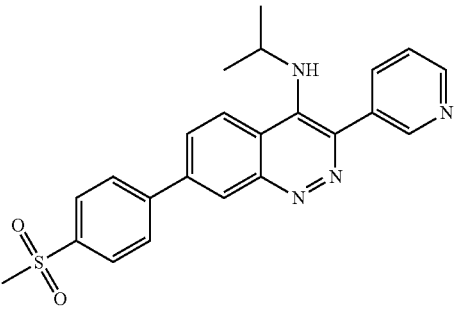 [SMILES: CC(C)Nc1c(-c2cccnc2)nnc2cc(-c3ccc(S(C)(=O)=O)cc3)ccc12] | MS: 419.1 m/z (M + H)⁺<br>$^1$H-NMR (400 MHz, CD$_3$OD) δ: 8.71-9.10 (m, 2H), 8.68 (d, J = 9.0 Hz, 1H), 8.11-8.26 (m, 7H), 7.73 (s, 1H), 4.14-4.17 (m, 1H), 3.20 (s, 3H), 1.32 (d, J = 5.4 Hz, 6H). |
| 187 | 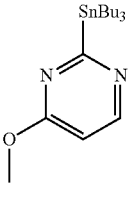 | 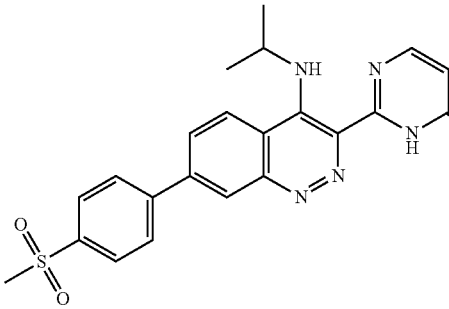 | MS: 436 m/z (M + H)⁺<br>$^1$H-NMR (400 MHz, CD$_3$OD) δ: 8.58 (d, J = 8.0 Hz, 1H), 8.23 (s, 1H), 8.07 (broad m, 7H), 6.45 (broad s, 1H), 4.65 (m, 1H), 3.12 (s, 3H), 1.59 (d, J = 6.0 Hz, 6H). |

Example 4

Synthesis of 4-(isopropylamino)-7-phenoxycinnoline-3-carboxamide (74) and 4-(isopropylamino)-7-phenoxycinnoline-3-carbonitrile (75)

4-(isopropylamino)-7-phenoxycinnoline-3-carboxamide (74) and 4-(isopropylamino)-7-phenoxycinnoline-3-carbonitrile (75) are prepared from 7-iodo-4-(isopropylamino)cinnoline-3-carboxamide (16, see Example 2) in 1 or 2 steps as follows:

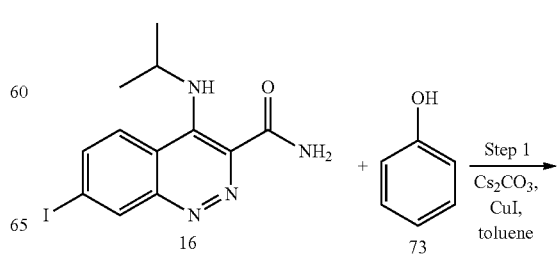

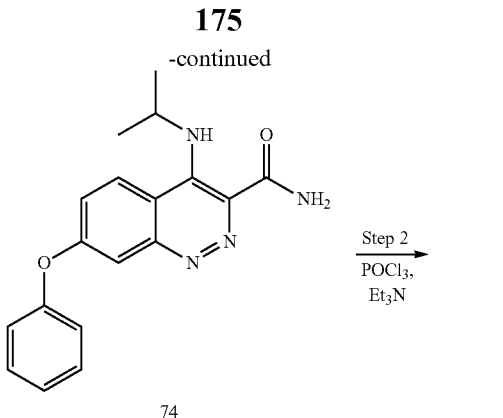

74

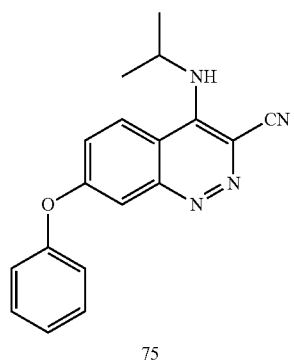

75

Step 1—synthesis of 4-(isopropylamino)-7-phenoxycinnoline-3-carboxamide (74): 7-Iodo-4-(isopropylamino)cinnoline-3-carboxamide (16, 0.05 g, 0.14 mmol) was suspended in 2 mL of toluene and phenol (73, 0.02 g, 0.21 mmol) was added, followed by iodocopper (0.001 g, 0.007 mmol) and cesium carbonate (0.09 g, 0.28 mmol). The reaction was heated in the microwave for 3 hours at 150° C. The reaction mixture was diluted with 10 mL of MeOH and was filtered and the filtrate concentrated. The resulting residue was purified by preparatory HPLC to provide 4-(isopropylamino)-7-phenoxycinnoline-3-carboxamide (74, 0.0017 g, 4%). $^1$H NMR (400 MHz, CDCl$_3$) δ: 8.21 (d, J=9.6 Hz, 1H), 7.97 (m, 2H), 7.74 (s, 1H), 7.49 (m, 2H), 7.40 (d, J=9.2 Hz, 1H), 7.34 (m, 1H), 7.16 (d, J=7.6 Hz, 2H), 5.76 (s, 1H), 4.50 (m, 1H), 1.56 (d, J=6.0 Hz, 6H). MS: 323.2 m/z (M+H)$^+$.

Step 2—synthesis of 4-(isopropylamino)-7-phenoxycinnoline-3-carbonitrile (75): 4-(isopropylamino)-7-phenoxycinnoline-3-carboxamide 74 is reacted similarly to step 7 of Example 2 to provide the desired compound 75.

4-(isopropylamino)-7-(phenylamino)cinnoline-3-carboxamide (78), and 4-(isopropylamino)-7-(phenylamino)cinnoline-3-carbonitrile (79),

78

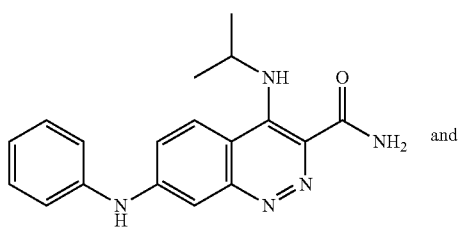

and

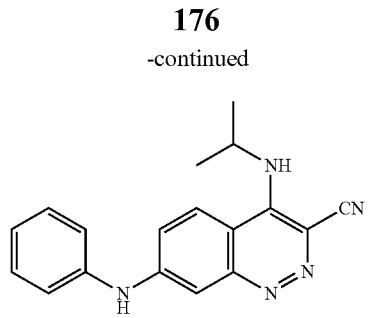

79 are prepared similarly, where phenol 73 is replaced with aniline according to the following Step 1a to provide 78, which is reacted according to Step 2 to provide 79.

Step 1a—synthesis of 4-(isopropylamino)-7-(phenylamino)cinnoline-3-carboxamide (78): 7-Iodo-4-(isopropylamino)cinnoline-3-carboxamide (16, 0.027 g, 0.076 mmol) was suspended in 1 mL of THF and 1,1'-bis(diphenylphosphino)ferrocene-palladium(II)dichloride (0.001 g, 0.0015 mmol), 1,1'-bis(diphenylphosphino)ferrocene (0.007 g, 0.0030 mmol), sodium tert-butoxide (0.009 g, 0.095 mmol), and aniline (0.008 g, 0.095 mmol) were added. The reaction mixture was heated in the microwave for 1 hour at 110° C. The reaction mixture was diluted with THF and filtered. The resulting residue was purified by preparative HPLC to provide 4-(isopropylamino)-7-(phenylamino)cinnoline-3-carboxamide (78, 0.008 g, 33%). $^1$H NMR (CD$_3$OD, 400 MHz) δ: 8.27 (d, J=9.6 Hz, 1H), 7.46 (m, 2H), 7.35 (m, 3H), 7.23 (m, 1H), 7.17 (s, 1H), 4.61 (m, 1H), 1.51 (d, J=6 Hz, 6H). MS: 322.1 m/z (M+H)$^+$.

Additional compounds are prepared similarly to this method, replacing phenol 73 with a suitable compound in Step 1 or replacing aniline with a suitable compound in Step 1a and/or replacing 7-iodo-4-(isopropylamino)cinnoline-3-carboxamide 16 with 6-iodo-4-(isopropylamino)cinnoline-3-carboxamide 16a in Step 1 or 1a and isolating the carboxamide. The following compounds are prepared:

4-(isopropylamino)-7-(phenylthio)cinnoline-3-carboxamide (76), 4-(isopropylamino)-7-(1H-pyrazol-1-yl)cinnoline-3-carboxamide (80), 4-(isopropylamino)-7-(2-oxopyrrolidin-1-yl)cinnoline-3-carboxamide (85), 4-(isopropylamino)-7-(4-methylpiperazin-1-yl)cinnoline-3-carboxamide (188), 4-(isopropylamino)-7-(2-methoxyphenylamino)cinnoline-3-carboxamide (189), 4-(isopropylamino)-7-(2-methoxypyridin-3-ylamino)cinnoline-3-carboxamide (190), 4-(isopropylamino)-6-morpholinocinnoline-3-carboxamide (191), and 4-(isopropylamino)-7-(3-methoxyphenylamino)cinnoline-3-carboxamide (192).

The following table provides the compound number (column 1), compound used in Step 1 or 1a (column 2) to give the compound shown in column 3. Identification data is provided in column 4.

| Comp. No. | Step 1 or 1a compound | Compound structure | Identification |
| --- | --- | --- | --- |
| 76* | SH-phenyl (Step 1) | 7-(phenylthio)-4-(isopropylamino)cinnoline-3-carboxamide | MS: 339.1 m/z (M + H)+<br>1H-NMR (400 MHz, CDCl3) δ: 8.01 (m, 1H), 7.85 (s, 1H), 7.59 (m, 2H), 7.53 (m, 3H), 7.37 (m, 1H), 5.63 (s, 1H), 4.47 (m, 1H), 1.53 (d, J = 6.0 Hz, 6H). |
| 80** | pyrazole (Step 1) | 7-(1H-pyrazol-1-yl)-4-(isopropylamino)cinnoline-3-carboxamide | MS: 297.1 m/z (M + H)+<br>1H-NMR (400 MHz, DMSO-d6) δ: 11.7 (s, 1H), 8.46 (s, 1H), 8.65 (s, 1H), 8.51 (d, J = 9.1 Hz, 1H), 8.41 (s, 1H), 8.27 (d, J = 9.1 Hz, 1H), 8.11 (s, 1H), 7.96 (s, 1H), 6.73 (s, 1H), 4.62-4.64 (m, 1H), 1.43 (d, J = 5.9 Hz, 6H). |
| 85 | 2-pyrrolidinone (Step 1a) | 7-(2-oxopyrrolidin-1-yl)-4-(isopropylamino)cinnoline-3-carboxamide | MS: 314.1 m/z (M + H))+<br>1H-NMR (400 MHz, CD3OD) δ: 8.49 (d, J = 9.6 Hz, 1H), 8.45 (s, 1H), 8.05 (d, J = 9.6 Hz, 1H), 4.71-4.73 (m, 1H), 4.05-4.09 (m, 2H), 2.68-2.72 (m, 2H), 2.24-2.27 (m, 2H), 1.54 (d, J = 6.0, 6H). |
| 188 | 1-methylpiperazine (Step 1a) | 7-(4-methylpiperazin-1-yl)-4-(isopropylamino)cinnoline-3-carboxamide | MS: 329.2 m/z (M + H)+<br>1H-NMR (400 MHz, CD3OD) δ: 8.33 (d, J = 9.7 Hz, 1H), 7.54 (d, J = 9.7 Hz, 1H), 7.08 (s, 1H), 4.61-4.64 (m, 1H), 3.80-3.90 (m, 4H), 3.42-3.52 (m, 4H), 2.96 (s, 3H), 1.50 (d, J = 6.0, 6H). |
| 189 | 2-methoxyaniline (Step 1a) | 7-((2-methoxyphenyl)amino)-4-(isopropylamino)cinnoline-3-carboxamide | MS: 352.2 m/z (M + H)+<br>1H-NMR (400 MHz, CD3OD) δ: 8.24 (d, J = 9.6 Hz, 1H), 7.34 (m, 3H), 7.16 (d, J = 8 Hz, 1H), 7.04 (m, 1H), 6.87 (s, 1H), 4.61 (m, 1H), 3.86 (s, 3H), 1.50 (d, J = 6.2 Hz, 6H). |
| 190 | 3-amino-2-methoxypyridine (Step 1a) | 7-((2-methoxypyridin-3-yl)amino)-4-(isopropylamino)cinnoline-3-carboxamide | MS: 353.1 m/z (M + H)+<br>1H-NMR (400 MHz, CD3OD) δ: 8.28 (d, J = 9.6 Hz, 1H), 8.05 (dd, J = 5.2, 1.6 Hz, 1H), 7.78 (dd, J = 7.6, 1.6 Hz, 1H), 7.38 (dd, J = 9.6, 2.4 Hz, 1H), 7.06 (dd, J = 7.6, 5.2 Hz, 1H), 2.4 Hz, 1H), 4.61 (m, 1H), 4.00 (s, 3H), 1.51 (d, J = 6.2 Hz, 6H). |

| Comp. No. | Step 1 or 1a compound | Compound structure | Identification |
|---|---|---|---|
| 191 | Step 1a using 16a | 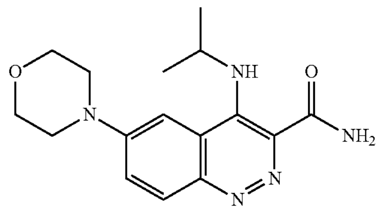 [SMILES: CC(C)Nc1c(C(N)=O)nnc2ccc(N3CCOCC3)cc12] | MS: 316.2 m/z (M + H)+<br>$^1$H-NMR (500 MHz, CD$_3$OD) δ: 7.98-7.96 (m, 1H), 7.96-7.91 (m, 1H), 7.54 (d, J = 2.0 Hz, 1H), 4.82-4.78 (m, 1H), 3.91 (t, J = 5.0 Hz, 2H), 3.44 (t, J = 5.0 Hz, 2H), 1.57 (d, J = 6.0 Hz, 6H). |
| 192 | Step 1a | 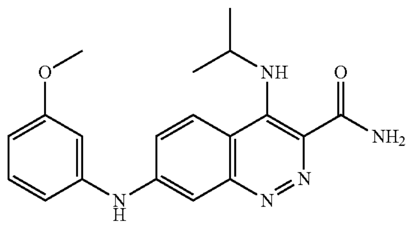 [SMILES: COc1cccc(Nc2ccc3c(NC(C)C)c(C(N)=O)nnc3c2)c1] | MS: 352.1 m/z (M + H)+<br>$^1$H-NMR (400 MHz, CD$_3$OD) δ: 8.27 (d, J = 9.6 Hz, 1H), 7.35 (m, 2H), 7.23 (d, J = 2.4 Hz, 1H), 6.93 (m, 1H), 6.89 (m, 1H), 6.81 (m, 1H), 4.61 (m, 1H), 3.82 (s, 3H), 1.51 (d, J = 6 Hz, 6H). |

*K$_2$CO$_3$ and ethylene glycol/IPA were used instead of Cs$_2$CO$_3$ and CuI in toluene.
**K$_2$CO$_3$ and trans-N1,N2-dimethylcyclohexane-1,2-diamine were used instead of CS$_2$CO$_3$ and CuI in toluene.

The carboxamides from this Example are further reacted through step 2 to provide the corresponding carbonitrile. The following compounds are prepared:
4-(isopropylamino)-7-(phenylthio)cinnoline-3-carbonitrile (77),
4-(isopropylamino)-7-(1H-pyrazol-1-yl)cinnoline-3-carbonitrile (81),
4-(isopropylamino)-7-(2-oxopyrrolidin-1-yl)cinnoline-3-carbonitrile (86),
4-(isopropylamino)-7-(4-methylpiperazin-1-yl)cinnoline-3-carbonitrile (193),
4-(isopropylamino)-7-(2-methoxyphenylamino)cinnoline-3-carbonitrile (194),
4-(isopropylamino)-7-(2-methoxypyridin-3-ylamino)cinnoline-3-carbonitrile (195),
4-(isopropylamino)-6-morpholinocinnoline-3-carbonitrile (196), and
4-(isopropylamino)-7-(3-methoxyphenylamino)cinnoline-3-carbonitrile (197).

Example 5

Synthesis of 4-(isopropylamino)-7-(triazol-4-yl)cinnoline-3-carboxamide (55), and 4-(isopropylamino)-7-(thiazol-4-yl)cinnoline-3-carbonitrile (56)

Compounds 4-(isopropylamino)-7-(thiazol-4-yl)cinnoline-3-carboxamide (55) are prepared from and 4-(isopropylamino)-7-(thiazol-4-yl)cinnoline-3-carbonitrile (56) are prepared from 7-iodo-4-(isopropylamino)cinnoline-3-carboxamide (16, see Example 2) in 1 or 2 steps as follows:

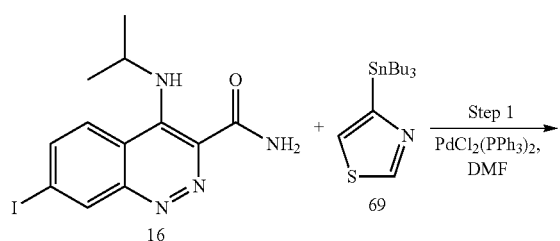

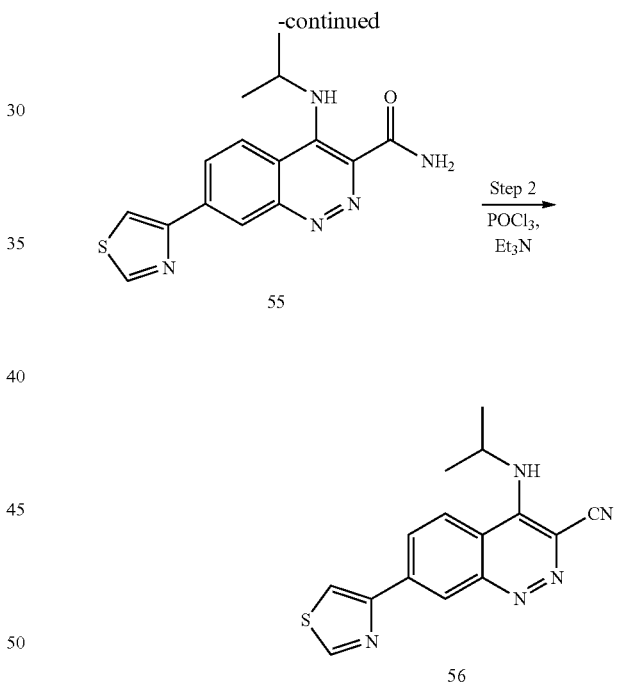

Step 1—synthesis of 4-(isopropylamino)-7-(thiazol-4-yl)cinnoline-3-carboxamide (55): 7-Iodo-4-(isopropylamino)cinnoline-3-carboxamide (16, 0.05 g, 0.14 mmol) was reacted with 4-(tributylstannyl)thiazole 69, following the protocol of step 10 of Example 3. $^1$H NMR (400 MHz, CD$_3$OD) δ: 9.19 (s, 1H), 8.52-8.55 (m, 2H), 8.42 (s, 1H), 8.36 (d, J=9.5 Hz, 1H), 4.76-4.80 (m, 1H), 1.57 (d, J=6.0, 6H). MS: 314.1 m/z (M+H)+.

Step 2—synthesis of 4-(isopropylamino)-7-(thiazol-4-yl)cinnoline-3-carbonitrile (56): 4-(isopropylamino)-7-(thiazol-4-yl)cinnoline-3-carboxamide 55 is reacted similarly to step 7 of Example 2 to provide the desired compound 56.

Example 6

Synthesis of N-isopropyl-3-methyl-7-(4-(methylsulfonyl)phenyl)cinnolin-4-amine (83)

N-isopropyl-3-methyl-7-(4-(methylsulfonyl)phenyl) cinnolin-4-amine (83) was prepared from 3-iodo-N-isopropyl-7-(4-(methylsulfonyl)phenyl)cinnolin-4-amine (68, see Example 3) in 1 step as follows:

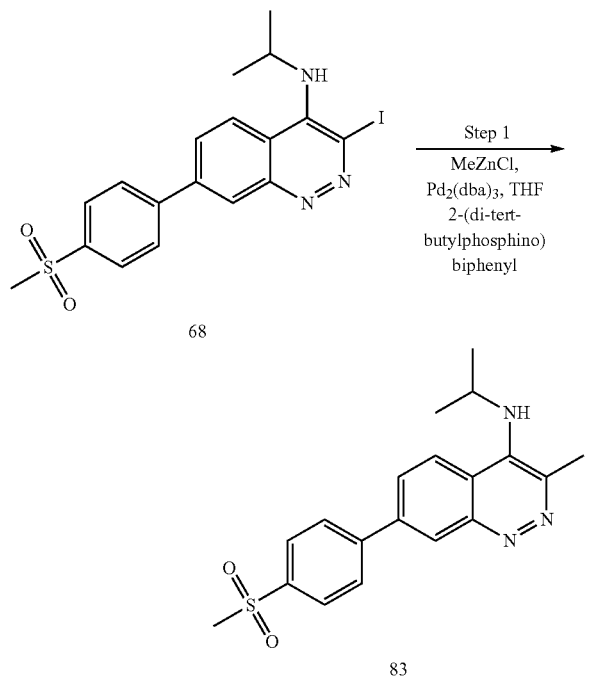

Step 1—synthesis of N-isopropyl-3-methyl-7-(4-(methylsulfonyl)phenyl) cinnolin-4-amine (83): 3-iodo-N-isopropyl-7-(4-(methylsulfonyl)phenyl)cinnolin-4-amine (68, 80 mg, 0.171 mmol), $Pd_2(dba)_3$ (15 mg, 0.0171 mmol) and 2-(di-tert-butylphosphino)biphenyl (10 mg, 0.0342 mmol) were placed in a screw cap vial and 1 mL of THF and methylzinc chloride (2M solution in THF, 171 μL, 0.342 mmol) were added. Nitrogen was bubbled through the resulting solution for 5 minutes. The vial was sealed and placed in a 90° C. oil bath. After stirring for 4 hours the reaction mixture was cooled to room temperature, diluted with EtOAc, washed with brine, dried with $Na_2SO_4$, filtered and the filtrate concentrated under vacuum. The resulting residue was purified by reverse phase HPLC to give N-isopropyl-3-methyl-7-(4-(methylsulfonyl)phenyl)cinnolin-4-amine 83. $^1H$ NMR (400 MHz, $CD_3OD$) δ: 8.52 (d, J=9.0 Hz, 1H), 8.04-8.16 (m, 6H), 4.80-4.84 (m, 1H), 3.19 (s, 3H), 2.73 (s, 3H), 1.61 (d, J=6.1 Hz, 6H). MS: 356.1 m/z (M+H)$^+$.

Example 7

Synthesis of 7-(2-hydroxyethyl)-4-(isopropylamino) cinnoline-3-carboxamide (198)

7-(2-Hydroxyethyl)-4-(isopropylamino)cinnoline-3-carboxamide (198) was prepared from 4-(isopropylamino)-7-vinylcinnoline-3-carboxamide (95, see Example 2) in 1 step as follows:

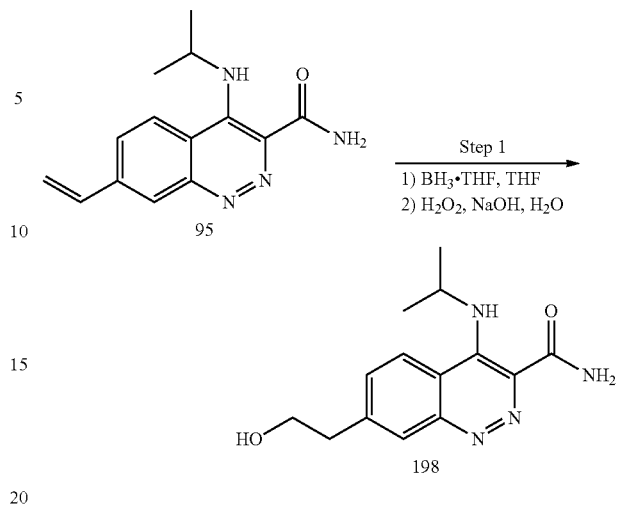

Step 1—synthesis of 7-(2-hydroxyethyl)-4-(isopropylamino)cinnoline-3-carboxamide (198): 4-(Isopropylamino)-7-vinylcinnoline-3-carboxamide (95, 0.28 g, 1.09 mmol) was dissolved in 5 mL of THF and the temperature was decreased to 0° C. Borane-THF complex (0.28 g, 3.29 mmol) was added and the reaction mixture was stirred at 0° C. for 1 hour. The reaction mixture was quenched with water, then 2 mL of 20% aqueous NaOH and 2 mL of hydrogen peroxide were added, and the reaction stirred for 1 hour at 0° C. The reaction mixture was saturated with NaCl and diluted with $CH_2Cl_2$. The organic layer was separated, concentrated under vacuum, and the residue dissolved in 5 mL of THF, then stirred with 20% NaOH and $H_2O_2$ overnight. The organic layer was separated and dried with $Na_2SO_4$, filtered and the filtrate concentrated under vacuum. The resulting residue was purified by preparative HPLC to afford 6 mg (2%) of compound 198. $^1H$ NMR ($CD_3OD$, 400 MHz) δ: 8.45 (d, J=9.2 Hz, 1H), 7.81 (s, 1H), 7.75 (d, J=9.2 Hz, 1H), 4.76 (m, 1H), 3.92 (m, 2H), 3.09 (m, 2H), 1.55 (d, J=6.4 Hz, 6H). MS: 275.1 m/z (M+H)$^+$. The 3-CN analog 7-(2-hydroxyethyl)-4-(isopropylamino)cinnoline-3-carbonitrile (199) is similarly prepared from 7-(2-hydroxyethyl)-4-(isopropylamino)cinnoline-3-carbonitrile 145.

Example 8

Synthesis of N-Isopropyl-7-(4-(methylsulfonyl)phenyl)-3-(1H-1,2,4-triazol-3-yl)cinnolin-4-amine (200)

N-Isopropyl-7-(4-(methylsulfonyl)phenyl)-3-(1H-1,2,4-triazol-3-yl)cinnolin-4-amine (200) was prepared from 4-(isopropylamino)-7-(4-(methylsulfonyl)phenyl)cinnoline-3-carboxamide (17, see Example 2) in 1 step as follows:

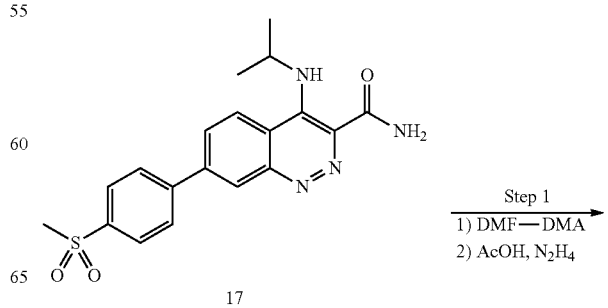

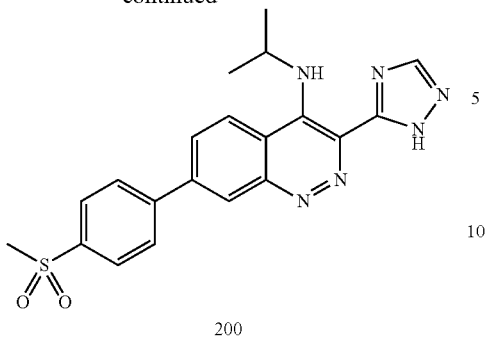

200

Step 1—synthesis of N-isopropyl-7-(4-(methylsulfonyl) phenyl)-3-(1H-1,2,4-triazol-3-yl)cinnolin-4-amine (200): 4-(Isopropylamino)-7-(4-(methylsulfonyl)phenyl)cinnoline-3-carboxamide (17, 0.028 g, 0.072 mmol) was suspended in 1 mL of N,N-dimethylformamide dimethyl acetal and the reaction mixture was plunged into a preheated 90° C. oil bath. The reaction mixture was stirred for 1.5 hours, then concentrated under vacuum. The resulting residue was placed on the high vacuum for 5 minutes and then dissolved in 1 mL of acetic acid. Hydrazine (0.011 g, 0.36 mmol) was added and the reaction mixture was stirred at room temperature for 30 minutes, transferred to a vial, and concentrated under vacuum. The resulting residue was purified by preparative HPLC to afford 0.017 g (56%) of compound 200. $^1$H NMR (CD$_3$OD, 400 MHz) δ: 8.71 (d, J=9.2 Hz, 1H), 8.25 (bs, 1H), 8.16 (m, 5H), 4.95 (m, 1H), 3.20 (s, 3H), 1.66 (d, J=6 Hz, 6H). MS: 409.1 m/z (M+H)$^+$.

Example 9

Synthesis of (R)-4-(1-cyclopropylethylamino)-7-(2-methoxy-5-(2-oxooxazolidin-3-yl)phenyl)cinnoline-3-carboxamide (206)

(R)-4-(1-Cyclopropylethylamino)-7-(2-methoxy-5-(2-oxooxazolidin-3-yl)phenyl)cinnoline-3-carboxamide (206) was prepared from (R)-7-(5-Bromo-2-methoxyphenyl)-4-(1-cyclopropylethylamino)cinnoline-3-carboxamide (109, see Example 2) in one Step as follows:

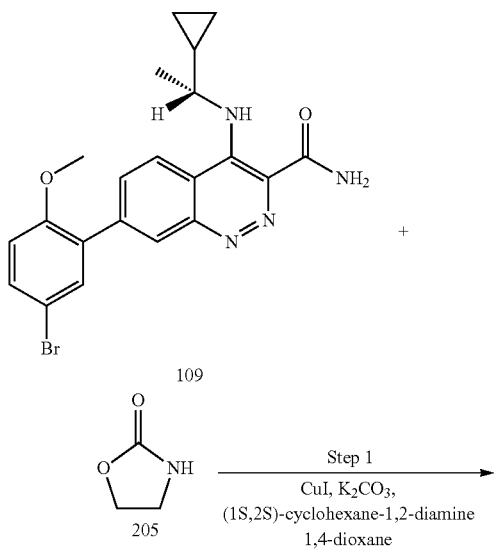

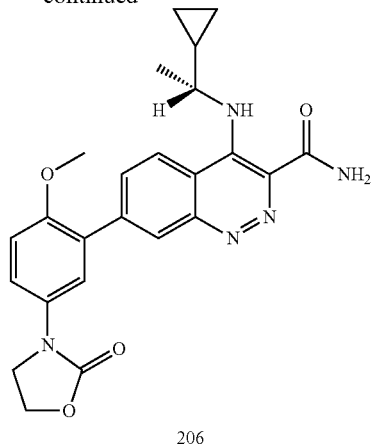

206

Step 1—synthesis of (R)-4-(1-cyclopropylethylamino)-7-(2-methoxy-5-(2-oxooxazolidin-3-yl)phenyl)cinnoline-3-carboxamide (206): (R)-7-(5-Bromo-2-methoxyphenyl)-4-(1-cyclopropylethylamino)cinnoline-3-carboxamide (109, 0.050 g; 0.11 mmol) was dissolved in 1 mL of 1,4-dioxane and oxazolidin-2-one (205, 0.099 g, 1.1 mmol) was added, followed by iodocopper (0.0004 g, 0.0023 mmol), K$_2$CO$_3$ (0.16 g, 1.1 mmol) and (1S,2S)-cyclohexane-1,2-diamine (0.0004 g, 0.0039 mmol). The reaction mixture was heated in the microwave for 1.5 hours at 150° C., then diluted with dioxane, filtered and the filtrate concentrated under vacuum. The resulting residue was purified by preparative HPLC to provide the desired compound (206, 0.012 g, 23%). $^1$H NMR (CD$_3$OD, 400 MHz) δ: 8.52 (d, J=8.8 Hz, 1H), 8.13 (d, J=1.6 Hz, 1H), 8.03 (dd, J=9.2, 1.6 Hz, 1H), 7.90 (d, J=2.4 Hz, 1H), 7.55 (dd, J=8.8, 2.4 Hz, 1H), 7.26 (d, J=9.2 Hz, 1H), 4.52 (m, 2H), 4.25 (m, 1H), 4.16 (m, 1H), 3.89 (s, 3H), 1.61 (d, J=6.4 Hz, 3H), 1.32 (m, 1H), 0.69 (m, 2H), 0.48 (m, 2H). MS: 448.2 m/z (M+H)$^+$.

Additional compounds are prepared similarly to this method, optionally replacing oxazolidin-2-one 205 with a suitable amine compound and/or replacing (R)-7-(5-bromo-2-methoxyphenyl)-4-(1-cyclopropylethylamino)cinnoline-3-carboxamide 109 with (R)-7-(4'-bromo-2',4-dimethoxybiphenyl-3-yl)-4-(1-cyclopropylethylamino)cinnoline-3-carboxamide 203 or (R)-7-(4-bromophenyl)-4-(1-cyclopropylethylamino)cinnoline-3-carboxamide 211. The following compounds are prepared:

(R)-4-(1-cyclopropylethylamino)-7-(2-methoxy-5-(1H-pyrazol-1-yl)phenyl)cinnoline-3-carboxamide (207), (R)-4-(1-cyclopropylethylamino)-7-(2',4-dimethoxy-4'-(2-oxooxazolidin-3-yl)biphenyl-3-yl)cinnoline-3-carboxamide (208), (R)-4-(1-cyclopropylethylamino)-7-(2-methoxy-5-(3-oxomorpholino)phenyl)cinnoline-3-carboxamide (209), (R)-4-(1-cyclopropylethylamino)-7-(2',4-dimethoxy-4'-(3-oxomorpholino)biphenyl-3-yl)cinnoline-3-carboxamide (210), and (R)-4-(1-cyclopropylethylamino)-7-(4-(2-oxooxazolidin-3-yl)phenyl)cinnoline-3-carboxamide (213).

The following table provides the compound number (column 1), amine and whether compound 109 or 203 or 211 was used (column 2), to give the compound shown in column 3. Identification data is provided in column 4.

| Comp. No. | amine + 109, 203, or 211 | Compound structure | Identification |
|---|---|---|---|
| 207 | 1H-pyrazole + 109 | (structure) | MS: 429.2 m/z (M + H)+<br>¹H-NMR (400 MHz, CD₃OD) δ: 8.54 (d, J = 9.2 Hz, 1H), 8.22 (d, J = 2 Hz, 1H), 8.18 (d, J = 2 Hz, 1H), 8.11 (dd, J = 9.2, 2.0 Hz, 1H), 7.91 (d, J = 2.8 Hz, 1H), 7.83 (dd, J = 8.8, 2.8 Hz, 1H), 7.74 (d, J = 1.6 Hz, 1H), 7.35 (d, J = 8.8 Hz, 1H), 6.54 (app. t, J = 2 Hz, 1H), 4.26 (m, 1H), 3.94 (s, 3H), 1.60 (m, 3H), 1.33 (m, 1H), 0.72 (m, 2H), 0.55 (m, 2H). |
| 208 | oxazolidin-2-one + 203 | (structure) | MS: 554.2 m/z (M + H)+<br>¹H-NMR (400 MHz, CD₃OD) δ: 8.51 (d, J = 8.8 Hz, 1H), 8.14 (d, J = 1.6 Hz, 1H), 8.06 (dd, J = 9.2, 1.6 Hz, 1H), 7.66 (m, 2H), 7.40 (dd, J = 8.8, 2.8 Hz, 1H), 7.26 (d, J = 8.8 Hz, 1H), 7.14 (d, J = 8.8 Hz, 1H), 4.49 (m, 2H), 4.25 (m, 1H), 4.12 (m, 2H), 3.93 (s, 3H), 3.82 (s, 3H), 1.58 (d, J = 6.4 Hz, 3H), 1.32 (m, 1H), 0.70 (m, 2H), 0.46 (m, 2H). |
| 209 | morpholin-3-one + 109 | (structure) | MS: 462.2 m/z (M + H)+<br>¹H-NMR (400 MHz, CD₃OD) δ: 8.51 (d, J = 8.8 Hz, 1H), 8.13 (d, J = 1.6 Hz, 1H), 8.01 (dd, J = 9.2, 2.0 Hz, 1H), 7.54 (d. J = 2.4 Hz, 1H), 7.49 (dd, J = 8.4, 2.4 Hz, 1H), 7.29 (d, J = 8.8 Hz, 1H), 4.28 (s, 2H), 4.23 (m, 1H), 4.06 (m, 2H), 3.91 (s, 3H), 3.82 (m, 2H), 1.60 (d, J = 6.4 Hz, 3H), 1.35 (m, 1H), 0.68 (m, 2H), 0.45 (m, 2H). |

| Comp. No. | amine + 109, 203, or 211 | Compound structure | Identification |
|---|---|---|---|
| 210 | 203 | 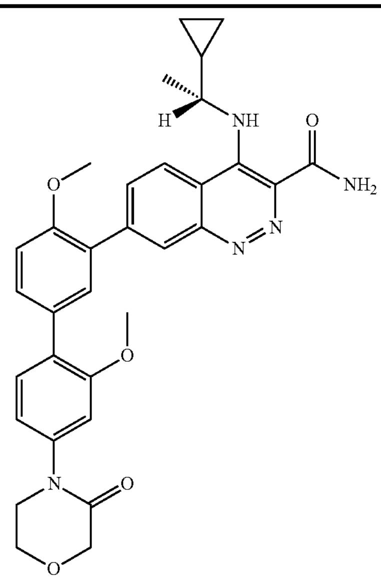 | MS: 568.3 m/z (M + H)+<br>¹H-NMR (400 MHz, CD₃OD) δ: 8.51 (d, J = 8.8 Hz, 1H), 8.14 (d, J = 1.6 Hz, 1H), 8.06 (dd. J = 9.2, 2Hz, 1H), 7.66 (m, 2H), 7.33 (m, 2H), 7.25 (d, J = 8.4 Hz, 1H), 7.16 (d, J = 8.8 Hz, 1H), 4.25 (m, 3H), 4.05 (m, 2H), 3.93 (s, 3H), 3.86 (s, 3H), 3.78 (m, 2H), 1.60 (d, J = 6.4 Hz, 3H), 1.35 (m, 1H), 0.75 (m, 2H), 0.50 (m, 2H). |
| 213 | 211 | 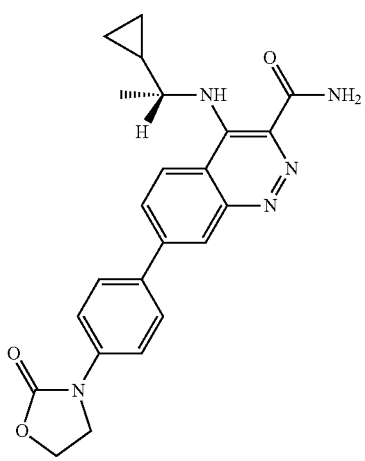 [SMILES: C[C@@H](Nc1c(C(N)=O)nnc2cc(-c3ccc(N4CCOC4=O)cc3)ccc12)C1CC1] | MS: 418.2 m/z (M + H)+<br>¹H-NMR (400 MHz, CD₃OD) δ: 8.53 (m, 1H), 8.10 (m, 2H), 7.91 (m, 2H), 7.83 (m, 2H), 4.55 (m, 2H), 4.21 (m, 3H), 1.59 (d, J = 3H), 1.33 (m, 1H), 0.74 (m, 2H), 0.48 (m, 2H). |

The carbonitriles analogous to the compounds from this Example may be prepared either by reacting the compounds of this example according to Example 2, Step 7, or by replacing the carboxamides 109, 203 or 211 with the carbonitriles 159, 204, and 212, respectively. The following compounds are prepared:

(R)-4-(1-cyclopropylethylamino)-7-(2-methoxy-5-(2-oxooxazolidin-3-yl)phenyl)cinnoline-3-carbonitrile (237), (R)-4-(1-cyclopropylethylamino)-7-(2-methoxy-5-(1H-pyrazol-1-yl)phenyl)cinnoline-3-carbonitrile (238), (R)-4-(1-cyclopropylethylamino)-7-(2',4-dimethoxy-4'-(2-oxooxazolidin-3-yl)biphenyl-3-yl)cinnoline-3-carbonitrile (239), (R)-4-(1-cyclopropylethylamino)-7-(2-methoxy-5-(3-oxomorpholino)phenyl)cinnoline-3-carbonitrile (240), (R)-4-(1-cyclopropylethylamino)-7-(2',4-dimethoxy-4'-(3-oxomorpholino)biphenyl-3-yl)cinnoline-3-carbonitrile (241), and (R)-4-(1-cyclopropylethylamino)-7-(4-(2-oxooxazolidin-3-yl)phenyl)cinnoline-3-carbonitrile (242).

Example 10

Synthesis of 3-ethynyl-N-isopropyl-7-(4-(methylsulfonyl)phenyl)cinnolin-4-amine (87)

3-Ethynyl-N-isopropyl-7-(4-(methylsulfonyl)phenyl) cinnolin-4-amine 87 was prepared from 3-iodo-N-isopropyl-7-(4-methylsulfonylphenyl)cinnolin-4-amine 68 (see Example 3) in one Step as follows:

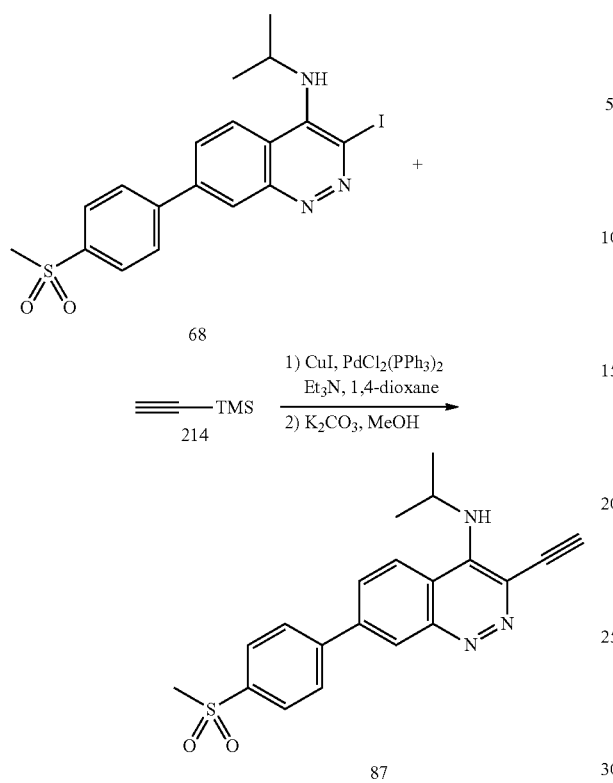

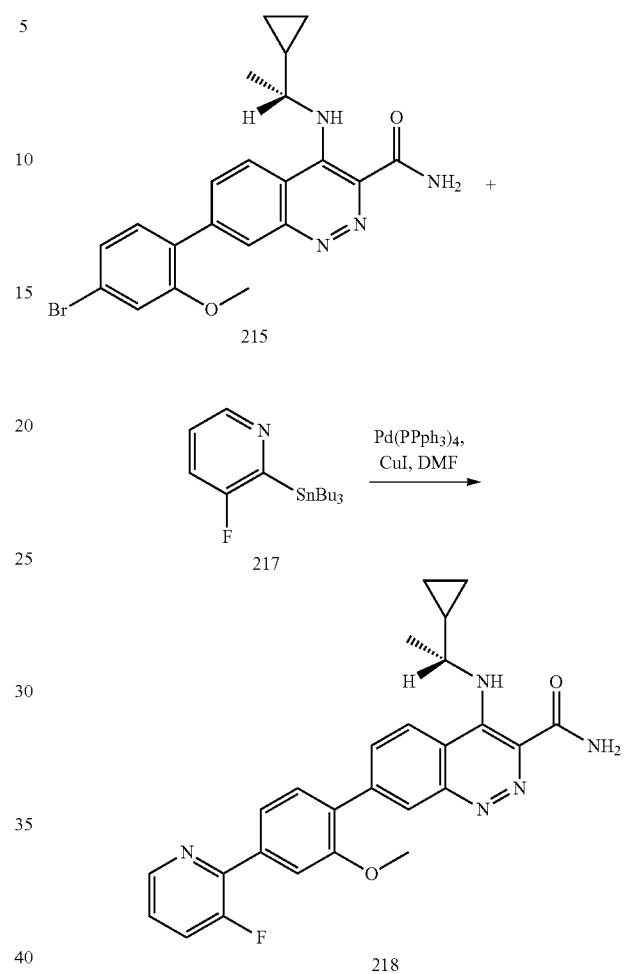

clopropylethylamino)cinnoline-3-carboxamide 215 (see Example 2) in one Step as follows:

Step 1—synthesis of 3-ethynyl-N-isopropyl-7-(4-(methylsulfonyl)phenyl) cinnolin-4-amine (87): 3-Iodo-N-isopropyl-7-(4-methylsulfonylphenyl)cinnolin-4-amine (68, 0.100 g, 0.214 mmol) was suspended in 1 mL of 1,4-dioxane and ethynyl(trimethyl)silane (214, 0.042 g, 0.428 mmol), iodocopper (0.001 g, 0.00642 mmol), Pd(PPh$_3$)$_4$ (0.004 g, 0.006 mmol), and 0.5 mL of triethylamine were added. The reaction mixture was heated in a microwave for 30 minutes at 130° C. The reaction mixture was diluted with 1:1 CH$_2$Cl$_2$:H$_2$O and the two layers were separated. The organic layer was dried with Na$_2$SO$_4$, filtered and the filtrate concentrated under vacuum. The resulting residue was dissolved in 2 mL of MeOH and K$_2$CO$_3$ (0.100 g, 0.72 mmol) was added. The reaction mixture was stirred for 15 minutes, then filtered and the filtrate concentrated under vacuum. The resulting residue was purified by preparative HPLC to give the desired compound (87, 2 mg 3%). $^1$H NMR (CD$_3$OD, 400 MHz) δ: 9.30 (s, 1H), 8.54 (d, J=8.4 Hz, 1H), 8.21 (d, J=8.4 Hz, 1H), 8.09 (m, 2H), 8.00 (m, 2H), 7.86 (s, 1H), 7.41 (s, 1H), 5.42 (m, 1H), 3.12 (s, 3H), 1.81 (d, J=6 Hz, 6H), 1.55 (s, 1H). MS: 366.1 m/z (M+H)$^+$.

Example 11

Synthesis of (R)-4-(1-cyclopropylethylamino)-7-(4 (3-fluoropyridin-2-yl)-2-methoxyphenyl)cinnoline-3-carboxamide (218)

(R)-4-(1-Cyclopropylethylamino)-7-(4-(3-fluoropyridin-2-yl)-2-methoxyphenyl)cinnoline-3-carboxamide 218 was prepared from (R)-7-(4-bromo-2-methoxyphenyl)-4-(1-cy- Step 1—synthesis of (R)-4-(1-Cyclopropylethylamino)-7-(4-(3-fluoropyridin-2-yl)-2-methoxyphenyl)cinnoline-3-carboxamide (218): (R)-7-(4-bromo-2-methoxyphenyl)-4-(1-cyclopropylethylamino)cinnoline-3-carboxamide (215, 0.030 g; 0.068 mmol) was dissolved in 0.5 mL of DMF and Pd(PPh$_3$)$_4$ (0.025 equiv.; 0.0017 mmol), CuI (0.025 equiv.; 0.0017 mmol) and 3-fluoro-2-(tributylstannyl)pyridine (217, 1.25 equiv.; 0.085 mmol) were added. The reaction mixture was heated in a microwave for 30 minutes at 115° C., then heated in the microwave for an additional 45 minutes at 125° C. A second aliquot of 3-fluoro-2-(tributylstannyl)pyridine (1.25 equiv.; 0.085 mmol), CuI (0.025 equiv.; 0.0017 mmol) and Pd(PPh$_3$)$_4$ (0.025 equiv.; 0.0017 mmol) were added. The reaction mixture was heated in the microwave for 45 minutes at 130° C., then filtered through a PTFE membrane and the filtrate concentrated under vacuum. The resulting residue was purified by HPLC to give the desired compound (218, 0.002 g, 5.5%). $^1$H NMR (CD$_3$OD, 400 MHz) δ: 8.55 (d, J=4.4 Hz, 1H), 8.51 (d, J=8.8 Hz, 1H), 8.21 (s, 1H), 8.06 (d, J=9.2 Hz, 1H), 7.76 (m, 2H), 7.66 (m, 2H), 7.50 (m, 1H), 4.24 (m, 1H), 3.97 (s, 3H), 1.60 (d, J=6.4 Hz, 3H), 1.32 (m, 2H), 0.70 (m, 2H), 0.53 (m, 2H). MS: 458.2 m/z (M+H)$^+$. This compound can be converted to the carbonitrile (R)-4-(1-cyclopropylethylamino)-7-(4-(3-fluoropyridin-2-yl)-2-methoxyphenyl)cinnoline-3-carbonitrile (219), for example, by following the procedure of Example 2 Step 7, or alternatively, the carbonitrile can be prepared by replacing the starting compound 215 with the corresponding (R)-7-(4-bromo-2-methoxyphenyl)-4-(1-cyclopropylethylamino)cinnoline-3-carbonitrile (216, see Example 2).

(R)-4-(1-cyclopropylethylamino)-7-(2-methoxy-4-(3-methoxypyrazin-2-yl)phenyl)cinnoline-3-carboxamide 220, and (R)-4-(1-cyclopropylethylamino)-7-(2-methoxy-4-(1-methyl-1H-imidazol-2-yl)phenyl)cinnoline-3-carboxamide 221:

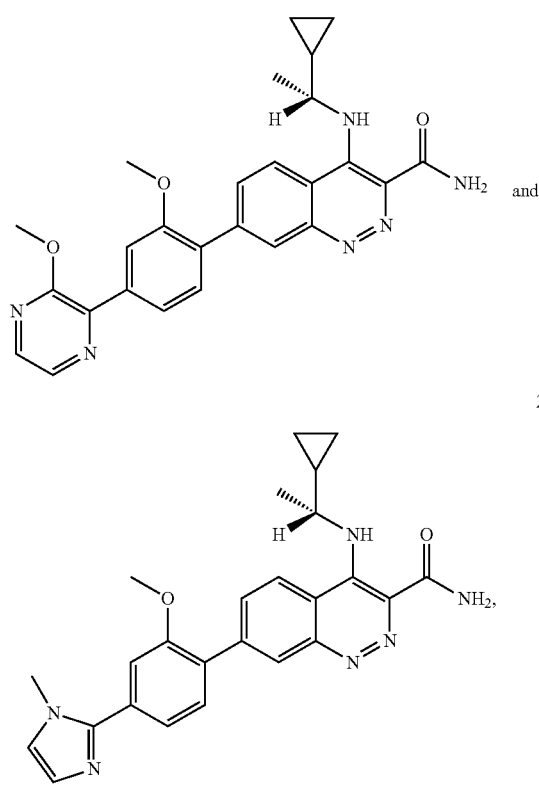

were prepared similarly, replacing 3-fluoro-2-(tributylstannyl)pyridine 217 with 2-methoxy-3-(tributylstannyl)pyrazine and 1-methyl-2-(tributylstannyl)-1H-imidazole, respectively. 220: $^1$H NMR (CD$_3$OD, 400 MHz) δ: 8.53 (d, J=9.2 Hz, 1H), 8.28 (d, J=2.8 Hz, 1H), 8.20 (d, J=2.4 Hz, 1H), 8.19 (d, J=1.6 Hz, 1H), 8.08 (dd, J=8.8, 1.6 Hz, 1H), 7.88 (m, 1H), 7.85 (m, 1H), 7.64 (d, J=8 Hz, 1H), 4.27 (m, 1H), 4.09 (s, 3H), 3.96 (s, 3H), 1.60 (d, J=6.4 Hz, 3H), 1.32 (m, 2H), 0.70 (m, 2H), 0.53 (m, 2H). MS: 471.2 m/z (M+H)$^+$. 221: $^1$H NMR (CD$_3$OD, 400 MHz) δ: 8.56 (d, J=9.2 Hz, 1H), 8.20 (d, J=2 Hz, 1H), 8.04 (dd, J=9.2, 2.0 Hz, 1H), 7.82 (d, J=8.0 Hz, 1H), 7.73 (m, 2H), 7.57 (m, 1H), 7.52 (m, 1H), 4.28 (m, 1H), 4.01 (m, 6H), 1.60 (d, J=6.4 Hz, 3H), 1.32 (m, 2H), 0.70 (m, 2H), 0.53 (m, 2H). MS: 443.2 m/z (M+H)$^+$. Similarly, the corresponding carbonitrile compounds are readily prepared to give (R)-4-(1-cyclopropylethylamino)-7-(2-methoxy-4-(3-methoxypyrazin-2-yl)phenyl)cinnoline-3-carbonitrile (222) and (R)-4-(1-cyclopropylethylamino)-7-(2-methoxy-4-(1-methyl-1H-imidazol-2-yl)phenyl)cinnoline-3-carbonitrile (223).

Example 12

Synthesis of 4-(Isopropylamino)-N-methyl-7-(4-(methylsulfonyl)phenyl) cinnoline-3-carboxamide (227)

4-(Isopropylamino)-N-methyl-7-(4-(methylsulfonyl)phenyl)cinnoline-3-carboxamide 227 was prepared from 4-hydroxy-7-iodocinnoline-3-carboxylic acid 13 (see Example 2) in four Steps as follows:

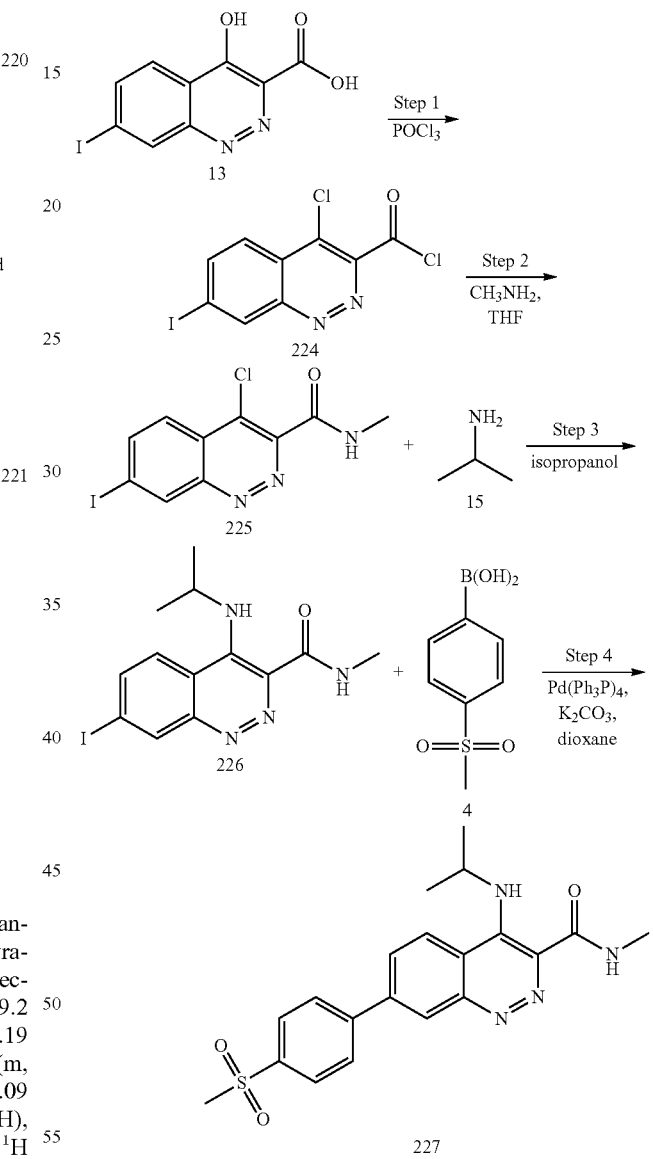

Step 1—synthesis of 4-chloro-7-iodocinnoline-3-carbonyl chloride (224): 4-hydroxy-7-iodocinnoline-3-carboxylic acid (13, 1.01 g, 3.20 mmol) in 10 mL of phosphorus(V) oxychloride was placed in a preheated oil bath at 100° C. and stirred for 2 hours, then concentrated under vacuum to provide the desired compound as a brown solid.

Step 2—synthesis of 4-chloro-7-iodo-N-methylcinnoline-3-carboxamide (225): 40% Methylamine in water (0.08 ml, 929 μmol) was added dropwise to a solution of 4-chloro-7-iodocinnoline-3-carbonyl chloride (224, 370 mg, 1.05 mmol) in 2 mL of THF at 0° C. After stirring for 1 hour, the solution was concentrated under vacuum and the residue was diluted with water. The resulting solid was collected by filtration to give the desired compound (225, 339 mg, 58%) as a brown solid.

Step 3—synthesis of 7-iodo-4-(isopropylamino)-N-methylcinnoline-3-carboxamide (226): 4-Chloro-7-iodo-N-methylcinnoline-3-carboxamide (339 mg, 961 μmol) and 2 mL of isopropylamine (15) in 10 mL of 2-propanol was placed into a preheated oil bath at 60° C. After stirring for 1 hour, the solution was concentrated under vacuum, the residue was diluted with water, and the resulting solid was collected by filtration to give the desired compound (226, 200 mg) as a brown solid.

Step 4—synthesis of 4-(isopropylamino)-N-methyl-7-(4-(methylsulfonyl)phenyl)cinnoline-3-carboxamide (227): 7-iodo-4-(isopropylamino)-N-methylcinnoline-3-carboxamide 226 is reacted with 4-(methylsulfonyl)phenylboronic acid 4 similarly to the method described in Example 2 Step 6. $^1$H NMR (DMSO-d$_6$, 400 MHz) δ: 11.95 (broad s, 1H), 9.28 (d, J=4.4 Hz, 1H), 8.57 (d, J=9.2 Hz, 1H), 8.34 (d, J=1.2 Hz, 1H), 8.16 (s, 5H), 8.06 (d, J=4.4 Hz, 1H), 4.70 (broad s, 1H), 3.33 (s, 3H), 2.88 (d, J=4.4 Hz, 3H), 1.47 (d, J=6.0 Hz, 6H). MS: 399 m/z (M+H)$^+$.

7-Iodo-N-methyl-4-(methylamino)cinnoline-3-carboxamide 228, N-methyl-4-(methylamino)-7-(4-(methylsulfonyl)phenyl)cinnoline-3-carboxamide 229, (R)-4-(1-cyclopropylethylamino)-7-iodo-N-methylcinnoline-3-carboxamide 230, and (R)-4-(1-cyclopropylethylamino)-N-methyl-7-(4-(methylsulfonyl)phenyl)cinnoline-3-carboxamide 231 are prepared using either methylamine or (R)-1-cyclopropylethanamine in place of isopropylamine in Step 3 where the 7-iodo analog is isolated after Step 3 or the 7-(4-(methylsulfonyl)phenyl) analog is isolated after Step 4:

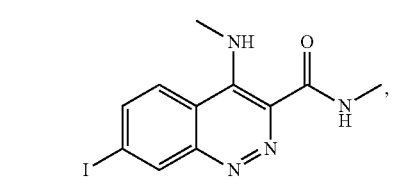
228

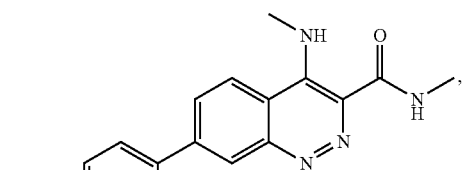
229

230
and

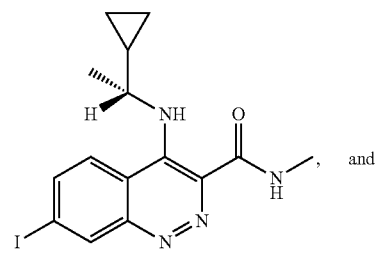

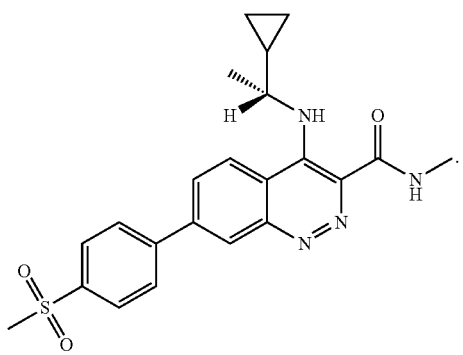
231

Example 13

Synthesis of 3-(1H-imidazol-2-yl)-N-isopropyl-7-(4-(methylsulfonyl)phenyl)cinnolin-4-amine (233)

3-(1H-imidazol-2-yl)-N-isopropyl-7-(4-(methylsulfonyl)phenyl)cinnolin-4-amine 233 was prepared from 3-iodo-N-isopropyl-7-(4-(methylsulfonyl)phenyl)cinnolin-4-amine 68 (see Example 3) in one Step as follows:

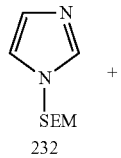
232

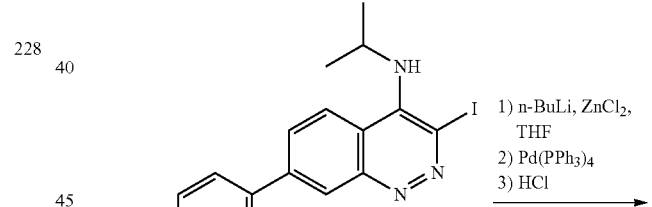
68

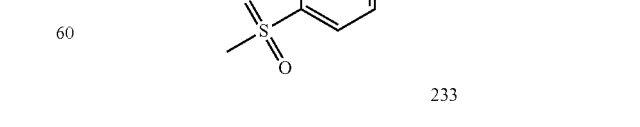
233

Step 1—synthesis of 3-(1H-imidazol-2-yl)-N-isopropyl-7-(4-(methylsulfonyl)phenyl)cinnolin-4-amine (233): 1-((2-(trimethylsilyl)ethoxy)methyl)-1H-imidazole (232, 0.253 g;

1.278 mmol) was dissolved in 3 mL of THF and the temperature was decreased to −78° C. A 2.5 M solution of n-butyllithium in THF (1.4 equiv.; 1.789 mmol) was added slowly and the reaction mixture was stirred for 30 minutes. Dichlorozinc (2.5 equiv.; 3.194 mmol) was added and the reaction mixture was stirred for 15 minutes at −78° C., then warmed to room temperature, and all of the ZnCl$_2$ dissolved. 3-Iodo-N-isopropyl-7-(4-methylsulfonylphenyl)cinnolin-4-amine (68, 1.0 equiv.; 1.278 mmol) was added followed by Pd(PPh$_3$)$_4$ (0.25 equiv.; 0.319 mmol). The reaction mixture was plunged into a preheated 90° C. oil bath and stirred for 2.5 hours, then stirred for 48 hours at room temperature and diluted with CH$_2$Cl$_2$ and saturated aqueous NH$_4$Cl. The layers were separated and the organic layer was dried over Na$_2$SO$_4$, filtered and the filtrate was concentrated under vacuum. The resulting residue was purified by silica flash chromatography eluting with EtOAc:Hex. Appropriate fractions were combined and concentrated under vacuum and the obtained material was dissolved in 10 mL of HCl (40 mmol; 4.0 M) and plunged into a preheated 85° C. oil bath. The reaction mixture was stirred for 1 hour, then cooled to room temperature and concentrated under vacuum. The resulting residue was suspended in CH$_2$Cl$_2$ and washed with H$_2$O to give a solid material that was sonicated with MeOH and then filtered. The filtrate was concentrated under vacuum and the resulting residue was purified by HPLC to give the desired compound (233, 0.030 g, 4.5%). $^1$H NMR (CDCl$_3$, 400 MHz) δ: 12.7 (s, 1H), 8.98 (d, J=1.6 Hz, 1H), 8.41 (d, J=9.2 Hz, 1H), 8.13 (d. J=8.4 Hz, 2H), 8.00 (d, J=8.4 Hz, 2H), 7.90 (dd, J=9.2, 1.6 Hz, 1H), 7.28 (s, 1H), 4.73 (m, 1H), 3.13 (s, 3H), 1.68 (d, J=6.4 Hz, 6H). MS: 408.1 m/z (M+H)$^+$.

Example 14

Synthesis of (R)-4-(1-cyclopropylethylamino)-N-methyl-7-(prop-1-en-2-yl)cinnoline-3-carboxamide (235)

(R)-4-(1-cyclopropylethylamino)-N-methyl-7-(prop-1-en-2-yl)cinnoline-3-carboxamide 235 was prepared from (R)-4-(1-cyclopropylethylamino)-7-iodo-N-methylcinnoline-3-carboxamide 230 (see Example 12) in one Step as follows:

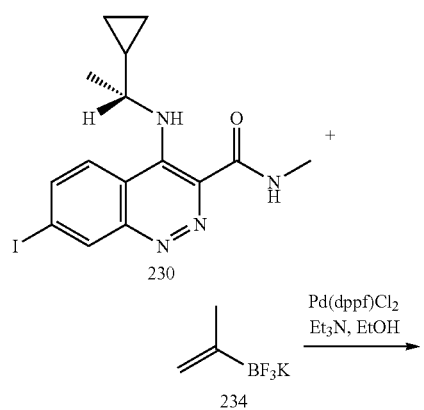

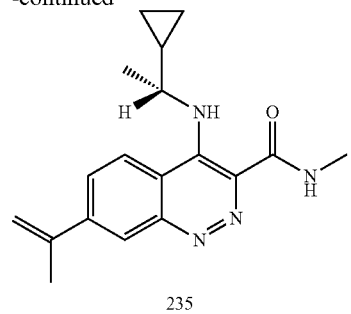

Step 1—synthesis of (R)-4-(1-cyclopropylethylamino)-N-methyl-7-(prop-1-en-2-yl)cinnoline-3-carboxamide (235): (R)-4-(1-cyclopropylethylamino)-7-iodo-N-methyl-cinnoline-3-carboxamide (230, 47 mg, 119 µmol), Pd(dppf)Cl$_2$ (18 mg, 24.6 µmol), potassium isopropenyltrifluoroborate (234, 182 mg, 1.23 mmol) and 1.0 mL of Et$_3$N in 3 mL of EtOH was heated in a microwave at 140° C. for 30 minutes. The solution was concentrated under vacuum and the resulting material was purified by HPLC to give the desired compound (235, 24 mg, 65%) as a white solid. $^1$H NMR (DMSO-d$_6$, 400 MHz) δ: 11.95 (broad s, 1H), 9.14 (d, J=4.8 Hz, 1H), 8.26 (d, J=9.2 Hz, 1H), 7.90 (m, 2H), 5.77 (s, 1H), 5.66 (s, 1H), 5.42 (s, 1H), 4.01 (broad s, 1H), 2.76 (d, J=4.8 Hz, 3H), 2.14 (s, 3H), 1.34 (d, J=6.4 Hz, 3H), 1.15 (broad m, 1H), 0.49 (broad m, 2H), 0.35 (broad m, 1H), 0.27 (broad m, 1H). MS: 311 m/z (M+H)$^+$.

(R)-7-cyclopropyl-4-(1-cyclopropylethylamino)-N-methylcinnoline-3-carboxamide 236 is prepared similarly, replacing potassium isopropenyltrifluoroborate 234 with potassium cyclopropyltrifluoroborate. $^1$H NMR (CD$_3$OD, 400 MHz) δ: 8.27 (d, J=9.2 Hz, 1H), 7.48 (d, J=1.6 Hz, 1H), 7.39 (dd, J=9.2 and 1.6 Hz, 1H), 4.11 (m, 1H), 2.87 (s, 3H), 2.14 (broad m, 1H), 1.47 (d, J=6.4 Hz, 3H), 1.24 (broad m, 3H), 0.90 (m, 2H), 0.62 (broad m, 2H), 0.42 (broad m, 2H). MS: 311 m/z (M+H)$^+$.

Example A

In Vitro Kinase Activities (LRRK2 TR-FRET Peptide Assay)

Compounds as described herein (compounds of Formula I, e.g., compounds of the above Examples) are tested for their in vitro kinase activities using various LRRK2 (including LRRK2 G2019S mutant) assays. For example, assays were performed in a total volume of 20 µL using the same kinase reaction buffer (50 mM HEPES pH 7.5, 10 mM MgCl$_2$, 1 mM EGTA, 2 mM DTT and 0.01% Tween-20) for wild-type or G2019S mutant LRRK2. Serially diluted compounds (1% DMSO as co-solvent) were pre-incubated with recombinant GST-LRRK2 (wild-type, or G2019S mutant, Invitrogen) for 15 minutes at room temperature in 384-well Corning black plates. Mixtures of ATP and biotin-LRRKtide substrate (biotin-RLGRDKYKTLRQIRQ) (SEQ ID NO: 1) were added to the wells at a final concentration of 100 µM ATP and 100 nM substrate, with final kinase concentration of 10 nM. The kinase reactions were carried out at room temperature for 60 minutes, then the reaction was stopped with the addition of 10 µL/well of stop/detection buffer (25 mM HEPES pH 7.5, 66 mM EDTA, 0.8 M KF and 0.1% BSA) that contains streptavidin-XL665 (12.5 nM) and europium-conjugated phospho-specific antibody (2nM). The plates were read 1 hour later and the time-resolved fluorescence (665 nm to 615 nm ratio) measured using an Envision reader. The inhibition of each well was calculated using the control and background readings for that plate. IC$_{50}$ values were determined from dose-response curves using eight concentrations from the serial dilution of the test compounds.

Many compounds of the Examples are demonstrated to be inhibitors of LRRK2, with most of the compounds tested typically measuring an IC$_{50}$ below 1 µM for both LRRK2 and G2019S mutant LRRK2 kinase activity. The following table summarizes exemplary compounds from the Examples above and their in vitro IC$_{50}$ values for LRRK2 as determined using the procedures of Example A. Compounds are identified by the Example number and compound number identification given in the Example.

| Example/Comp. No. | LRRK2 wild-type IC$_{50}$ (µM) |
|---|---|
| 1-5 | 0.14 |
| 1-6 | 0.12 |
| 1-7 | 0.13 |
| 1-8 | 0.25 |
| 1-9 | 29.7 |
| 1-186 | 4.0 |
| 2-17 | 0.015 |
| 2-18 | 0.62 |
| 2-19 | 0.010 |
| 2-21 | 0.18 |
| 2-23 | 0.017 |
| 2-25 | 0.023 |
| 2-27 | 0.18 |
| 2-29 | 0.047 |
| 2-31 | 0.014 |
| 2-33 | 0.21 |
| 2-35 | 0.009 |
| 2-37 | <0.006 |
| 2-38 | 0.55 |
| 2-39 | 1.0 |
| 2-41 | <0.006 |
| 2-42 | 0.56 |
| 2-43 | 0.055 |
| 2-45 | 0.084 |
| 2-47 | 0.21 |
| 2-49 | 0.009 |
| 2-51 | 0.017 |
| 2-53 | 0.009 |
| 2-57 | 0.033 |
| 2-88 | 0.42 |
| 2-89 | 0.11 |
| 2-90 | 0.063 |
| 2-91 | 0.045 |
| 2-92 | 0.017 |
| 2-93 | 0.046 |
| 2-94 | 0.12 |
| 2-95 | 0.12 |
| 2-96 | 0.35 |
| 2-97 | 0.046 |
| 2-98 | 0.59 |
| 2-99 | 0.076 |
| 2-100 | <0.006 |
| 2-101 | 0.001 |
| 2-102 | <0.006 |
| 2-103 | 0.14 |
| 2-104 | 0.33 |
| 2-105 | 0.38 |
| 2-106 | 0.011 |
| 2-107 | 0.048 |
| 2-108 | 4.3 |
| 2-109 | 0.71 |
| 2-110 | 0.010 |
| 2-111 | 0.001 |
| 2-112 | <0.006 |
| 2-113 | 0.051 |
| 2-114 | 0.0005 |
| 2-115 | 0.050 |
| 2-116 | 0.01 |
| 2-117 | 0.46 |
| 2-118 | 0.010 |
| 2-119 | 0.018 |
| 2-120 | 0.001 |
| 2-121 | 0.002 |
| 2-122 | 0.008 |
| 2-123 | 0.43 |
| 2-124 | 0.63 |
| 2-125 | 2.9 |
| 2-126 | 0.030 |
| 2-127 | <0.006 |
| 2-128 | 0.12 |
| 2-129 | 0.38 |
| 2-130 | 0.57 |
| 2-131 | 0.11 |
| 2-132 | 0.74 |
| 2-133 | 1.03 |
| 2-134 | 0.026 |
| 2-135 | 1.06 |
| 2-136 | 0.12 |
| 2-137 | 0.15 |
| 2-203 | 8.7 |
| 2-243 | 12 |
| 3-68 | 0.95 |
| 3-70 | >100 |
| 3-71 | >100 |
| 3-72 | 13 |
| 3-84 | 1.60 |
| 3-187 | 0.28 |
| 4-74 | 0.49 |
| 4-76 | 0.56 |
| 4-78 | 0.072 |
| 4-80 | 0.031 |
| 4-85 | 0.17 |
| 4-188 | 0.053 |
| 4-189 | 0.068 |
| 4-190 | 0.031 |
| 4-191 | 1.3 |
| 4-192 | 0.24 |
| 5-55 | 0.013 |
| 6-83 | 21.6 |
| 7-198 | 0.94 |
| 8-200 | 0.42 |
| 9-206 | 0.054 |
| 9-207 | 0.28 |
| 9-208 | 1.1 |
| 9-209 | 0.063 |
| 9-210 | 0.49 |
| 9-213 | 0.001 |
| 10-87 | 0.99 |
| 11-218 | 0.043 |
| 11-220 | 0.025 |
| 11-221 | 0.009 |

| Example/Comp. No. | LRRK2 wild-type IC$_{50}$ (μM) |
|---|---|
| 12-227 | 0.41 |
| 12-229 | >1 |
| 12-231 | 0.17 |
| 13-233 | 0.051 |
| 14-235 | 1.6 |
| 14-236 | 1.95 |

Additional assays for LRRK2 kinase activity are known, for example, assays involving monitoring of the phosphorylation of the substrate Nictide, or LRRK2 autophosphorylation or phosphorylation of myelin basic protein are known (Deng et al., Nature Chemical Biology 2011, 7(4): 203-5; Dzamko et al., Biochemical Journal 2010, 430(3): 405-13; and Lee et al., Nature Medicine 2010, 16(9):998-1000, the disclosures of which are hereby incorporated by reference with respect to LRRK2 biochemical, cell based and in vivo assays). Compounds can also be readily assayed using other kinases in order to determine IC$_{50}$ values against these kinases and determine selectivity of the compound activity against LRRK2 relative to these other kinases. Alternatively, compounds can be similarly tested at a particular concentration, such as at 1 μM or 10 μM test compound, against a variety of kinases, including LRRK2 and LRRK2 G2019S, and the % inhibition of the kinase activity at the given concentration can be used to assess the selectivity of compounds for LRRK2 relative to other kinases.

Example B

Cell Activities

Compounds as described herein (compounds of Formula I, e.g., compounds of the above Examples) may also be tested for their activity in a cell based assay. For example, LRRK2, both wild-type and G2019S mutant, is stably transfected into HEK-293. It is known that LRRK2 binds to isoforms of 14-3-3 proteins, an interaction that depends on the phosphorylation of LRRK2 at serine 910 (ser910) and serine 935 (ser935), and further that LRRK2 kinase indirectly affects this phosphorylation of ser910 and ser935. As such, the transfected HEK-293 cells may be used to assess the cellular activity of LRRK2 inhibitors. Three separate readouts may be monitored to assess the compounds for ability to inhibit LRRK2 kinase. Firstly, antibodies to phosphorylated ser910 and ser935 can be used to assess the affect of compounds on ser910 and ser935 phosphorylation, which decreases with inhibition of LRRK2 kinase activity. Secondly, the dephosphorylated LRRK2 has reduced binding of 14-3-3 protein, such that the binding of 14-3-3 protein may be monitored to assess LRRK2 inhibition. Thirdly, LRRK2 that is not bound to 14-3-3 protein is seen to localize within cytoplasmic pools. Green fluorescent protein labeled LRRK2 (GFP-LRRK2) can be used in order to monitor the LRRK2, where LRRK2 kinase activity inhibition results in observation of GFP-LRRK2 localized in such cytoplasmic pools (Deng et al., op. cit., p 203-5; and Dzamko et al., op. cit., p 405-13). These studies also demonstrate the use of other cell lines, for example, compounds can be assessed for inhibition of endogenous LRRK2 in human-derived neuroblastoma SHSY5Y cells, mouse Swiss 3T3 cells, and human lymphoblastoid cells, where the latter are derived from a control individual, or from an individual with Parkinson's disease who is homozygous for the LRRK2 G2019S mutation (Deng et al., op. cit., p 203-5; and Dzamko et al., op. cit., p 405-13). It was also observed that overexpression of LRRK2, both wild-type and G2019S, in cortical cell cultures led to primary cortical neuron injury, as assessed by neurite shortening, and cell death, as assessed by DNA fragmentation (Lee et al., op. cit., p 998-1000). Thus LRRK2 inhibitors can be assessed for their ability to reduce neuron injury and cell death in such cortical cell cultures.

Example C

In Vivo Activities

Pharmacokinetics of compounds as described herein (compounds of Formula I, e.g., compounds of the above Examples) can be assessed in animal models. For example, half-life and bioavailability can be assessed after intraperitoneal injection of compound into mice, and the phosphorylation of ser910 and ser935 can be assessed in tissues, such as kidney or brain tissue, where brain tissue can be used to assess whether compound can efficiently cross the blood-brain barrier (Deng et al., op. cit., p 204). In a herpes simplex virus (HSV) amplicon-based mouse model, it was shown that HSV amplicon mediated delivery of LRRK2 G2019S mutant induced a loss of tyrosine hydroxylase-positive neurons as compared to control mice expressing wild-type LRRK2. LRRK2 inhibitors can be assessed in this model for their ability to provide neuroprotection, i.e. attenuation of the loss of tyrosine hydroxylase-positive neurons (Lee et al., op. cit., p 999).

The disclosures in this document of all articles and references, including patents, are incorporated herein by reference in their entirety.

What is claimed is:

1. A compound having Formula I:

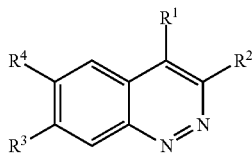

or a pharmaceutically acceptable salt thereof, wherein:

$R^1$ is $-C(=O)R^8$, $-SR^{10}$, $-S(=O)_n R^{11}$, or $-NR^{12}R^{13}$;

n is 1 or 2;

$R^8$, $R^{10}$, and $R^{11}$ are independently selected from the group consisting of $C_1$-$C_6$ alkyl optionally substituted with one or more substituents $R^{14}$, cycloalkyl optionally substituted with one or more substituents $R^{15}$, heterocycloalkyl optionally substituted with one or more substituents $R^{16}$, aryl optionally substituted with one or more substituents $R^{17}$, and heteroaryl optionally substituted with one or more substituents $R^{18}$;

$R^{12}$ is hydrogen or $C_1$-$C_6$ alkyl optionally substituted with one or more substituents $R^{14}$;

$R^{13}$ is selected from the group consisting of $C_1$-$C_6$ alkyl optionally substituted with one or more substituents $R^{14}$, cycloalkyl optionally substituted with one or more substituents $R^{15}$, and heterocycloalkyl optionally substituted with one or more substituents $R^{16}$;

or $R^{12}$ and $R^{13}$, together with the nitrogen to which they are attached, form a 5-7 membered heterocycloalkyl optionally substituted with one or more substituents $R^{16}$;

$R^{14}$ at each occurrence is independently selected from the group consisting of halogen, $-OH$, $C_1$-$C_6$ alkoxy, $-S(=O)-$, $-S(=O)_m-C_1$-$C_6$ alkyl, $-NH_2$, $C_1$-$C_6$ alkylamino, $C_1$-$C_6$ dialkylamino, cycloalkyl optionally substituted with one or more substituents $R^{15}$, heterocycloalkyl optionally substituted with one or more substituents $R^{16}$, aryl optionally substituted with one or more substituents $R^{17}$, and heteroaryl optionally substituted with one or more substituents $R^{18}$, wherein the alkyl chain of $C_1$-$C_6$ alkoxy, $-S(=O)_m-C_1$-$C_6$ alkyl, $C_1$-$C_6$ alkylamino, or $C_1$-$C_6$ dialkylamino is optionally substituted with one or more substituents independently selected from the group consisting of halogen, $-OH$, $C_1$-$C_6$ alkoxy, $C_1$-$C_6$ haloalkoxy, $-SH$, $-S(=O)_m-C_1$-$C_6$ alkyl, $-S(=O)_m-C_1$-$C_6$ haloalkyl, $-NH_2$, $C_1$-$C_6$ alkylamino, $C_1$-$C_6$ dialkylamino, and N-linked-heterocycloalkyl;

$R^{15}$ and $R^{16}$, at each occurrence, are independently selected from the group consisting of halogen, $C_1$-$C_6$ alkyl, $-OH$, $=O$, $C_1$-$C_6$ alkoxy, $-SH$, $-S(=O)_m-C_1$-$C_6$ alkyl, $-NH_2$, $C_1$-$C_6$ alkylamino, $C_1$-$C_6$ dialkylamino, and N-linked-heterocycloalkyl, wherein the alkyl chain of $C_1$-$C_6$ alkyl, $C_1$-$C_6$ alkoxy, $-S(=O)_m-C_1$-$C_6$ alkyl, $C_1$-$C_6$ alkylamino, or $C_1$-$C_6$ dialkylamino is optionally substituted with one or more substituents independently selected from the group consisting of halogen, $-OH$, $C_1$-$C_6$ alkoxy, $C_1$-$C_6$ haloalkoxy, $-SH$, $-S(=O)_m-C_1$-$C_6$ alkyl, $-S(=O)_m-C_1$-$C_6$ haloalkyl, $-NH_2$, $C_1$-$C_6$ alkylamino, $C_1$-$C_6$ dialkylamino, and N-linked-heterocycloalkyl;

$R^{17}$ and $R^{18}$ at each occurrence are independently selected from the group consisting of halogen, $-CN$, $-NO_2$, $C_1$-$C_6$ alkyl, $-OH$, $C_1$-$C_6$ alkoxy, $-SH$, $-S(=O)_m-C_1$-$C_6$ alkyl, $-NH_2$, $C_1$-$C_6$ alkylamino, $C_1$-$C_6$ dialkylamino, and N-linked-heterocycloalkyl, wherein the alkyl chain of $C_1$-$C_6$ alkyl, $C_1$-$C_6$ alkoxy, $-S(=O)_m-C_1$-$C_6$ alkyl, $C_1$-$C_6$ alkylamino, or $C_1$-$C_6$ dialkylamino is optionally substituted with one or more substituents independently selected from the group consisting of halogen, $-OH$, $C_1$-$C_6$ alkoxy, $C_1$-$C_6$ haloalkoxy, $-SH$, $-S(=O)_m-C_1$-$C_6$ alkyl, $-S(=O)_m-C_1$-$C_6$ haloalkyl, $-NH_2$, $C_1$-$C_6$ alkylamino, $C_1$-$C_6$ dialkylamino, and N-linked-heterocycloalkyl;

m is 0, 1 or 2;

$R^2$ is selected from the group consisting of $R^{19}$, $L_1$-$R^{20}$, $C_2$-$C_6$ alkenyl, $C_2$-$C_6$ alkynyl, cycloalkyl, heterocycloalkyl, aryl, and heteroaryl, wherein $C_2$-$C_6$ alkenyl and $C_2$-$C_6$ alkynyl are optionally substituted with one or more substituents independently selected from the group consisting of $R^{19}$, $L_1$-$R^{20}$, cycloalkyl, heterocycloalkyl, aryl, and heteroaryl, and wherein cycloalkyl and heterocycloalkyl, as $R^2$ or as a substituent of $C_2$-$C_6$ alkenyl or $C_2$-$C_6$ alkynyl, are optionally substituted with one or more substituents independently selected from the group consisting of $R^{19}$, $=O$, $=NR^{21}$, $=NOR^{21}$, $L_1$-$R^{20}$, and $R^{23}$, and wherein aryl and heteroaryl, as $R^2$ or as a substituent of $C_2$-$C_6$ alkenyl or $C_2$-$C_6$ alkynyl, are optionally substituted with one or more substituents independently selected from the group consisting of $R^{19}$, $L_1$-$R^{20}$, and $R^{23}$;

one of $R^3$ and $R^4$ is hydrogen;

the other of $R^3$ and $R^4$ is selected from the group consisting of $R^{24}$, $L_3$-$R^{20}$, $-OR^{25}$, $-SR^{25}$, methyl, $C_2$-$C_6$ alkyl, $C_2$-$C_6$ alkenyl, $C_2$-$C_6$ alkynyl, cycloalkyl, heterocycloalkyl, aryl, and heteroaryl, wherein methyl is substituted with one or more substituents independently selected from the group consisting of $R^{19}$, $L_1$-$R^{20}$, cycloalkyl, heterocycloalkyl, aryl, and heteroaryl, and wherein $C_2$-$C_6$ alkyl, $C_2$-$C_6$ alkenyl, and $C_2$-$C_6$ alkynyl are optionally substituted with one or more substituents independently selected from the group consisting of $R^{19}$, $L_1$-$R^{20}$, cycloalkyl, heterocycloalkyl, aryl, and heteroaryl, and wherein cycloalkyl and heterocycloalkyl, as $R^3$ or $R^4$ or as a substituent of methyl, $C_2$-$C_6$ alkyl, $C_2$-$C_6$ alkenyl, or $C_2$-$C_6$ alkynyl, are optionally substituted with one or more substituents independently selected from the group consisting of $R^{19}$, $=O$, $=NR^{21}$, $=NOR^{21}$, $L_1$-$R^{20}$, and $R^{23}$, and wherein aryl and heteroaryl, as $R^3$ or $R^4$ or as a substituent of methyl, $C_2$-$C_6$ alkyl, $C_2$-$C_6$ alkenyl, or $C_2$-$C_6$ alkynyl, are optionally substituted with one or more substituents independently selected from the group consisting of $R^{19}$, $L_1$-$R^{20}$, and $R^{23}$;

$R^{19}$ at each occurrence is independently selected from the group consisting of halogen, —CN, —NO$_2$, —OH, —SH, —NH$_2$, —NHOH, —C(=X)OH, —C(=X)NH$_2$, —C(=X)NHOH, —OC(=X)NH$_2$, —NHC(=X)NH$_2$, —NHC(=X)OH, —S(=O)$^2$NH$_2$, —S(=O)$^2$NHOH, —NHS(=O)$^2$NH$_2$, and —NHC(NH$_2$)=NH;

$R^{24}$ at each occurrence is independently selected from the group consisting of —CN, —NH$_2$, —NHOH, —C(=X)OH, —C(=X)NH$_2$, —C(=X)NHOH, —OC(=X)NH$_2$, —NHC(=X)NH$_2$, —NHC(=X)OH, —S(=O)$_2$NH$_2$, —S(=O)$_2$NHOH, —NHS(=O)$_2$NH$_2$, and —NHC(NH$_2$)=NH;

$R^{20}$ at each occurrence is independently selected from the group consisting of $C_1$-$C_6$ alkyl, $C_2$-$C_6$ alkenyl, $C_2$-$C_6$ alkynyl, cycloalkyl, heterocycloalkyl, aryl, and heteroaryl, wherein $C_1$-$C_6$ alkyl, $C_2$-$C_6$ alkenyl, and $C_2$-$C_6$ alkynyl are optionally substituted with one or more substituents independently selected from the group consisting of $R^{19}$, $L_4$-$R^{26}$, cycloalkyl, heterocycloalkyl, aryl, and heteroaryl, and wherein cycloalkyl and heterocycloalkyl, as $R^{20}$ or as a substituent of $C_1$-$C_6$ alkyl, $C_2$-$C_6$ alkenyl, or $C_2$-$C_6$ alkynyl, are optionally substituted with one or more substituents independently selected from the group consisting of $R^{19}$, $L_4$-$R^{26}$, =O, =NR$^{21}$, =NOR$^{21}$, and $R^{27}$, and wherein aryl and heteroaryl, as $R^{20}$ or as a substituent of $C_1$-$C_6$ alkyl, $C_2$-$C_6$ alkenyl, or $C_2$-$C_6$ alkynyl, are optionally substituted with one or more substituents independently selected from the group consisting of $R^{19}$, $L_4$-$R^{26}$, and $R^{27}$;

$R^{23}$ at each occurrence is independently selected from the group consisting of $C_1$-$C_6$ alkyl, $C_2$-$C_6$ alkenyl, $C_2$-$C_6$ alkynyl, cycloalkyl, heterocycloalkyl, aryl, and heteroaryl, wherein $C_1$-$C_6$ alkyl, $C_2$-$C_6$ alkenyl, and $C_2$-$C_6$ alkynyl are optionally substituted with one or more substituents independently selected from the group consisting of $R^{19}$, $L_4$-$R^{26}$, cycloalkyl, heterocycloalkyl, aryl, and heteroaryl, and wherein cycloalkyl and heterocycloalkyl as $R^{23}$ or as a substituent of $C_1$-$C_6$ alkyl, $C_2$-$C_6$ alkenyl, or $C_2$-$C_6$ alkynyl, are optionally substituted with one or more substituents independently selected from the group consisting of $R^{19}$, =O, =NR$^{21}$, =NOR$^{21}$, $L_4$-$R^{26}$, and $R^{28}$, and wherein aryl and heteroaryl, as $R^{23}$ or as a substituent of $C_1$-$C_6$ alkyl, $C_2$-$C_6$ alkenyl, or $C_2$-$C_6$ alkynyl, are optionally substituted with one or more substituents independently selected from the group consisting of $R^{19}$, $L_4$-$R^{26}$, and $R^{28}$;

$R^{25}$ at each occurrence is independently selected from the group consisting of methyl, $C_2$-$C_6$ alkyl, $C_2$-$C_6$ alkenyl, $C_2$-$C_6$ alkynyl, cycloalkyl, heterocycloalkyl, aryl, and heteroaryl, wherein methyl is substituted with one or more substituents independently selected from the group consisting of $R^{19}$, $L_4$-$R^{26}$, cycloalkyl, heterocycloalkyl, aryl, and heteroaryl, and wherein $C_2$-$C_6$ alkyl, $C_2$-$C_6$ alkenyl, and $C_2$-$C_6$ alkynyl are optionally substituted with one or more substituents independently selected from the group consisting of $R^{19}$, $L_4$-$R^{26}$, cycloalkyl, heterocycloalkyl, aryl, and heteroaryl, and wherein cycloalkyl and heterocycloalkyl, as $R^{25}$ or as a substituent of methyl, $C_2$-$C_6$ alkyl, $C_2$-$C_6$ alkenyl, or $C_2$-$C_6$ alkynyl, are optionally substituted with one or more substituents independently selected from the group consisting of $R^{19}$, $L_4$-$R^{26}$, =O, =NR$^{21}$, =NOR$^{21}$, and $R^{27}$, and wherein aryl and heteroaryl, as $R^{25}$ or as a substituent of methyl, $C_2$-$C_6$ alkyl, $C_2$-$C_6$ alkenyl, or $C_2$-$C_6$ alkynyl, are optionally substituted with one or more substituents independently selected from the group consisting of $R^{19}$, $L_4$-$R^{26}$, and $R_{27}$;

$R^{26}$ at each occurrence is independently selected from the group consisting of $C_1$-$C_6$ alkyl, $C_2$-$C_6$ alkenyl, $C_2$-$C_6$ alkynyl, cycloalkyl, heterocycloalkyl, aryl, and heteroaryl, wherein $C_1$-$C_6$ alkyl, $C_2$-$C_6$ alkenyl, $C_2$-$C_6$ alkynyl are optionally substituted with one or more substituents independently selected from the group consisting of $R^{19}$, $L_5$-$R^{29}$, cycloalkyl, heterocycloalkyl, aryl, and heteroaryl, wherein cycloalkyl and heterocycloalkyl as $R^{26}$ or as a substituent of $C_1$-$C_6$ alkyl, $C_2$-$C_6$ alkenyl, or $C_2$-$C_6$ alkynyl, are optionally substituted with one or more substituents independently selected from the group consisting of $R^{19}$, =O, =NR$^{21}$, =NOR$^{21}$, $L_5$-$R^{29}$, and $R^{28}$, and wherein aryl and heteroaryl, as $R^{26}$ or as a substituent of $C_1$-$C_6$ alkyl, $C_2$-$C_6$ alkenyl, or $C_2$-$C_6$ alkynyl, are optionally substituted with one or more substituents independently selected from the group consisting of $R^{19}$, $L_5$-$R^{29}$, and $R^{28}$;

$R^{27}$ at each occurrence is independently selected from the group consisting of $C_1$-$C_6$ alkyl, $C_2$-$C_6$ alkenyl, $C_2$-$C_6$ alkynyl, cycloalkyl, heterocycloalkyl, aryl, and heteroaryl, wherein $C_1$-$C_6$ alkyl, $C_2$-$C_6$ alkenyl, $C_2$-$C_6$ alkynyl are optionally substituted with one or more substituents independently selected from the group consisting of $R^{19}$, $L_4$-$R^{26}$, cycloalkyl, heterocycloalkyl, aryl, and heteroaryl, wherein cycloalkyl and heterocycloalkyl as $R^{27}$ or as a substituent of $C_1$-$C_6$ alkyl, $C_2$-$C_6$ alkenyl, or $C_2$-$C_6$ alkynyl, are optionally substituted with one or more substituents independently selected from the group consisting of $R^{19}$, =O, =NR$^{21}$, =NOR$^{21}$, $L_4$-$R^{26}$, and $R^{28}$, and wherein aryl and heteroaryl, as $R^{27}$ or as a substituent of $C_1$-$C_6$ alkyl, $C_2$-$C_6$ alkenyl, or $C_2$-$C_6$ alkynyl, are optionally substituted with one or more substituents independently selected from the group consisting of $R^{19}$, $L_4$-$R^{26}$, and $R^{28}$;

$R^{28}$ at each occurrence is independently selected from the group consisting of $C_1$-$C_6$ alkyl, $C_2$-$C_6$ alkenyl, or $C_2$-$C_6$ alkynyl, cycloalkyl, heterocycloalkyl, aryl, and heteroaryl, wherein $C_1$-$C_6$ alkyl, $C_2$-$C_6$ alkenyl, or $C_2$-$C_6$ alkynyl are optionally substituted with one or more substituents independently selected from the group consisting of $R^{19}$, $L_5$-$R^{29}$, cycloalkyl, heterocycloalkyl, aryl, and heteroaryl, and wherein cycloalkyl and heterocycloalkyl as $R^{28}$ or as a substituent of $C_1$-$C_6$ alkyl, $C_2$-$C_6$ alkenyl, or $C_2$-$C_6$ alkynyl, are optionally substituted with one or more substituents independently selected from the group consisting of $R^{19}$, =O, =NR$^{21}$, =NOR$^{21}$, $L_5$-$R^{29}$, and $R^{29}$, and wherein aryl and heteroaryl, as $R^{28}$ or a substituent of $C_1$-$C_6$ alkyl, $C_2$-$C_6$ alkenyl, or $C_2$-$C_6$ alkynyl, are optionally substituted with one or more substituents independently selected from the group consisting of $R^{19}$, $L_5$-$R^{29}$, and $R^{29}$;

$R^{29}$ at each occurrence is independently selected from the group consisting of $C_1$-$C_6$ alkyl, $C_2$-$C_6$ alkenyl, or $C_2$-$C_6$ alkynyl, cycloalkyl, heterocycloalkyl, aryl, and heteroaryl, wherein $C_1$-$C_6$ alkyl, $C_2$-$C_6$ alkenyl, and $C_2$-$C_6$ alkynyl are optionally substituted with one or more substituents $R^{30}$, and wherein cycloalkyl and heterocycloalkyl are optionally substituted with one or more substituents $R^{31}$, and wherein aryl and heteroaryl are optionally substituted with one or more substituents $R^{32}$;

$L_1$, $L_4$, and $L_5$, at each occurrence, are independently selected from the group consisting of —O—, —S—, —$NR^{21}$—, —$NR^{21}$O—, —C(=X)—, —C(=X)O—, —OC(=X)—, —C(=X)$NR^{21}$—, —C(=X)$NR^{21}$O—, —$NR^{21}$C(=X)—, —OC(=X)$NR^{21}$—, —$NR^{21}$C(=X)$NR^{21}$—, —$NR^{21}$C(=X)O—, —S(=O)—, —S(=O)$_2$—, —S(=O)$_2$$NR^{21}$—, —S(=O)$_2$$NR^{21}$O—, —$NR^{21}$S(=O)$_2$—, —$NR^{21}$S(=O)$_2$$NR^{21}$—, —$NR^{21}$C(=$NR^{21}$)$NR^{21}$—, and —$NR^{21}$C($NR^{21}R^{21}$)=N—;

$L_3$ at each occurrence is independently selected from the group consisting of —$NR^{21}$—, —$NR^{21}$O—, —C(=X)—, —C(=X)O—, —OC(=X)—, —C(=X)$NR^{21}$—, —C(=X)$NR^{21}$O—, —$NR^{21}$C(=X)—, —OC(=X)$NR^{21}$—, —$NR^{21}$C(=X)$NR^{21}$—, —$NR^{21}$C(=X)O—, —S(=O)—, —S(=O)$_2$—, —S(=O)$_2$$NR^{21}$—, —S(=O)$_2$$NR^{21}$O—, —$NR^{21}$S(=O)$_2$—, —$NR^{21}$S(=O)$_2$$NR^{21}$—, —$NR^{21}$C(=$NR^{21}$)$NR^{21}$—, and —$NR^{21}$C($NR^{21}R^{21}$)=N—;

X is O or S;

$R^{21}$ at each occurrence is independently selected from the group consisting of hydrogen, $C_1$-$C_6$ alkyl, $C_2$-$C_6$ alkenyl, $C_2$-$C_6$ alkynyl, cycloalkyl, heterocycloalkyl, aryl, and heteroaryl, wherein $C_1$-$C_6$ alkyl, $C_2$-$C_6$ alkenyl, and $C_2$-$C_6$ alkynyl are optionally substituted with one or more substituents $R^{30}$, cycloalkyl and heterocycloalkyl are optionally substituted with one or more substituents $R^{31}$, and aryl and heteroaryl are optionally substituted with one or more substituents $R^{32}$;

$R^{30}$ at each occurrence is independently selected from the group consisting of halogen, —OH, $C_1$-$C_6$ alkoxy, —SH, —S(=O)$_m$—$C_1$-$C_6$ alkyl, —$NH_2$, $C_1$-$C_6$ alkylamino, $C_1$-$C_6$ dialkylamino, cycloalkyl, heterocycloalkyl, aryl, and heteroaryl, wherein the alkyl chain of $C_1$-$C_6$ alkoxy, —S(=O)$_m$—$C_1$-$C_6$ alkyl, $C_1$-$C_6$ alkylamino, or $C_1$-$C_6$ dialkylamino is optionally substituted with one or more substituents independently selected from the group consisting of halogen, —OH, $C_1$-$C_6$ alkoxy, $C_1$-$C_6$ haloalkoxy, —SH, —S(=O)$_m$—$C_1$-$C_6$ alkyl, —S(=O)$_m$—$C_1$-$C_6$ haloalkyl, —$NH_2$, $C_1$-$C_6$ alkylamino, $C_1$-$C_6$ dialkylamino, and N-linked-heterocycloalkyl, and wherein cycloalkyl and heterocycloalkyl are optionally substituted with one or more substituents $R^{31}$, and aryl and heteroaryl are optionally substituted with one or more substituents $R^{32}$;

$R^{31}$ at each occurrence is independently selected from the group consisting of halogen, $C_1$-$C_6$ alkyl, —OH, =O, $C_1$-$C_6$ alkoxy, —SH, —S(=O)$_m$—$C_1$-$C_6$ alkyl, —$NH_2$, $C_1$-$C_6$ alkylamino, $C_1$-$C_6$ dialkylamino, and N-linked-heterocycloalkyl, wherein the alkyl chain of $C_1$-$C_6$ alkyl, $C_1$-$C_6$ alkoxy, —S(=O)$_m$—$C_1$-$C_6$ alkyl, $C_1$-$C_6$ alkylamino, or $C_1$-$C_6$ dialkylamino is optionally substituted with one or more substituents selected from the group consisting of halogen, —OH, $C_1$-$C_6$ alkoxy, $C_1$-$C_6$ haloalkoxy, —SH, —S(=O)$_m$—$C_1$-$C_6$ alkyl, —S(=O)$_m$—$C_1$-$C_6$ haloalkyl, —$NH_2$, $C_1$-$C_6$ alkylamino, $C_1$-$C_6$ dialkylamino, and N-linked-heterocycloalkyl; and $R^{32}$ at each occurrence is independently selected from the group consisting of halogen, $C_1$-$C_6$ alkyl, —OH, —CN, $C_1$-$C_6$ alkoxy, —SH, —S(=O)$_m$—$C_1$-$C_6$ alkyl, —$NH_2$, $C_1$-$C_6$ alkylamino, $C_1$-$C_6$ dialkylamino, and N-linked-heterocycloalkyl, wherein the alkyl chain of $C_1$-$C_6$ alkyl, $C_1$-$C_6$ alkoxy, —S(=O)$_m$—$C_1$-$C_6$ alkyl, $C_1$-$C_6$ alkylamino, or $C_1$-$C_6$ dialkylamino is optionally substituted with one or more substituents selected from the group consisting of halogen, —OH, $C_1$-$C_6$ alkoxy, $C_1$-$C_6$ haloalkoxy, —SH, —S(=O)$_m$—$C_1$-$C_6$ alkyl, —S(=O)$_m$—$C_1$-$C_6$ haloalkyl, —$NH_2$, $C_1$-$C_6$ alkylamino, $C_1$-$C_6$ dialkylamino, and N-linked-heterocycloalkyl.

2. The compound according to claim 1, wherein:

$R^1$ is —$NR^{12}R^{13}$;

$R^{12}$ is hydrogen or $C_1$-$C_6$ alkyl;

$R^{13}$ is selected from the group consisting of $C_1$-$C_6$ alkyl optionally substituted with one or more substituents $R^{14}$, $C_3$-$C_8$ cycloalkyl optionally substituted with one or more substituents $R^{15}$, and 4-7 membered heterocycloalkyl optionally substituted with one or more substituents $R^{16}$;

or $R^{12}$ and $R^{13}$, together with the nitrogen to which they are attached, form a 5-7 membered heterocycloalkyl optionally substituted with one or more substituents $R^{16}$;

$R^{14}$ at each occurrence is independently selected from the group consisting of halogen, —OH, $C_1$-$C_6$ alkoxy, —SH, —S(=O)$_m$—$C_1$-$C_6$ alkyl, —$NH_2$, $C_1$-$C_6$ alkylamino, $C_1$-$C_6$ dialkylamino, $C_3$-$C_8$ cycloalkyl optionally substituted with one or more substituents $R^{15}$, 4-7 membered heterocycloalkyl optionally substituted with one or more substituents $R^{16}$, phenyl optionally substituted with one or more substituents $R^{17}$, and 5 or 6 membered heteroaryl optionally substituted with one or more substituents $R^{18}$, wherein the alkyl chain of $C_1$-$C_6$ alkoxy, —S(=O)$_m$—$C_1$-$C_6$ alkyl, $C_1$-$C_6$ alkylamino, or $C_1$-$C_6$ dialkylamino is optionally substituted with one or more substituents independently selected from the group consisting of halogen, —OH, $C_1$-$C_6$ alkoxy, $C_1$-$C_6$ haloalkoxy, —SH, —S(=O)$_m$—$C_1$-$C_6$ alkyl, —S(=O)$_m$—$C_1$-$C_6$ haloalkyl, —$NH_2$, $C_1$-$C_6$ alkylamino, $C_1$-$C_6$ dialkylamino, and N-linked-heterocycloalkyl; and $R^2$ is selected from the group consisting of $R^{19}$, $L_1$-$R^{20}$, $C_2$-$C_6$ alkynyl, 4-7 membered heterocycloalkyl, and 5 or 6 membered heteroaryl, wherein $C_2$-$C_6$ alkynyl is optionally substituted with one or more substituents independently selected from the group consisting of $R^{19}$ and $L_1$-$R^{20}$, and wherein 4-7 membered heterocycloalkyl is optionally substituted with one or more substituents independently selected from the group consisting of $R^{19}$, =O, =$NR^{21}$, =$NOR^{21}$, $L_1$-$R^{20}$, and $R^{23}$, and wherein 5 or 6 membered heteroaryl is optionally substituted with one or more substituents independently selected from the group consisting of $R^{19}$, $L_1$-$R^{20}$, and $R^{23}$.

3. The compound according to claim 1, wherein $R^1$ is selected from the group consisting of:

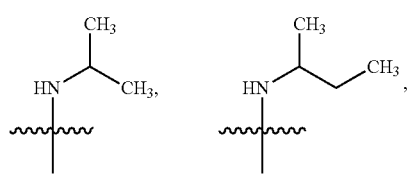

-continued

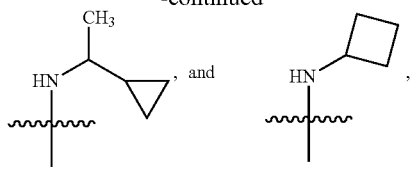

wherein

indicates the point of attachment of $R^1$ to the 4-position of the cinnoline ring.

4. The compound according to claim 3, wherein $R^1$ is selected from the group consisting of:

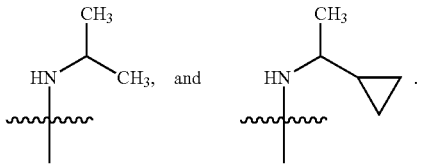

5. The compound according to claim 1, wherein
$R^1$ is —$NR^{12}R^{13}$, where
$R^{12}$ is hydrogen; and
$R^{13}$ is selected from the group consisting of $C^3$-$C^{10}$ cycloalkyl, 4-7 membered heterocycloalkyl optionally substituted with one $C_1$-$C_6$ alkyl, and $C_1$-$C_6$ alkyl optionally substituted with one substituent selected from the group consisting of —OH, $C_3$-$C_8$ cycloalkyl, 4-7 membered heterocycloalkyl, phenyl and pyridyl.

6. The compound according to claim 1, wherein $R^2$ is selected from the group consisting of —I, —Cl, —C≡CH, —CN, —C(=O)NH$_2$, —C(=O)NHCH$_3$, imidazolyl, triazolyl, thiazolyl, oxazolyl, pyridinyl, and pyrimidin-4(3H)-onyl.

7. The compound according to claim 6, wherein $R^2$ is selected from the group consisting of —CN, —C(=O)NH$_2$, —C(=O)NHCH$_3$, imidazolyl, 1,2,4-triazolyl, and pyrimidin-4(3H)-onyl.

8. The compound according to claim 1, wherein $R^2$ is —C(=O)NH$_2$.

9. The compound according to claim 1, wherein one of $R^3$ and $R^4$ is hydrogen and the other of $R^3$ and $R^4$ is selected from the group consisting of —$OR^{25}$, —$SR^{25}$, $C_2$-$C_4$ alkyl, $C_2$-$C_3$ alkenyl, $C_3$-$C_6$ cycloalkyl, phenyl, heteroaryl, and heterocycloalkyl selected from the group consisting of piperazinyl, morpholinyl, pyrrolidinyl, oxazolidinyl, dihydropyridinyl, and indolinyl, wherein $C_2$-$C_4$ alkyl is optionally substituted with one OH, and wherein heterocycloalkyl is optionally substituted with one or more =O or $C_1$-$C_6$ alkyl, and wherein phenyl and heteroaryl are optionally substituted with one or more substituents independently selected from the group consisting of halogen, —$OR^{20}$, —$S(=O)^2R^{20}$, —$NR^{21}R^{20}$, —$C(=O)NR^{21}R^{20}$, $C_1$-$C_6$ alkyl optionally substituted with one or more $C_1$-$C_6$ alkoxy, piperazinyl optionally substituted with one or more =O or $C_1$-$C_6$ alkyl, morpholinyl optionally substituted with one or more =O or $C_1$-$C_6$ alkyl, pyrrolidinyl optionally substituted with one or more =O or $C_1$-$C_6$ alkyl, oxazolidinyl optionally substituted with one or more =O or $C_1$-$C_6$ alkyl, phenyl optionally substituted with one or more substituents selected from the group consisting of halogen, $C_1$-$C_6$ alkoxy, morpholinyl optionally substituted with one or more =O or $C_1$-$C_6$ alkyl, and oxazolidinyl optionally substituted with one or more =O or $C_1$-$C_6$ alkyl, and heteroaryl optionally substituted with one or more substituents selected from the group consisting of halogen, $C_1$-$C_6$ alkyl, or $C_1$-$C_6$ alkoxy;
$R^{25}$ is phenyl optionally substituted with one or more $C_1$-$C_3$ alkoxy or $C_1$-$C_3$ haloalkoxy, or pyridinyl optionally substituted with one or more $C_1$-$C_3$ alkoxy or $C_1$-$C_3$ haloalkoxy;
$R^{20}$ at each occurrence is independently $C_1$-$C_6$ alkyl optionally substituted with one $C_3$-$C_6$ cycloalkyl or with one or more fluoro; and
$R^{21}$ at each occurrence is independently hydrogen or $C_1$-$C_6$ alkyl.

10. The compound according to claim 1, wherein $R^3$ is hydrogen.

11. The compound according to claim 1, wherein $R^4$ is hydrogen.

12. The compound according to claim 1, wherein the compound has Formula Ia:

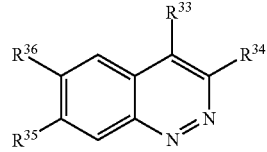

Ia or a pharmaceutically acceptable salt thereof, wherein:
$R^{33}$ is —$SR^{41}$ or —$NR^{42}R^{43}$;
$R^{41}$ is $C_1$-$C_6$ alkyl optionally substituted with one or more substituents $R^{44}$, $C_3$-$C_8$ cycloalkyl optionally substituted with one or more substituents $R^{45}$, or 4-7 membered heterocycloalkyl optionally substituted with one or more substituents $R^{46}$;
$R^{42}$ is hydrogen or $C_1$-$C_6$ alkyl;
$R^{43}$ is $C_1$-$C_6$ alkyl optionally substituted with one or more substituents $R^{44}$, $C_3$-$C_8$ cycloalkyl optionally substituted with one or more substituents $R^{45}$, or 4-7 membered heterocycloalkyl optionally substituted with one or more substituents $R^{46}$;
or $R^{42}$ and $R^{43}$, together with the nitrogen to which they are attached, form a 5-7 membered heterocycloalkyl optionally substituted with one or more substituents $R^{46}$;
$R^{34}$ is selected from the group consisting of halogen, —CN, —C≡CH, —C(=O)NH$_2$, $L_6$-$R^{47}$, 4-7 membered heterocycloalkyl optionally substituted with one or more substituents $R^{48}$, or 5 or 6 membered heteroaryl optionally substituted with one or more substituents $R^{49}$;
one of $R^{35}$ and $R^{36}$ is hydrogen;
the other of $R^{35}$ and $R^{36}$ is selected from the group consisting of $R^{54}$, $L_8$-$R^{51}$, —$OR^{55}$, —$SR^{55}$, methyl, $C_2$-$C_6$ alkyl, $C_2$-$C_6$ alkenyl, $C_2$-$C_6$ alkynyl, cycloalkyl, heterocycloalkyl, aryl, and heteroaryl, wherein methyl is substituted with one or more substituents independently selected from the group consisting of $R^{50}$, $L_7$-$R^{51}$, cycloalkyl, heterocycloalkyl, aryl, and heteroaryl, and wherein $C_2$-$C_6$ alkyl, $C_2$-$C_6$ alkenyl, and $C_2$-$C_6$ alkynyl are optionally substituted with one or more substituents independently selected from the group consisting of $R^{50}$, $L_7$-$R^{51}$, cycloalkyl, heterocycloalkyl, aryl, and heteroaryl, and wherein cycloalkyl and heterocycloalkyl, as $R^{35}$ or $R^{36}$ or as a substituent of methyl, $C_2$-$C_6$ alkyl, $C_2$-$C_6$ alkenyl, or $C_2$-$C_6$ alkynyl, are optionally substituted with one or more substituents independently selected from the group consisting of $R^{50}$, =O, =$NR^{52}$, =$NOR^{52}$, $L_7$-$R^{51}$, and $R^{53}$, and wherein aryl and heteroaryl, as $R^{35}$ or $R^{36}$ or as a substituent of methyl, $C_2$-$C_6$ alkyl, $C_2$-$C_6$ alkenyl, or $C_2$-$C_6$ alkynyl, are optionally substituted with one or more substituents independently selected from the group consisting of $R^{50}$, $L_7$-$R^{51}$, and $R^{53}$;

$R^{44}$ at each occurrence is independently selected from the group consisting of halogen, —OH, $C_1$-$C_6$ alkoxy, $C_1$-$C_6$ haloalkoxy, —SH, —S(=O)$_m$—$C_1$-$C_6$ alkyl, —S(=O)$_m$—$C_1$-$C_6$ haloalkyl, —NH$_2$, $C_1$-$C_6$ alkylamino, $C_1$-$C_6$ dialkylamino, $C_3$-$C_8$ cycloalkyl optionally substituted with one or more substituents $R^{45}$, and 4-7 membered heterocycloalkyl optionally substituted with one or more substituents $R^{46}$;

$R^{45}$ at each occurrence is independently selected from the group consisting of halogen, $C_1$-$C_6$ alkyl, $C_1$-$C_6$ haloalkyl, —OH, =O, $C_1$-$C_6$ alkoxy, $C_1$-$C_6$ haloalkoxy, —SH, —S(=O)$_m$, —$C_1$-$C_6$ alkyl, —S(=O)$_m$—$C_1$-$C_6$ haloalkyl, —NH$_2$, $C_1$-$C_6$ alkylamino, $C_1$-$C_6$ dialkylamino, and N-linked-heterocycloalkyl;

$R^{46}$ at each occurrence is independently selected from the group consisting of halogen, $C_1$-$C_6$ alkyl, $C_1$-$C_6$ haloalkyl, —OH, =O, $C_1$-$C_6$ alkoxy, $C_1$-$C_6$ haloalkoxy, —SH, —S(=O)$_m$—$C_1$-$C_6$ alkyl, —S(=O)$_m$—$C_1$-$C_6$ haloalkyl, —NH$_2$, $C_1$-$C_6$ alkylamino, $C_1$-$C_6$ dialkylamino, and N-linked-heterocycloalkyl;

$R^{48}$ at each occurrence, are independently selected from the group consisting of $R^{50}$, =O, =$NR^{52}$, =$NOR^{52}$, $L_7$-$R^{51}$, $C_1$-$C_6$ alkyl, $C_2$-$C_6$ alkenyl, $C_2$-$C_6$ alkynyl, cycloalkyl, heterocycloalkyl, aryl, and heteroaryl, wherein $C_1$-$C_6$ alkyl, $C_2$-$C_6$ alkenyl, and $C_2$-$C_6$ alkynyl are optionally substituted with one or more substituents independently selected from the group consisting of $R^{50}$, $L_9$-$R^{56}$, cycloalkyl, heterocycloalkyl, aryl, and heteroaryl, and wherein cycloalkyl and heterocycloalkyl, as $R^{48}$ or as a substituent of $C_1$-$C_6$ alkyl, $C_2$-$C_6$ alkenyl, or $C_2$-$C_6$ alkynyl, are optionally substituted with one or more substituents independently selected from the group consisting of $R^{50}$, =O, =$NR^{52}$, =$NOR^{52}$, -$L_9$-$R^{56}$, and $R^{56}$, and wherein aryl and heteroaryl, as $R^{48}$ as a substituent of $C_1$-$C_6$ alkyl, $C_2$-$C_6$ alkenyl, or $C_2$-$C_6$ alkynyl, are optionally substituted with one or more substituents independently selected from the group consisting of $R^{50}$, -$L_9$-$R^{56}$, and $R^{56}$;

$R^{49}$ at each occurrence, are independently selected from the group consisting of $R^{50}$, $L_7$-$R^{51}$, $C_1$-$C_6$ alkyl, $C_2$-$C_6$ alkenyl, $C_2$-$C_6$ alkynyl, cycloalkyl, heterocycloalkyl, aryl, and heteroaryl, wherein $C_1$-$C_6$ alkyl, $C_2$-$C_6$ alkenyl, and $C_2$-$C_6$ alkynyl are optionally substituted with one or more substituents independently selected from the group consisting of $R^{50}$, $L_9$-$R^{56}$, cycloalkyl, heterocycloalkyl, aryl, and heteroaryl, and wherein cycloalkyl and heterocycloalkyl, as $R^{49}$ or as a substituent of $C_1$-$C_6$ alkyl, $C_2$-$C_6$ alkenyl, or $C_2$-$C_6$ alkynyl, are optionally substituted with one or more substituents independently selected from the group consisting of $R^{50}$, =O, =$NR^{52}$, =$NOR^{52}$, $L_9$-$R^{56}$, and $R^{56}$, and wherein aryl and heteroaryl, as $R^{49}$ or as a substituent of $C_1$-$C_6$ alkyl, $C_2$-$C_6$ alkenyl, or $C_2$-$C_6$ alkynyl, are optionally substituted with one or more substituents independently selected from the group consisting of $R^{50}$, $L_9$-$R^{56}$, and $R^{56}$;

$R^{50}$ at each occurrence is independently selected from the group consisting of halogen, —CN, —NO$_2$, —OH, —SH, —NH$_2$, —NHOH, —C(=X)OH, —C(=X)NH$_2$, —C(=X)NHOH, —OC(=X)NH$_2$, —NHC(=X)NH$_2$, —NHC(=X)OH, —S(=O)$_2$NH$_2$, —S(=O)$_2$NHOH, —NHS(=O)$_2$NH$_2$, and —NHC(NH$_2$)=NH;

$R^{54}$ at each occurrence is independently selected from the group consisting of —CN, —NH$_2$, —NHOH, —C(=X)OH, —C(=X)NH$_2$, —C(=X)NHOH, —OC(=X)NH$_2$, —NHC(=X)NH$_2$, —NHC(=X)OH, —S(=O)$_2$NH$_2$, —S(=O)$_2$NHOH, —NHS(=O)$_2$NH$_2$) and —NHC(NH$_2$)=NH;

$R^{47}$, $R^{51}$, and $R^{53}$, at each occurrence, are independently selected from the group consisting of $C_1$-$C_6$ alkyl, $C_2$-$C_6$ alkenyl, $C_2$-$C_6$ alkynyl, cycloalkyl, heterocycloalkyl, aryl, and heteroaryl, wherein $C_1$-$C_6$ alkyl, $C_2$-$C_6$ alkenyl, and $C_2$-$C_6$ alkynyl are optionally substituted with one or more substituents independently selected from the group consisting of $R^{50}$, $L_9$-$R^{56}$, cycloalkyl, heterocycloalkyl, aryl, and heteroaryl, and wherein cycloalkyl and heterocycloalkyl as $R^{47}$, $R^{51}$, or $R^{53}$, or as a substituent of $C_1$-$C_6$ alkyl, $C_2$-$C_6$ alkenyl, or $C_2$-$C_6$ alkynyl, are optionally substituted with one or more substituents independently selected from the group consisting of $R^{50}$, =O, =$NR^{52}$, =$NOR^{52}$, $L_9$-$R^{56}$, and $R^{56}$, and wherein aryl and heteroaryl, as $R^{47}$, $R^{51}$, or $R^{53}$, or as a substituent of $C_1$-$C_6$ alkyl, $C_2$-$C_6$ alkenyl, or $C_2$-$C_6$ alkynyl, are optionally substituted with one or more substituents independently selected from the group consisting of $R^{50}$, $L_9$-$R^{56}$, and $R^{56}$;

$R^{55}$ at each occurrence is independently selected from the group consisting of methyl, $C_2$-$C_6$ alkyl, $C_2$-$C_6$ alkenyl, $C_2$-$C_6$ alkynyl, cycloalkyl, heterocycloalkyl, aryl, and heteroaryl, wherein methyl is substituted with one or more substituents independently selected from the group consisting of $R^{50}$, $L_9$-$R^{56}$, cycloalkyl, heterocycloalkyl, aryl, and heteroaryl, and wherein $C_2$-$C_6$ alkyl, $C_2$-$C_6$ alkenyl, and $C_2$-$C_6$ alkynyl are optionally substituted with one or more substituents independently selected from the group consisting of $R^{50}$, $L_9$-$R^{56}$, cycloalkyl, heterocycloalkyl, aryl, and heteroaryl, and wherein cycloalkyl and heterocycloalkyl as $R^{55}$ or as a substituent of methyl, $C_2$-$C_6$ alkyl, $C_2$-$C_6$ alkenyl, or $C_2$-$C_6$ alkynyl, are optionally substituted with one or more substituents independently selected from the group consisting of $R^{50}$, =O, =$NR^{52}$, =$NOR^{52}$, $L_9$-$R^{56}$, and $R^{56}$, and wherein aryl and heteroaryl, as $R^{55}$ or as a substituent of methyl, $C_2$-$C_6$ alkyl, $C_2$-$C_6$ alkenyl, or $C_2$-$C_6$ alkynyl, are optionally substituted with one or more substituents independently selected from the group consisting of $R^{50}$, $L_9$-$R^{56}$, and $R^{56}$;

$L_6$ at each occurrence is independently selected from the group consisting of —O—, —S—, —$NR^{52}$—, —$NR^{52}$O—, —C(=X)—, —C(=X)$NR^{52}$—, —C(=X)$NR^{52}$O—, —NR↑C(=X)—, —OC(=X)$NR^{52}$—, —$NR^{52}$C(=X)$NR^{52}$—, —$NR^{52}$C(=X)O—, —S(=O)—, —S(=O)$_2$—, —S(=O)$_2$$NR^{52}$—, —S(=O)$_2$$NR^{52}$O—, —$NR^{52}$S(=O)$_2$—, —$NR^{52}$S $(=O)_2NR^{52}-$, $-NR^{52}C(=NR^{52})NR^{52}-$, and $-NR^{52}C(NR^{52}R^{52})=N-$;

$L_7$ and $L_9$, at each occurrence, are independently selected from the group consisting of $-O-$, $-S-$, $-NR^{52}-$, $-NR^{52}O-$, $-C(=X)-$, $-C(=X)O-$, $-OC(=X)-$, $-C(=X)NR^{52}-$, $-C(=X)NR^{52}O-$, $-NR^{52}C(=X)-$, $-OC(=X)NR^{52}-$, $-NR^{52}C(=X)NR^{52}-$, $-NR^{52}C(=X)C$ $-S(=O)-$, $-S(=O)_2-$, $-S(=O)_2NR^{52}-$, $-S(=O)_2NR^{52}O-$, $-NR^{52}S(=O)_2-$, $-NR^{52}S(=O)_2NR^{52}-$, $-NR^{52}C(=NR^{52})NR^{52}-$, and $-NR^{52}C(NR^{52}R^{52})=N-$;

$L_8$ at each occurrence is independently selected from the group consisting of $-NR^{52}-$, $-NR^{52}O-$, $-C(=X)-$, $-C(=X)O-$, $-OC(=X)-$, $-C(=X)NR^{52}-$, $-C(=X)NR^{52}O-$, $-NR^{52}C(=X)-$, $-OC(=X)NR^{52}-$, $-NR^{52}C(=X)NR^{52}-$, $-NR^{52}C(=X)O-$, $-S(=O)-$, $-S(=O)_2-$, $-S(=O)_2NR^{52}-$, $-S(=O)_2NR^{52}O-$, $-NR^{52}S(=O)_2-$, $-NR^{52}S(=O)_2NR^{52}-$, $-NR^{52}C(=NR^{52})NR^{52}-$, and $-NR^{52}C(NR^{52}R^{52})=N-$;

X is O or S;

$R^{52}$ at each occurrence is independently selected from the group consisting of hydrogen, $C_1$-$C_6$ alkyl, $C_2$-$C_6$ alkenyl, $C_2$-$C_6$ alkynyl, cycloalkyl, heterocycloalkyl, aryl, and heteroaryl, wherein $C_1$-$C_6$ alkyl, $C_2$-$C_6$ alkenyl, and $C_2$-$C_6$ alkynyl are optionally substituted with one or more substituents $R^{57}$, and wherein cycloalkyl and heterocycloalkyl are optionally substituted with one or more substituents $R^{58}$, and wherein aryl and heteroaryl are optionally substituted with one or more substituents $R^{59}$;

$R^{56}$ at each occurrence is independently selected from the group consisting of $C_1$-$C_6$ alkyl, $C_2$-$C_6$ alkenyl, $C_2$-$C_6$ alkynyl, cycloalkyl, heterocycloalkyl, aryl, and heteroaryl, wherein $C_1$-$C_6$ alkyl, $C_2$-$C_6$ alkenyl, and $C_2$-$C_6$ alkynyl are optionally substituted with one or more substituents $R^{57}$, and wherein cycloalkyl and heterocycloalkyl are optionally substituted with one or more substituents $R^{58}$, and wherein aryl and heteroaryl are optionally substituted with one or more substituents $R^{59}$;

$R^{57}$ at each occurrence is independently selected from the group consisting of halogen, $-OH$, C, $-C_6$ alkoxy, $-SH$, $-S(=O)_m-C_1$-$C_6$ alkyl, $-NH_2$, $C_1$-$C_6$ alkylamino, $C_1$-$C_6$ dialkylamino, cycloalkyl, heterocycloalkyl, aryl, and heteroaryl, wherein the alkyl chain of $C_1$-$C_6$ alkoxy, $-S(=O)_m-C_1$-$C_6$ alkyl, $C_1$-$C_6$ alkylamino, or $C_1$-$C_6$ dialkylamino is optionally substituted with one or more substituents selected from the group consisting of halogen, $-OH$, $C_1$-$C_6$ alkoxy, $C_1$-$C_6$ haloalkoxy, $-SH$, $-S(=O)_m-C_1$-$C_6$ alkyl, $-S(=O)_m-C_1$-$C_6$ haloalkyl, $-NH_2$, $C_1$-$C_6$ alkylamino, $C_1$-$C_6$ dialkylamino, and N-linked-heterocycloalkyl, and wherein cycloalkyl and heterocycloalkyl are optionally substituted with one or more substituents $R^{58}$, and aryl and heteroaryl are optionally substituted with one or more substituents $R^{59}$;

$R^{58}$ at each occurrence is independently selected from the group consisting of halogen, $C_1$-$C_6$ alkyl, $-OH$, $=O$, $C_1$-$C_6$ alkoxy, $-SH$, $-S(=O)_m-C_1$-$C_6$ alkyl, $-NH_2$, $C_1$-$C_6$ alkylamino, $C_1$-$C_6$ dialkylamino, and N-linked-heterocycloalkyl, wherein the alkyl chain of $C_1$-$C_6$ alkyl, $C_1$-$C_6$ alkoxy, $-S(=O)_m-C_1$-$C_6$ alkyl, $C_1$-$C_6$, alkylamino, or $C_1$-$C_6$ dialkylamino is optionally substituted with one or more substituents selected from the group consisting of halogen, $-OH$, $C_1$-$C_6$ alkoxy, $C_1$-$C_6$ haloalkoxy, $-SH$, $-S(=O)_m-C_1$-$C_6$ alkyl, $-S(=O)_m-C_1$-$C_6$ haloalkyl, $-NH_2$, $C_1$-$C_6$ alkylamino, $C_1$-$C_6$ dialkylamino, and N-linked-heterocycloalkyl; and $R^{59}$ at each occurrence is independently selected from the group consisting of halogen, $C_1$-$C_6$ alkyl, $-OH$, $-CN$, $C_1$-$C_6$ alkoxy, $-SH$, $-S(=O)_m-C_1$-$C_6$ alkyl, $-NH_2$, $C_1$-$C_6$ alkylamino, $C_1$-$C_6$ dialkylamino, and N-linked-heterocycloalkyl, wherein the alkyl chain of $C_1$-$C_6$ alkyl, $C_1$-$C_6$ alkoxy, $-S(=O)_m-C_1$-$C_6$ alkyl, $C_1$-$C_6$ alkylamino, or $C_1$-$C_6$ dialkylamino is optionally substituted with one or more substituents selected from the group consisting of halogen, $-OH$, $C_1$-$C_6$ alkoxy, $C_1$-$C_6$ haloalkoxy, $-SH$, $-S(=O)_m-C_1$-$C_6$ alkyl, $-S(=O)_m-C_1$-$C_6$ haloalkyl, $-NH_2$, $C_1$-$C_6$ alkylamino, $C_1$-$C_6$ dialkylamino, and N-linked-heterocycloalkyl.

13. The compound according to claim 12, wherein:
$R^{33}$ is $-NR_{42}R_{43}$.

14. The compound according to claim 12, wherein $R^{33}$ is $-NR^{42}R^{43}$, where
$R^{42}$ is hydrogen; and
$R^{43}$ is selected from the group consisting of $C_3$-$C_8$ cycloalkyl, 4-7 membered heterocycloalkyl optionally substituted with one $C_1$-$C_6$ alkyl, and $C_1$-$C_6$ alkyl optionally substituted with one substituent selected from the group consisting of $-OH$, $C_3$-$C_8$ cycloalkyl, and 4-7 membered heterocycloalkyl.

15. The compound according to claim 12, wherein $R^{34}$ is selected from the group consisting of $-I$, $-Cl$, $-C\equiv CH$, $-CN$, $-C(=O)NH_2$, $-C(=O)NHCH_3$, imidazolyl, triazolyl, thiazolyl, oxazolyl, pyridinyl, and pyrimidin-4(3H)-onyl.

16. The compound according to claim 15, wherein $R^{34}$ is selected from the group consisting of $-CN$, $-C(=O)NH_2$, $-C(=O)NHCH_3$, imidazolyl, 1,2,4-triazolyl, and pyrimidin-4(3H)-onyl.

17. The compound according to claim 12, wherein one of $R^{35}$ and $R^{36}$ is hydrogen and the other of $R^{35}$ and $R^{36}$ is selected from the group consisting of $-OR^{55}$, $-SR^{55}$, $C_2$-$C_4$ alkyl, $C_2$-$C_3$ alkenyl, $C_3$-$C_6$ cycloalkyl, phenyl, heteroaryl, and heterocycloalkyl selected from the group consisting of piperazinyl, morpholinyl, pyrrolidinyl, oxazolidinyl, dihydropyridinyl, and indolinyl, wherein $C_2$-$C_4$ alkyl is optionally substituted with one OH, and wherein heterocycloalkyl is optionally substituted with one or more $=O$ or $C_1$-$C_6$ alkyl, and wherein phenyl and heteroaryl are optionally substituted with one or more substituents independently selected from the group consisting of halogen, $-OR^{51}$, $-S(=O)_2R^{51}$, $-NR^{52}R^{51}$, $-C(=O)NR^{52}R^{51}$, $C_1$-$C_6$ alkyl optionally substituted with one or more $C_1$-$C_6$ alkoxy, piperazinyl optionally substituted with one or more $=O$ or $C_1$-$C_6$ alkyl, morpholinyl optionally substituted with one or more $=O$ or $C_1$-$C_6$ alkyl, pyrrolidinyl optionally substituted with one or more $=O$ or $C_1$-$C_6$ alkyl, oxazolidinyl optionally substituted with one or more $=O$ or $C_1$-$C_6$ alkyl, phenyl optionally substituted with one or more substituents selected from the group consisting of halogen, $C_1$-$C_6$ alkoxy, morpholinyl optionally substituted with one or more $=O$ or $C_1$-$C_6$ alkyl, and oxazolidinyl optionally substituted with one or more $=O$ or $C_1$-$C_6$ alkyl, and heteroaryl optionally substituted with one or more substituents selected from the group consisting of halogen, $C_1$-$C_6$ alkyl, or $C_1$-$C_6$ alkoxy;

$R^{55}$ is phenyl optionally substituted with one or more $C_1$-$C_3$ alkoxy or $C_1$-$C_3$ haloalkoxy, or pyridinyl optionally substituted with one or more $C_1$-$C_3$ alkoxy or $C_1$-$C_3$ haloalkoxy;

$R^{51}$ at each occurrence is independently $C_1$-$C_6$ alkyl optionally substituted with one $C_3$-$C_6$ cycloalkyl or with one or more fluoro; and $R^{52}$ at each occurrence is independently hydrogen or $C_1$-$C_6$ alkyl.

18. The compound according to claim 1, wherein the compound has Formula Ib:

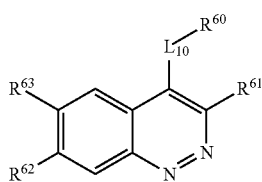

or a pharmaceutically acceptable salt thereof, wherein:
$L_{10}$ is —S— or —NH—;
$R^{60}$ is $C_1$-$C_6$ alkyl optionally substituted with one or more substituents $R^{64}$, $C_3$-$C_{10}$ cycloalkyl, or 4-7 membered heterocycloalkyl optionally substituted with one $C_1$-$C_6$ alkyl;
$R^{61}$ is selected from the group consisting of halogen, —CN, $C_2$-$C_6$ alkenyl, $C_2$-$C_6$ alkynyl, —C(=O)NHR$^{65}$, pyrimidinonyl, or 5 or 6 membered heteroaryl;
one of $R^{62}$ and $R^{63}$ is hydrogen;
the other of $R^{62}$ and $R^{63}$ is selected from the group consisting of —NHR$^{66}$, —OR$^{66}$, —SR$^{66}$, $C_2$-$C_6$ alkyl optionally substituted with one OH, $C_2$-$C_6$ alkenyl, $C_3$-$C_6$ cycloalkyl, heterocycloalkyl optionally substituted with one or more =O or $C_1$-$C_6$ alkyl, phenyl, and heteroaryl, wherein phenyl and heteroaryl are optionally substituted with one or more substituents independently selected from the group consisting of halogen, —OR$^{67}$, —S(=O)$_2$R$^{68}$, —NR$^{69}$R$_{70}$, —C(=O)NR$^{69}$R$^{70}$, $C_1$-$C_6$ alkyl optionally substituted with one or more R$^{71}$, heterocycloalkyl optionally substituted with one or more =O or $C_1$-$C_6$ alkyl, phenyl optionally substituted with one or more R$^{72}$, and heteroaryl optionally substituted with one or more R$^{73}$;
$R^{64}$ at each occurrence is independently selected from the group consisting of —OH, $C_3$-$C_8$ cycloalkyl, 4-7 membered heterocycloalkyl, phenyl and pyridyl;
$R^{65}$ is hydrogen or $C_1$-$C_6$ alkyl;
$R^{66}$ is phenyl optionally substituted with one or more R$^{70}$, or 5 or 6 membered heteroaryl optionally substituted with one or more R$^{71}$;
$R^{67}$, $R^{68}$ and $R^{69}$ are independently $C_1$-$C_6$ alkyl optionally substituted with one or more R$^{71}$;
$R^{70}$ is hydrogen or $C_1$-$C_6$ alkyl optionally substituted with one or more R$^{71}$;
$R^{71}$ is halogen, $C_1$-$C_6$ alkoxy, $C_1$-$C_6$ haloalkoxy, or $C_3$-$C_6$ cycloalkyl;
$R^{72}$ is halogen, $C_1$-$C_6$ alkyl, $C_1$-$C_6$ haloalkyl, $C_1$-$C_6$ alkoxy, $C_1$-$C_6$ haloalkoxy, or 4-7 membered heterocycloalkyl optionally substituted with one or more =O or $C_1$-$C_6$ alkyl; and
$R^{73}$ is halogen, $C_1$-$C_6$ alkyl, $C_1$-$C_6$ haloalkyl, $C_1$-$C_6$ alkoxy, $C_1$-$C_6$ haloalkoxy, or 4-7 membered heterocycloalkyl optionally substituted with one or more =O or $C_1$-$C_6$ alkyl.

19. The compound according to claim 18, wherein:
$R^{61}$ is selected from the group consisting of —I, —Cl, , —C≡CH, —CN, —C(=O)NH$_2$, —C(=O)NHCH$_3$, imidazolyl, triazolyl, thiazolyl, oxazolyl, pyridinyl, and pyrimidin-4(3H)-onyl.

20. The compound according to claim 19, wherein:
$L_{10}$ is —NH—; and
$R^{61}$ is selected from the group consisting of —CN, —C(=O)NH$_2$, —C(=O)NHCH$_3$, imidazolyl, 1,2,4-triazolyl, and pyrimidin-4(3H)-onyl.

21. The compound according to claim 18, wherein one of $R^{62}$ and $R^{63}$ is hydrogen and the other of $R^{62}$ and $R^{63}$ is selected from the group consisting of —NHR$^{66}$, —OR$^{66}$, —SR$^{66}$, $C_2$-$C_4$ alkyl, $C_2$-$C_3$ alkenyl, $C_3$-$C_6$ cycloalkyl, phenyl, heteroaryl, and heterocycloalkyl selected from the group consisting of piperazinyl, morpholinyl, pyrrolidinyl, oxazolidinyl, dihydropyridinyl, and indolinyl, wherein $C_2$-$C_4$ alkyl is optionally substituted with one OH, and wherein heterocycloalkyl is optionally substituted with one or more =O or $C_1$-$C_6$ alkyl, and wherein phenyl and heteroaryl are optionally substituted with one or more substituents independently selected from the group consisting of halogen, —OR$^{67}$, —S(=O)$_2$R$^{68}$, —NR$^{69}$R$^{70}$, —C(=O)NR$^{69}$R$^{70}$, $C_1$-$C_6$ alkyl optionally substituted with one or more $C_1$-$C_6$ alkoxy, piperazinyl optionally substituted with one or more =O or $C_1$-$C_6$ alkyl, morpholinyl optionally substituted with one or more =O or $C_1$-$C_6$ alkyl, pyrrolidinyl optionally substituted with one or more =O or $C_1$-$C_6$ alkyl, oxazolidinyl optionally substituted with one or more =O or $C_1$-$C_6$ alkyl, phenyl optionally substituted with one or more R$^{72}$, and heteroaryl optionally substituted with one or more R$^{73}$;
$R^{66}$ is phenyl optionally substituted with one or more $C_1$-$C_3$ alkoxy or $C_1$-$C_3$ haloalkoxy, or pyridinyl optionally substituted with one or more $C_1$-$C_3$ alkoxy or $C_1$-$C_3$ haloalkoxy;
$R^{67}$ at each occurrence is independently $C_1$-$C_6$ alkyl optionally substituted with one $C_3$-$C_6$ cycloalkyl or with one or more fluoro;
$R^{68}$ and $R^{69}$ at each occurrence are independently $C_1$-$C_6$ alkyl;
$R^{70}$ at each occurrence is independently hydrogen or $C_1$-$C_6$ alkyl;
$R^{72}$ at each occurrence is independently halogen, $C_1$-$C_6$ alkoxy, morpholinyl optionally substituted with one or more =O or $C_1$-$C_6$ alkyl, or oxazolidinyl optionally substituted with one or more =O or $C_1$-$C_6$ alkyl; and
$R^{73}$ at each occurrence is independently halogen, $C_1$-$C_6$ alkyl, or $C_1$-$C_6$ alkoxy.

22. The compound according to claim 1, wherein the compound is selected from the group consisting of:
4-(isopropylamino)-7-(4-(methylsulfonyl)phenyl)cinnoline-3-carboxamide,
4-(isopropylamino)-7-(4-(methylsulfonyl)phenyl)cinnoline-3-carbonitrile,
4-(cyclobutylamino)-7-(4-(methylsulfonyl)phenyl)cinnoline-3-carboxamide,
4-(cyclobutylamino)-7-(4-(methylsulfonyl)phenyl)cinnoline-3-carbonitrile,
4-(1-methylpiperidin-4-ylamino)-7-(4-(methylsulfonyl)phenyl)cinnoline-3-carboxamide,
4-(1-methylpiperidin-4-ylamino)-7-(4-(methylsulfonyl)phenyl)cinnoline-3-carbonitrile,
7-(4-(methylsulfonyl)phenyl)-4-(tetrahydrofuran-3-ylamino)cinnoline-3-carboxamide,
7-(4-(methylsulfonyl)phenyl)-4-(tetrahydrofuran-3-ylamino)cinnoline-3-carbonitrile,
7-(4-(methylsulfonyl)phenyl)-4-(tetrahydro-2H-pyran-4-ylamino)cinnoline-3-carboxamide,
7-(4-(methylsulfonyl)phenyl)-4-(tetrahydro-2H-pyran-4-ylamino)cinnoline-3-carbonitrile, 7-(4-(methylsulfonyl)phenyl)-4-(oxetan-3-ylamino)cinnoline-3-carboxamide,
7-(4-(methylsulfonyl)phenyl)-4-(oxetan-3-ylamino)cinnoline-3-carbonitrile,
4-(cyclopropylamino)-7-(4-(methylsulfonyl)phenyl)cinnoline-3-carboxamide,
4-(cyclopropylamino)-7-(4-(methylsulfonyl)phenyl)cinnoline-3-carbonitrile,
(R)-4-(sec-butylamino)-7-(4-(methylsulfonyl)phenyl)cinnoline-3-carboxamide,
(R)-4-(sec-butylamino)-7-(4-(methylsulfonyl)phenyl)cinnoline-3-carbonitrile,
(R)-7-(4-(methylsulfonyl)phenyl)-4-(1-phenylethylamino)cinnoline-3-carboxamide,
(R)-7-(4-(methylsulfonyl)phenyl)-4-(1-phenylethylamino)cinnoline-3-carbonitrile,
(R)-4-(1-cyclopropylethylamino)-7-(4-(methylsulfonyl)phenyl)cinnoline-3-carboxamide,
(R)-4-(1-cyclopropylethylamino)-7-(4-(methylsulfonyl)phenyl)cinnoline-3-carbonitrile,
4-(isopropylamino)-7-(pyridin-4-yl)cinnoline-3-carboxamide,
4-(isopropylamino)-7-(pyridin-4-yl)cinnoline-3-carbonitrile,
4-(isopropylamino)-7-(pyrimidin-5-yl)cinnoline-3-carboxamide,
4-(isopropylamino)-7-(pyrimidin-5-yl)cinnoline-3-carbonitrile,
4-(isopropylamino)-7-(1-methyl-1H-pyrazol-4-yl)cinnoline-3-carboxamide,
4-(isopropylamino)-7-(1-methyl-1H-pyrazol-4-yl)cinnoline-3-carbonitrile,
7-(4-fluorophenyl)-4-(isopropylamino)cinnoline-3-carboxamide,
7-(4-fluorophenyl)-4-(isopropylamino)cinnoline-3-carbonitrile,
7-(3-fluorophenyl)-4-(isopropylamino)cinnoline-3-carboxamide,
7-(3-fluorophenyl)-4-(isopropylamino)cinnoline-3-carbonitrile,
7-(2-fluorophenyl)-4-(isopropylamino)cinnoline-3-carboxamide,
7-(2-fluorophenyl)-4-(isopropylamino)cinnoline-3-carbonitrile,
4-(isopropylamino)-7-(4-morpholinophenyl)cinnoline-3-carboxamide,
4-(isopropylamino)-7-(4-morpholinophenyl)cinnoline-3-carbonitrile,
4-(isopropylamino)-7-(3-morpholinophenyl)cinnoline-3-carboxamide,
4-(isopropylamino)-7-(3-morpholinophenyl)cinnoline-3-carbonitrile,
4-(isopropylamino)-7-(1H-pyrazol-4-yl)cinnoline-3-carboxamide,
4-(isopropylamino)-7-(1H-pyrazol-4-yl)cinnoline-3-carbonitrile,
4-(isopropylamino)-7-(pyridin-3-yl)cinnoline-3-carboxamide,
4-(isopropylamino)-7-(pyridin-3-yl)cinnoline-3-carbonitrile,
N-isopropyl-7-(4-(methylsulfonyl)phenyl)-3-(thiazol-4-yl)cinnolin-4-amine,
3-iodo-N-isopropyl-7-(4-(methylsulfonyl)phenyl)cinnolin-4-amine,
N-isopropyl-7-(4-(methylsulfonyl)phenyl)-3-(oxazol-2-yl)cinnolin-4-amine,
N-isopropyl-7-(4-(methylsulfonyl)phenyl)-3-(pyridin-3-yl)cinnolin-4-amine,
4-(isopropylamino)-7-phenoxycinnoline-3-carboxamide,
4-(isopropylamino)-7-phenoxycinnoline-3-carbonitrile,
4-(isopropylamino)-7-(phenylthio)cinnoline-3-carboxamide,
4-(isopropylamino)-7-(phenylthio)cinnoline-3-carbonitrile,
4-(isopropylamino)-7-(phenylamino)cinnoline-3-carboxamide,
4-(isopropylamino)-7-(phenylamino)cinnoline-3-carbonitrile,
4-(isopropylamino)-7-(1H-pyrazol-1-yl)cinnoline-3-carboxamide,
4-(isopropylamino)-7-(1H-pyrazol-1-yl)cinnoline-3-carbonitrile,
4-(isopropylamino)-7-(thiazol-4-yl)cinnoline-3-carboxamide,
4-(isopropylamino)-7-(thiazol-4-yl)cinnoline-3-carbonitrile,
3-chloro-N-isopropyl-7-(4-(methylsulfonyl)phenyl)cinnolin-4-amine,
4-(isopropylamino)-7-(2-oxopyrrolidin-1-yl)cinnoline-3-carboxamide,
4-(isopropylamino)-7-(2-oxopyrrolidin-1-yl)cinnoline-3-carbonitrile,
3-ethynyl-N-isopropyl-7-(4-(methylsulfonyl)phenyl)cinnolin-4-amine,
(R)-4-(1-cyclopropylethylamino)-7-(pyridin-4-yl)cinnoline-3-carboxamide,
(R)-4-(1-cyclopropylethylamino)-7-(pyridin-4-yl)cinnoline-3-carbonitrile,
4-(isopropylamino)-7-(4-methylpiperazin-1-yl)cinnoline-3-carboxamide,
4-(isopropylamino)-7-(4-methylpiperazin-1-yl)cinnoline-3-carbonitrile,
4-(isopropylamino)-7-vinylcinnoline-3-carboxamide,
4-(isopropylamino)-7-vinylcinnoline-3-carbonitrile,
7-(2-hydroxyethyl)-4-(isopropylamino)cinnoline-3-carboxamide,
7-(2-hydroxyethyl)-4-(isopropylamino)cinnoline-3-carbonitrile,
(R)-4-(1-cyclopropylethylamino)-7-(1-methyl-1H-pyrazol-4-yl)cinnoline-3-carboxamide,
(R)-4-(1-cyclopropylethylamino)-7-(1-methyl-1H-pyrazol-4-yl)cinnoline-3-carbonitrile,
4-(isopropylamino)-7-(2-methoxyphenylamino)cinnoline-3-carboxamide,
4-(isopropylamino)-7-(2-methoxyphenylamino)cinnoline-3-carbonitrile,
4-(isopropylamino)-6-phenylcinnoline-3-carboxamide,
4-(isopropylamino)-6-phenylcinnoline-3-carbonitrile,
4-(isopropylamino)-6-(4-(methylsulfonyl)phenyl)cinnoline-3-carboxamide,
4-(isopropylamino)-6-(4-(methylsulfonyl)phenyl)cinnoline-3-carbonitrile,
4-(isopropylamino)-6-(pyridin-4-yl)cinnoline-3-carboxamide,
4-(isopropylamino)-6-(pyridin-4-yl)cinnoline-3-carbonitrile,
4-(isopropylamino)-6-(1H-pyrazol-4-yl)cinnoline-3-carboxamide,
4-(isopropylamino)-6-(1H-pyrazol-4-yl)cinnoline-3-carbonitrile,
4-(isopropylamino)-6-(1-methyl-1H-pyrazol-4-yl)cinnoline-3-carboxamide, 4-(isopropylamino)-6-(1-methyl-1H-pyrazol-4-yl)cinnoline-3-carbonitrile,
4-(isopropylamino)-6-(thiazol-2-yl)cinnoline-3-carboxamide,
4-(isopropylamino)-6-(thiazol-2-yl)cinnoline-3-carbonitrile,
4-(isopropylamino)-6-(thiazol-5-yl)cinnoline-3-carboxamide,
4-(isopropylamino)-6-(thiazol-5-yl)cinnoline-3-carbonitrile,
(R)-4-(1-phenylethylamino)-7-(pyridin-4-yl)cinnoline-3-carboxamide,
(R)-4-(1-phenylethylamino)-7-(pyridin-4-yl)cinnoline-3-carbonitrile,
(S)-4-(1-phenylethylamino)-7-(pyridin-4-yl)cinnoline-3-carboxamide,
(S)-4-(1-phenylethylamino)-7-(pyridin-4-yl)cinnoline-3-carbonitrile,
4-(pentan-3-ylamino)-7-(pyridin-4-yl)cinnoline-3-carboxamide,
4-(pentan-3-ylamino)-7-(pyridin-4-yl)cinnoline-3-carbonitrile,
4-(1-(pyridin-3-yl)ethylamino)-7-(pyridin-4-yl)cinnoline-3-carboxamide,
4-(1-(pyridin-3-yl)ethylamino)-7-(pyridin-4-yl)cinnoline-3-carbonitrile,
N-isopropyl-7-(4-(methylsulfonyl)phenyl)-3-(1H-1,2,4-triazol-3-yl)cinnolin-4-amine,
4-(isopropylamino)-7-(2-methoxypyridin-3-ylamino)cinnoline-3-carboxamide,
4-(isopropylamino)-7-(2-methoxypyridin-3-ylamino)cinnoline-3-carbonitrile,
2-(4-(isopropylamino)-7-(4-(methylsulfonyl)phenyl)cinnolin-3-yl)pyrimidin-4(3H)-one,
4-(isopropylamino)-6-morpholinocinnoline-3-carboxamide,
4-(isopropylamino)-6-morpholinocinnoline-3-carbonitrile,
4-(3-hydroxypropylamino)-7-(pyridin-4-yl)cinnoline-3-carboxamide,
4-(3-hydroxypropylamino)-7-(pyridin-4-yl)cinnoline-3-carbonitrile,
4-(2-hydroxyethylamino)-7-(pyridin-4-yl)cinnoline-3-carboxamide,
4-(2-hydroxyethylamino)-7-(pyridin-4-yl)cinnoline-3-carbonitrile,
4-(isopropylamino)-7-(3-methoxyphenylamino)cinnoline-3-carboxamide,
4-(isopropylamino)-7-(3-methoxyphenylamino)cinnoline-3-carbonitrile,
4-(isopropylamino)-7-(2-methoxyphenyl)cinnoline-3-carboxamide,
4-(isopropylamino)-7-(2-methoxyphenyl)cinnoline-3-carbonitrile,
4-(isopropylamino)-7-(3-methoxyphenyl)cinnoline-3-carboxamide,
4-(isopropylamino)-7-(3-methoxyphenyl)cinnoline-3-carbonitrile,
7-(5-fluoro-2-methoxyphenyl)-4-(isopropylamino)cinnoline-3-carboxamide,
7-(5-fluoro-2-methoxyphenyl)-4-(isopropylamino)cinnoline-3-carbonitrile,
4-(tert-butylamino)-7-(4-(methylsulfonyl)phenyl)cinnoline-3-carboxamide,
4-(tert-butylamino)-7-(4-(methylsulfonyl)phenyl)cinnoline-3-carbonitrile,
4-(sec-butylthio)-7-(4-(methylsulfonyl)phenyl)cinnoline-3-carboxamide,
4-(sec-butylthio)-7-(4-(methylsulfonyl)phenyl)cinnoline-3-carbonitrile,
4-(1-adamantylamino)-7-(4-(methylsulfonyl)phenyl)cinnoline-3-carboxamide,
4-(1-adamantylamino)-7-(4-(methylsulfonyl)phenyl)cinnoline-3-carbonitrile,
7-(4-(methylsulfonyl)phenyl)-4-((tetrahydro-2H-pyran-4-yl)methylamino)cinnoline-3-carboxamide,
7-(4-(methylsulfonyl)phenyl)-4-((tetrahydro-2H-pyran-4-yl)methylamino)cinnoline-3-carbonitrile,
4-(isopropylamino)-7-(prop-1-en-2-yl)cinnoline-3-carboxamide,
4-(isopropylamino)-7-(prop-1-en-2-yl)cinnoline-3-carbonitrile,
(R)-4-(1-cyclopropylethylamino)-7-(3-(dimethylcarbamoyl)phenyl)cinnoline-3-carboxamide,
(R)-4-(1-cyclopropylethylamino)-7-(3-(dimethylcarbamoyl)phenyl)cinnoline-3-carbonitrile,
(R)-4-(1-cyclopropylethylamino)-7-(2-methoxyphenyl)cinnoline-3-carboxamide,
(R)-4-(1-cyclopropylethylamino)-7-(2-methoxyphenyl)cinnoline-3-carbonitrile,
(R)-4-(1-cyclopropylethylamino)-7-(2-(methoxymethyl)phenyl)cinnoline-3-carboxamide,
(R)-4-(1-cyclopropylethylamino)-7-(2-(methoxymethyl)phenyl)cinnoline-3-carbonitrile,
(R)-4-(1-cyclopropylethylamino)-7-(isoquinolin-4-yl)cinnoline-3-carboxamide,
(R)-4-(1-cyclopropylethylamino)-7-(isoquinolin-4-yl)cinnoline-3-carbonitrile,
(R)-4-(1-cyclopropylethylamino)-7-(2-methoxy-5-(1H-pyrazol-1-yl)phenyl)cinnoline-3-carboxamide,
(R)-4-(1-cyclopropylethylamino)-7-(2-methoxy-5-(1H-pyrazol-1-yl)phenyl)cinnoline-3-carbonitrile,
(R)-7-(4-(methylsulfonyl)phenyl)-4-(1-(tetrahydro-2H-pyran-4-yl)ethylamino)cinnoline-3-carboxamide,
(R)-7-(4-(methylsulfonyl)phenyl)-4-(1-(tetrahydro-2H-pyran-4-yl)ethylamino)cinnoline-3-carbonitrile,
(R)-4-(1-cyclopropylethylamino)-7-(2-oxoindolin-5-yl)cinnoline-3-carboxamide,
(R)-4-(1-cyclopropylethylamino)-7-(2-oxoindolin-5-yl)cinnoline-3-carbonitrile,
(R)-4-(1-cyclopropylethylamino)-7-(5-(dimethylcarbamoyl)-2-methoxyphenyl)cinnoline-3-carboxamide,
(R)-4-(1-cyclopropylethylamino)-7-(5-(dimethylcarbamoyl)-2-methoxyphenyl)cinnoline-3-carbonitrile,
(R)-4-(1-cyclopropylethylamino)-7-(2-methoxy-5-(2-oxooxazolidin-3-yl)phenyl)cinnoline-3-carboxamide,
(R)-4-(1-cyclopropylethylamino)-7-(2-methoxy-5-(2-oxooxazolidin-3-yl)phenyl)cinnoline-3-carbonitrile,
(R)-4-(1-cyclopropylethylamino)-7-(2',4-dimethoxy-4'-(2-oxooxazolidin-3-yl)biphenyl-3-yl)cinnoline-3-carboxamide,
(R)-4-(1-cyclopropylethylamino)-7-(2',4-dimethoxy-4'-(2-oxooxazolidin-3-yl)biphenyl-3-yl)cinnoline-3-carbonitrile,
(R)-4-(1-cyclopropylethylamino)-7-(2-(trifluoromethoxy)phenyl)cinnoline-3-carboxamide,
(R)-4-(1-cyclopropylethylamino)-7-(2-(trifluoromethoxy)phenyl)cinnoline-3-carbonitrile,
(R)-7-(5-bromo-2-methoxyphenyl)-4-(1-cyclopropylethylamino)cinnoline-3-carboxamide,
(R)-7-(5-bromo-2-methoxyphenyl)-4-(1-cyclopropylethylamino)cinnoline-3-carbonitrile, (R)-7-(4'-bromo-2',4-dimethoxybiphenyl-3-yl)-4-(1-cyclopropylethylamino)cinnoline-3-carboxamide, (R)-7-(4'-bromo-2',4-dimethoxybiphenyl-3-yl)-4-(1-cyclopropylethylamino)cinnoline-3-carbonitrile, (R)-4-(1-cyclopropylethylamino)-7-(2-methoxy-5-(3-oxomorpholino)phenyl)cinnoline-3-carboxamide, (R)-4-(1-cyclopropylethylamino)-7-(2-methoxy-5-(3-oxomorpholino)phenyl)cinnoline-3-carbonitrile, (R)-4-(1-cyclopropylethylamino)-7-(2',4-dimethoxy-4'-(3-oxomorpholino)biphenyl-3-yl)cinnoline-3-carboxamide, (R)-4-(1-cyclopropylethylamino)-7-(2',4-dimethoxy-4'-(3-oxomorpholino)biphenyl-3-yl)cinnoline-3-carbonitrile, (R)-4-(1-cyclopropylethylamino)-7-phenylcinnoline-3-carboxamide, (R)-4-(1-cyclopropylethylamino)-7-phenylcinnoline-3-carbonitrile, (R)-4-(1-cyclopropylethylamino)-7-(3-(methylsulfonyl)phenyl)cinnoline-3-carboxamide, (R)-4-(1-cyclopropylethylamino)-7-(3-(methylsulfonyl)phenyl)cinnoline-3-carbonitrile, (R)-4-(1-cyclopropylethylamino)-7-(1-methyl-6-oxo-1,6-dihydropyridin-3-yl)cinnoline-3-carboxamide, (R)-4-(1-cyclopropylethylamino)-7-(1-methyl-6-oxo-1,6-dihydropyridin-3-yl)cinnoline-3-carbonitrile, (R)-4-(1-cyclopropylethylamino)-7-(3-(cyclopropylmethoxy)phenyl)cinnoline-3-carboxamide, (R)-4-(1-cyclopropylethylamino)-7-(3-(cyclopropylmethoxy)phenyl)cinnoline-3-carbonitrile, (R)-4-(1-cyclopropylethylamino)-7-(4-(dimethylcarbamoyl)phenyl)cinnoline-3-carboxamide, (R)-4-(1-cyclopropylethylamino)-7-(4-(dimethylcarbamoyl)phenyl)cinnoline-3-carbonitrile, (R)-4-(1-cyclopropylethylamino)-7-(2-methoxy-5-(methylsulfonyl)phenyl)cinnoline-3-carboxamide, (R)-4-(1-cyclopropylethylamino)-7-(2-methoxy-5-(methylsulfonyl)phenyl)cinnoline-3-carbonitrile, (R)-4-(1-cyclopropylethylamino)-7-(4-(3-oxomorpholino)phenyl)cinnoline-3-carboxamide, (R)-4-(1-cyclopropylethylamino)-7-(4-(3-oxomorpholino)phenyl)cinnoline-3-carbonitrile, (R)-4-(1-cyclopropylethylamino)-7-(4-(2-oxooxazolidin-3-yl)phenyl)cinnoline-3-carboxamide, (R)-4-(1-cyclopropylethylamino)-7-(4-(2-oxooxazolidin-3-yl)phenyl)cinnoline-3-carbonitrile, (R)-7-(2-chlorophenyl)-4-(1-cyclopropylethylamino)cinnoline-3-carboxamide, (R)-7-(2-chlorophenyl)-4-(1-cyclopropylethylamino)cinnoline-3-carbonitrile, (R)-4-(1-cyclopropylethylamino)-7-(4-(dimethylcarbamoyl)-2-methoxyphenyl)cinnoline-3-carboxamide, (R)-4-(1-cyclopropylethylamino)-7-(4-(dimethylcarbamoyl)-2-methoxyphenyl)cinnoline-3-carbonitrile, (R)-4-(1-cyclopropylethylamino)-7-(2-oxoindolin-4-yl)cinnoline-3-carboxamide, (R)-4-(1-cyclopropylethylamino)-7-(2-oxoindolin-4-yl)cinnoline-3-carbonitrile, (R)-4-(1-cyclopropylethylamino)-7-(2-oxoindolin-6-yl)cinnoline-3-carboxamide, (R)-4-(1-cyclopropylethylamino)-7-(2-oxoindolin-6-yl)cinnoline-3-carbonitrile, (R)-4-(1-cyclopropylethylamino)-7-(2-oxoindolin-7-yl)cinnoline-3-carboxamide, (R)-4-(1-cyclopropylethylamino)-7-(2-oxoindolin-7-yl)cinnoline-3-carbonitrile, (R)-4-(1-cyclopropylethylamino)-7-(1-methyl-2-oxo-1,2-dihydropyridin-4-yl)cinnoline-3-carboxamide, (R)-4-(1-cyclopropylethylamino)-7-(1-methyl-2-oxo-1,2-dihydropyridin-4-yl)cinnoline-3-carbonitrile, (R)-4-(1-cyclopropylethylamino)-7-(2-(methylsulfonyl)phenyl)cinnoline-3-carboxamide, (R)-4-(1-cyclopropylethylamino)-7-(2-(methylsulfonyl)phenyl)cinnoline-3-carbonitrile, 4-(cyclopropylmethylamino)-7-(4-(methylsulfonyl)phenyl)cinnoline-3-carboxamide, 4-(cyclopropylmethylamino)-7-(4-(methylsulfonyl)phenyl)cinnoline-3-carbonitrile, 4-(ethylamino)-7-(4-(methylsulfonyl)phenyl)cinnoline-3-carboxamide, 4-(ethylamino)-7-(4-(methylsulfonyl)phenyl)cinnoline-3-carbonitrile, 4-(methylamino)-7-(4-(methylsulfonyl)phenyl)cinnoline-3-carboxamide, 4-(methylamino)-7-(4-(methylsulfonyl)phenyl)cinnoline-3-carbonitrile, (R)-4-(1-cyclopropylethylamino)-7-(4-(3-fluoropyridin-2-yl)-2-methoxyphenyl)cinnoline-3-carboxamide, (R)-4-(1-cyclopropylethylamino)-7-(4-(3-fluoropyridin-2-yl)-2-methoxyphenyl)cinnoline-3-carbonitrile, (R)-7-(4-bromo-2-methoxyphenyl)-4-(1-cyclopropylethylamino)cinnoline-3-carboxamide, (R)-7-(4-bromo-2-methoxyphenyl)-4-(1-cyclopropylethylamino)cinnoline-3-carbonitrile, (R)-4-(1-cyclopropylethylamino)-7-(2-methoxy-4-(3-methoxypyrazin-2-yl)phenyl)cinnoline-3-carboxamide, (R)-4-(1-cyclopropylethylamino)-7-(2-methoxy-4-(3-methoxypyrazin-2-yl)phenyl)cinnoline-3-carbonitrile, (R)-4-(1-cyclopropylethylamino)-7-(2-methoxy-4-(1-methyl-1H-imidazol-2-yl)phenyl)cinnoline-3-carboxamide, (R)-4-(1-cyclopropylethylamino)-7-(2-methoxy-4-(1-methyl-1H-imidazol-2-yl)phenyl)cinnoline-3-carbonitrile, N-methyl-4-(methylamino)-7-(4-(methylsulfonyl)phenyl)cinnoline-3-carboxamide, 4-(isopropylamino)-N-methyl-7-(4-(methylsulfonyl)phenyl)cinnoline-3-carboxamide, 3-(1H-imidazol-2-yl)-N-isopropyl-7-(4-(methylsulfonyl)phenyl)cinnolin-4-amine, (R)-4-(1-cyclopropylethylamino)-N-methyl-7-(prop-1-en-2-yl)cinnoline-3-carboxamide, (R)-4-(1-cyclopropylethylamino)-N-methyl-7-(4-(methylsulfonyl)phenyl)cinnoline-3-carboxamide, and (R)-7-cyclopropyl-4-(1-cyclopropylethylamino)-N-methylcinnoline-3-carboxamide.

23. A pharmaceutical composition comprising a compound according to claim 1 and a pharmaceutically acceptable carrier.

\* \* \* \* \*